US009938354B2

(12) United States Patent
Gregory et al.

(10) Patent No.: US 9,938,354 B2
(45) Date of Patent: Apr. 10, 2018

(54) LIN28-MEDIATED CONTROL OF LET-7 BIOGENESIS

(71) Applicants: Children's Medical Center Corporation, Boston, MA (US); Dana-Farber Cancer Institute, Inc., Boston, MA (US)

(72) Inventors: Richard I. Gregory, Brookline, MA (US); Elena Piskounova, Dallas, TX (US); Dimitrios Iliopoulos, Los Angeles, CA (US)

(73) Assignees: Dana-Farber Cancer Institute, Inc., Boston, MA (US); Children's Medical Center Corporation, Boston, MA (US)

( * ) Notice: Subject to any disclaimer, the term of this patent is extended or adjusted under 35 U.S.C. 154(b) by 0 days.

(21) Appl. No.: 14/269,041

(22) Filed: May 2, 2014

(65) Prior Publication Data
US 2014/0328858 A1 Nov. 6, 2014

Related U.S. Application Data

(63) Continuation of application No. 14/007,465, filed as application No. PCT/US2012/030497 on Mar. 26, 2012, now abandoned.

(60) Provisional application No. 61/562,706, filed on Nov. 22, 2011, provisional application No. 61/467,427, filed on Mar. 25, 2011.

(51) Int. Cl.
| *A61K 31/713* | (2006.01) |
| *C12N 15/113* | (2010.01) |
| *C07K 16/40* | (2006.01) |
| *A61K 31/7105* | (2006.01) |
| *C12N 15/11* | (2006.01) |
| *C07K 2/00* | (2006.01) |
| *C12N 15/115* | (2010.01) |

(52) U.S. Cl.
CPC ............ *C07K 16/40* (2013.01); *A61K 31/713* (2013.01); *A61K 31/7105* (2013.01); *C07K 2/00* (2013.01); *C12N 15/111* (2013.01); *C12N 15/115* (2013.01); *C12N 15/1137* (2013.01); *C12N 2310/14* (2013.01); *C12N 2310/141* (2013.01); *C12N 2320/10* (2013.01); *C12N 2320/50* (2013.01)

(58) Field of Classification Search
None
See application file for complete search history.

(56) References Cited

U.S. PATENT DOCUMENTS

2010/0221266 A1    9/2010 Gregory et al.

FOREIGN PATENT DOCUMENTS

WO    WO 2011/015829 A1    2/2011

OTHER PUBLICATIONS

International Search Report and Written Opinion for PCT/US2012/030497 dated Oct. 23, 2012.
International Preliminary Report on Patentability for PCT/US2012/030497 dated Oct. 10, 2013.
Extended European Search Report for EP 12763967.2 dated Nov. 10, 2014.
Hagan et al., Lin28 recruits the TUTase Zcchc11 to inhibit let-7 maturation in mouse embryonic stem cells. Nat Struct Mol Biol. Oct. 2009;16(10):1021-5. doi: 10.1038/nsmb.1676. Epub Aug. 27, 2009.
Heo et al., TUT4 in concert with Lin28 suppresses microRNA biogenesis through pre-microRNA uridylation. Cell. Aug. 21, 2009;138(4):696-708. doi: 10.1016/j.cell.2009.08.002.
Heo et al., Lin28 mediates the terminal uridylation of let-7 precursor MicroRNA. Mol Cell. Oct. 24, 2008;32(2):276-84. doi: 10.1016/j.molcel.2008.09.014.
Minoda et al., A novel Zinc finger protein, ZCCHC11, interacts with TIFA and modulates TLR signaling. Biochem Biophys Res Commun. Jun. 9, 2006;344(3):1023-30. Epub Apr. 19, 2006.
Piskounova et al., Lin28A and Lin28B inhibit let-7 microRNA biogenesis by distinct mechanisms. Cell. Nov. 23, 2011;147(5):1066-79. doi: 10.1016/j.cell.2011.10.039.
Blahna et al., Terminal uridyltransferase enzyme Zcchc11 promotes cell proliferation independent of its uridyltransferase activity. J Biol Chem. Dec. 9, 2011;286(49):42381-9. doi:10.1074/jbc.M111.259689. Epub Oct. 17, 2011.
Guo et al., Identification and characterization of lin-28 homolog B (LIN28B) in human hepatocellular carcinoma. Gene. Dec. 15, 2006;384:51-61. Epub Jul. 28, 2006.
Jones et al., Zcchc11-dependent uridylation of microRNA directs cytokine expression. Nat Cell Biol. Sep. 2009;11(9):1157-63. doi: 10.1038/ncb1931. Epub Aug. 23, 2009.
Kwak et al., A family of poly(U) polymerases. RNA. Jun. 2007;13(6):860-7. Epub Apr. 20, 2007.
Lehrbach et al., LIN-28 and the poly(U) polymerase PUP-2 regulate let-7 microRNA processing in Caenorhabditis elegans. Nat Struct Mol Biol. Oct. 2009;16(10):1016-20. doi: 10.1038/nsmb.1675. Epub Aug. 27, 2009.
Nam et al., Molecular basis for interaction of let-7 microRNAs with Lin28. Cell. Nov. 23, 2011;147(5):1080-91. doi:10.1016/j.cell.2011.10.020. Epub Nov. 10, 2011.
Newman et al., Lin-28 interaction with the Let-7 precursor loop mediates regulated microRNA processing. RNA. Aug. 2008;14(8):1539-49. doi: 10.1261/rna.1155108. Epub Jun. 19, 2008.
Piskounova et al., Determinants of microRNA processing inhibition by the developmentally regulated RNA-binding protein Lin28. J Biol Chem. Aug. 1, 2008;283(31):21310-4. doi: 10.1074/jbc.C800108200. Epub Jun. 12, 2008.
Rissland et al., Efficient RNA polyuridylation by noncanonical poly(A) polymerases. Mol Cell Biol. May 2007;27(10):3612-24. Epub Mar. 12, 2007.
Schmidt et al., The human cytoplasmic RNA terminal U-transferase ZCCHC11 targets histone mRNAs for degradation. RNA. Jan. 2011;17(1):39-44. doi: 10.1261/rna.2252511. Epub Nov. 4, 2010.

(Continued)

*Primary Examiner* — Tracy Vivlemore
(74) *Attorney, Agent, or Firm* — Wolf, Greenfield & Sacks, P.C.

(57) ABSTRACT

The present embodiments provide for compositions and methods that regulate microRNA-binding protein-mediated miRNA biogenesis; for example Lin28-mediated biogenesis of let-7; and in particular Lin28A-recruited 3' terminal uridylyl transferase (TUTase) uridylation of pre-let-7. A particular embodiment provide compositions and methods for screening for agents that inhibit TUTase-dependent Lin28A-mediated repression of let-7 miRNA.

8 Claims, 56 Drawing Sheets

(56) References Cited

OTHER PUBLICATIONS

Scott et al., Characterization and prediction of protein nucleolar localization sequences. Nucleic Acids Res. Nov. 2010;38(21):7388-99. doi: 10.1093/nar/gkq653. Epub Jul. 26, 2010.
Stagno et al., Structure of the mitochondrial editosome-like complex associated TUTase 1 reveals divergent mechanisms of UTP selection and domain organization. J Mol Biol. Jun. 11, 2010;399(3):464-75. doi: 10.1016/j.jmb.2010.04.021. Epub Apr. 18, 2010.
Thorton et al., Lin28-mediated control of let-7 microRNA expression by alternative TUTases Zcchc11 (TUT4) and Zcchc6 (TUT7), RNA Oct. 2012, vol. 18, No. 10, pp. 1875-1885.
Tomlins et al., Integrative molecular concept modeling of prostate cancer progression. Nat Genet. Jan. 2007;39(1):41-51. Epub Dec. 17, 2006.
Van Wynsberghe et al., LIN-28 co-transcriptionally binds primary let-7 to regulate miRNA maturation in Caenorhabditis elegans. Nat Struct Mol Biol. Mar. 2011;18(3):302-8. doi:10.1038/nsmb.1986. Epub Feb. 6, 2011.
Viswanathan et al., Selective blockade of microRNA processing by Lin28. Science. Apr. 4, 2008;320(5872):97-100. doi:10.1126/science.1154040. Epub Feb. 21, 2008.
Wyman et al., Post-transcriptional generation of miRNA variants by multiple nucleotidyl transferases contributes to miRNA transcriptome complexity. Genome Res. Sep. 2011;21(9):1450-61. doi: 10.1101/gr.118059.110. Epub Aug. 3, 2011.

```
hZcchc11    YDEKARLCLFGSSKNGFGFRDS DLDI CMTLEGHENAEKLNCKEIIENLAKILLKRHPGLRN  1012
hZcchc6     FPG-TKLSLFGSSKNGFGFKQS DLDV CMTINGLETAEGLDCVRTIEELARVLRKHSGLRN   1060
            :*:*************:***  ::**  ****:* :*::**  *:**:::*::***:****

hZcchc11    ILPITTAKVPIVKFEHRRSGLEG DI SLYNTLAQHNTRMLATYAAIDPRVQYLGYTMKVFA  1072
hZcchc6     ILPITTAKVPIVKFFHLRSGLEV DI SLYNTLALHNTRLLSAYSAIDPRVKYLCYLCYTMKVFT  1120
            **************  *:***  ** ******* ****::::*:*****:** **:****:
```

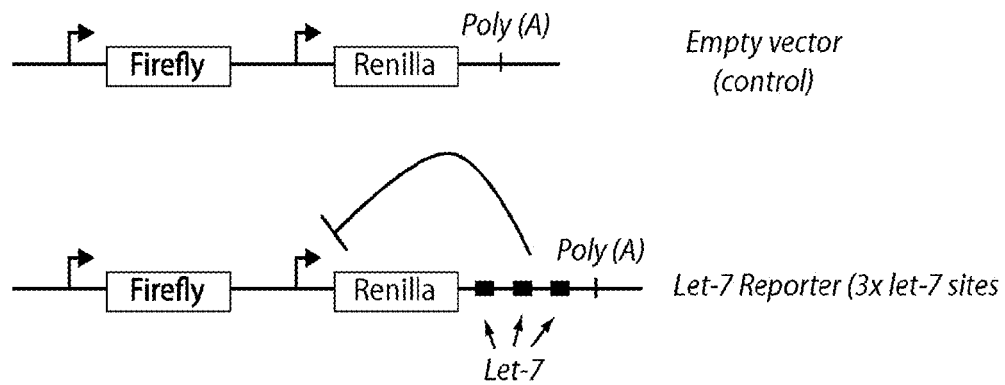
Fig. 23A
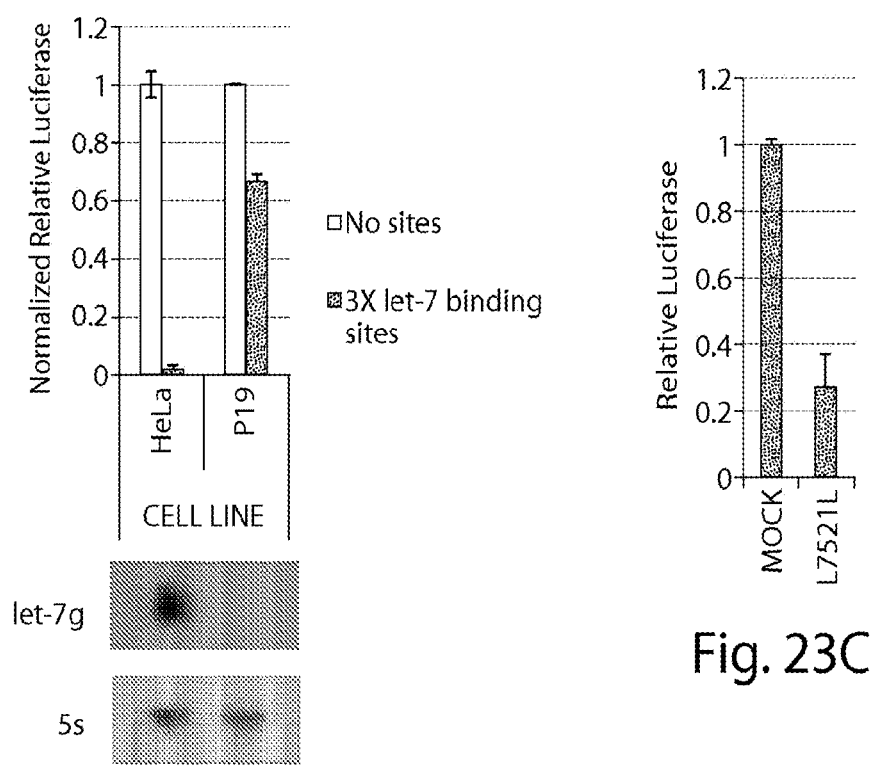
Fig. 23B
Fig. 23C

SEQUENCE LISTING

<160> NUMBER OF SEQ ID NOS: 101

<210> SEQ ID NO 1
<211> LENGTH: 12
<212> TYPE: PRT
<213> ORGANISM: Artificial Sequence
<220> FEATURE:
<223> OTHER INFORMATION: Synthetic Polypeptide

<400> SEQUENCE: 1

Lys Lys Gly Pro Ser Val Gln Lys Arg Lys Lys Thr
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Synthetic Polypeptide

<400> SEQUENCE: 2

Arg Arg Pro Lys Gly Lys Thr Leu Gln Lys Arg Lys Pro Lys
1               5                   10

<210> SEQ ID NO 3
<211> LENGTH: 7
<212> TYPE: RNA
<213> ORGANISM: Artificial Sequence
<220> FEATURE:
<223> OTHER INFORMATION: Synthetic Polynucleotide

<400> SEQUENCE: 3 aggagau                                                                     7

<210> SEQ ID NO 4
<211> LENGTH: 9
<212> TYPE: RNA
<213> ORGANISM: Artificial Sequence
<220> FEATURE:
<223> OTHER INFORMATION: Synthetic Polynucleotide

<400> SEQUENCE: 4 guaguuugu                                                                   9

<210> SEQ ID NO 5
<211> LENGTH: 77
<212> TYPE: RNA
<213> ORGANISM: Artificial Sequence
<220> FEATURE:
<223> OTHER INFORMATION: Synthetic Polynucleotide

<400> SEQUENCE: 5
gagguaguag uuuguacagu uugagggucu augauaccac ccgguacagg agauaacugu          60
acaggccacu gccuugc                                                         77

<210> SEQ ID NO 6
<211> LENGTH: 60
<212> TYPE: RNA
<213> ORGANISM: Artificial Sequence
<220> FEATURE:
<223> OTHER INFORMATION: Synthetic Polynucleotide

<400> SEQUENCE: 6
uagcuuauca gacugauguu gacuguugaa ucucauggca acagcagucg augggcuguc        60

<210> SEQ ID NO 7
<211> LENGTH: 77
<212> TYPE: RNA
<213> ORGANISM: Artificial Sequence
<220> FEATURE:
<223> OTHER INFORMATION: Synthetic Polynucleotide

<400> SEQUENCE: 7
uagcuuauca gacugauguu gaugaggguc uaugauacca cccgguacag gagaucaaca        60
gcagucgaug ggcuguc                                                       77

<210> SEQ ID NO 8
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 8

Tyr Leu Cys Lys Leu Cys Leu Ile His Ile Glu Asn Ile Gln Gly Ala
1               5                   10                  15

His Lys His Ile Lys Glu Lys Arg His
            20                  25

<210> SEQ ID NO 9
<211> LENGTH: 25
<212> TYPE: PRT
<213> ORGANISM: Artificial Sequence
<220> FEATURE:
<223> OTHER INFORMATION: Synthetic Polypeptide

<400> SEQUENCE: 9

Tyr Thr Cys Arg Leu Cys Asp Val Leu Ile Glu Ser Ile Ala Phe Ala
1               5                   10                  15

His Lys His Ile Lys Glu Lys Arg His
            20                  25

<210> SEQ ID NO 10
<211> LENGTH: 119
<212> TYPE: PRT
<213> ORGANISM: Artificial Sequence
<220> FEATURE:
<223> OTHER INFORMATION: Synthetic Polypeptide

<400> SEQUENCE: 10

Tyr Asp Glu Lys Ala Arg Leu Cys Leu Phe Gly Ser Ser Lys Asn Gly
1               5                   10                  15

Phe Gly Phe Arg Asp Ser Asp Leu Asp Ile Cys Met Thr Leu Glu Gly
            20                  25                  30

His Glu Asn Ala Glu Lys Leu Asn Cys Lys Glu Ile Ile Glu Asn Leu
        35                  40                  45

Ala Lys Ile Leu Lys Arg His Pro Gly Leu Arg Asn Ile Leu Pro Ile
    50                  55                  60

Thr Thr Ala Lys Val Pro Ile Val Lys Phe Glu His Arg Arg Ser Gly
65                  70                  75                  80

Leu Glu Gly Asp Ile Ser Leu Tyr Asn Thr Ala Gln His Asn Thr Arg
                85                  90                  95

```
Met Leu Ala Thr Tyr Ala Ala Ile Asp Pro Arg Val Gln Tyr Leu Gly
            100                 105                 110

Tyr Thr Met Lys Val Phe Ala
            115

<210> SEQ ID NO 11
<211> LENGTH: 118
<212> TYPE: PRT
<213> ORGANISM: Artificial Sequence
<220> FEATURE:
<223> OTHER INFORMATION: Synthetic Polypeptide

<400> SEQUENCE: 11

Phe Pro Gly Thr Lys Leu Ser Leu Phe Gly Ser Ser Lys Asn Gly Phe
1               5                   10                  15

Gly Phe Lys Gln Ser Asp Leu Asp Val Cys Met Thr Ile Asn Gly Leu
            20                  25                  30

Glu Thr Ala Glu Gly Leu Asp Cys Val Arg Thr Ile Glu Glu Leu Ala
        35                  40                  45

Arg Val Leu Arg Lys His Ser Gly Leu Arg Asn Ile Leu Pro Ile Thr
    50                  55                  60

Thr Ala Lys Val Pro Ile Val Lys Phe Phe His Leu Arg Ser Gly Leu
65                  70                  75                  80

Glu Val Asp Ile Ser Tyr Asn Thr Leu Ala Leu His Asn Thr Arg Leu
                85                  90                  95

Leu Ser Ala Tyr Ser Ala Ile Asp Pro Arg Val Lys Tyr Leu Cys Tyr
            100                 105                 110

Thr Met Lys Val Phe Thr
            115

<210> SEQ ID NO 12
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 12
ugagguagua guuugugcug uu                                        22

<210> SEQ ID NO 13
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 13
cugcgcaagc uacugccuug cu                                        22

<210> SEQ ID NO 14
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 14
uagucgcugc auuugugcug uu                                        22

<210> SEQ ID NO 15
<211> LENGTH: 22
```

```
<212> TYPE: RNA
<213> ORGANISM: Artificial Sequence
<220> FEATURE:
<223> OTHER INFORMATION: Synthetic Polynucleotide

<400> SEQUENCE: 15
ugagguaugc agccuagcug uu                                              22

<210> SEQ ID NO 16
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 16
uagucgcugc agccuagcug uu                                              22

<210> SEQ ID NO 17
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 17
uuacauacua auuucuacuc uu                                              22

<210> SEQ ID NO 18
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 18
ucgaaguauu ccgcguacgu u                                               21

<210> SEQ ID NO 19
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 19 ucgagugua guuuguacgu u                                                21

<210> SEQ ID NO 20
<211> LENGTH: 23
<212> TYPE: RNA
<213> ORGANISM: Artificial Sequence
<220> FEATURE:
<223> OTHER INFORMATION: Synthetic Polynucleotide

<400> SEQUENCE: 20
uacccuguag auccgaauuu gug                                             23

<210> SEQ ID NO 21
<211> LENGTH: 22
<212> TYPE: RNA
<213> ORGANISM: Artificial Sequence
<220> FEATURE:
<223> OTHER INFORMATION: Synthetic Polynucleotide

<400> SEQUENCE: 21
```
uuccaaguaa uccaggauag gc                                              22

<210> SEQ ID NO 22
<211> LENGTH: 23
<212> TYPE: RNA
<213> ORGANISM: Artificial Sequence
<220> FEATURE:
<223> OTHER INFORMATION: Synthetic Polynucleotide

<400> SEQUENCE: 22
uacccuugca auccgaagcc uag                                             23

<210> SEQ ID NO 23
<211> LENGTH: 59
<212> TYPE: DNA
<213> ORGANISM: Artificial Sequence
<220> FEATURE:
<223> OTHER INFORMATION: Synthetic Polynucleotide

<400> SEQUENCE: 23
tgcagaccgg tgagcagaaa ctcataagcg aagaggacct gggctccgtg tccaaccag      59

<210> SEQ ID NO 24
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 24
gacatgaagc tttcaattct gtgcctccgg gag                                  33

<210> SEQ ID NO 25
<211> LENGTH: 58
<212> TYPE: DNA
<213> ORGANISM: Artificial Sequence
<220> FEATURE:
<223> OTHER INFORMATION: Synthetic Polynucleotide

<400> SEQUENCE: 25
tgcagaccgg tgagcagaaa ctcataagcg aagaggacct ggccgaaggc ggggctag       58

<210> SEQ ID NO 26
<211> LENGTH: 43
<212> TYPE: DNA
<213> ORGANISM: Artificial Sequence
<220> FEATURE:
<223> OTHER INFORMATION: Synthetic Polynucleotide

<400> SEQUENCE: 26
tacgattcta gattatgtct ttttcctttt ttgaactgaa ggc                       43

<210> SEQ ID NO 27
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 27
agtctatcta gattagcttt gctcttctgg tgc                                  33

<210> SEQ ID NO 28
<211> LENGTH: 33
<212> TYPE: DNA
<213> ORGANISM: Artificial Sequence

```
<220> FEATURE:
<223> OTHER INFORMATION: Synthetic Polynucleotide

<400> SEQUENCE: 28
gacactacag ggaagaggac caggggggaga tag                              33

<210> SEQ ID NO 29
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 29
ctatctcccc ctggtcctct tccctgtagt gtc                               33

<210> SEQ ID NO 30
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 30
ggaagtgaaa gaggacccgg agggaagaca cta                               33

<210> SEQ ID NO 31
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 31
tagtgtcttc cctccgggtc ctctttcact tcc                               33

<210> SEQ ID NO 32
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 32
tatcgatcta gaggctccgt gtccaaccag cag                               33

<210> SEQ ID NO 33
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 33
tatcgaggat ccttaattct gtgcctccgg gagcaggg                          38

<210> SEQ ID NO 34
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 34
tatcgatcta gagccgaagg cggggctagc aaag                              34
```

<210> SEQ ID NO 35
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 35
ctcgcaggat ccttatgtct ttttcctttt ttgaactg         38

<210> SEQ ID NO 36
<211> LENGTH: 33
<212> TYPE: DNA
<213> ORGANISM: Artificial Sequence
<220> FEATURE:
<223> OTHER INFORMATION: Synthetic Polynucleotide

<400> SEQUENCE: 36
cgtcagggat ccttagcttt gctcttctgg tgc              33

<210> SEQ ID NO 37
<211> LENGTH: 28
<212> TYPE: DNA
<213> ORGANISM: Artificial Sequence
<220> FEATURE:
<223> OTHER INFORMATION: Synthetic Polynucleotide

<400> SEQUENCE: 37
gccgccatgg gctccgtgtc caaccagc                    28

<210> SEQ ID NO 38
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 38
cattctgtgc ctccgggagc ag                          22

<210> SEQ ID NO 39
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 39
gccgccatgg ccgaaggcgg ggctagc                     27

<210> SEQ ID NO 40
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 40
ctgtcttttt cctttttga actg                         24

<210> SEQ ID NO 41
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 41
aaactgaagg cccctttttg c                                           21

<210> SEQ ID NO 42
<211> LENGTH: 47
<212> TYPE: DNA
<213> ORGANISM: Artificial Sequence
<220> FEATURE:
<223> OTHER INFORMATION: Synthetic Polynucleotide

<400> SEQUENCE: 42
gccgccatga aaaagggggcc ttcagttcaa aaaggaaaa agacaga                47

<210> SEQ ID NO 43
<211> LENGTH: 48
<212> TYPE: DNA
<213> ORGANISM: Artificial Sequence
<220> FEATURE:
<223> OTHER INFORMATION: Synthetic Polynucleotide

<400> SEQUENCE: 43 tctgtcttt tccttttttg aactgaaggc ccctttttca tggcggca                48

<210> SEQ ID NO 44
<211> LENGTH: 56
<212> TYPE: DNA
<213> ORGANISM: Artificial Sequence
<220> FEATURE:
<223> OTHER INFORMATION: Synthetic Polynucleotide

<400> SEQUENCE: 44
gccgccatgg gaagaagacc caaagggaag acactacaga aagaaaacc aaagga       56

<210> SEQ ID NO 45
<211> LENGTH: 56
<212> TYPE: DNA
<213> ORGANISM: Artificial Sequence
<220> FEATURE:
<223> OTHER INFORMATION: Synthetic Polynucleotide

<400> SEQUENCE: 45
cctttggttt tcttttctgt agtgtcttcc ctttgggtct tcttcccatg gcggca      56

<210> SEQ ID NO 46
<211> LENGTH: 45
<212> TYPE: DNA
<213> ORGANISM: Artificial Sequence
<220> FEATURE:
<223> OTHER INFORMATION: Synthetic Polynucleotide

<400> SEQUENCE: 46
ggatcccatc atcaccatca ccacggctcc gtgtccaacc agcag                  45

<210> SEQ ID NO 47
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 47
gcggccgctt acagtttgcg taccaataag                                   30

<210> SEQ ID NO 48

-continued

```
<211> LENGTH: 46
<212> TYPE: DNA
<213> ORGANISM: Artificial Sequence
<220> FEATURE:
<223> OTHER INFORMATION: Synthetic Polynucleotide

<400> SEQUENCE: 48
ggatcccatc atcaccatca ccacgccgaa ggcggggcta gcaaag           46

<210> SEQ ID NO 49
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 49
ttatgtcttt ttcctttttt gaac                                   24

<210> SEQ ID NO 50
<211> LENGTH: 18
<212> TYPE: DNA
<213> ORGANISM: Artificial Sequence
<220> FEATURE:
<223> OTHER INFORMATION: Synthetic Polynucleotide

<400> SEQUENCE: 50
agcgctccgt ttccttt                                           18

<210> SEQ ID NO 51
<211> LENGTH: 16
<212> TYPE: DNA
<213> ORGANISM: Artificial Sequence
<220> FEATURE:
<223> OTHER INFORMATION: Synthetic Polynucleotide

<400> SEQUENCE: 51
ccccacttgg cagctg                                            16

<210> SEQ ID NO 52
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 52
cctggatgtt ctcttcactg                                        20

<210> SEQ ID NO 53
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 53
gcctggatgc agactttct                                         20

<210> SEQ ID NO 54
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 54
```

```
gcttatcaga ctgatgttga ctg                                        23

<210> SEQ ID NO 55
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 55
cagcccatcg actggtg                                               17

<210> SEQ ID NO 56
<211> LENGTH: 17
<212> TYPE: DNA
<213> ORGANISM: Artificial Sequence
<220> FEATURE:
<223> OTHER INFORMATION: Synthetic Polynucleotide

<400> SEQUENCE: 56
ctcgcttcgg cagcaca                                               17

<210> SEQ ID NO 57
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 57
aacgcttcac gaatttgcgt                                            20

<210> SEQ ID NO 58
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 58
aagcgcagat caaaaggaga                                            20

<210> SEQ ID NO 59
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 59
ctgatgctct ggcagaagtg                                            20

<210> SEQ ID NO 60
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 60
tgataaaccg agagggaagc                                            20

<210> SEQ ID NO 61
<211> LENGTH: 21
<212> TYPE: DNA
```

<213> ORGANISM: Artificial Sequence
<220> FEATURE:
<223> OTHER INFORMATION: Synthetic Polynucleotide

<400> SEQUENCE: 61
tgtgaattcc actggttctc c                                            21

<210> SEQ ID NO 62
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 62
atgttcgtca tgggtgtgaa                                              20

<210> SEQ ID NO 63
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 63
ggtgctaagc agttggtggt                                              20

<210> SEQ ID NO 64
<211> LENGTH: 64
<212> TYPE: DNA
<213> ORGANISM: Artificial Sequence
<220> FEATURE:
<223> OTHER INFORMATION: Synthetic Polynucleotide

<400> SEQUENCE: 64
accggcaaca agatgaagag caccaactcg agttggtgct cttcatcttg ttgtttttga   60
attc                                                               64

<210> SEQ ID NO 65
<211> LENGTH: 71
<212> TYPE: DNA
<213> ORGANISM: Artificial Sequence
<220> FEATURE:
<223> OTHER INFORMATION: Synthetic Polynucleotide

<400> SEQUENCE: 65
accgggcccg caagctgacc ctgaagttca ttcaagagat gaacttcagg gtcagcttgc   60
tttttgaatt c                                                       71

<210> SEQ ID NO 66
<211> LENGTH: 64
<212> TYPE: DNA
<213> ORGANISM: Artificial Sequence
<220> FEATURE:
<223> OTHER INFORMATION: Synthetic Polynucleotide

<400> SEQUENCE: 66
accgggtcgg cttacggcgg tgatttctcg agaaatcacc gccgtaagcc gactttttga   60
attc                                                               64

<210> SEQ ID NO 67
<211> LENGTH: 65
<212> TYPE: DNA
<213> ORGANISM: Artificial Sequence
<220> FEATURE:
<223> OTHER INFORMATION: Synthetic Polynucleotide

<400> SEQUENCE: 67
accgggtcag ttacattcag cagaaactcg agtttctgct gaatgtaact gactttttg    60 aattc                                                                65

<210> SEQ ID NO 68
<211> LENGTH: 65
<212> TYPE: DNA
<213> ORGANISM: Artificial Sequence
<220> FEATURE:
<223> OTHER INFORMATION: Synthetic Polynucleotide

<400> SEQUENCE: 68
accggcgtga tagtgatctg gatattctcg agaatatcca gatcactatc acgttttttg   60
aattc                                                                65

<210> SEQ ID NO 69
<211> LENGTH: 65
<212> TYPE: DNA
<213> ORGANISM: Artificial Sequence
<220> FEATURE:
<223> OTHER INFORMATION: Synthetic Polynucleotide

<400> SEQUENCE: 69
accgggcttc tgaccttaat gatgatctcg agatcatcat taaggtcaga agctttttg    60 aattc                                                                65

<210> SEQ ID NO 70
<211> LENGTH: 65
<212> TYPE: DNA
<213> ORGANISM: Artificial Sequence
<220> FEATURE:
<223> OTHER INFORMATION: Synthetic Polynucleotide

<400> SEQUENCE: 70
accgggcaac agacatgtac agataactcg agttatctgt acatgtctgt tgctttttg    60 aattc                                                                65

<210> SEQ ID NO 71
<211> LENGTH: 64
<212> TYPE: DNA
<213> ORGANISM: Artificial Sequence
<220> FEATURE:
<223> OTHER INFORMATION: Synthetic Polynucleotide

<400> SEQUENCE: 71
accgggaacc cttccatgtg cagcttttcg aagctgcaca tggaagggtt ccttttttga   60
attc                                                                 64

<210> SEQ ID NO 72
<211> LENGTH: 59
<212> TYPE: DNA
<213> ORGANISM: Artificial Sequence
<220> FEATURE:
<223> OTHER INFORMATION: Synthetic Polynucleotide

<400> SEQUENCE: 72
ccgggccttg agtcaatacg ggtaactcga gttacccgta ttgactcaag gctttttg     59

<210> SEQ ID NO 73

```
<211> LENGTH: 39
<212> TYPE: DNA
<213> ORGANISM: Artificial Sequence
<220> FEATURE:
<223> OTHER INFORMATION: Synthetic Polynucleotide

<400> SEQUENCE: 73
tgccgcctcg aggtttctat ggataaaagg aagagtgaa                            39

<210> SEQ ID NO 74
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 74
tgccgcctcg agcttcggtc tcttccatct cctt                                 34

<210> SEQ ID NO 75
<211> LENGTH: 38
<212> TYPE: DNA
<213> ORGANISM: Artificial Sequence
<220> FEATURE:
<223> OTHER INFORMATION: Synthetic Polynucleotide

<400> SEQUENCE: 75
tgccgcctcg agtgcttact tggaagttgg attgaagg                             38

<210> SEQ ID NO 76
<211> LENGTH: 35
<212> TYPE: DNA
<213> ORGANISM: Artificial Sequence
<220> FEATURE:
<223> OTHER INFORMATION: Synthetic Polynucleotide

<400> SEQUENCE: 76
tgccgcgtcg acttgcttta agtcactgcc tccac                                35

<210> SEQ ID NO 77
<211> LENGTH: 44
<212> TYPE: DNA
<213> ORGANISM: Artificial Sequence
<220> FEATURE:
<223> OTHER INFORMATION: Synthetic Polynucleotide

<400> SEQUENCE: 77
tgccgcctcg agtcccagga attatattat gtgtttgata agtt                      44

<210> SEQ ID NO 78
<211> LENGTH: 37
<212> TYPE: DNA
<213> ORGANISM: Artificial Sequence
<220> FEATURE:
<223> OTHER INFORMATION: Synthetic Polynucleotide

<400> SEQUENCE: 78
tgccgcgtcg acttctgaag actgtctggt ccttatg                              37

<210> SEQ ID NO 79
<211> LENGTH: 30
<212> TYPE: DNA
<213> ORGANISM: Artificial Sequence
<220> FEATURE:
<223> OTHER INFORMATION: Synthetic Polynucleotide

<400> SEQUENCE: 79
```

```
gtcgacgtca cgggagtctt tttcttcttc                                        30

<210> SEQ ID NO 80
<211> LENGTH: 41
<212> TYPE: DNA
<213> ORGANISM: Artificial Sequence
<220> FEATURE:
<223> OTHER INFORMATION: Synthetic Polynucleotide

<400> SEQUENCE: 80
tgccgcgtcg acatgattca agtcaaaagg atcttcaatt g                           41

<210> SEQ ID NO 81
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 81
gtcgactctc tgcggaatct gcttccc                                           27

<210> SEQ ID NO 82
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 82
tgccgctatc tagccaaact tgccttaatt cacatt                                 36

<210> SEQ ID NO 83
<211> LENGTH: 36
<212> TYPE: DNA
<213> ORGANISM: Artificial Sequence
<220> FEATURE:
<223> OTHER INFORMATION: Synthetic Polynucleotide

<400> SEQUENCE: 83
aatgtgaatt aaggcaagtt tggctagata gcggca                                 36

<210> SEQ ID NO 84
<211> LENGTH: 43
<212> TYPE: DNA
<213> ORGANISM: Artificial Sequence
<220> FEATURE:
<223> OTHER INFORMATION: Synthetic Polynucleotide

<400> SEQUENCE: 84
cgatgcgtcg acgactacaa ggatgacgat gacaaagttt cta                         43

<210> SEQ ID NO 85
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 85
tggataaaag gaagagtgaa                                                   20

<210> SEQ ID NO 86
<211> LENGTH: 33
<212> TYPE: DNA
```

<213> ORGANISM: Artificial Sequence
<220> FEATURE:
<223> OTHER INFORMATION: Synthetic Polynucleotide

<400> SEQUENCE: 86
gcggccgctt ctgaagactg tctggtcctt atg                      33

<210> SEQ ID NO 87
<211> LENGTH: 43
<212> TYPE: DNA
<213> ORGANISM: Artificial Sequence
<220> FEATURE:
<223> OTHER INFORMATION: Synthetic Polynucleotide

<400> SEQUENCE: 87
gtagcggaat tcgtttgttt ctatggataa aaggaagagt gaa           43

<210> SEQ ID NO 88
<211> LENGTH: 39
<212> TYPE: DNA
<213> ORGANISM: Artificial Sequence
<220> FEATURE:
<223> OTHER INFORMATION: Synthetic Polynucleotide

<400> SEQUENCE: 88
gtcgataagc tttccttgtt cttttgctaa ctcaacaac                39

<210> SEQ ID NO 89
<211> LENGTH: 22
<212> TYPE: DNA
<213> ORGANISM: Artificial Sequence
<220> FEATURE:
<223> OTHER INFORMATION: Synthetic Polynucleotide

<400> SEQUENCE: 89
ggtactgggc aaagctttgc ag                                  22

<210> SEQ ID NO 90
<211> LENGTH: 34
<212> TYPE: DNA
<213> ORGANISM: Artificial Sequence
<220> FEATURE:
<223> OTHER INFORMATION: Synthetic Polynucleotide

<400> SEQUENCE: 90
cgtagcggat ccttatgatt cctgctgggt cctc                     34

<210> SEQ ID NO 91
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 91
gaagacagaa acagacaacc aag                                 23

<210> SEQ ID NO 92
<211> LENGTH: 21
<212> TYPE: DNA
<213> ORGANISM: Artificial Sequence
<220> FEATURE:
<223> OTHER INFORMATION: Synthetic Polynucleotide

<400> SEQUENCE: 92
cctccaaagc aaaatccagt g                                   21

<210> SEQ ID NO 93
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 93
aggcggtgga gttcaccttt aaga                                          24

<210> SEQ ID NO 94
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 94
agcttgcatt ccttggcatg atgg                                          24

<210> SEQ ID NO 95
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 95
cagaaggaga ttactgctct ggct                                          24

<210> SEQ ID NO 96
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 96
tactcctgct tgctgatcca catc                                          24

<210> SEQ ID NO 97
<211> LENGTH: 21
<212> TYPE: RNA
<213> ORGANISM: Artificial Sequence
<220> FEATURE:
<223> OTHER INFORMATION: Synthetic Polynucleotide

<400> SEQUENCE: 97
ggguugugau gacaggcaau u                                             21

<210> SEQ ID NO 98
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 98
gggcuaagcu gugcuauau                                                19

<210> SEQ ID NO 99
<211> LENGTH: 19
<212> TYPE: RNA
<213> ORGANISM: Artificial Sequence
<220> FEATURE:

```
<223> OTHER INFORMATION: Synthetic Polynucleotide

<400> SEQUENCE: 99
ccaaagugcc uauuguaaa                                                  19

<210> SEQ ID NO 100
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 100
agaucaggcu ucaacguaa                                                  19

<210> SEQ ID NO 101
<211> LENGTH: 19
<212> TYPE: RNA
<213> ORGANISM: Artificial Sequence
<220> FEATURE:
<223> OTHER INFORMATION: Synthetic Polynucleotide

<400> SEQUENCE: 101
gaaagugagg cgacggaga                                                  19
```

LIN28-MEDIATED CONTROL OF LET-7 BIOGENESIS

CROSS REFERENCE TO RELATED APPLICATIONS

This application is a continuation of U.S. patent application Ser. No. 14/007,465, filed Sep. 25, 2013, which application is a national stage filing under 35 U.S.C. 371 of International Application PCT/US2012/030497, filed Mar. 26, 2012, which claims the benefit under 35 U.S.C. §119(e) of U.S. Patent Applications No. 61/467,427, filed Mar. 25, 2011, and No. 61/562,706, filed Nov. 22, 2011, the contents of which are incorporated herein by reference in their entirety. International Application PCT/US2012/030497 was published under PCT Article 21(2) in English.

FEDERAL FUNDING

This invention was made with U.S. government support under grant 1RO1GM086386, awarded by the National Institute of General Medical Sciences. The U.S. government has certain rights in the invention.

FIELD

The present invention relates to molecular biology. More specifically, the present embodiments provide for compositions and methods that regulate Lin28-mediated let-7 miRNA biogenesis. A particular embodiment provides compositions and methods for screening for agents that inhibit TUTase-dependent Lin28A-mediated repression of let-7 miRNA.

BACKGROUND

Cancer claimed the lives of more than 500,000 Americans in 2011. Although the Lin28 oncogenic pathway has been recognized as factor in many cancerous states, the characterization of the molecular biology involved with Lin28-associated pathogenesis is not well characterized. Moreover, there remains a need for "druggable" targets for therapeutic intervention of the Lin28-mediated oncogenic pathway.

SUMMARY

The present invention provides for compositions and methods to regulate miRNA biogenesis, in particular for modulating the distinct functions of Lin28A and Lin28B. As shown herein, Lin28B functions in the nucleus and inhibits the miRNA Microprocessor by sequestering primary let-7 transcripts. In contrast, Lin28A-mediated inhibition of let-7 expression involves recruitment of a 3' terminal uridylyl transferase (TUTase) (e.g., Zcchc11/TUTase4/TUT4) to let-7 precursor RNA to block processing by Dicer in the cell cytoplasm. As shown herein, biochemical dissection and reconstitution assays reveal the TUTase domains necessary and sufficient for Lin28-enhanced pre-let-7 uridylation by, for example, TUTase Zcchc11. In particular, a single C2H2-type zinc finger domain of Zcchc11 is responsible for the functional interaction with Lin28A: Lin28 dramatically enhanced C2H2 binding to the terminal loop region of pre-let-7. Additionally, Zcchc6 (TUTase7) acts as an alternative TUTase that functions with Lin28A in vitro, and Zcchc11 and Zcchc6 redundantly control let-7 biogenesis in embryonic stem cells. Importantly, the inhibitory effects of Zcchc11 depletion on the tumorigenic capacity and metastatic potential of human breast cancer cells and xenografts is restricted to Lin28A-expressing tumors. Overall, the present invention provides compositions and methods for modulating the mechanism of Lin28A-mediated TUTase-dependent and Lin28B-mediated TUTase-independent control of let-7 expression in development of stem cells and cancers, supporting the development of new strategies for cancer therapy.

Some embodiments of the present invention relates to compositions and methods to inhibit TUTases associated with Lin28-enhanced pre-let-7 uridylation. Accordingly, some embodiments of the present invention provides methods to inhibit Lin28A-enhanced TUTase activity to thus increase of miRNA biogenesis. Such embodiments are desirable to increase the level of miRNAs in the cell, such as for example, to increase the level of a tumor suppressor miRNAs in a cell, such as the let-7 family of miRNA molecules. More specific embodiments address the TUTase domains necessary and sufficient for Lin28-enhanced pre-let-7 uridylation, for example by TUTase Zcchc11.

Another embodiment provides compositions and methods for the treatment or prevention of cancer, by administering to a subject a pharmaceutical composition comprising agents that inhibit the expression and/or activity of a TUTase that represses miRNA biogenesis, such as a TUTase that associates with Lin28A to repress let-7 biogenesis (e.g., Zcchc11 or Zcchc6). In some embodiments, the subjects have cancer, or are at increased risk of developing cancer, as indicated by increased levels of Lin28A as compared to a reference level of Lin28A. In further embodiments, the subjects are identified to have decreased levels of tumor suppressor miRNA molecules, such as let-7 miRNA, as compared to a reference levels of such tumor suppressor miRNA molecule. In some embodiments, a subject amenable to treatment or prevention of cancer is a mammal, for example a human.

In some embodiments, agents useful in the methods and compositions as disclosed herein for inhibition of TUTase expression (protein or gene expression) or activity include for example, but are not limited to, a small molecule, nucleic acid, nucleic acid analogue, aptamer, ribosome, peptide, protein, antibody or a portion, analog, variant, derivative or fragment thereof. In some embodiments, an agent is an antibody, for example, a recombinant antibody, humanized antibody, chimeric antibody, modified antibody, monoclonal antibody, polyclonal antibody, miniantibody, dimeric miniantibody, minibody, diabody or tribody, or portionsm variants, analogues, fragments or modified versions thereof. In other embodiments, agents useful for inhibition of TUTase expression are nucleic acid molecules, such as DNA, RNA, nucleic acid analogue, peptide nucleic acid (PNA), pseudo-complementary PNA (pcPNA), locked nucleic acid (LNA), antagomir or analogue thereof. In particular embodiments, an agent can be a RNA molecule, for example a small inhibitory RNA (RNAi) such as siRNA, microRNA, shRNA, miRNA molecules and analogues and homologues and variants thereof. In some embodiments, the TUTase is Zcchc11 or Zcchc6.

In some embodiments, a pharmaceutical composition comprising at least one agent that inhibits TUTase domains necessary and sufficient for Lin28A-enhanced pre-let-7 uridylation by, for example, an agent that inhibits TUTase Zcchc11 or Zcchc6, are administered intravenous, intradermal, intramuscular, intraarterial, intralesional, percutaneous, subcutaneous, or by aerosol. In some embodiments, a subject can also administered one or more additional therapies simultaneously, before or after administration of agents which inhibit the TUTase, for example subjects are administered additional therapies such as surgery, chemotherapy, radiotherapy, thermotherapy, immunotherapy, hormone therapy or laser therapy. For example, a pharmaceutical composition as disclosed herein comprising at least one agent which inhibits the activity or expression of TUTase (e.g., Zcchc11 or Zcchc6) can be administered concurrently with, or before, or after, the delivery of a let-7 miRNA, for example where a let-7 miRNA is being used as a therapeutic strategy for cancer in a subject.

Another aspect of the present invention relates to a method for treating cancer in a subject comprising measuring the level of the expression or activity of Lin28A in a biological sample obtained from the subject, wherein a clinician reviews the results and if the expression or activity level of Lin28A is higher than the expression or activity of a reference level, the clinician directs the subject to be treated with an anti-cancer therapy and/or a pharmaceutical composition comprising an effective amount of at least one agent that inhibits the activity and/or expression of TUTase Zcchc11 or Zcchc6.

Another embodiment of the present invention provides for the identification of small molecule inhibitors of a newly discovered Lin28 oncogenic pathway, more specifically the identification of small molecules that specifically target the Lin28A pathway to restore expression of tumor suppressor let-7 microRNA in cancer. In a particular embodiment, the identification utilizes high throughput screening. A related embodiment provides for methods of establishing the efficacy of these compounds as potential chemotherapeutics.

DESCRIPTION OF THE DRAWINGS

FIGS. 1A-D show Lin28B regulates let-7 biogenesis through a Zcchc11 TUTase-independent mechanism. FIG. 1A shows a schematic representation of human Lin28A and Lin28B. FIG. 1B reflects Western Blot analysis of Zcchc11, Lin28A, and Lin28B in extracts prepared from human cancer cell lines. FIG. 1C shows co-immunoprecipitation (co-IP): Hela cells were co-transfected with Human myc-Lin28A, myc-Lin28B, or myc-Ago2 with either Flag-Zcchc11 or Flag-EIF6. Flag-IP and Flag- and Myc-western blots were performed to detect expression and interaction respectively. See also FIG. 2. FIG. 1D-1 through D-4 indicates that stable knockdown of Zcchc11 leads to upregulation of mature let-7g levels in Lin28A-expressing cells but not Lin28B-expressing cell lines. miRNA levels were measured by q.RT-PCR. Error bars represent SEM (n=3). Protein knockdown was monitored by Western blot.

(FIG. 2A) Co-immunoprecipitation (co-IP): Hela cells were co-transfected with Human myc-Lin28A, or myc-Lin28B with a titration of Flag-Zcchc11 plasmid (1×), Flag-Zcchc11 (5×), or control (Mock). Flag-IP and Flag- and Myc-western blots were performed to detect expression and interaction respectively. (FIG. 2B) Flag-Zcchc11 interacts with endogenous Lin28A. Igrov1 cells were transfected with Flag-Zcchc11 (or Mock) and the IP was analyzed by Western blot using antibodies to detect Lin28A.

FIG. 3A: Immunoflourescent staining for endogenous Lin28A in Igrov1 and Lin28B in H1299 cell lines. Fibrillarin, a known nucleolar protein, was used as a positive control. FIG. 3B: immunofluorescence analysis of control- and Lin28B-knockdown H1299 cell lines. FIG. 3C: Biochemical fractionation of Igrov1 and H1299 cell lines. Endogenous levels of Lin28A, Lin28B and Zcchc11 in each fraction were detected by western blot. Fibrillarin was used as a nuclear marker; Tubulin was used as a cytoplasmic marker. FIG. 3D: Schematic of nuclear localization signals in the Lin28B protein. NLS#1 is SEQ ID NO: 1 and NLS#2 is SEQ ID NO: 2. FIG. 3E: Localization of GFP-Lin28 proteins in Hela cells. DGCR8 NLS was used as a positive control for nuclear localization. hrGFP was used as a control for GFP expression. FIG. 3F: Fractionation of Flag-Lin28 proteins, exogenously expressed in Hela cells. Proteins were detected by Flag western blot. The same control proteins were used as in the fractionation in FIG. 3C.

FIG. 4A: pri-let-7 microRNAs accumulate and mature let-7 levels decrease in Hela cells overexpressing Lin28B. pri-microRNA and mature microRNA levels were analyzed by q.RT-PCR. FIG. 4B: Levels of pri-let-7g are higher in Lin28B-expressing cancer cell lines in comparison to Lin28A-expressing cell lines. Levels of pri-let-7g were detected by qPCR. FIG. 4C: RNA-Immunoprecipiation (RIP) of RNA associated with exogenously expressed immunopurified Flag-Lin28A, Lin28B and Lin28BANLS#1 from Hela cells. RNA was extracted from IP material and analyzed by q.RT-PCR. Ability of all three immunopurified proteins to bind to pre-let-7 microRNAs equally was validated by EMSA.

FIG. 5A: Co-localization of Microprocessor components GFP-Drosha and mCherry-DGCR8 in Hela cells reveals their distribution throughout the nucleus and exclusion from nucleoli. FIG. 5B: Localization of GFP-Lin28A, Lin28B, or mutant Lin28B proteins with mCherry-DGCR8 in Hela cells reveals non-overlapping localization of Lin28B and DGCR8. FIG. 5C: Fractionation of a Flag-Lin28B Hela stable cell line. Flag-Lin28B and endogenous DGCR8 were detected western blot and shows a non-overlapping subcellular localization of Lin28B and the Microprocessor. Fibrillarin was used as a control for nucleolar localization.

FIG. 6B: Transient knockdown of DGCR8 in Hela cells with siRNA. Effect of knockdown was detected by western blot. FIG. 6C: Knockdown of DGCR8 leads to stabilization of different pri-microRNAs, detected as an increased Renilla luciferase signal. Firefly luciferase signal was used as a normalizer. FIG. 6D: Overexpression of Lin28B in Hela cells leads to stabilization of pri-let-7 microRNAs, but not pri-miR-125. Levels of pri-miRNA stabilization were detected as increased Renilla luciferase signal as in FIG. 6C. FIG. 6E: Pri-let-7 microRNAs are stabilized more efficiently in Lin28B-expressing cell line, H1299, than Lin28A-expressing cell line, Igrov1. Renilla/Firefly ratios for each pri-microRNAs were normalized to the stabilization of each pri-microRNA in Hela cells, which lack any Lin28 protein.

FIG. 7A: Colloidal Blue staining of purified recombinant His-Lin28A and His-Lin28B proteins. (7B) Binding of r.Lin28A and r.Lin28B to pre-let-7g was assessed by EMSA performed with 0.5 nM 5'-end labeled pre-let-7g RNA and the indicated concentration of recombinant protein. Band intensities were quantitated from three independent experiments and represented as the fraction of bound pre-let-7g RNA in the plots. Values are given as average±S.E.M. (n=3). See also FIG. 8. FIG. 7C: EMSA performed indicated concentration of r.Lin28A and r.Lin28B with in vitro transcribed uniformly labeled pri-let- 7g. FIG. 7D: RNA-Immunoprecipitation (RIP) analysis of RNA associated with immunopurified Flag-Lin28A and Flag-Lin28B from Hela cells. RNA was extracted from IP material and analyzed by q.RT-PCR. Error bars±S.E.M. (n=3). Lower panel indicates relative Lin28A and Lin28B expression levels by Flag-Western blot. FIG. 7E: Accumulation of pri-let-7 by transient Lin28B expression in Hela cell detected by q.RT-PCR. Error bars±S.E.M. (n=3). Lower panel indicates relative expression levels of Lin28A and Lin28B proteins detected by Flag-Western blot in transfected cells. FIG. 7F: pri-let-7 accumulates (top panel) and mature let-7 levels decrease (bottom panel) in Hela cells stably overexpressing Lin28B. Error bars±S.E.M. (n=3)

FIG. 9A: Lin28B mRNA expression levels are increased during transformation of MCF10A ER-Src cells. Lin28B mRNA expression was evaluated at 1, 4, 12, 24, 36 hours post-tamoxifen (TAM) treatment of MCF10A ER-Src cells by real-time PCR analysis. Error bars±S.E.M. (n=3) FIG. 9B: Inhibition of Lin28B expression does not block the transformation ability of MCF10A ER-Src cells. Phase-contract images of MCF10A ER-Src treated with TAM for 36 h in the presence or absence of a siRNA against Lin28B (siLin28B), a monoclonal antibody against IL6 (Ab-IL6) or a siRNA against Zcchc11 (siZcchc11#1). FIG. 9C: Inhibition of Lin28B but not Zcchc11 blocks the tumorigenicity of MCF10A ER-Src cells. MCF10A ER-Src transformed cells untreated or treated with siRNA negative control (siRNA NC), two different siRNAs against Zcchc11 (siZcchc11#1, siZcchc11#2), Ab-IL6 and siLin28B were plated in soft agar and their ability to form colonies was evaluated 20 days later. The experiment was repeated thrice and the statistical significance was calculated using Student's t test. FIG. 9D: Effectiveness of siRNA inhibition of Zcchc11 expression in MCF10A ER-Src cells. MCF10A ER-Src cells were treated with siRNA NC or siZcchc11#1 or siZcchc11#2 and Zcchc11 mRNA expression was tested by real-time PCR 24 hours post-transfection. Error bars±S.E.M. (n=3) (FIG. 9E) Inhibition of Lin28B but not of Zcchc11 allows up-regulation of let-7a microRNA expression in MCF10A ER-Src transformed cells. Let-7a expression level was tested by real-time PCR analysis 24 h post transfection. Error bars±S.E.M. (n=3) (FIG. 9F) Inhibition of Lin28B but not of Zcchc11 results in increased IL6 production levels expression in MCF10A ER-Src transformed cells. IL6 production was examined by ELISA assay in MCF10A ER-Src transformed cells 48 h post transfection. mean±SD n=3 (FIG. 9G) Inhibition of Lin28B but not of Zcchc11 suppresses MCF10A ER-Src tumor growth in xenografts. The treatments with siRNA NC, siZcchc11#1 and siLin28B were performed intraperitoneally (i.p.) for 5 cycles starting on day 15. Error bars±S.E.M. (n=3). (FIG. 9H) Efficiency of siRNA inhibition of Zcchc11 in xenograft tumors (day 39). Zcchc11 mRNA expression levels were tested by real-time PCR on tumors untreated or treated with siRNA NC or siZcchc11#1. Error bars±S.E.M. (n=3) (FIG. 9I) Inhibition of Lin28B but not of Zcchc11 allows up-regulation of let-7a expression levels in xenograft tumors (day 30). Let-7a expression levels were tested by real-time PCR on tumors untreated or treated with siRNA NC or siZcchc11#1 or siLin28B. Error bars±S.E.M. (n=3)

FIG. 10A: q.RT-PCR analysis of Zcchc11 knockdown in MDA-MB-231 and T47D breast cancer cells. Error bars±S.E.M. (n=3) FIG. 10B: Inhibition of Zcchc11 expression does not affect let-7a expression in Lin28B-expressing cells (MDA-MB-231), while it up-regulates let-7a expression in Lin28A-expressing cells (T47D). Let-7a expression levels measured by q.RT-PCR in cells treated with siRNAs for 48 hours. Error bars±S.E.M. (n=3) FIG. 10C: Inhibition of Zcchc11 expression did not affect the colony formation ability of MDA-MB-231 cells, but suppressed the colony formation ability of T47D cells. The number of colonies was evaluated 20 days post plating in soft agar. The experiment was repeated thrice and the statistical significance was calculated using Student's t test. FIG. 10D: Inhibition of Zcchc11 expression did not affect the invasiveness of MDA-MB-231 cells, but suppressed the invasive ability of T47D cells. The number of invasive cells was measured 16 hr post transfection with indicated siRNAs. In all assays, ten fields per insert were scored and SD was measured. The experiment was repeated thrice and the statistical significance was calculated using Student's t test. FIG. 10E: Inhibition of Zcchc11 expression did not suppress tumor growth of MDA-MB-231 cells in xenografts, however it inhibited tumor growth of T47D cells in xenografts. The treatments with indicated siRNA were performed intraperitoneally (i.p.) for five cycles starting on day 15. Each treatment group consisted of five mice. FIG. 10F: q.RT-PCR analysis of siRNA inhibition of Lin28B, Lin28A, and Zcchc11 in xenograft tumors (day 30) derived from MDA-MB-231 and T47D cells. Error bars±S.E.M. (n=3). FIG. 10G: Inhibition of Lin28B but not of Zcchc11 allows up-regulation of let-7a expression levels in MDA-MB-231 xenograft tumors (day 30). Inhibition of Lin28A or Zcchc11 results in let-7a up-regulation in T47D xenograft tumors. Let-7a expression levels measured by q.RT-PCR on tumors untreated or treated with indicated siRNA. Error bars±S.E.M. (n=3).

(FIG. 11A) Xenograft experiments were performed with a variety of different human cancer cell lines. Mice were treated with the indicated siRNA for 5 cycles starting on day 15. For all cells lines tested each treatment group consisted of 5 mice. While inhibition of Lin28A or Lin28B suppressed tumor growth in the relevant xenografts, inhibition of Zcchc11 inhibited growth only of Lin28A- but not Lin28B-expressing tumors. Error bars±S.E.M. (n=3) (FIG. 11B) Analysis of siRNA inhibition of Zcchc11 in xenograft tumors (day 30) derived from the indicated cells. (FIG. 11C) Analysis of siRNA inhibition of Lin28B in xenograft tumors (day 30) derived from the indicated cells. (FIG. 11D) Analysis of siRNA inhibition of Lin28A in xenograft tumors (day 30) derived from IGROV1 cells. mRNA expression levels were measured by q.RT-PCR on tumors untreated or treated with the indicated siRNA. Error bars±S.E.M. (n=3)

(FIG. 12A) q.RT-PCR analysis of Lin28A, Lin28B and let-7a expression levels in normal and colon cancer tissues. Tumor samples were further classified into two groups expressing either high Lin28A or Lin28B. Data expressed as mean±SE. n=3. (FIG. 12B) Immunohistochemistry for Lin28A, Lin28B and in situ hybridization for let-7a and U6 in normal colon tissues and colon adenocarcinomas. (FIG. 12C) q.RT-PCR analysis of Lin28A, Lin28B and let-7a in human normal and breast cancer tissues. Tumor samples were further classified into two groups expressing either high Lin28A or Lin28B. Data expressed as mean±SE. n=3. (FIG. 12D) Lin28A, Lin28B and let-7a expression levels in different breast cancer subtypes. (FIG. 12E) Correlation between Lin28A and Lin28B mRNA levels assessed by q.RT-PCR with NF-κB phosphorylation status assessed by ELISA assay. (FIG. 12F) Heatmap representation of Lin28A and Lin28B in carcinomas of different origin measured by q.RT-PCR.

FIG. 13A: A subset of colon adenocarcinomas expresses significantly higher levels of Lin28A compared to the uninvolved normal tissues. Sections were subjected to immunohistochemistry for Lin28A and counterstained with haematoxylin. FIG. 13B: A different subset of adenocarcinomas expresses significantly higher levels of Lin28B compared to the uninvolved tissues. Sections were subjected to immunohistochemistry for Lin28B and counterstained with haematoxylin. FIG. 13C: Let-7a levels are decreased in colon adenocarcinomas in comparison to normal tissue. Sections were subjected to in situ hybridization for let-7a and counterstained with nuclear fast red. Bar, 50 μm.

FIG. 14A: Schematic representation of Zcchc11 and truncations used for in vitro uridylation assays. FIG. 14B: Uridylation assays with synthetic pre-let-7g carried out using Flag immunopurified (IP) Zcchc11 variants and IP Lin28. α-Flag Western blots show similar amounts of IP Zcchc11 within experiments. FIG. 14C: Summary of Zcchc11 domain requirements from in vitro uridylation assays.

FIG. 16A: Colloidal blue stain of recombinant Lin28A and recombinant Zcchc11 C2H2 zinc finger domain. (16B) EMSA experiment using the indicated recombinant protein and 0.5 nM 5' end-labeled pre-let-7g. FIG. 16C: EMSA using sub-saturating binding conditions with the indicated recombinant proteins and 5 nM 5' end-labeled preE-let-7g.

FIG. 17A: Diagram of synthetic RNAs used for in vitro uridylation assays. Pre-let-7g: endogenous precursorlet-7g miRNA sequence (SEQ ID NO: 5). Pre-miR-21: endogenous precursor miR-21 sequence (SEQ ID NO: 6). Pre-21S7L: synthetic RNA consisting of the let-7g preE and miR-21 stem sequences (SEQ ID NO: 7). FIG. 17B: Left: 5' end-labeled RNAs showing equal amounts. Right: Uridylation assay using WT Flag IP-mZcchc11, with or without Flag IP-mLin28, and the indicated precursor miRNAs.

FIG. 18A: Schematic showing the domain similarities between hZcchc11 (SEQ ID NO: 8) and hZcchc6 (SEQ ID NO: 9) with the N-terminal C2H2 zinc finger highlighted and critical zinc finger residues in bold. FIG. 18B: Uridylation assay with Flag-IP WT mZcchc11 and a mutant harboring point mutations in two conserved asparates required for catalysis, with or without Flag-IP Lin28. FIG. 18C: Alignment of the nucleotidyl transferase (Ntr) domains of hZcchc11 (SEQ ID NO: 10) and hZcchc6 (SEQ ID NO: 11). Aspartic acid residues critical for catalysis are boxed.

FIG. 19A: α-Flag WB showing relative amounts of Flag-hZcchc11 and Flag-hZcchc6 (left) or Flag-hLin28A and Flag-hLin28B (right). FIG. 19B: EMSA showing similar amounts of functional Flag-hLin28A and Flag-hLin28B used in uridylation assays. (19C) Uridylation assays using Flag-hZcchc11 or Flag-hZcchc6 with either Flag-hLin28A or Flag-hLin28B. (19D) Uridylation assay with Flag-hZcchc6 and r.Lin28A.

FIG. 20A: q.RT-PCR analysis of mature let-7g and mature miR-21 levels in P19 embryonal carcinoma cells after transfection with the indicated siRNAs (left). mRNA levels of the indicated genes in P19 cells after transfection with the indicated siRNAs (right). FIG. 20B: qRT-PCR as in FIG. 20A in V6.5 mouse embryonic stem cells. For all experiments, miRNA levels were normalized to sno-142 and mRNA levels were normalized to β-actin. Error bars represent s.d. of experiments in triplicate.

FIGS. 23A-C present a let-7 sensitive reporter gene. FIG. 23A is a schematic representation of reporter constructs. FIG. 23B shows luciferase activity assay performed on cells transfected with either a control vector or one with the let-7 reporter. Below is a Northern Blot of let-7 levels. FIG. 23C shows luciferase activity assay performed on Stable H1299 cell line was transfected with 1 μg control plasmid or 1 μg pri-let-7g stem/miR-21 loop plasmid. Luciferase activity was measured 2 days after transfection. N=3.

FIG. 24A shows Western blot analysis of Lin28A, Lin28B and Zcchc11 in various human cancer cell lines. FIG. 24B is q.RT-PCR analysis of let-7g and miR-21 levels after Lin28A, or Zcchc11 knockdown in IGROV1 ovarian cancer cells.

DETAILED DESCRIPTION

Figure 1A:
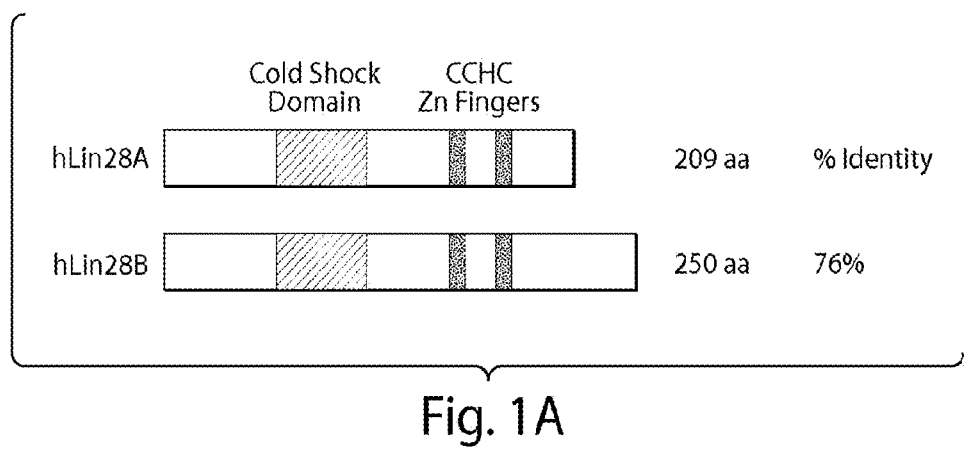

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

As used herein and in the claims, the singular forms include the plural reference and vice versa unless the context clearly indicates otherwise. The term "or" is inclusive unless modified, for example, by "either." Other than in the operating examples, or where otherwise indicated, all numbers expressing quantities of ingredients or reaction conditions used herein should be understood as modified in all instances by the term "about" "About" when used in connection with percentages means±1% unless otherwise specified.

Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Although any known methods, devices, and materials may be used in the practice or testing of the invention, the methods, devices, and materials in this regard are described herein.

Disruption of microRNA (miRNA) gene regulatory pathways can lead to cancer. The paralogous RNA-binding proteins Lin28A and Lin28B selectively block the expression of the let-7 family of miRNAs and function as oncogenes in a variety of human cancers. See U.S. Patent Pub. No. 2010/0221266. For example, the majority of human colon and breast tumors analyzed exclusively express either Lin28A or Lin28B: Lin28A is expressed in HER2-overexpressing breast tumors while Lin28B expression characterizes triple-negative breast tumors.

The present invention provides for compositions and methods for modulating the distinct mechanisms of Lin28A and Lin28B function. As shown herein, Lin28B functions in the nucleus and inhibits the Microprocessor by sequestering primary let-7 transcripts. Lin28B represses let-7 processing through a 3' terminal uridylyl transferase (TUTase)-independent mechanism. In contrast, Lin28A-mediated inhibition of let-7 expression involves recruitment of a TUTase (e.g., Zcchc11/TUTase4/TUT4) to let-7 precursor RNA to block processing by Dicer in the cell cytoplasm. As shown herein, biochemical dissection and reconstitution assays reveal the TUTase domains necessary and sufficient for Lin28-enhanced pre-let-7 uridylation by the example TUTAse Zcchc11. In particular, a single C2H2-type zinc finger domain of Zcchc11 was found to be responsible for the functional interaction with Lin28. Lin28 dramatically enhanced C2H2 binding to the terminal loop region of pre-let-7. Additionally, Zcchc6 (TUTase7) acts as an alternative TUTase that functions with Lin28 in vitro, and accordingly Zcchc11 and Zcchc6 redundantly control let-7 biogenesis in embryonic stem cells. Importantly, the inhibitory effects of Zcchc11 depletion on the tumorigenic capacity and metastatic potential of human breast cancer cells and xenografts is restricted to Lin28A-expressing tumors. Overall, the present invention provides insight into the mechanism of Lin28-mediated TUTase-dependent and Lin28B-mediated TUTase-independent control of let-7 expression in development of stem cells and cancers. As shown herein, Lin28A and Lin28B function by distinct mechanisms, which has implications for the development of new strategies for cancer therapy.

More specifically by way of introduction, control of gene expression by microRNAs (miRNAs) comprise a large family of regulatory RNAs that have important roles in normal development. Zhao & Srivastava, 32 Trends Biochem. Sci. 189 (2007). miRNAs are small, 22-nucleotide (nt) noncoding RNAs that repress the expression of many target messenger RNAs (mRNAs). Wightman et al., 75 Cell 855 (1993). Their requirement in mammals is demonstrated by the severe developmental consequences of global loss of miRNAs, and more recently by the phenotypes observed in individual miRNA knockout mice. Hundreds of miRNAs have been identified, many of which are developmentally regulated. Altered miRNA expression is linked with various diseases including cancer. Small & Olson, 469 Nature 336 (2011).

The canonical process of miRNA biogenesis is well understood and is characterized by successive cleavage events by RNase III enzymes. Winter et al., 11 Nat. Cell Biol. 228 (2009). The miRNA biogenesis pathway begins with transcription of primary miRNAs (pri-miRNAs); long transcripts that contain a stem-loop structure with single-stranded flanking sequences. In the cell nucleus, pri-miRNAs are processed by the Microprocessor protein complex, which contains an RNaseIII endonuclease, Drosha, and the double-stranded RNA-binding protein, DGCR8. The Microprocessor cleaves the double-stranded RNA towards the base of the stem-loop structure to release a 60-80 nucleotide (nt) hairpin-shaped precursor (pre-miRNA) from the flanking RNA sequences. Denli et al., 432 Nature 231 (2004); Gregory et al., 432 Nature 235 (2004); Han et al., 136 Cell 75 (2009). Pre-miRNAs are exported to the cell cytoplasm by Exportin5, where they are subsequently cleaved by another double-stranded ribonuclease, Dicer. Hutvagner et al., 293 Science 834 (2001); Krol et al., 11 Nat. Rev. Genet. 597 (2010). This cleavage step generates a 22 nt miRNA duplex consisting of a guide and a passenger strand. The guide strand is bound by Argonaute proteins and is incorporated into the RNA-induced silencing complex (RISC). Gregory et al., 123 Cell 631 (2005); Liu et al., 305 Science 1437 (2004). Base-pairing between the miRNA and the target mRNA guides the RISC complex to complementary transcripts leading to target gene repression through mRNA degradation and/or translational repression. Krol et al., 2010. Proper temporal and spatial expression of miRNAs is essential for normal development and physiology, as perturbations in specific miRNAs or miRNA processing factors can lead to aberrant development and cancer. Calin & Croce, 6 Nat. Rev. Cancer 857 (2006); Esquela-Kerscher & Slack, 7 Cell Cycle 759 (2006); Small & Olson, 2011. Altered miRNA expression is directly associated with cancer initiation, progression, and metastasis and has been observed in a wide variety of human malignancies. Di Leva & Croce, 16 Trends 257 (2010).

The relationship between Lin28 proteins and the expression of miRNA let-7 is central to the control of normal mammalian development, stem cell pluripotency, and cancer biology. Viswanathan & Daley, 140 Cell 445 (2010). In embryonic cells, the RNA-binding protein Lin28 coordinately represses the let-7 family of miRNAs by binding to the terminal loop of pre- and pri-let-7 miRNAs, thereby inhibiting let-7 biogenesis. Heo et al., 32 Mol. Cell 276 (2008); Newman et al., 14 RNA 1539 (2008); Rybak et al., 10 Nat. Cell Biol. 987 (2008); Viswanathan et al., 320 Science 320 (2008). As cells undergo differentiation Lin28 levels decrease, leading to a corresponding increase in mature let-7, which is retained in many adult tissues. As such, the posttranscriptional regulation of let-7 expression by Lin28 contributes to the maintenance of the pluripotent state by preventing let-7 mediated ES cell differentiation. Martinez & Gregory, 7 Cell 31 (2010). Furthermore, Lin28 mRNA is repressed by let-7 miRNAs, leading to an inversely correlated expression pattern between let-7 and Lin28 and a double negative feedback loop that controls cell differentiation. Wu & Belasco, 25 Mol. Cell Biol (2005). Lin28 is required for normal development and contributes to the pluripotent state by preventing let-7-mediated differentiation of embryonic stem cells (ESCs). Ambros & Horvitz, 226 Science 409 (1984); Moss et al., 88 Cell 637 (1997); Viswanathan & Daley, 2010. Lin28 overexpression or let-7 inhibition with antisense RNAs promotes reprogramming of human and mouse fibroblasts to induced pluripotent stem cells (iPSCs). Ambros & Horvitz, 1984; Melton et al., 463 Nature 621 (2010); Yu et al., 318 Science 1917 (2007b).

The Lin28/let-7 axis is also relevant to a wide variety of human cancers as well as the control of glucose homeostasis in mammals. Frost & Olson, PNAS (2011); Iliopoulos et al., 139 Cell 693 (2009); Piskounova et al., 147 Cell 1066 (2011); Viswanathan et al., 41 nat. Genet. 843 (2009); Zhu et al., 147 Cell 81 (2011). In particular, the let-7 miRNA family members act as tumor suppressors in multiple different tumor types by inhibiting expression of oncogenes and key regulators of mitogenic pathways including RAS, MYC, and HMGA2. Bussing et al., 14 Trends Mol. Med. 400 (2008). Let-7 is downregulated in numerous different cancers and low let-7 correlates with poor prognosis. Boyerinas et al., 17 Endrocr. Relat. Cancer F19 (2010); She et al., (2007); Takamizawa et al., 64 Cancer Res. 3753 (2004). Restoration of let-7 expression was shown to effectively inhibit cancer growth in mouse models of lung and breast cancers. Barh et al., 17 Curr. Oncol. 70 (2010); Esquela-Kerscher et al., 2008; Slack, 8 Cell Cycle 1823 (2009); Trang et al., 29 Oncol. 1580 (2010); Yu et al., 131 Cell 1109 (2007a). In humans, there are twelve let-7 family members (let-7a-1, -2, -3; let-7b; let-7c; let-7d; let-7e; let-7f-1, -2; let-7g; let-7i; miR-98) located at eight unlinked chromosomal loci. Of note, many tumors are characterized by the coordinate downregulation of all let-7 family members that are typically expressed in the corresponding normal tissue. Shell et al., 104 PNAS 11400 (2007). Previously, mechanisms controlling let-7 expression remained largely unknown.

Further regarding Lin 28, there are two Lin28 paralogs in mammals: Lin28A (Lin28) and Lin28B. Guo et al., 384 Gene 51 (2006); Lehrbach et al., 16 Nat. Str. Mol. Biol. 1016 (2009); Moss et al., 1997; Van Wynsberghe et al., 18 Nat. Str. Mol. Biol 302 (2011); Viswanathan & Daley, 2010. Lin28B has also been shown to regulate expression of multiple let-7 family members, and genome-wide association studies (GWAS) have linked Lin28B with the determination of human height, as well as control of the age of onset of puberty and menopause. Lin28B (and less frequently Lin28A) contribute to oncogenesis by coordinately inactivating multiple let-7 family miRNAs. Iliopoulos et al., 2009; Viswanathan et al., 2009. This finding is consistent with the fact that activation of Lin28A/Lin28B occurs in many different primary human tumors with an overall frequency of –15% and these tumors display downregulation let-7 expression, suggesting an important role in tumorigenesis. Indeed Lin28A/Lin28B are classical oncogenes that can promote cellular transformation when ectopically expressed. Iliopoulos et al., 2009; Viswanathan et al., 41 Nat. Genet. 843 (2009); West et al., 460 Nature 909 (2009). Importantly, this effect can be abrogated when let-7 is reintroduced into these cells. Iliopoulos et al., 2009; Viswanathan et al., 2009. Therefore, Lin28-mediated cellular transformation is directly dependent on let-7 levels.

Conversely, depletion of Lin28A or Lin28B in human cancer cells lines results in decreased cell proliferation. Chang et al., 106 PNAS 3384 (2009); Iliopoulos et al., 2009; Viswanathan et al., 2009. Lin28A/Lin28B may contribute to the development of an aggressive, poorly differentiated tumor. Lin28A or Lin28B expression is associated with advanced disease in hepatocellular carcinoma (HCC), chronic myeloid leukemia (CML), Wilms' tumor, ovarian carcinoma, and germ cell tumors. Dangi-Garimella et al., 28 EMBO J. 347 (2009); Guo et al., 2006; Iliopoulos et al., 2009; Ji & Wang, 53 J. Hepatol. 974 (2010); Lu et al., 45 Eur. J. Cancer 2212 (2009); Oh et al. 76 Intl. J. Rad. Oncol. Biol. Phys. 5; Peng et al., 29 Oncol. 2153 (2010); Viswanathan et al., 2009; Wang et al., 31 Carcinogenesis 1516 (2010); West et al., 2009; Yang et al., 70 cancer Res. 9463 (2010). Lin28A/Lin28B expression is associated with poor clinical outcome and patient survival in HCC and ovarian cancer. Lu et al., 2009; Viswanathan et al., 2009. In the case of LIN28B, rare amplification or translocation events might explain activation in some cases. A more common mechanism, however, might be transcriptional activation by upstream factors during tumor progression. In support of this notion, c-Myc binds to both Lin28A and Lin28B loci and activates expression of these genes. Chang et al., 2009. Also, in a breast cancer model system, transient expression of Src oncoprotein in the MCF10A cell line results in a transformed breast cancer cell line that forms self-renewing mammospheres harboring tumor initiating cells. Iliopoulos et al., 2009. The transformation process involves NF-κB activation leading to direct transcriptional upregulation of Lin28B, consequent let-7 loss, and de-repression of the let-7 target gene IL-6. Because IL-6 activates NF-κB, this regulatory circuit represents a positive feedback loop, providing a molecular link between inflammation and cancer.

Lin28A has been shown to recognize and selectively bind the terminal loop of let-7 precursors, a molecular recognition that requires both the cold-shock domain (CSD) and CCHC-type zinc finger RNA-binding domains of the Lin28A protein. Piskounova et al., 2008. Lin28A recognizes pre-let-7 in the cytoplasm and recruits the terminal uridyl transferase (TUTase) Zcchc11 (TUTase4/TUT4) to add an oligouridine tail to the 3' end of pre-let-7, blocking Dicer cleavage and leading to the degradation of the pre-miRNA. Hagan et al., 16 Nat. Str. Mol. Biol. 1021 (2009); Heo et al., 2008; Heo et al., 138 Cell 696 (2009). Although both Lin28A and Lin28B have been shown to have the ability to recruit Zcchc11/TUTase4 to uridylate pre-let-7 in vitro, the molecular mechanism of the Lin28B-mediated blockade of let-7 expression was unknown previously. Heo et al., 2008; Heo et al., 2009. The recently-identified TUTase Zcchc11 may also regulate IL-6 levels by uridylating mature miR-26a, promote the cell-cycle-dependent degradation of a subset of histone mRNAs, and is required for the growth of Lin28A-driven cancers in vitro and in vivo. Jones et al., 11 Nat. Cell Biol 1157 (2009); Piskounova et al., 2011; Schmidt et al., 17 RNA 39 (2011). Given its central role in processes ranging from the inflammatory response, to cell cycle regulation and Lin28-mediated repression of let-7, TUTases, such as Zcchc11 and Zcchc6, are important RNA-modifying enzyme that may have essential roles in diverse aspects of human biology. The present invention characterizes the molecular cis-acting elements of mammalian TUTases and how these TUTases interact with their binding partners.

The present invention provides, surprisingly, that despite their high degree of homology, Lin28A and Lin28B function through distinct mechanisms in human cancer cell lines. Lin28A and Lin28B are differentially localized in cells with Lin28A present predominantly in the cell cytoplasm whereas Lin28B accumulates in the nucleus due to the presence of functional nuclear localization signals in the Lin28B protein. Lin28B localizes to the nucleus where it binds pri-let-7 miRNAs to block processing by the Microprocessor through a TUTase-independent mechanism. In contrast, Lin28A functions in the cytoplasm by blocking at the Dicer step and recruiting the TUTase to uridylate pre-let-7, as previously reported in mouse ES cells. Depletion of Zcchc11 has an effect on let-7 expression only in Lin28A-expressing cancer cell lines, and Zcchc11 depletion selectively inhibits the tumorigenic capacity and metastatic potential of Lin28A-expressing human breast cancer cells and xenografts. Because Zcchc11 has been shown to regulate let-7 it has been identified as a potential therapeutic target in Lin28B-expressing cancers. The present embodiments support the therapeutic potential of Zcchc11 inhibition in treating Lin28A-expressing cancers.

Nuclear Lin28B blocks processing of pri-let-7 miRNAs. Lin28A localizes to the cytoplasm and blocks Dicer processing of pre-let-7 microRNAs, by recruiting Zcchc11. Lin28B localizes to the nucleus, where it blocks the Microprocessor complex, possibly by binding and sequestering pri-let-7 microRNAs in the nucleoli.

More specifically, the present invention provides for the mechanism by which Zcchc11 represses pre-let-7 in a Lin28-dependent manner. Mutational analyses of Zcchc11 identified domains required for activity both in the absence and presence of Lin28, and use of recombinant proteins shows, herein, that Lin28 and Zcchc11 proteins are sufficient for uridylation of pre-let-7 in vitro. Furthermore, the single C2H2-type zinc finger at the N-terminus of Zcchc11 mediates the interaction with Lin28, and that this domain synergizes with Lin28 in binding to pre-let-7. Comparing the domain architecture of Zcchc11 with other mammalian TUTases identified Zcchc6, another TUTase with extensive homology to Zcchc11, that also mediates Lin28-dependent uridylation of pre-let-7 in vitro. Accordingly, Zcchc6 deple- tion in embryonic cells synergized with Zcchc11 knockdown to upregulate let-7 miRNAs, implying that these two TUTases work redundantly to repress let-7 expression. These findings provide insight into the mechanism of Lin28-mediated TUTase control of let-7 expression in development, stem cells, and cancer.

Figure 1B:
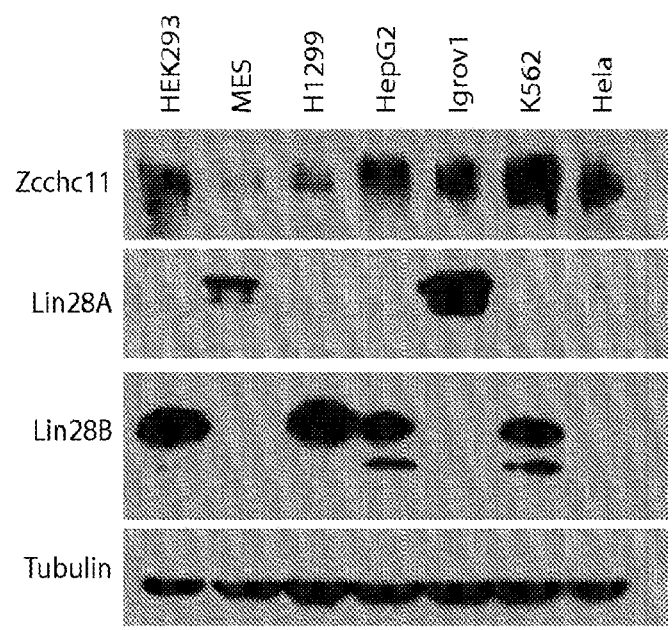

As determined herein, Lin28B regulates let-7 expression through a Zcchc11-independent mechanism. The paralogous RNA-binding proteins Lin28A and Lin28B have a high degree of sequence identity and conserved domain organization (FIG. 1A) and both proteins selectively block let-7 expression. See Newman et al., 2008; Viswanathan et al., 2008. Here, several human cancer cell lines were screened, revealing that some express Lin28A, whereas others express Lin28B (FIG. 1B). The co-expression of both Lin28A and Lin28B was not observed in any cell line, suggesting that their expression may be mutually exclusive. Zcchc11 expression, however, was ubiquitous. More specifically, Hela cells express Zcchc11 but neither Lin28A nor Lin28B. Because Lin28A-mediated repression of let-7 in mouse ESCs involves the TUTase Zcchc11, whether Lin28A and Lin28B function through the same mechanism to block let-7 processing was determined. Previous reports have used recombinant Lin28A and Lin28B interchangeably in biochemical assays demonstrating that Lin28B is capable of enhancing Zcchc11 activity in vitro, however the physiological relevance of these observations remained unknown. Heo et al., 2009.

Figure 1C:
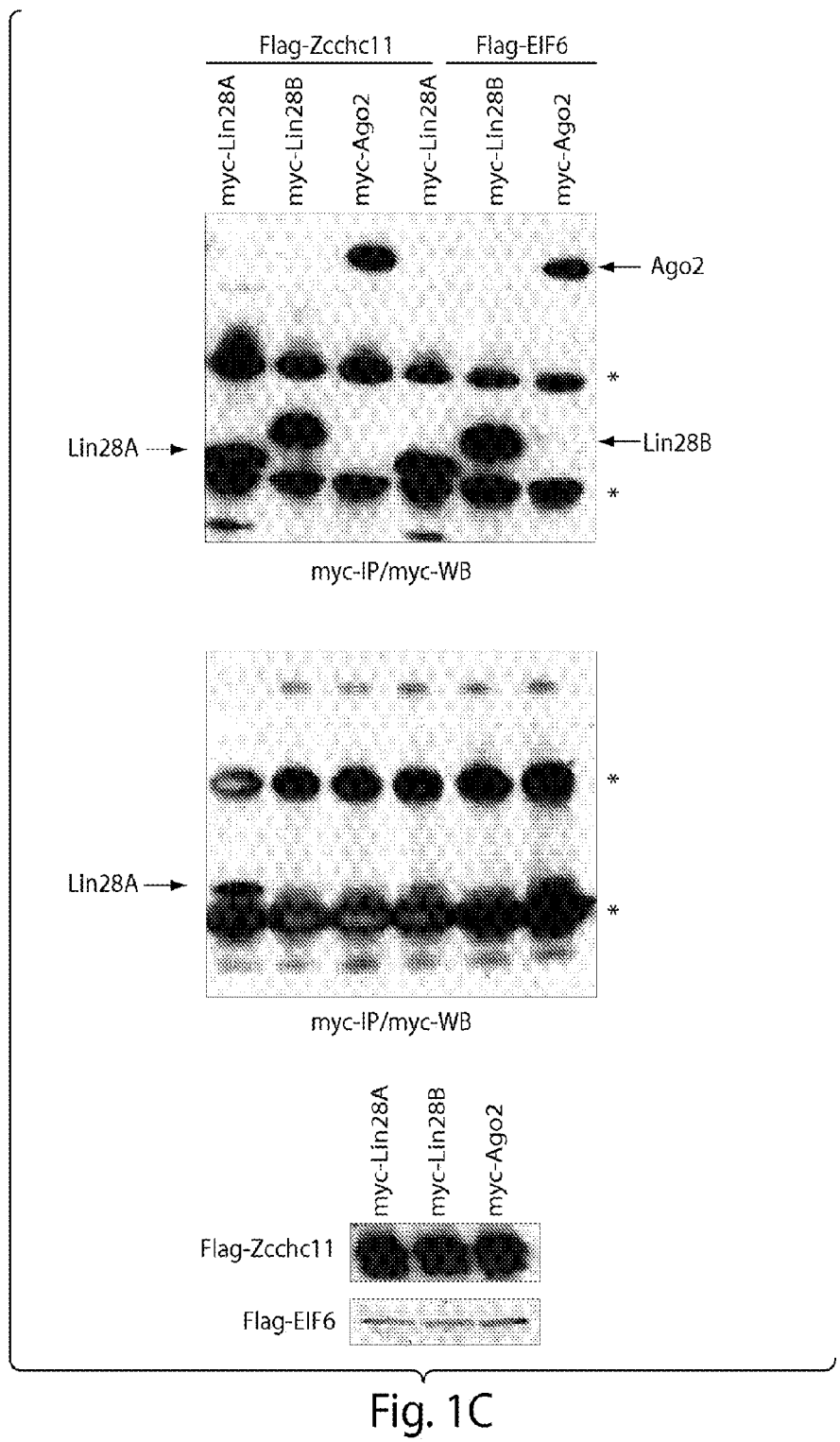
Figure 2A:
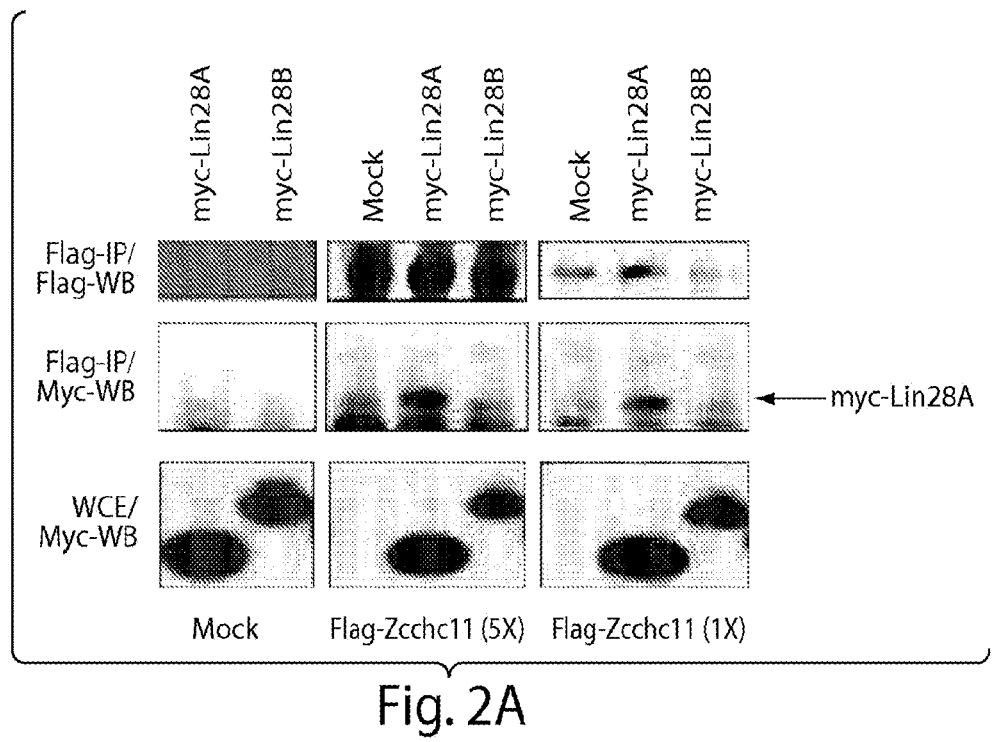
FIGS. 2A-B show that Lin28A physically interacts with Zcchc11.
Figure 2B:
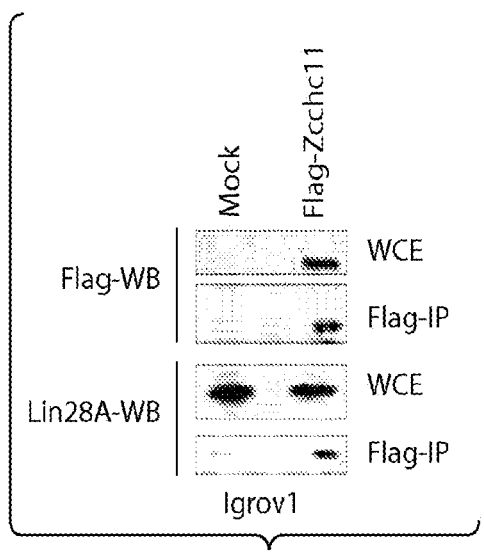

Whether both Lin28A and Lin28B function through a Zcchc11 TUTase-dependent mechanism was investigated using co-immunoprecipitation (co-IP) experiments. Myc-tagged Lin28A, Lin28B, or Ago2 were co-expressed with either Flag-tagged Zcchc11 or Flag-EIF6 control (FIG. 1C). Because the Lin28A-Zcchc11 interaction has been shown to be RNA-dependent we also co-expressed pri-let-7g. Heo et al., 2009. Consistent with earlier reports, myc-Lin28A was found to be associated with affinity-purified Flag-Zcchc11. Heo et al., 2009. A physical interaction between myc-Lin28B and Flag-Zcchc11 was not detected. Additional co-IP experiments were performed in which the amount of exogenously expressed Flag-Zcchc11 was titrated. These experiments confirmed the specific physical interaction Zcchc11 and Lin28A, whereas myc-Lin28B was not detected in any of the Flag-Zcchc11 IPs (FIG. 2A). This was confirmed additionally by the co-IP of endogenous Lin28A in Igrov1 cells (FIG. 2B). Together, these results indicate that unlike Lin28A, there was no detectable physical interaction between Lin28B and Zcchc11.

Figures 1, 1D:
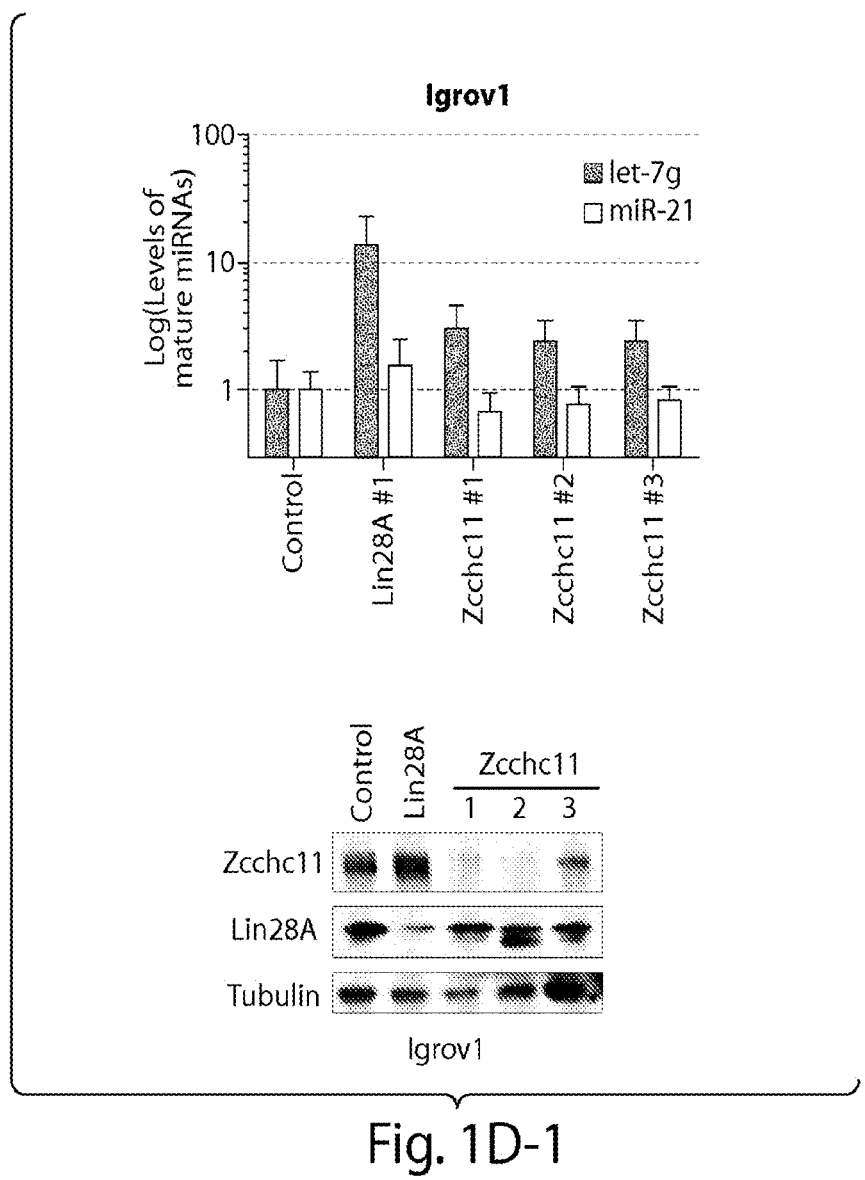
Figures 1, 1D, 2:
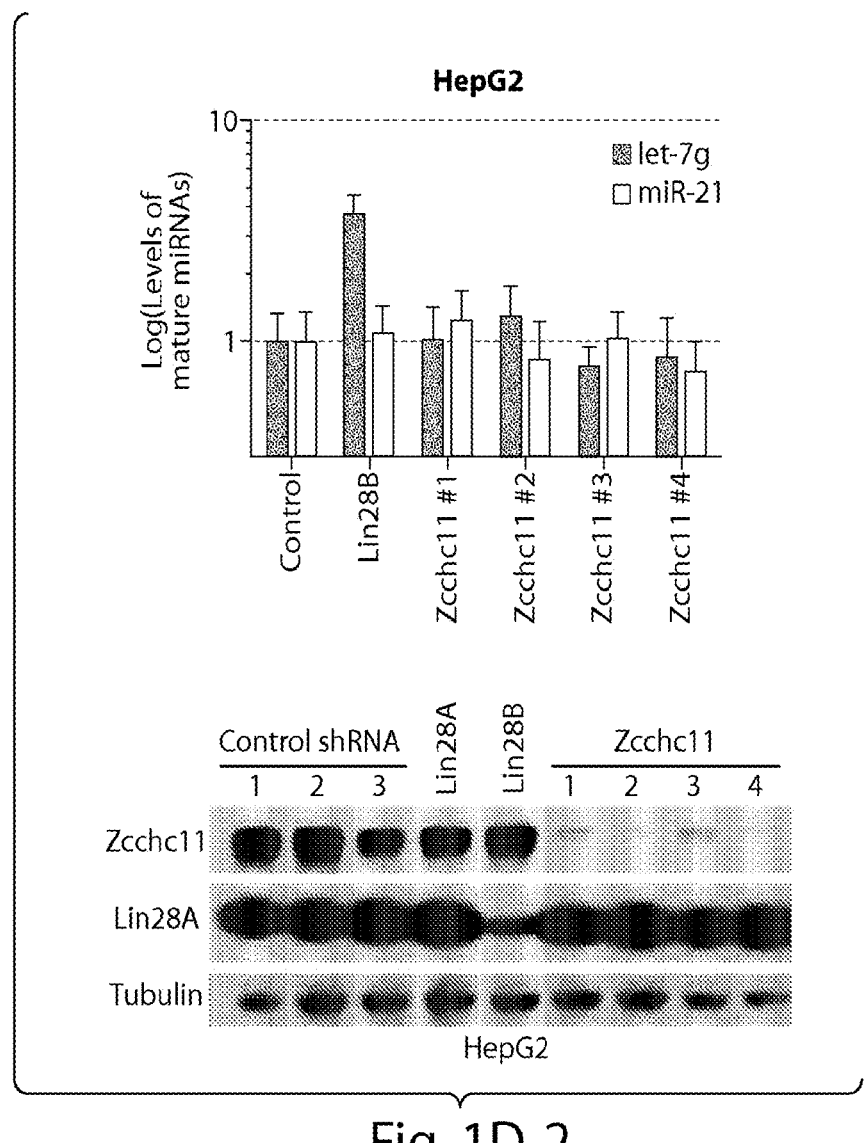
Figures 1, 1D, 2, 3:
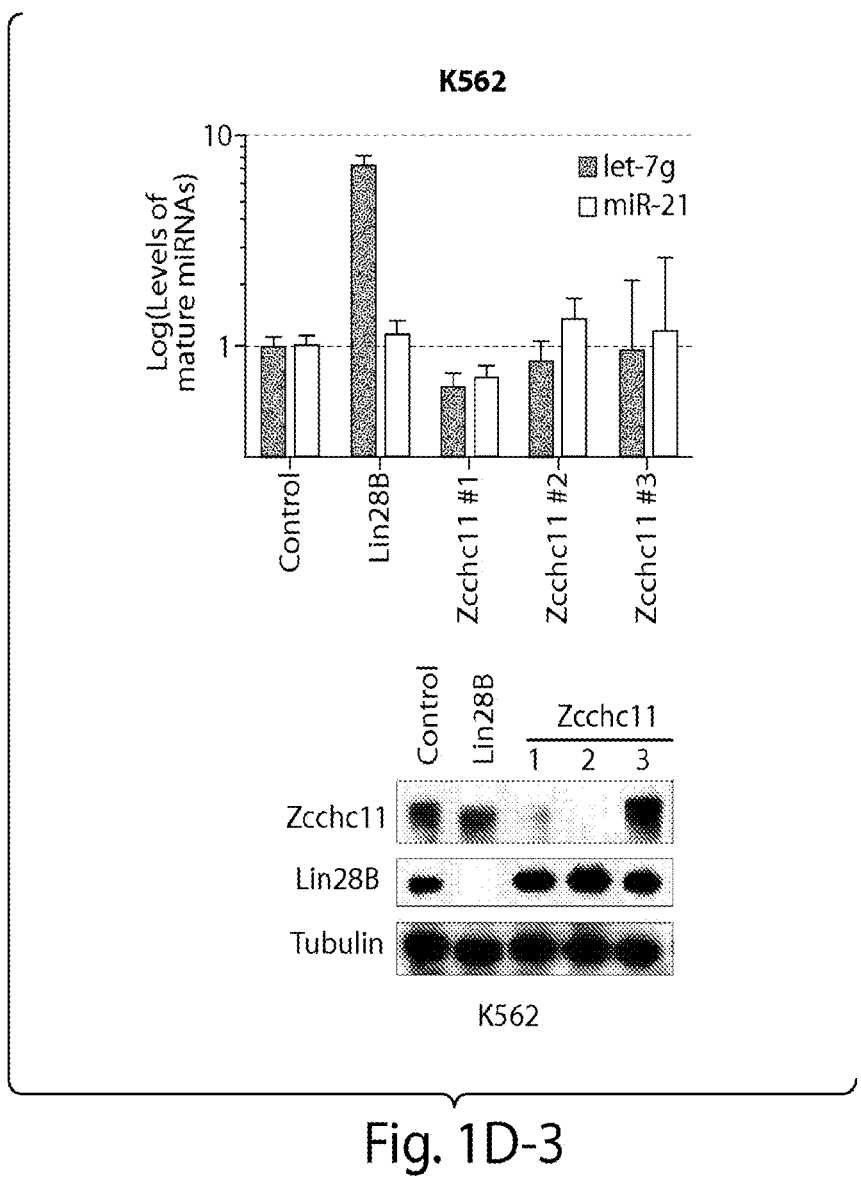

The functional requirement of Zcchc11 in the Lin28A- and Lin28B-mediated repression of let-7 expression was addressed using a series of knockdown experiments to deplete Zcchc11 in a panel of human cancer cell lines. shRNAs were used to deplete Lin28A or Zcchc11 expression in Igrov cells and measured the effect on let-7 expression by quantitative reverse transcription PCR (q.RT-PCR). As expected, depletion of Lin28A led to ~10-fold increase in let-7 levels. Knockdown of Zcchc11 with three independent shRNAs also led to elevated mature let-7 levels (FIG. 1D). Therefore Zcchc11 is involved in the repression of let-7 expression in this Lin28A-expressing human cancer cell line as has been previously reported in mESCs and P19 embryonal carcinoma cells. Hagan et al., 2009; Heo et al., 2009. Analogous experiments were performed in three different Lin28B-expressing cancer cell lines: HepG2, K562 and H1299 (FIG. 1D) and found no significant effect on mature let-7 levels in any of the cell lines when Zcchc11 was depleted. In contrast, knockdown of Lin28B consistently led to the expected increase in mature let-7. Overall our results indicate that Zcchc11 negatively regulates let-7 expression in Lin28A- but not Lin28B-expressing cell lines suggesting that Lin28B employs a Zcchc11-independent mechanism to block let-7 processing.

Figure 3A:
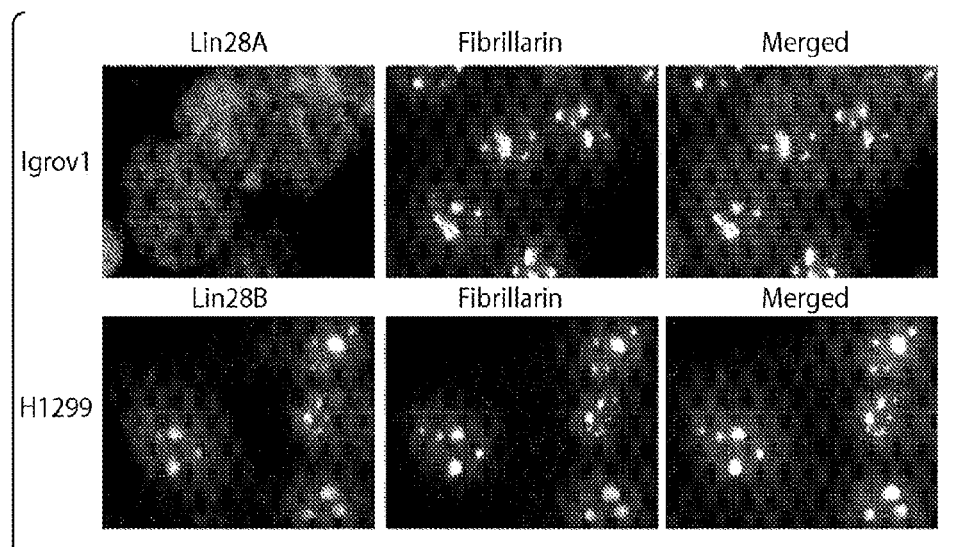
FIGS. 3A-F show that Lin28A and Lin28B are differentially localized within the cell.
Figure 3B:
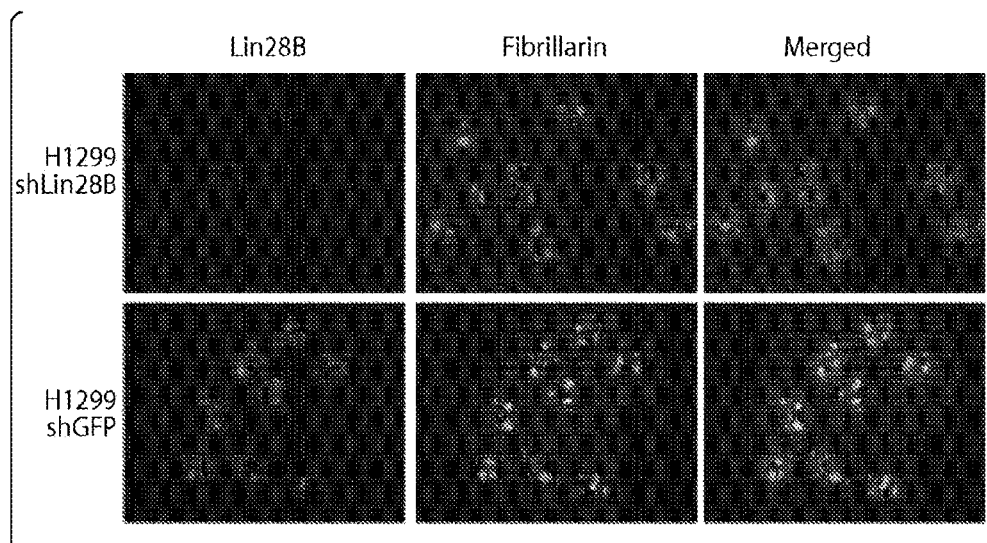
Figure 3C:
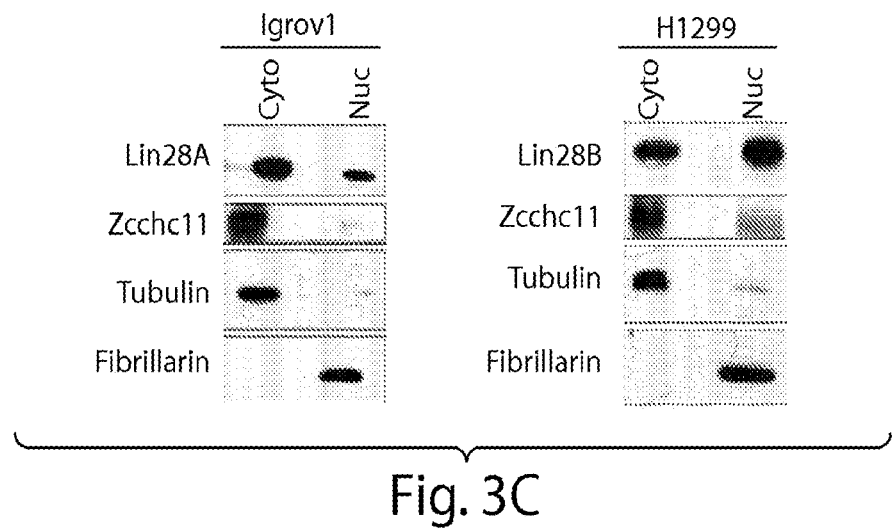

Lin28B localizes to the nucleus, in contrast to Lin28A that is mostly present in the cell cytoplasm. Potential explanations for the functional differences between Lin28A and Lin28B were examined, first, by comparing the subcellular localization of the endogenous Lin28A with Lin28B proteins using immunofluorescence assays (FIG. 3A). Lin28A was mostly localized to the cytoplasm of Igrov1 cells whereas Lin28B localized to specific foci in the nucleus of H1299 cells where it co-localized with the nucleolar marker Fibrillarin. Localization of Lin28B in the nucleoli was confirmed by immunofluorescence assays on H1299 cells in which Lin28B expression (or control) was stably knocked down by shRNA and showed that the observed nucleolar staining pattern is specific to Lin28B (FIG. 3B). These data were further confirmed by biochemical fractionation and Western blot of both cell lines (FIG. 3C). Consistent with published data we found Zcchc11 only in the cytoplasmic fraction in both the Lin28A- and Lin28B-expressing cell lines (FIG. 3C). These data suggest that the divergence in the mechanisms by which Lin28A and Lin28B block let-7 biogenesis derives from their differential subcellular localization. The lack of physical and functional interactions between Zcchc11 and Lin28B is therefore likely due to their localization to distinct cellular compartments, even though recombinant Lin28B has the capacity to enhance Zcchc11 activity in vitro. Heo et al., 2009).

Figure 3D:
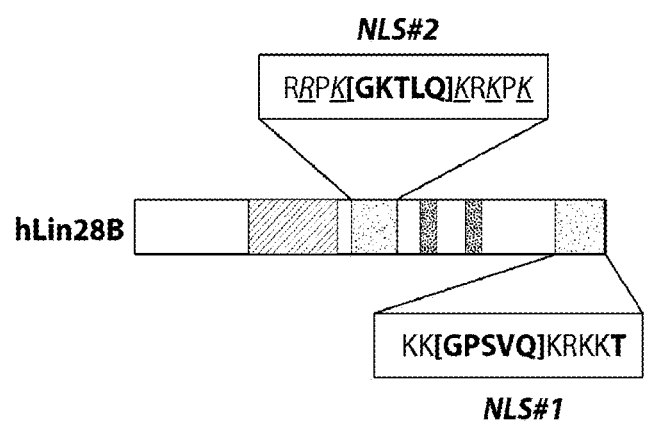
Figure 3E:
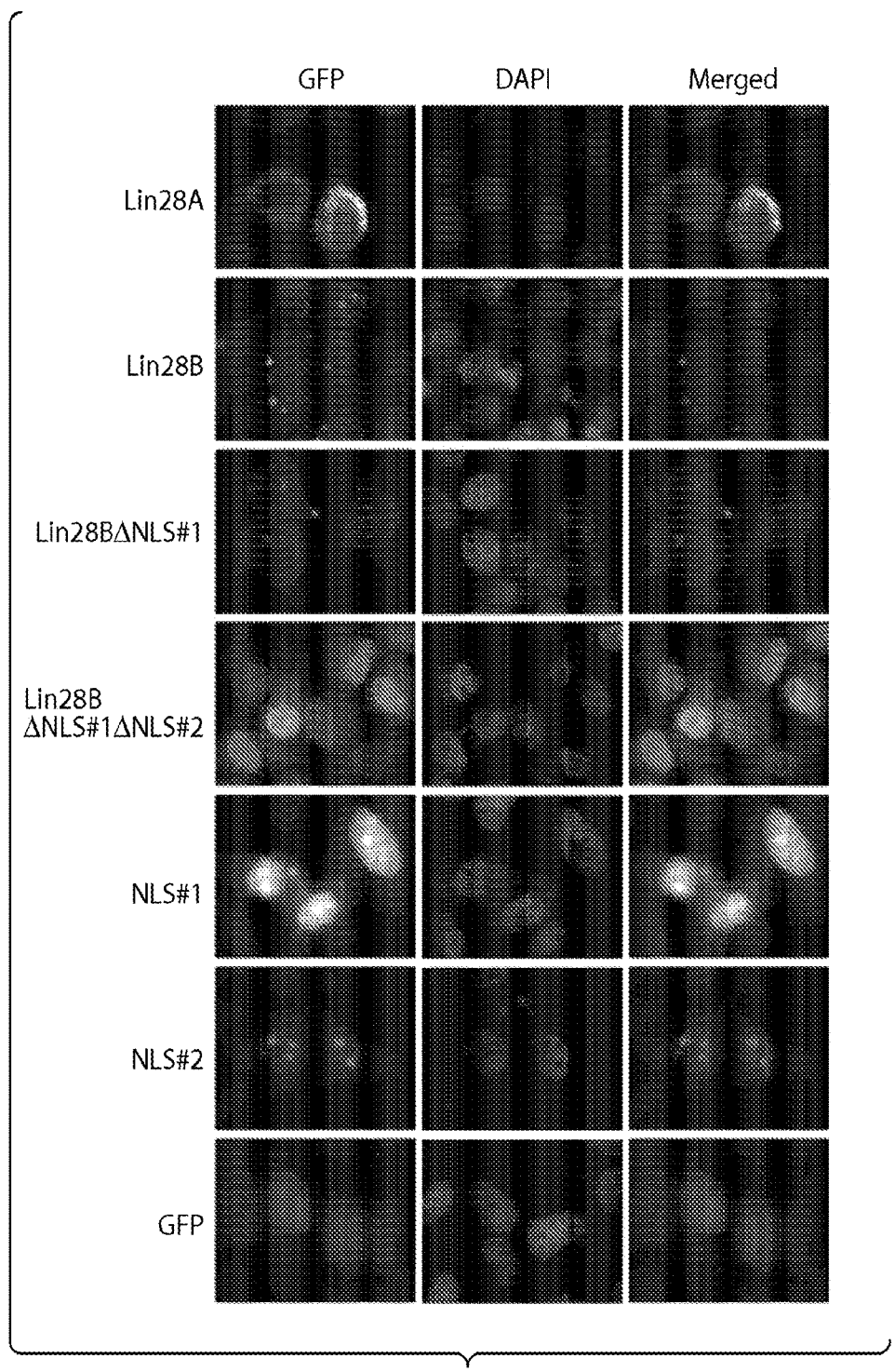
Figure 3F:
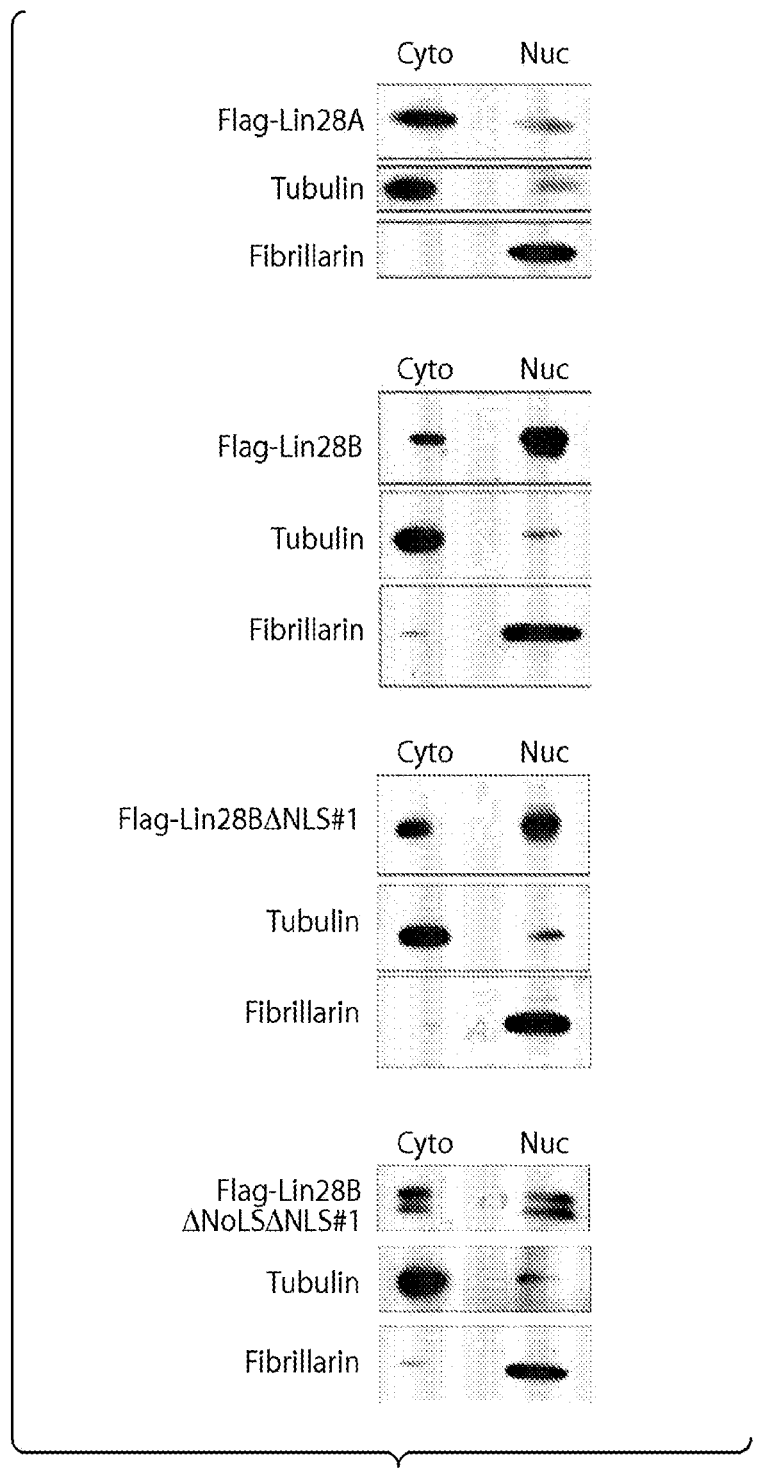

Lin28B contains functional nuclear localization signals. Lin28B protein has an extended C-terminus compared to Lin28A which upon closer inspection contains a putative bipartite nuclear localization signal (NLS), KK[GPSVQ]KRKK (SEQ ID NO:1). Another potential NLS, RRPK[GKTLQ]KRKPK (SEQ ID NO:2), was identified in the linker region that connects the two functional RNA-binding domains (FIG. 3D). To test the function of these putative NLS constructs for the expression of a series of GFP fusion proteins were generated. Hela cells were infected transiently with these constructs and analyzed the subcellular localization of the GFP-Fusion proteins by microscopy (FIG. 3E). Consistent with the localization of endogenous Lin28A in Igrov1 cells, we found Lin28A-GFP localized mainly to the cytoplasm. Lin28B-GFP predominantly localized to specific foci in the nucleus, again recapitulating the nucleolar localization of endogenous Lin28B observed in H1299 cells. Exogenously expressed truncated Lin28BΔNLS#1 increased the signal in the cytoplasm, however some nucleolar localization still remained consistent with the presence of a second NLS. Indeed, the double mutant Lin28B-GFP protein lacking both NLS showed cellular localization similar to that of GFP alone suggesting that both NLS elements are important for nuclear and nucleolar localization of Lin28B (FIG. 3E). Whether these sequences represent functional NLS was examined in the localization of the NLS#1-GFP and NLS#2-GFP (FIG. 3E). When exogenously expressed in Hela cells, NLS#1-GFP localized nearly entirely throughout the nucleus including the nucleoli. This is in contrast to the control GFP construct that is broadly distributed throughout the cell. Localization of NLS#2-GFP the signal was nearly entirely localized to the nucleoli (FIG. 3E). Together these results identify that NLS#1 amino acid sequence represents a bona fide NLS, and that NLS#2 is a functional nucleolar localization signal (NoLS). NoLS properties are less well known and have only recently been studied at the amino acid sequence level. Scott et al., 38 Nucl. Acids Res. 7388 (2010). Several reports suggest that proteins with a NoLS also contain an NLS that allows them to cross the nuclear membrane before localizing to the nucleoli. These results were confirmed by biochemical fractionation of Hela cells transiently expressing either Flag-Lin28A, full-length-, truncated-, or double mutant-Flag-Lin28B. As expected Flag-Lin28A was predominantly present in the cytoplasmic fraction, Flag-Lin28B was mostly nuclear, NLS#1 mutant only showed marginal increase of signal in the cytoplasmic fraction, whereas the double mutant Flag-Lin28B showed a more significant increase in cytoplasmic signal (FIG. 3F).

Figures 1, 1D, 2, 3, 4:
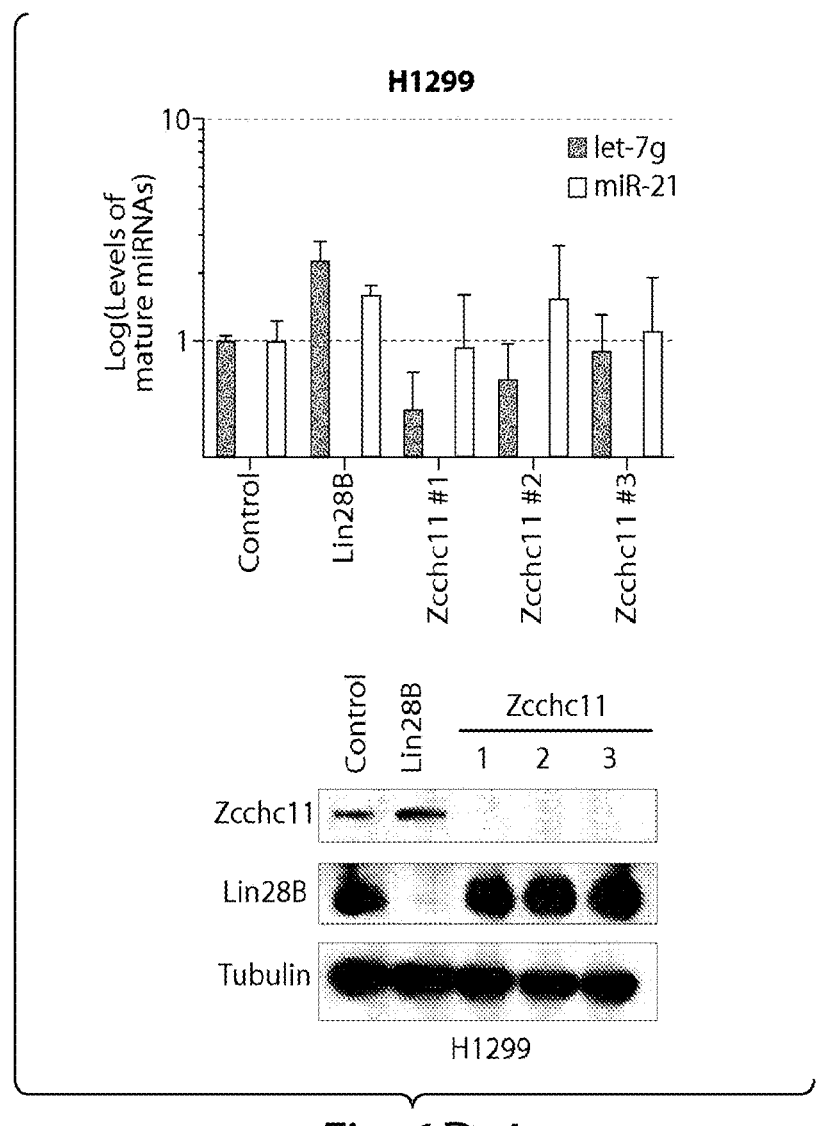
Figure 4A:
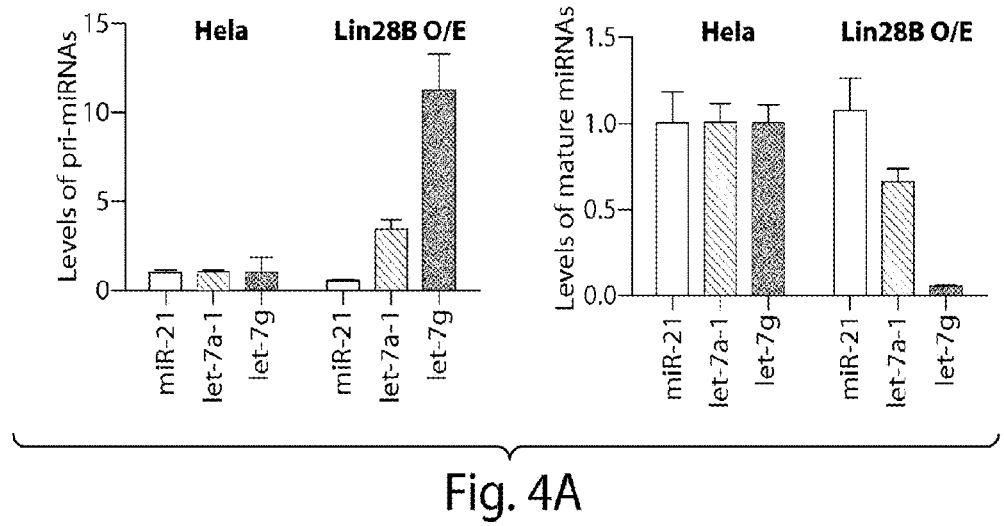
FIGS. 4A-C show that Lin28B directly associates with pri-let-7 microRNAs.
Figure 4B:
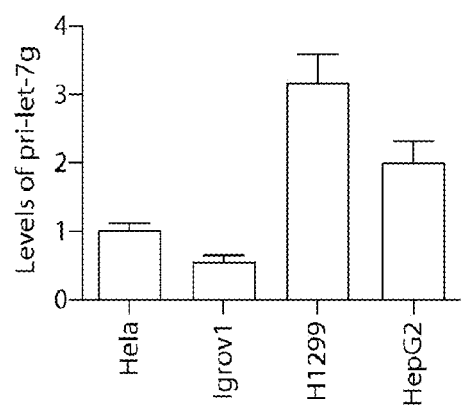

Lin28B directly associates with pri-let-7 miRNAs. To further dissect the exact mechanism of the Lin28B-mediated let-7 processing block, a stable Flag-Lin28B expressing HeLa cell line was created. Analysis of several pri-miRNAs by q.RT-PCR in this cell line demonstrated a dramatic accumulation of pri-let-7 miRNAs, over 10-fold for pri-let-7g and over 3-fold for pri-let-7a-1. There was no effect, however, on levels of pri-miR-21 (FIG. 4). Consistent with this observation there was a corresponding decrease in the levels of mature let-7 miRNAs, with over 90% decrease for mature let-7g, and about 40% decrease for mature let-7a. Again no effect was observed on levels of mature miR-21 (FIG. 4A). Also consistent with the Lin28B localization data, overexpression of Lin28B in Hela cells causes a selective accumulation of pri-let-7 miRNAs (and corresponding decrease in mature let-7 miRNA) presumably by blocking processing of pri-let-7 by the Microprocessor. Because wild-type Hela cells do not express either Lin28A or Lin28B, pri-let-7 levels were measured in the context of endogenous Lin28A- and Lin28B-expressing cell lines. Indeed, the levels of pri-let-7g in a Lin28A-expressing cell line, Igrov1, and two Lin28B-expressing cell lines, H1229 and HepG2, showed higher levels of pri-let-7 miRNAs in Lin28B-expressing cell lines compared with Igrov1 or Hela cells (FIG. 4B). This is consistent with the notion that endogenous Lin28B blocks let-7 processing at the level of the Microprocessor leads to accumulation of pri-let-7.

Figure 4C:
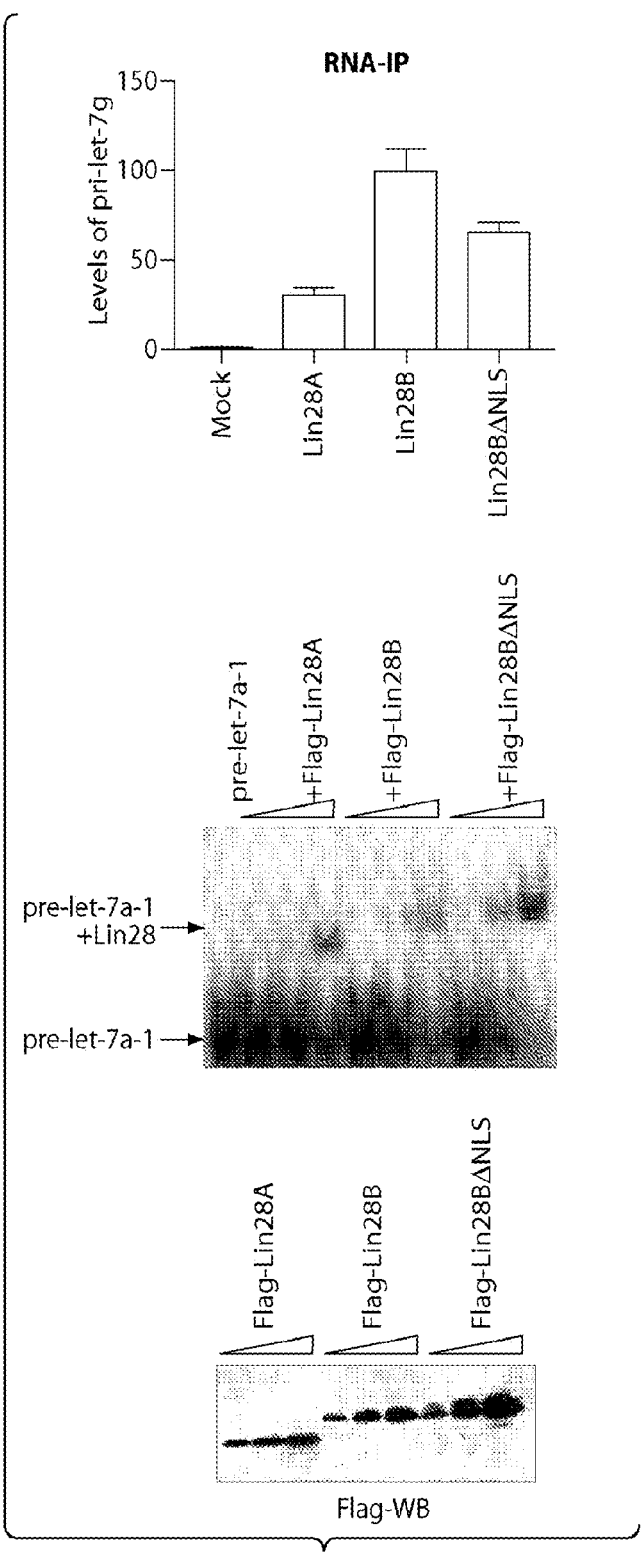

To gain further support for the model in which Lin28B functions in the cell nucleus to block the Microprocessor, the RNA that is associated with Lin28B protein was examined. Flag-Lin28A, Flag-Lin28B, and Flag-Lin28BΔNLS#1 were expressed individually in Hela cells and analyzed by Flag-immunoprecipitations. The RNA immunoprecipitation (RIP) was performed by extracting the RNA associated with the immunopurified proteins and analyzing relative levels of pri-let-7g by q.RT-PCR. This analysis revealed that Lin28B directly associates with pri-let-7g RNA (FIG. 4C). Indeed, in comparison to mock IP, there was a ~70-fold enrichment of pri-let-7 associated with Lin28B. Furthermore, substantially more pri-let-7 RNA was associated with Lin28B than with Lin28A or with Lin28BΔNLS#1, which is consistent with the data showing differential localization of these proteins. As a control, the immunopurified proteins were also used in an in vitro electromobility shift assay (EMSA) to ensure that these Lin28 proteins had similar RNA-binding capacity. For this we performed EMSA with radiolabeled synthetic pre-let-7a-1. Indeed purified Lin28A, Lin28B, and Lin28BΔNLS#1 protein all displayed very similar binding affinity to pre-let-7 RNA (FIG. 4C). Taken together, these results indicate that the preferential association of Lin28B with pri-let-7g detected in the RIP assays likely reflects the distinct molecular mechanism of Lin28-mediated repression of let-7 biogenesis and nuclear localization of Lin28B rather than any possible intrinsic differential binding affinity to let-7 precursors. Therefore Lin28B, likely due to its nuclear localization, directly associates with pri-let-7 and corresponds with the accumulation of pri-let-7 detected in Lin28B-expressing cells. This further supports the model of the Lin28B-mediated block in let-7 biogenesis, in which Lin28B blocks pri-let-7 processing by directly binding to the pri-let-7 and sequestering it from cleavage by the Microprocessor.

Figure 5A:
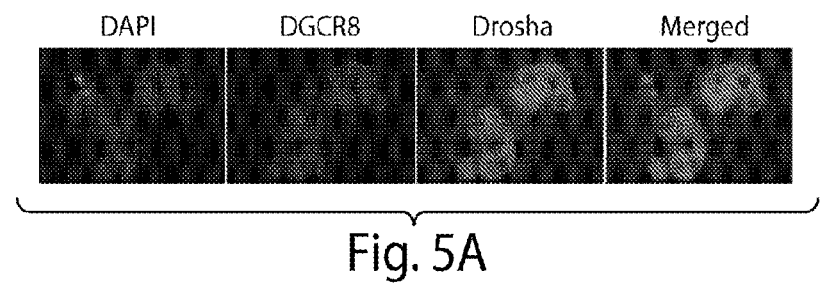
FIGS. 5A-C demonstrate that Lin28B localizes to nucleoli where Microprocessor is absent.
Figure 5B:
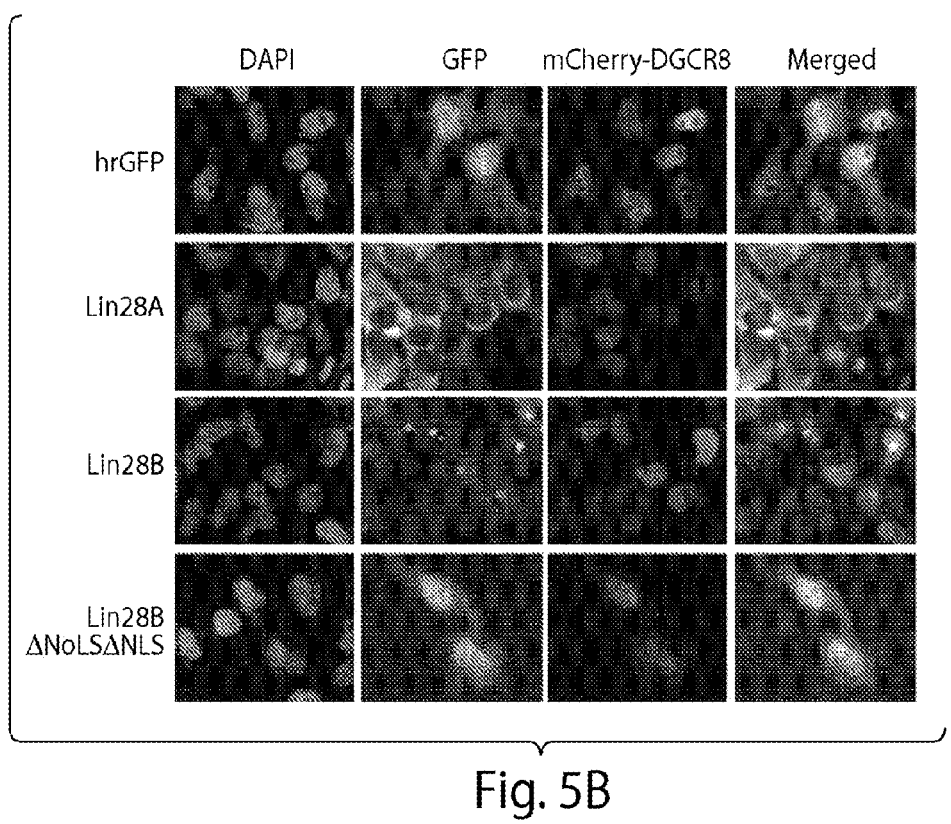
Figure 5C:
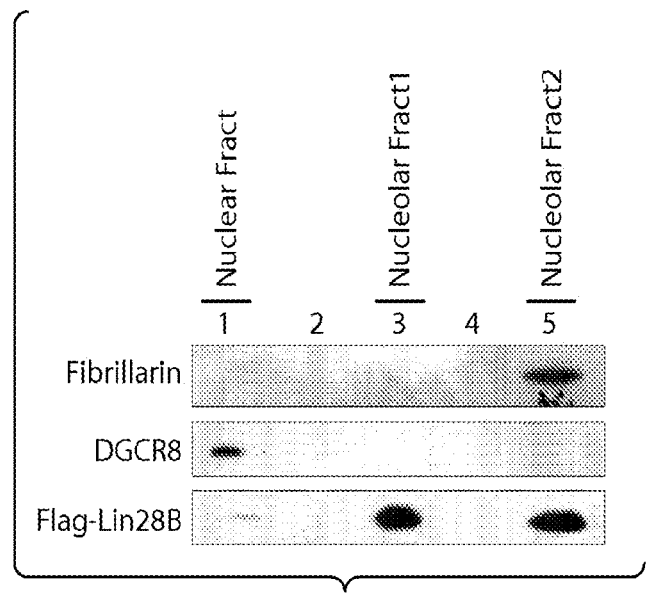

Additionally, Lin28B localizes to nucleoli where Microprocessor is absent. The specific localization of Lin28B with that of the nuclear miRNA processing machinery. The Microprocessor components, DGCR8 and Drosha, co-localize in the nucleoplasm but are excluded from nucleoli (FIG. 5A). To further confirm that localization of Lin28B is distinct and non-overlapping with the Microprocessor, the co-localization of mCherry-DGCR8 and GFP-Lin28A/B proteins in transfected cells was visualized (FIG. 5B). Lin28A localized mostly to the cytoplasm and therefore showed no overlap with the nuclear DGCR8. Lin28B localized to nucleoli and did not overlap with DGCR8 either. In contrast, the localization of the Lin28B NLS/NoLS mutant showed a broadly dispersed localization throughout the nucleus and cytoplasm (similar to GFP control) and displayed co-localization with DGCR8 in the nucleoplasm. That Lin28B and Microprocessor normally occupy distinct compartments in the nucleus was confirmed by performing large-scale biochemical fractionation and Western blot of a stable Hela cell line expressing Flag-Lin28B. Lin28B was specifically present in the nucleolar-enriched fractions whereas DGCR8 was only detectable in the nuclear fraction and not in the nucleolar fractions (FIG. 5C). Overall, these findings suggest a possible mechanism by which Lin28B blocks let-7 processing in the nucleus by sequestering pri-let-7 miRNAs in the nucleoli away from the Microprocessor.

Figure 6A:
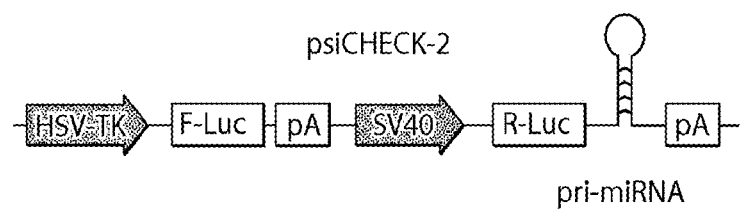
FIGS. 6A-E show that Lin28B blocks processing of pri-let-7 microRNAs. (6A) Schematic of the dual luciferase vector with pri-microRNA sequence 3' of the Renilla luciferase ORF.
Figure 6B:
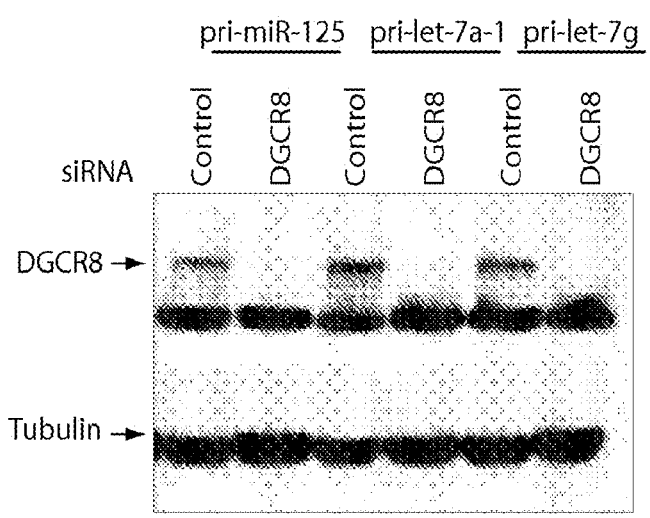
Figure 6C:
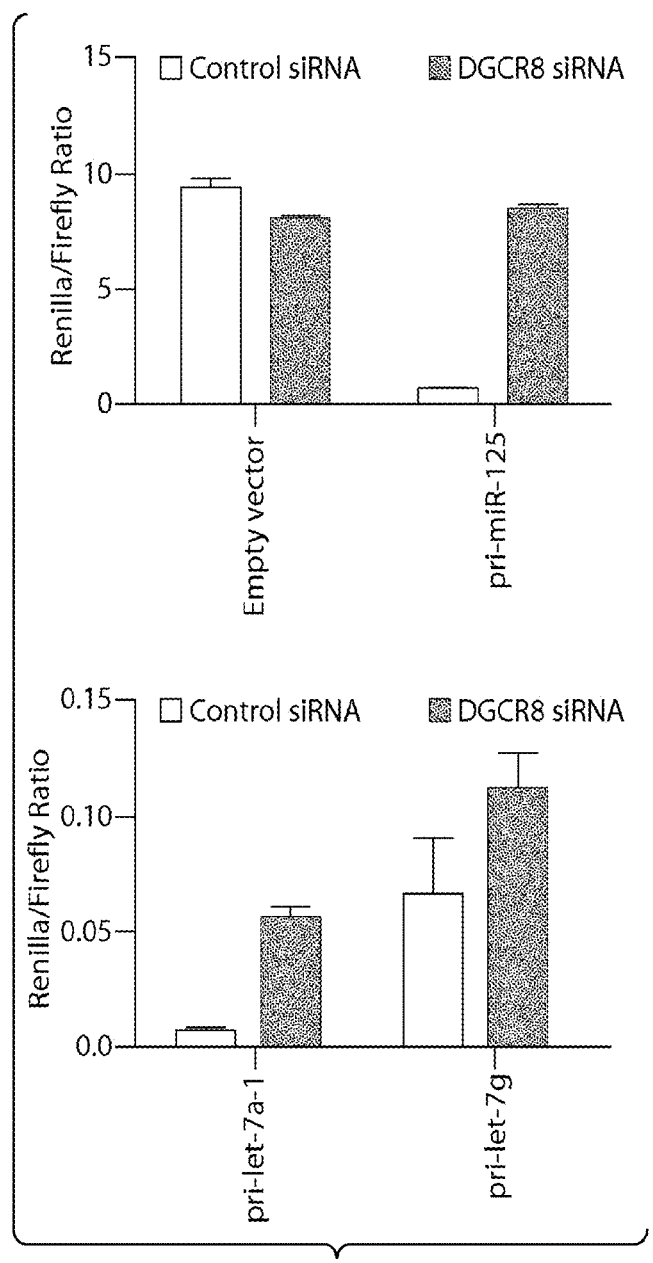
Figure 6D:
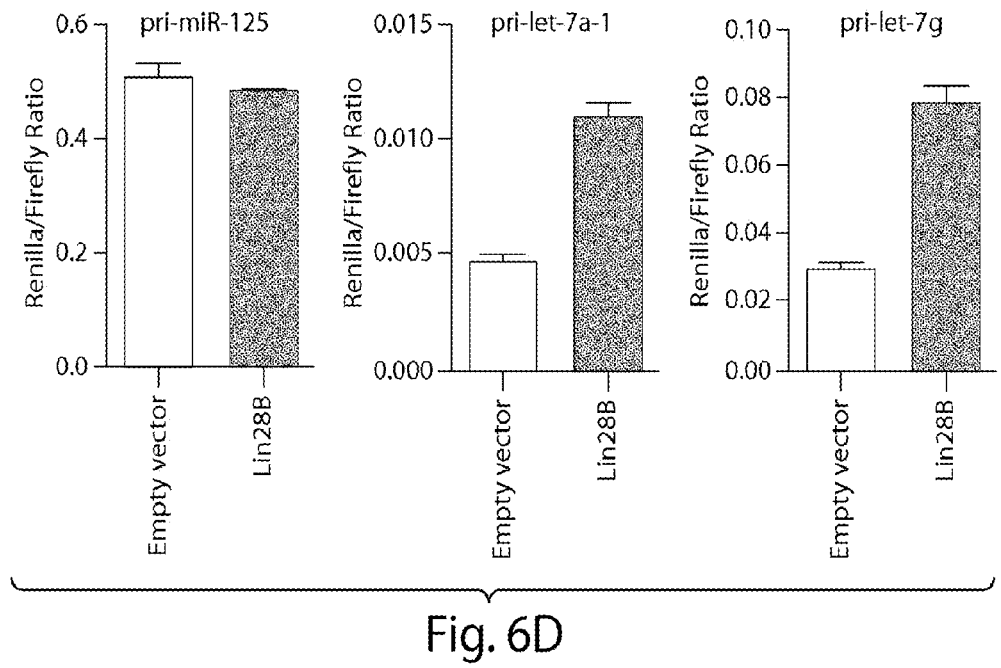
Figure 6E:
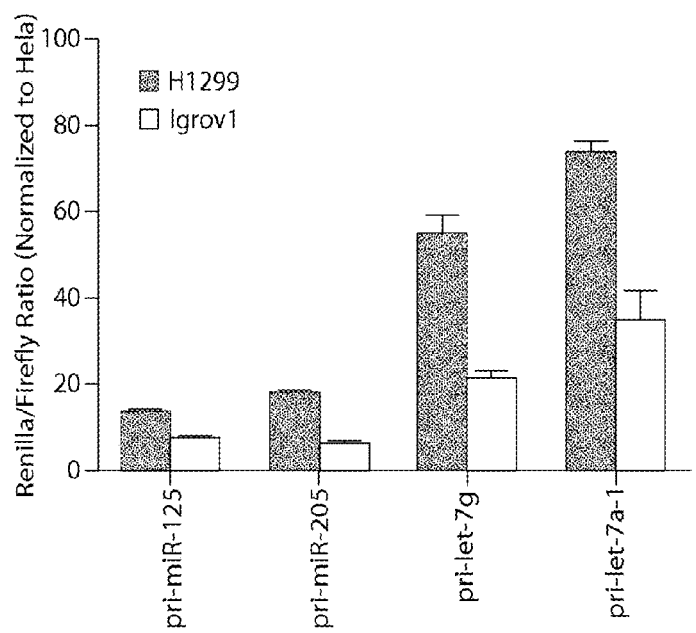

More specifically, that Lin28B blocks processing of pri-let-7 miRNAs by the Microprocessor was confirmed using a novel dual luciferase reporter system to monitor Microprocessor activity in transfected cells (FIG. 6A). A psiCHECK2 vector was used and several reporter constructs generated by placing particular pri-miRNA sequences between the Renilla Luciferase open reading frame and the polyA site. This novel reporter allows monitoring of Microprocessor activity in vivo. In the presence of an active Microprocessor complex the pri-miRNA should be processed regularly and Renilla protein expression would be consequently low. Inhibition of the Microprocessor should lead to stabilization of the Renilla mRNA and thereby lead to accumulation of Renilla protein. The Renilla Luciferase signal can be normalized to the Firefly luciferase that is encoded in the same plasmid but expressed ubiquitously regardless of Microprocessor activity. To validate this system as a reliable sensor of Microprocessor activity, DGCR8 levels were depleted by transient knockdown with siRNAs in Hela cells, which co-expressed the dual luciferase plasmid (FIG. 6B). A scrambled siRNA was used as a negative control. Three different dual luciferase constructs were used containing pri-let-7g, pri-let-7a-1, or pri-miR-125 (FIG. 6C). This showed that for all three constructs, Renilla Luciferase was stabilized, when DGCR8 was depleted. As a control for the luciferase system we used an empty vector with no pri-miRNA sequence, and showed that the relative Luciferase levels were unchanged by DGCR8 depletion (FIG. 6C). As the next step to address the question of whether Lin28B directly inhibits the action of the Microprocessor, Lin28B was transiently overexpressed in Hela cells in the presence the dual luciferase plasmids containing the different pri-miRNAs. The results demonstrate that overexpression of Lin28B caused stabilization of both pri-let-7 reporters, but had no effect on the pri-miR-125 construct (FIG. 6D). This result further supports the hypothesis that Lin28B inhibits the action of the Microprocessor in the nucleus. To confirm that the same mechanism is functional in cell lines that express endogenous Lin28B, was confirmed using the dual luciferase system in Lin28A- and Lin28B-expressing cell lines. Consistent with the observations for exogenously expressed Lin28B, pri-let-7 constructs were more stable in Lin28B-expressing cell lines than in Lin28A expressing cells (FIG. 6E). This confirmed that endogenous Lin28B operates via a mechanism distinct to that of Lin28A, and blocks let-7 processing by inhibiting the action of the Microprocessor complex.

Figure 7A:
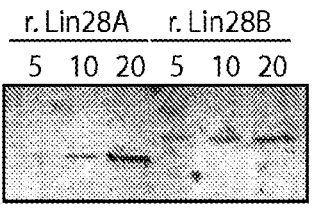
FIGS. 7A-F present data showing that Lin28B directly binds and sequesters pri-let-7.
Figure 7B:
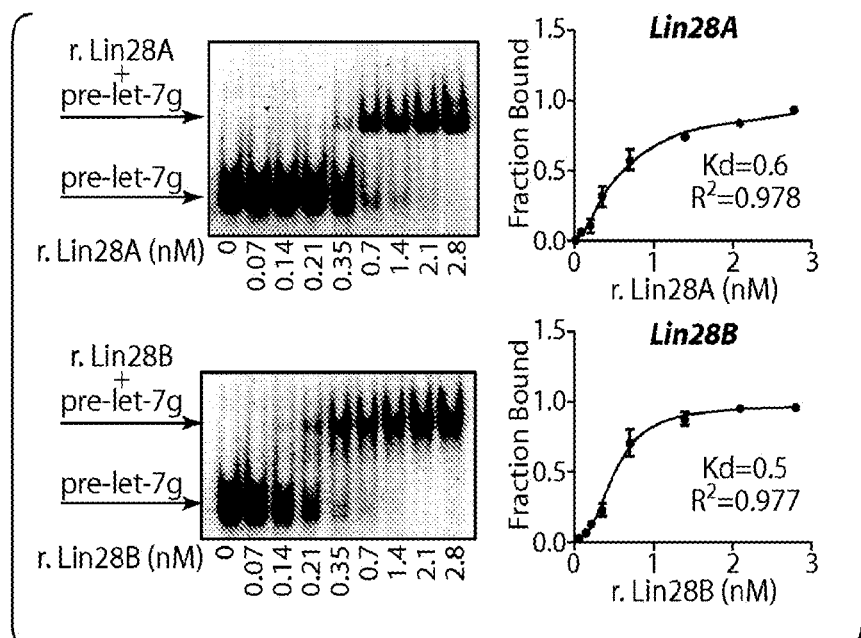
Figure 7C:
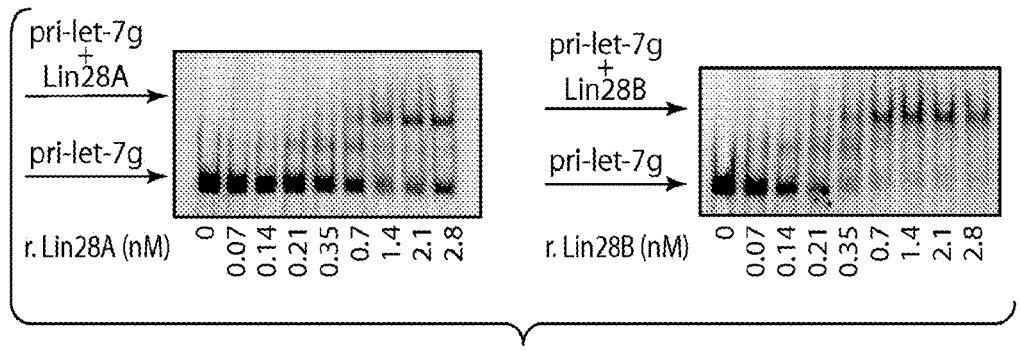
Figure 8:
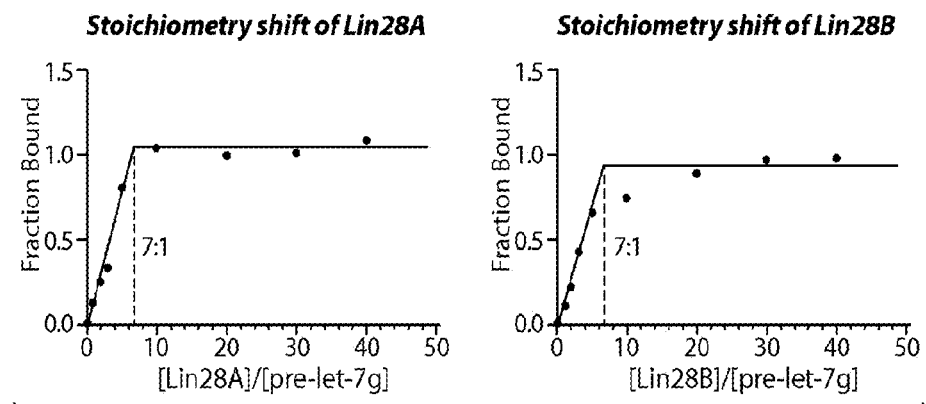
FIG. 8 demonstrates stoichiometry shifts of Lin28A and Lin28B. The data are plotted as the fraction of bound labeled RNA versus molar equivalents of recombinant protein. The 7:1 curve most closely approximates the data for both proteins.

Furthermore, Lin28B directly binds and sequesters pri-let-7. To further dissect the mechanism of the Lin28B-mediated let-7 processing block, the relative abilities of recombinant human Lin28A and Lin28B proteins to bind pre-let-7 were compared. (FIG. 7A, 7B and FIG. 8). EMSA was performed with pre-let-7g to analyze the relative binding affinities of the two recombinant proteins. Lin28A and Lin28B have apparent Kds of approximately 0.6 nM and 0.5 nM, respectively (FIG. 7B). Both these estimated Kds are much lower than a previously reported for recombinant mouse Lin28A. This difference is likely due to the omission here of nonspecific yeast tRNA competitor used previously in the binding buffer. Piskounova et al., 2008. An EMSA with pri-let-7g was performed and demonstrated that both recombinant Lin28A and Lin28B are able to bind pri-let-7g with similar affinities (FIG. 7C). Collectively, these assays reveal that both Lin28 proteins can directly bind to let-7 precursors with high-affinity in vitro.

Figure 7D:
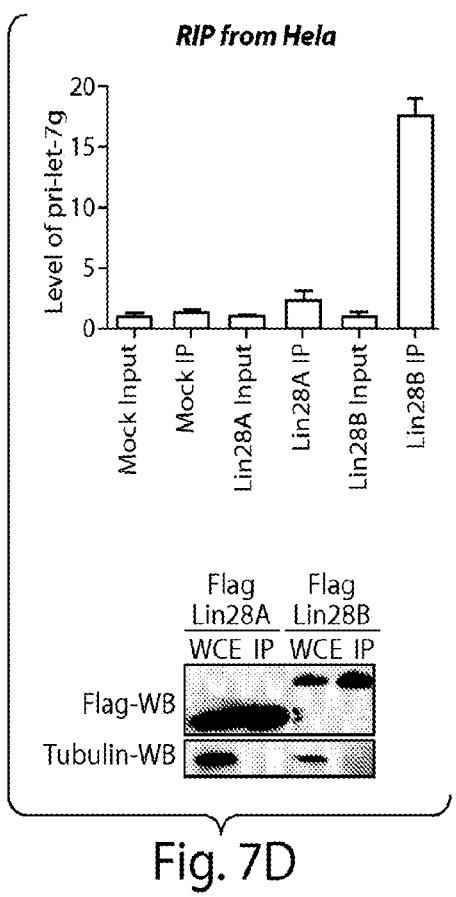

To gain further support for our model in which Lin28B binds and sequesters pri-let-7 in the nucleus to inhibit the Microprocessor, the RNA associated with Lin28B was examined. Flag-Lin28A and Flag-Lin28B were individually expressed and purified, and the associated RNA extracted and analyzed relative levels of pri-let-7g by q.RT-PCR. This RNA immune-precipitation (RIP) analysis revealed that Lin28B directly associates with pri-let-7g RNA (FIG. 7D), revealing an ~18-fold enrichment of pri-let-7 associated with Lin28B. Furthermore, substantially more pri-let-7 associated with Lin28B than with Lin28A, which is consistent with the differential subcellular localization of these proteins. Taken together, these results indicate that this preferential association of pri-let-7g with Lin28B likely reflects the distinct mechanism by which Lin28B represses let-7 expression rather than any possible intrinsic differences in the relative RNA-binding affinities of Lin28A and Lin28B proteins.

Figure 7E:
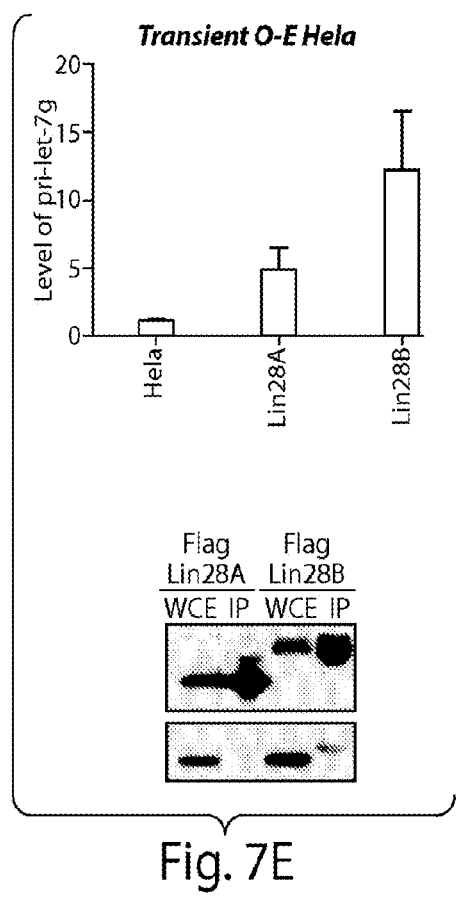
Figure 7F:
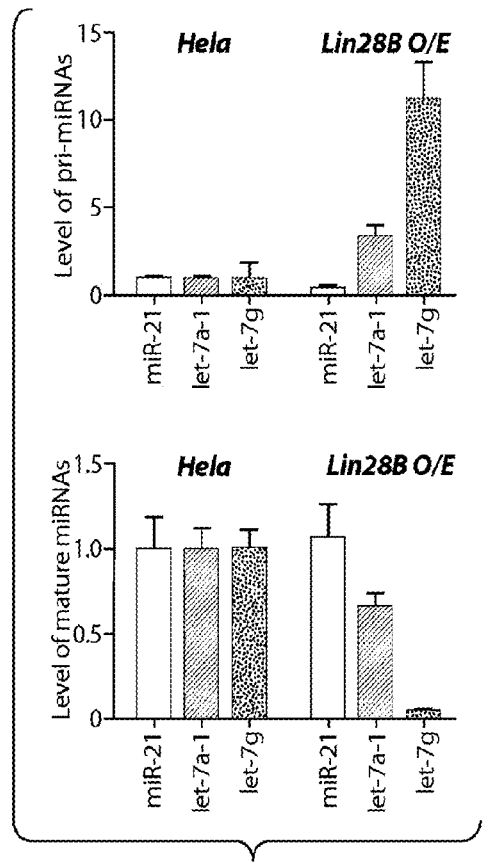

The effect of transient Lin28B overexpression on pri-let-7g levels was also studied by q.RT-PCR. Transient Lin28B overexpression led to ~12-fold accumulation of pri-let-7g levels (FIG. 7E). In contrast, overexpression of Lin28A only had a more modest effect on pri-let-7g levels consistent with its predominantly cytoplasmic localization. In order to further assess the effects of Lin28B overexpression on both pri- and mature miRNA levels, a Flag-Lin28B expressing Hela stable cell line was used. Analysis of several pri-miRNAs by q.RT-PCR in this cell line demonstrated a substantial accumulation of pri-let-7 miRNAs, >10-fold for pri-let-7g and >3-fold for pri-let-7a-1. There was however no effect on levels of pri-miR-21 (FIG. 4A). A corresponding decrease in the levels of mature let-7, with >90% decrease for mature let-7g, and ~40% decrease for mature let-7a was observed. Again no effect was observed on levels of mature miR-21 (FIG. 4A). Together, these data support our model whereby nuclear Lin28B directly associates with pri-let-7 sequestering it from cleavage by the Microprocessor to selectively inhibit let-7 maturation, and underscore our findings that the paralogous RNA-binding proteins, Lin28A and Lin28B, operate by distinct mechanisms to selectively repress let-7 expression.

Zcchc11 inhibition blocks the tumorigenicity and invasiveness of Lin28A- but not Lin28B-expressing breast cancer cells in vitro and in vivo. The mechanistic studies showed that Lin28A and Lin28B block let-7 processing through distinct mechanisms: Lin28A recruits Zcchc11 to uridylate pre-let-7 miRNAs in the cytoplasm, whereas Lin28B functions in the nucleus through a Zcchc11-independent mechanism by blocking pri-let-7 biogenesis at the Microprocessor step. Next, the physiological and disease relevance of these distinct mechanisms were explored in the context of the role of Zcchc11 in human Lin28A- and Lin28B-expressing cancer, more specifically, the effect of Zcchc11 inhibition on the tumorigenicity and invasiveness of breast cancer cells expressing either Lin28A or Lin28B.

Figure 9A:
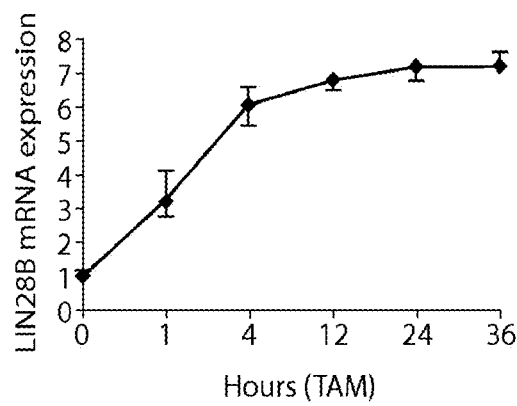
FIGS. 9A-J show that Lin28B-mediated transformation and tumorigenicity is Zcchc11-independent.
Figure 9B:
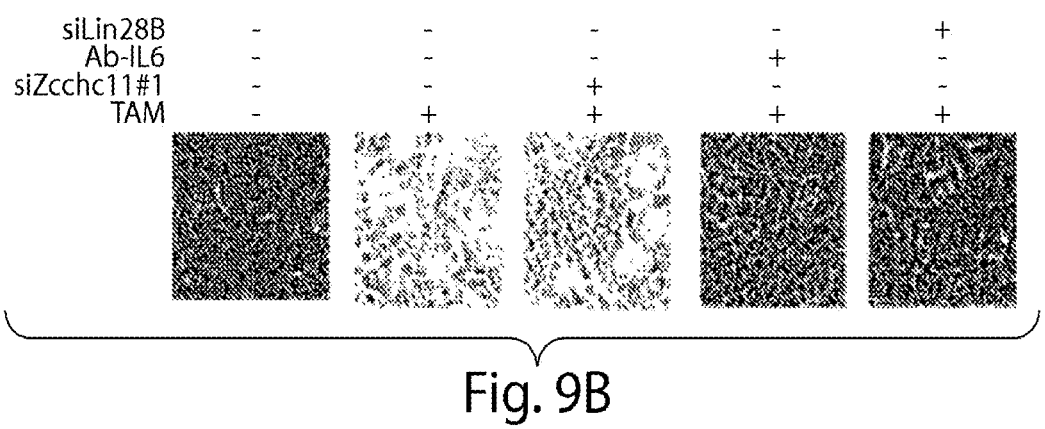
Figure 9C:
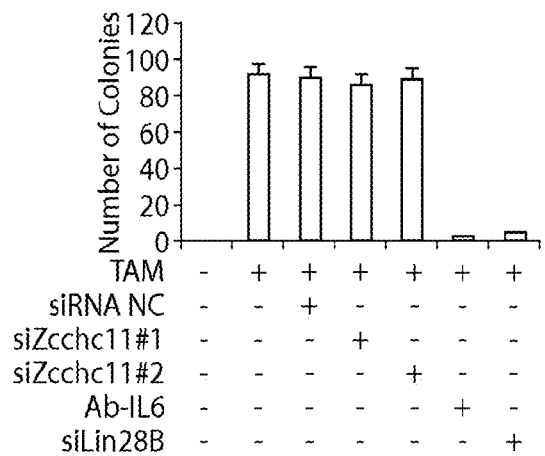
Figure 9D:
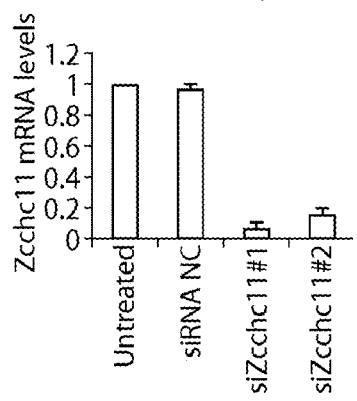
Figure 9E:
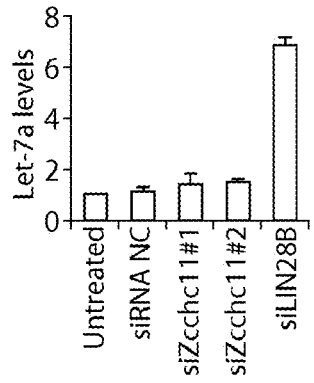
Figure 9F:
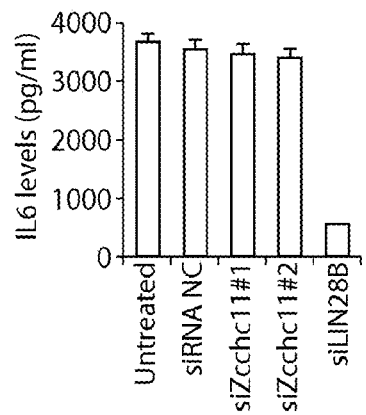

Initially, the effects of Zcchc11 inhibition in MCF10A ER-Src inducible model of cellular transformation were tested, where MCF10A immortalized breast epithelial cells become transformed 36 h post tamoxifen (TAM) treatment, Iliopoulos et al., 2009. During transformation of MCF10A ER-Src cells, there is activation of a negative feedback loop, consisting of NF-κB, Lin28B, let-7a and 1L6, which is essential for induction and maintenance of the transformed phenotype. During the transformation process, there is an increase in the expression levels of Lin28B, while these cells do not express Lin28A (FIG. 9A). Furthermore, when the MCF10A ER-Src cells are transformed (36 h post TAM treatment) they have a substantial change in their morphology (FIG. 9B). Zcchc11 depletion by siRNA did not affect MCF10A ER-Src transformation, while in contrast depletion of Lin28B by siRNA or inhibition of IL6 by a monoclonal antibody (Ab-IL6) suppressed this transformation. In addition, in order to confirm these findings, we tested the effects of Zcchc11 inhibition on the colony formation ability of the transformed MCF10A ER-Src cells. Interestingly, Zcchc11 suppression did not affect the colony formation ability of the transformed MCF10A ER-Src cells, while inhibition of Lin28B blocked their tumorigenicity (FIG. 9C, 9D). Furthermore, Zcchc11 inhibition did not affect the expression levels of let-7a miRNA and its direct downstream target 1L6 (FIG. 9D, 9E, 9F).

Figure 9G:
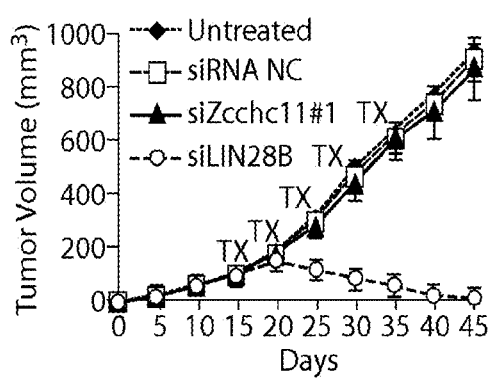
Figure 9H:
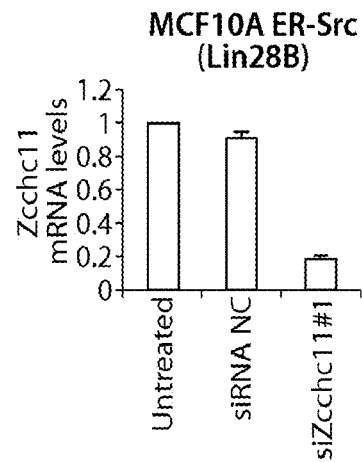
Figure 9I:
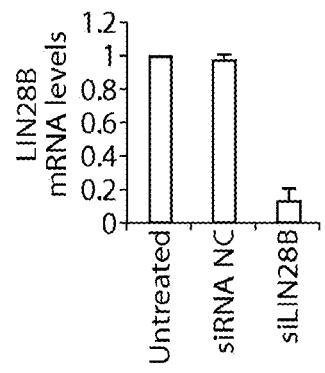
Figure 9J:
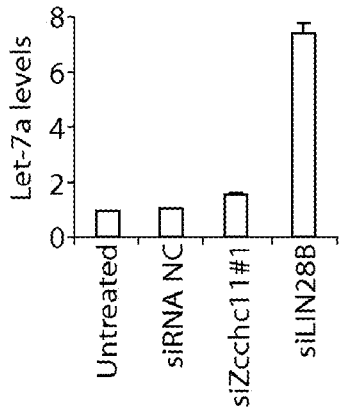

In addition to the in vitro data, the effects of Zcchc11 inhibition in was tested in xenografts (FIG. 9G). Specifically, MCF10A ER-Src transformed cells were injected in immunodeficient (nu/nu) mice and when the tumors reached the size of 100 mm3, the mice were randomly distributed into four groups (five mice/group). The first group of mice did not receive any treatment (untreated), the second group of mice was treated intraperitoneously (i.p.) with siRNA negative control (siRNA NC) the third group of mice was treated i.p. with siRNA against Zcchc11 (siZcchc11#1) and the fourth group of mice was treated i.p. with siRNA against Lin28B (siLin28B). All the treatments started at day 15 for 5 cycles (days 15, 20, 25, 30, 35). In accordance with the in vitro data, Zcchc11 inhibition did not affect MCF10A ER-Src tumor growth, while Lin28B inhibition suppressed tumor growth (FIG. 9G, 9H). The tumors were excised from the mice at day 30 (after three cycles of treatment) and were tested for let-7a expression. siZcchc11 treatment did not affect let-7a expression levels in these tumors, while siLin28B treatment led to a 7-fold increase in let-7a expression levels (FIG. 9J). Overall, these data suggest that inhibition of Zcchc11 does not have an inhibitory effect on the tumorigenicity and invasiveness of Lin28B-expressing MCF10A ER-Src cells.

Figure 10A:
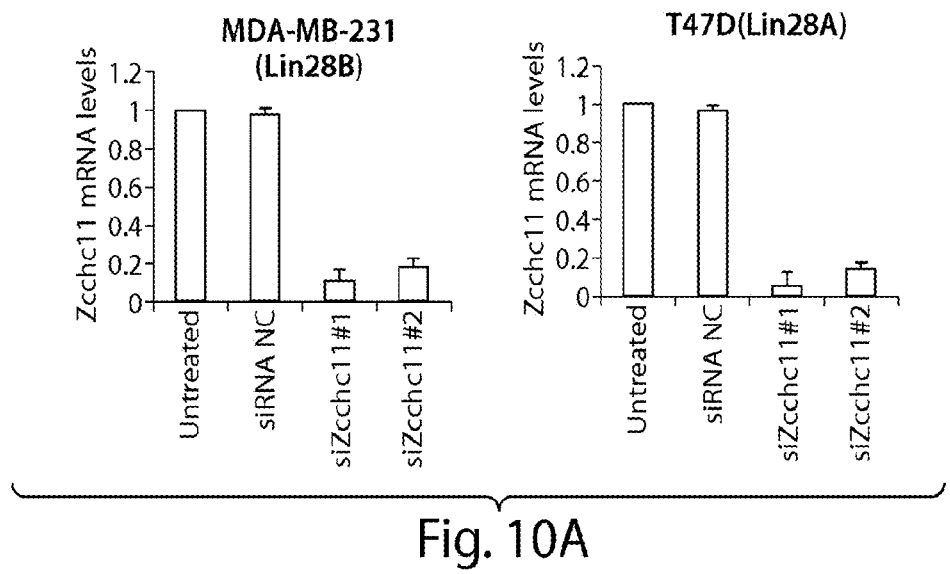
FIGS. 10A-G demonstrate that Zcchc11 inhibition blocks tumorigenicity and invasiveness of Lin28A-expressing breast cancer cells.
Figure 10B:
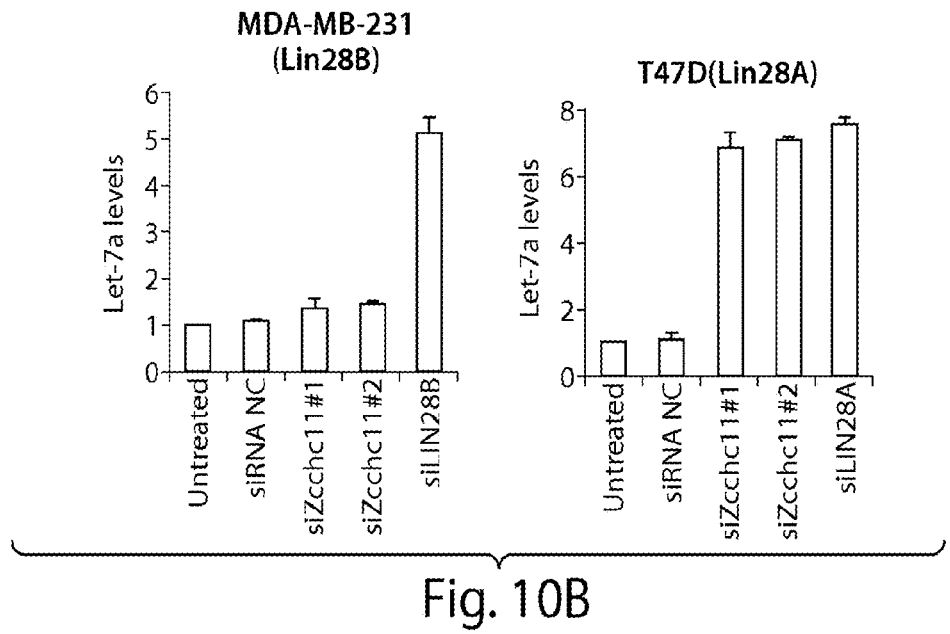
Figure 10C:
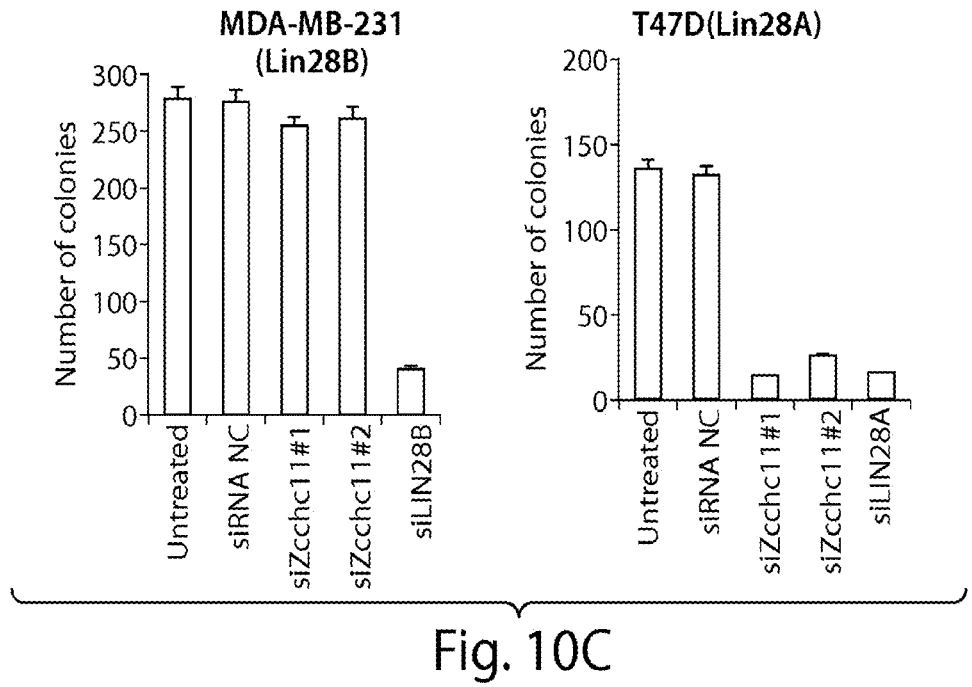
Figure 10D:
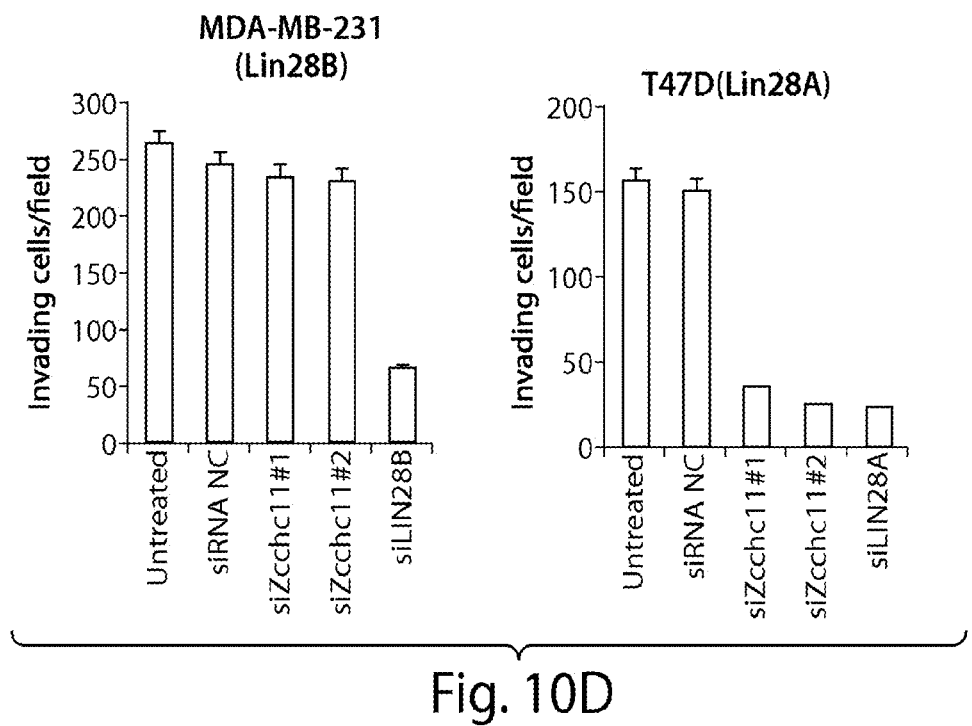
Figure 10E:
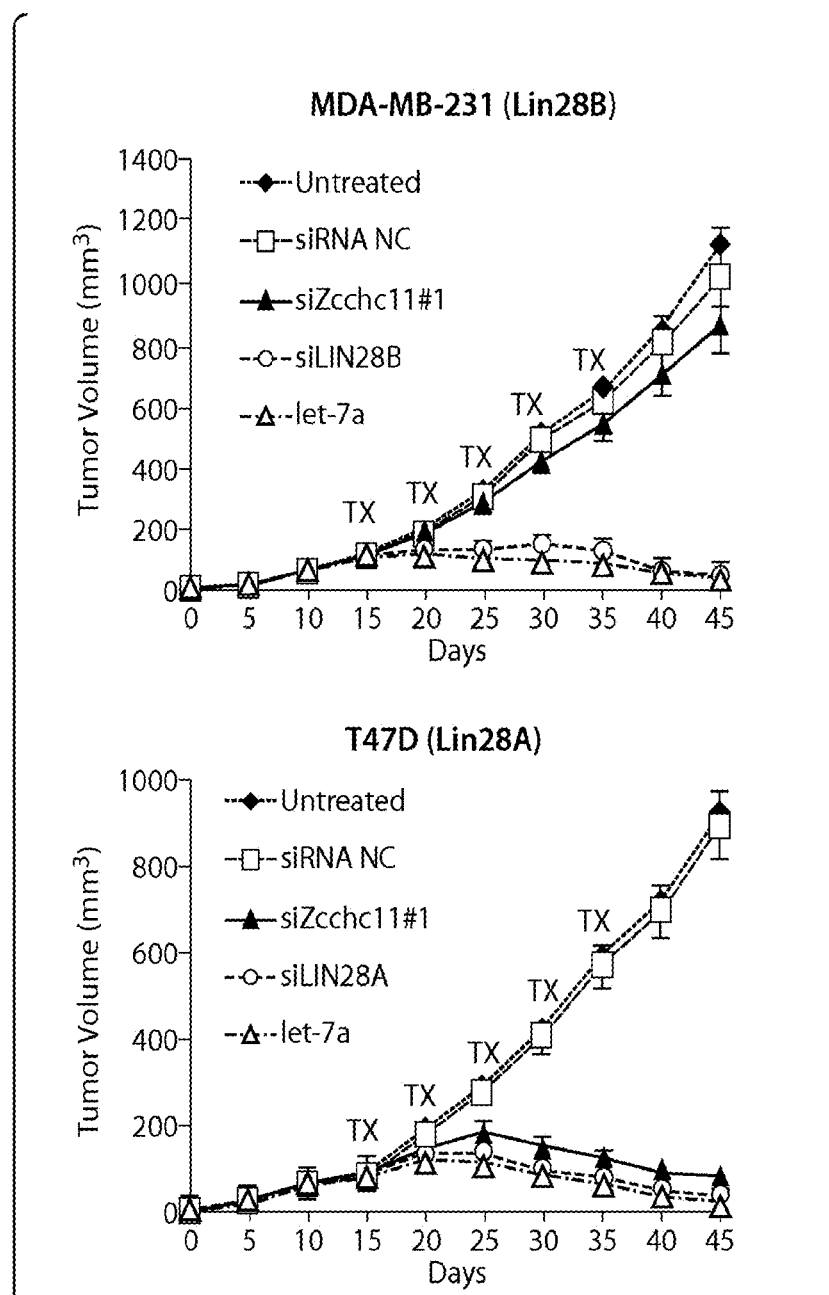
Figure 10F:
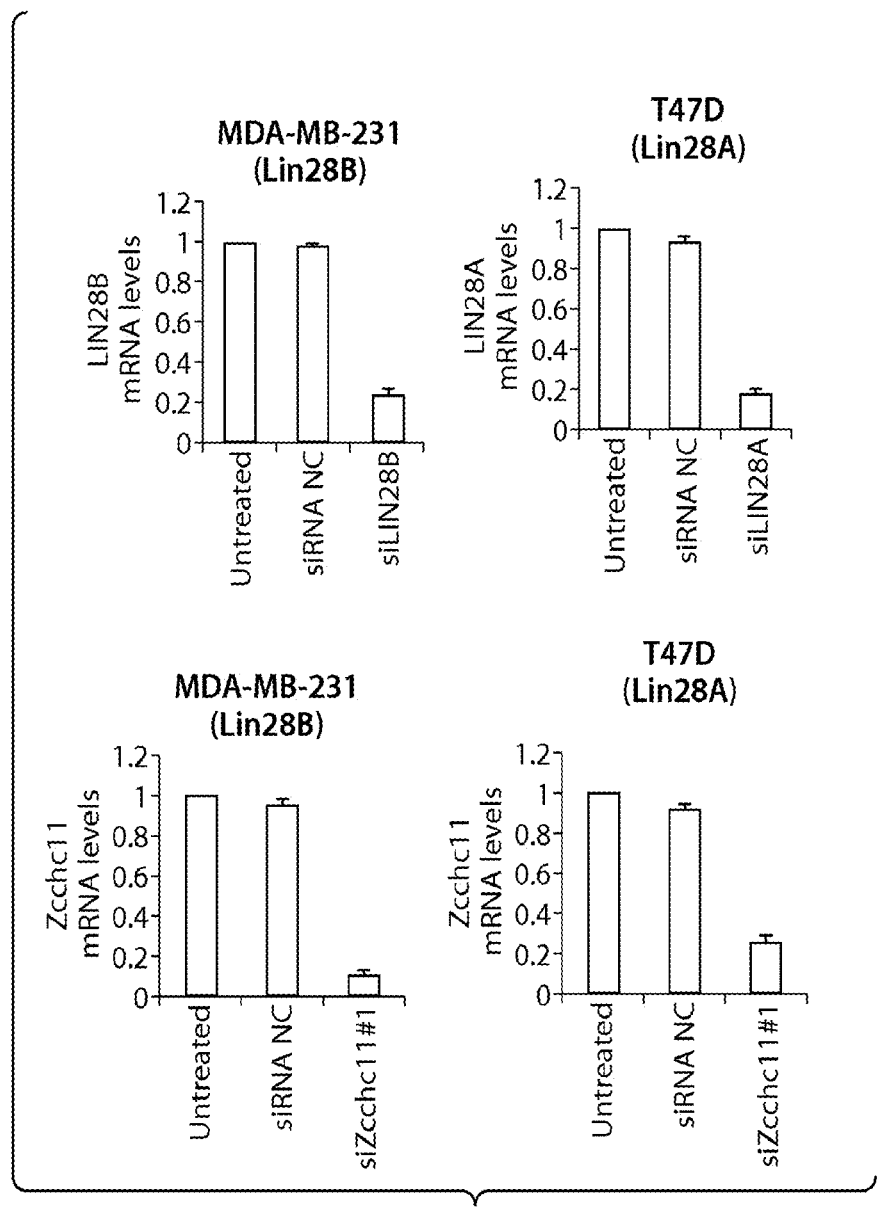
Figure 10G:
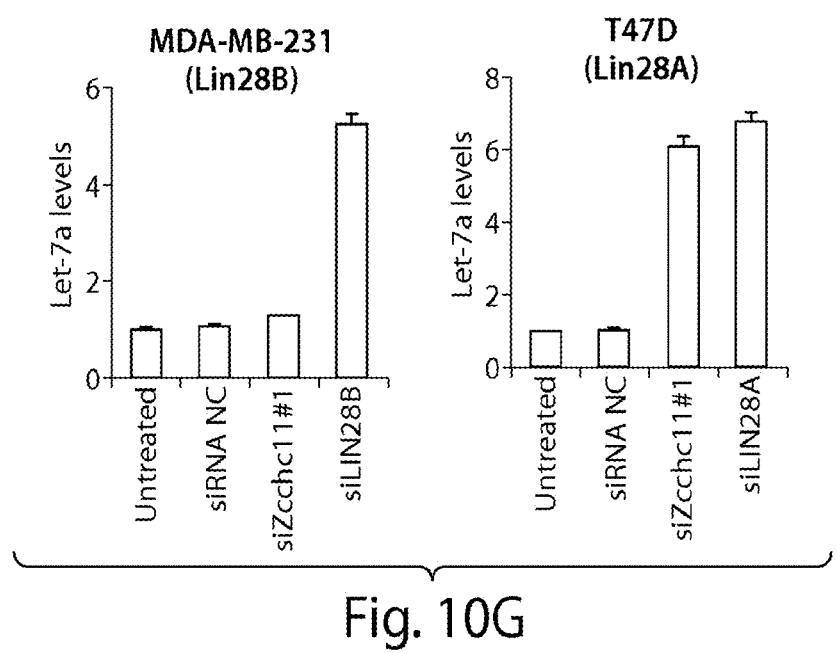

To further explore the distinct requirements for Zcchc11 in Lin28A- and Lin28B-expressing cancer, the effects of Zcchc11 inhibition on the tumorigenicity and invasiveness of MDA-MB-231 breast cancer cells (Lin28B-expressing cells) relative to T47D breast cancer cells (Lin28A-expressing cells) were compared. Suppression of Zcchc11 expression did not affect let-7a expression in MDA-MB-231 cells, but led to 7-fold increase in mature let-7a levels in T47D cells (FIG. 10A, 10B). Furthermore, Zcchc11 inhibition did not affect the tumorigenicity and invasiveness of MDA-MB-231 cells, while it suppressed both the colony formation ability and invasiveness of T47D cells (FIGS. 10C, 10D). Zcchc11 inhibition had similar effects on the tumor growth of these cell lines in xenografts. Specifically, Zcchc11 knockdown did not affect tumor growth of MDA-MB-231 while it suppressed T47D tumor growth (FIG. 10E). Synthetic let-7a miRNA suppressed both MDA-MB-231 and T47D tumor growth (FIG. 10E). Also, in the tumors derived from MDA-MB-231 xenografts (day 30), let-7a expression was not affected by inhibition of Zcchc11, while Lin28B suppression increased let-7a levels about 5-fold (FIG. 5F P2, 5GP2 nFIG. 10F, nFIG. 10G). On the other hand, both Zcchc11 and Lin28A inhibition resulted in up-regulation of let-7a expression to similar levels in T47D-derived tumors (day 30) (FIG. 10F, 10G).

Figure 11A:
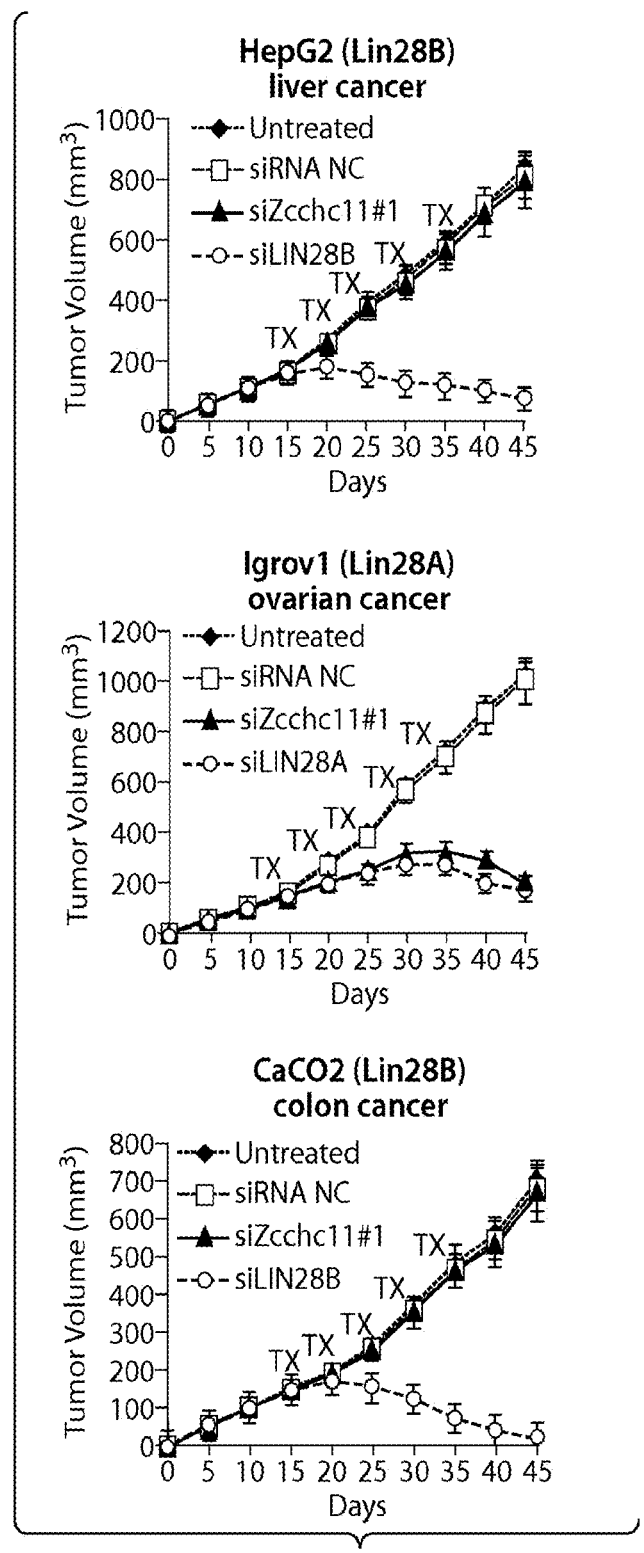
FIGS. 11A-D demonstrate that inhibition of Zcchc11 expression suppresses tumor growth of Lin28A- but not Lin28B-expressing xenografts.
Figure 11A:
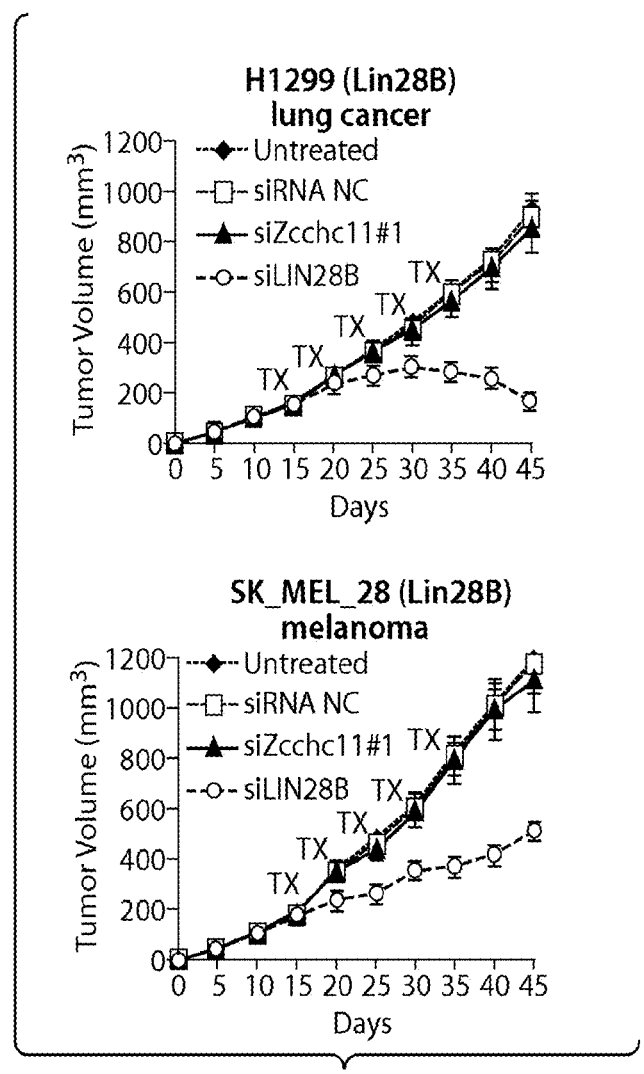
Figure 11B:
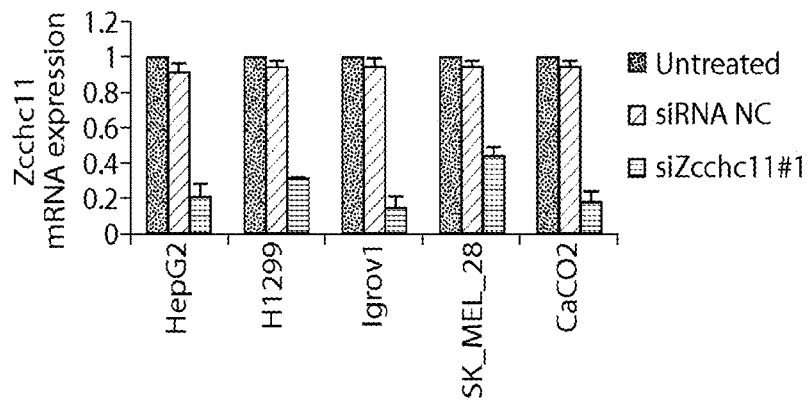
Figure 11C:
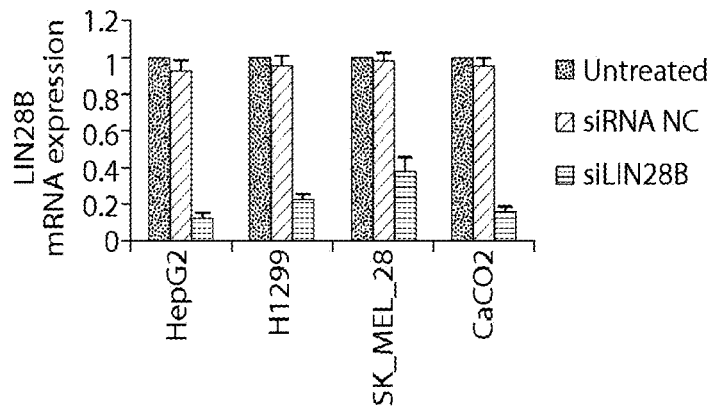
Figure 11D:
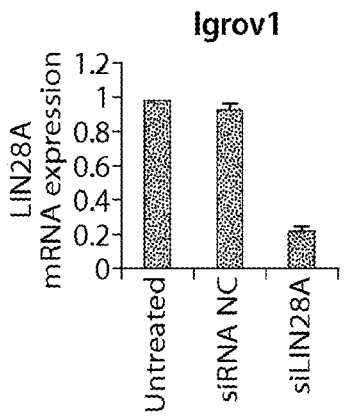

In addition to the breast cancer cells, the effects of Zcchc11 inhibition on tumor growth of several other (liver, lung, ovarian, melanoma, colon) cancer cell types were tested (FIG. 11A). Zcchc11 inhibition (FIG. 11B) blocked the growth of LIN28A-expressing tumors (Igrov1) and did not affect the growth of Lin28B-expressing tumors (HepG2, H1299, SK_MEL_28, CaCO2) (FIG. 11A). Lin28A and Lin28B inhibition suppressed the growth of the corresponding tumors (FIG. 11C, 11D). Taken together, these data suggest that Zcchc11 plays a role in the tumorigenicity and invasiveness of Lin28A-expressing cancer cells but depletion of Zcchc11 in Lin28B-expressing cancer cell lines has no effect on cancer growth.

Figure 12A:
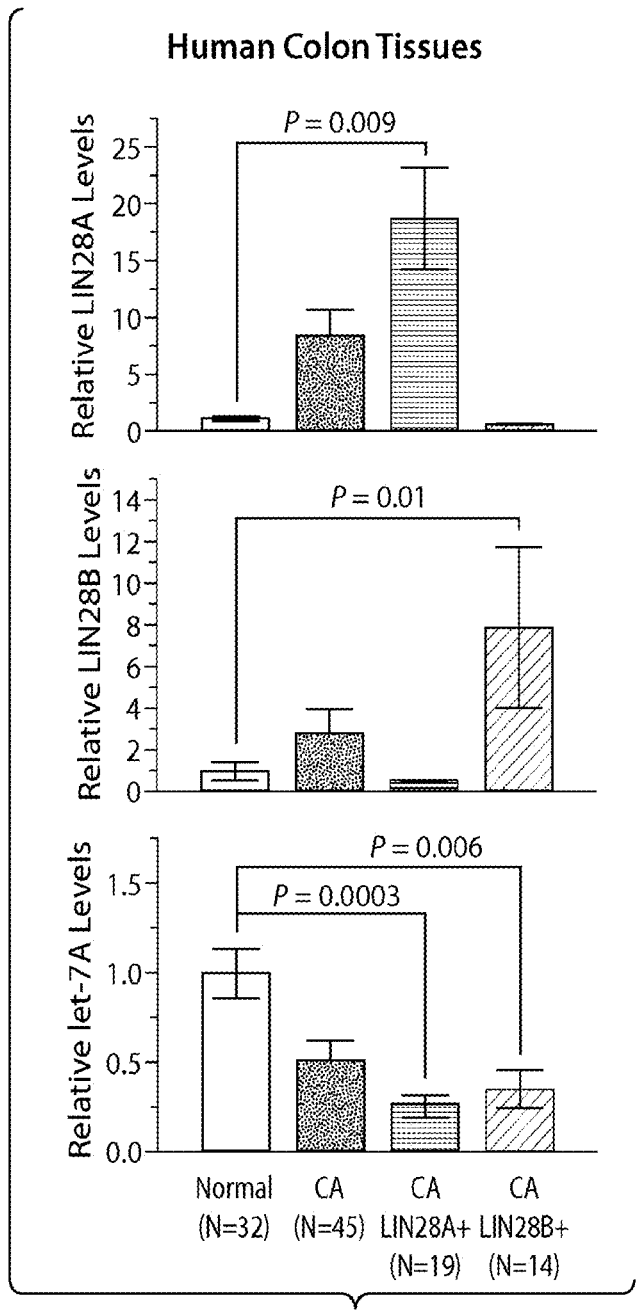
FIGS. 12A-F depict Lin28A and Lin28B expression in primary human cancers.
Figure 12B:
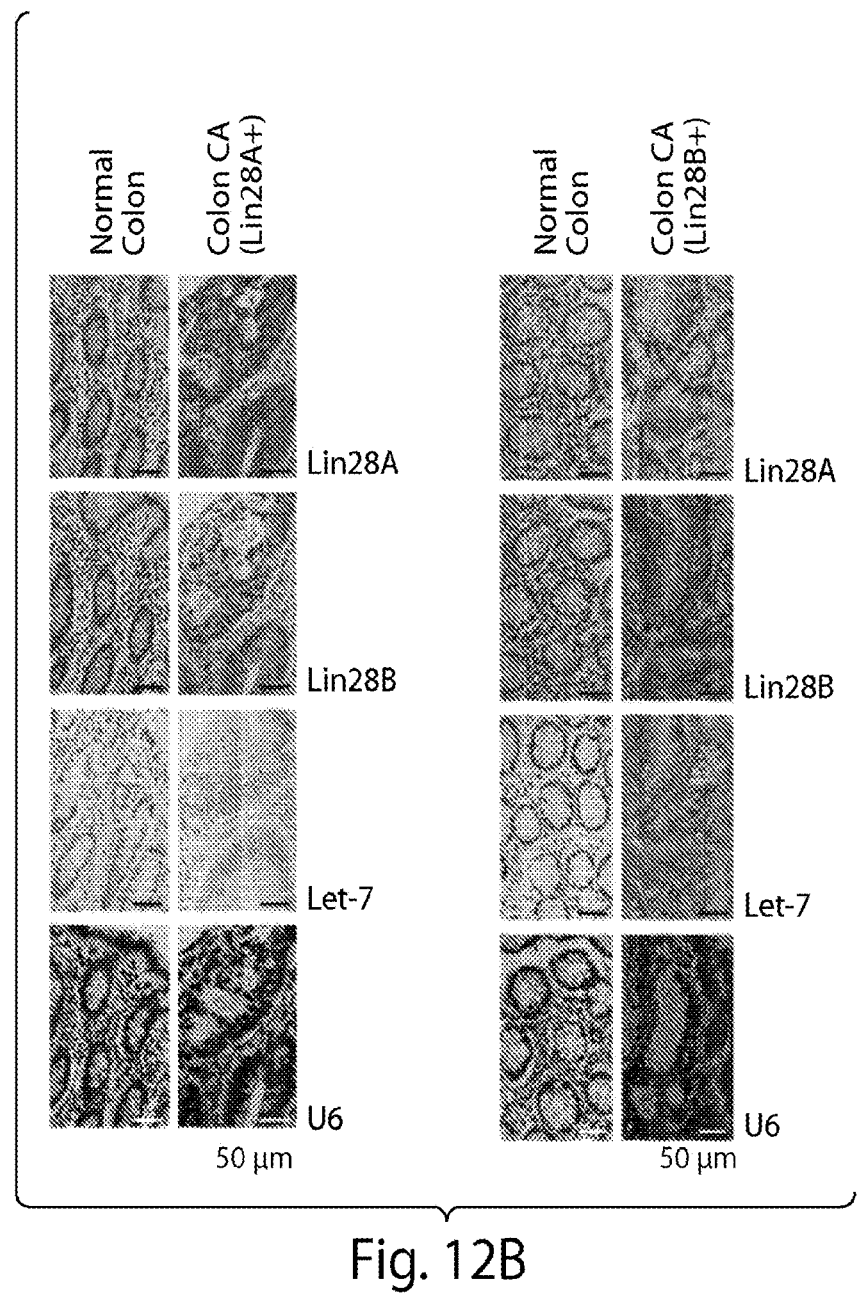
Figure 13A:
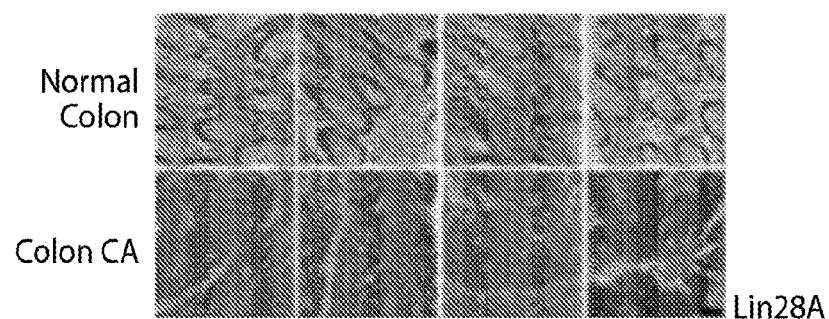
FIGS. 13A-C show that Lin28A, Lin28B and let-7a expression in colon adenocarcinomas.
Figure 13B:
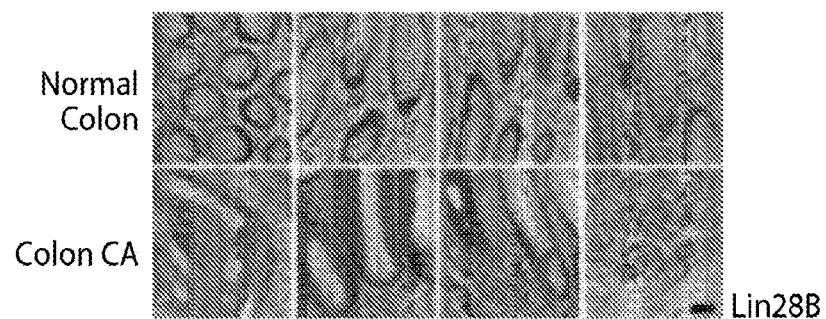
Figure 13C:
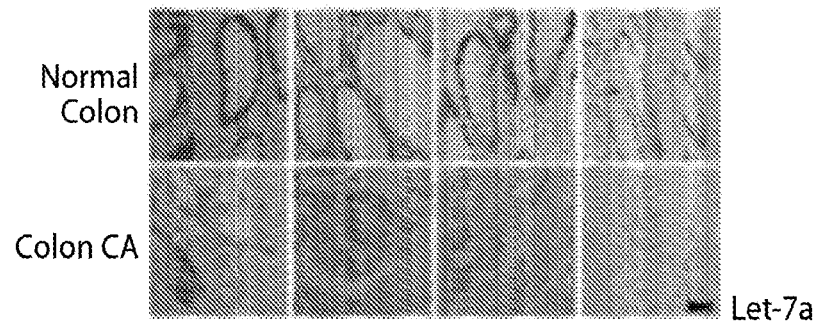

The disease relevance of these findings were further confirmed by measuring Lin28A and Lin28B expression in human colon and breast tissues. Lin28A or Lin28B are upregulated while let-7a was downregulated in colon adenocarcinomas relative to normal colon tissues (FIG. 12A). Specifically, Lin28A was upregulated in 19/45 colon adenocarcinomas while Lin28B was upregulated in 14/45 colon adenocarcinomas. The colon tumors with Lin28A overexpression had very low levels of Lin28B and vice versa. Furthermore, immunohistochemistry and in situ hybridization analyses in normal and colon cancer tissues revealed that Lin28A or Lin28B proteins were upregulated while let-7a was downregulated in colon carcinomas relative to normal colon tissues (FIG. 12B, FIG. 13). Similar to the mRNA data, immunohistochemistry revealed that tumors that expressed high Lin28A protein levels had low levels for Lin28B and vice versa. This is consistent with our analysis of human cancer cell lines where we did not find cells that express both Lin28A and Lin28B (FIG. 1B).

Figure 12C:
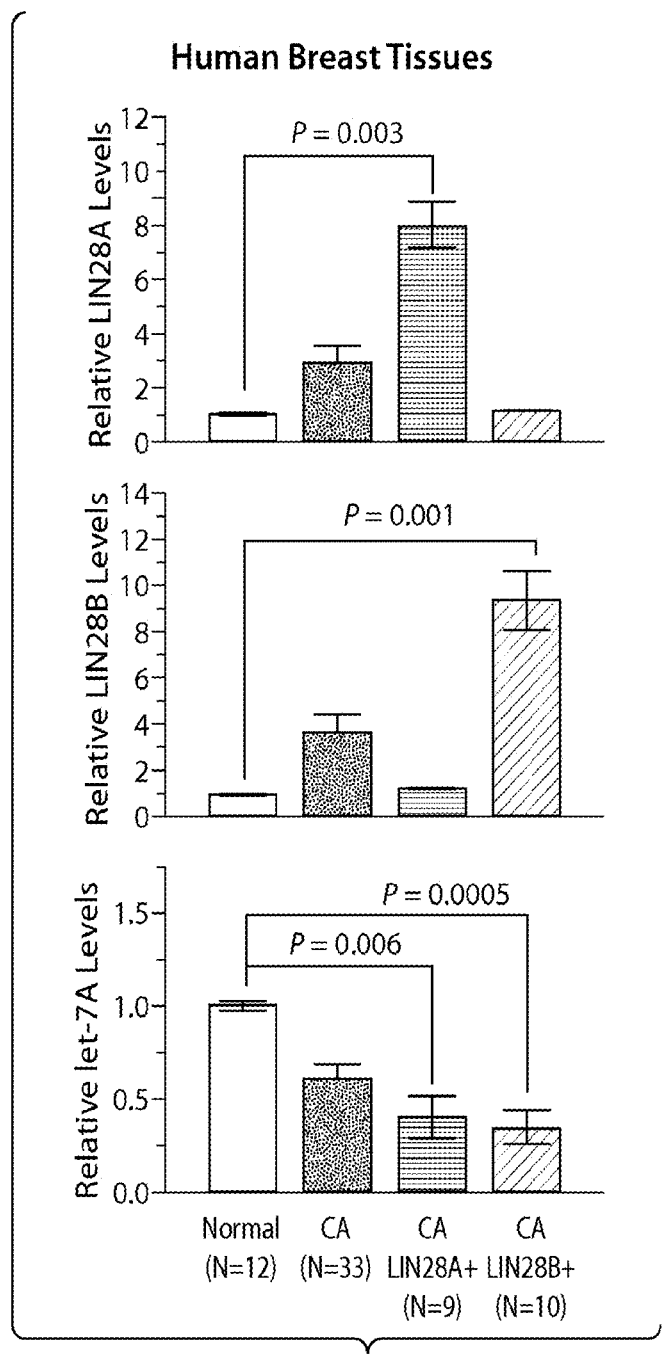
Figure 12D:
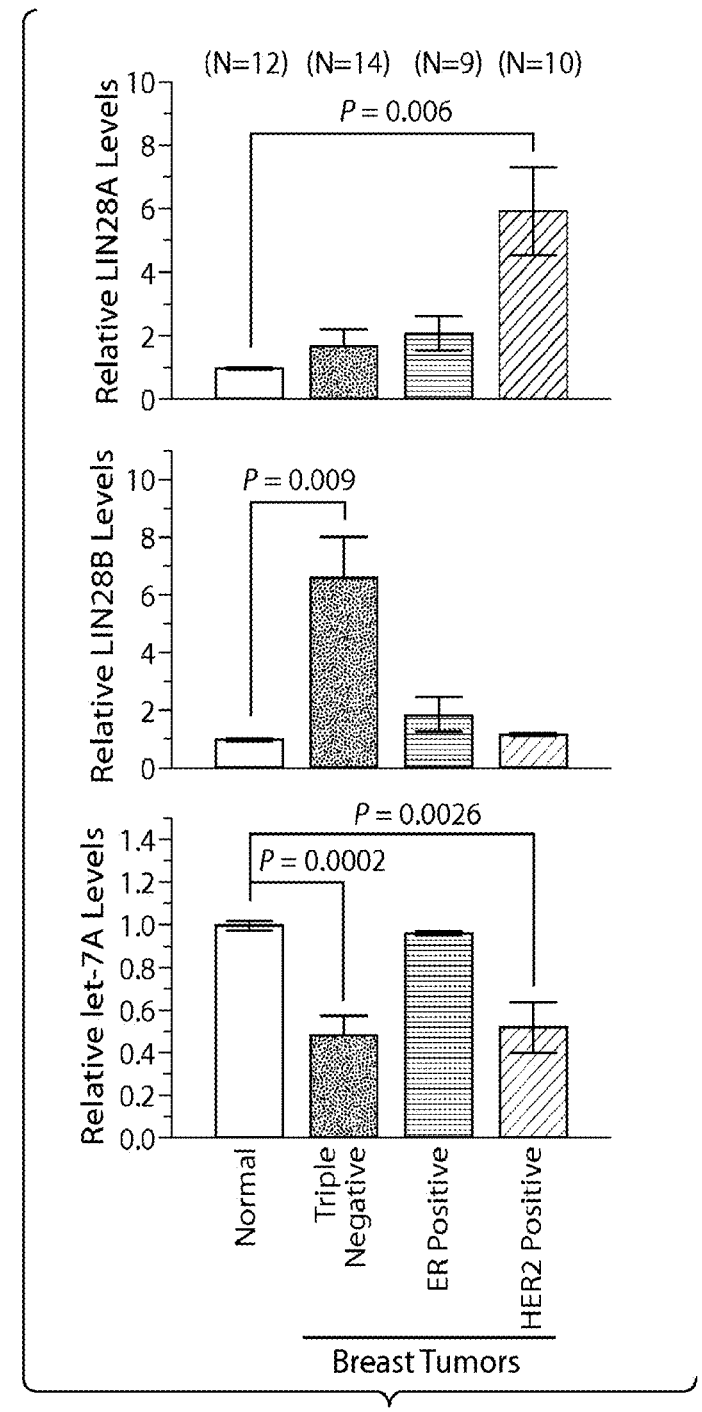
Figure 12E:
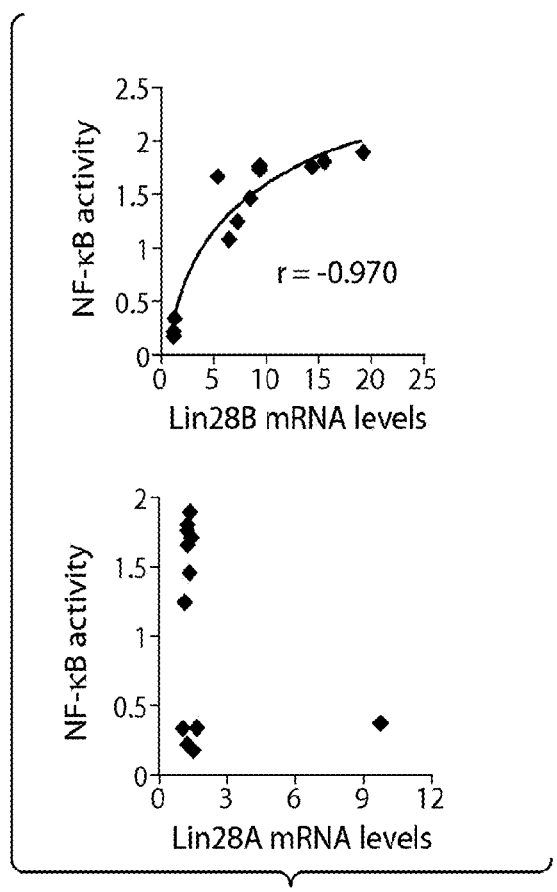
Figure 12F:
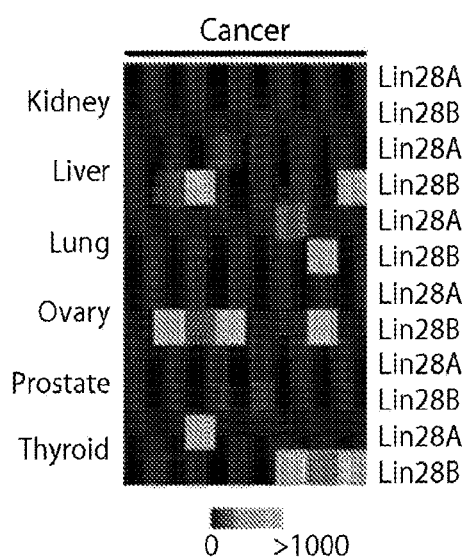

Additionally, Lin28A or Lin28B were upregulated while let-7a was down-regulated in breast cancer relative to normal breast tissues (FIG. 12C). Specifically, Lin28A was upregulated in 9/33 breast carcinomas while Lin28B was upregulated in 10/33 breast carcinomas. Similar to the colon tissues, the breast tumors that overexpressed Lin28A had very low levels of Lin28B and vice versa. In addition, Lin28A was significantly upregulated in HER2-overexpressing breast tumors while Lin28B was significantly upregulated in triple-negative (ER-, PR-, HER2-) breast tumors (FIG. 12D). Furthermore, according to previous studies Lin28B expression is a part of an inflammatory circuit and is regulated by NF-κB transcription factor. Iliopoulos et al., Cell, 2009. Thus, how NF-κB activity correlates with Lin28A or Lin28B mRNA levels in human breast tumors was tested, and revealed a statistically significant correlation between NF-κB nuclear levels and Lin28B but not Lin28A expression levels (FIG. 12E). These data suggest that NF-κB regulates Lin28B but not Lin28A pathway. Also, in order to have a broader view of Lin28A and Lin28B expression levels in human cancer tissues, their expression levels in kidney, liver, lung, ovarian, prostate, and thyroid cancer were compared (FIG. 12F). These data reveal that Lin28B is upregulated in liver, ovarian and thyroid carcinomas.

The present invention also provides the domains of Zcchc11 required for Lin28-enhanced pre-miRNA uridylation. As described herein and elsewhere, Zcchc11 is a cytoplasmic Lin28-interacting TUTase in embryonic and cancer cells. Hagan et al., 2009; Heo et al., 2009; Piskounova et al., 2011. Its depletion in Lin28-expressing cells leads to the specific upregulation of let-7 family members similar to the depletion of Lin28 and its expression is required for potent let-7 repression and rapid cell growth in Lin28A-expressing cancers. Piskounova et al., 2011. Zcchc11 encodes a 184 kDa non-canonical poly(A) polymerase that is highly conserved across vertebrates. The Zcchc11 active site is located within the Nucleotidyl Transferase (Ntr) domain, which is paired with a Poly(A)-Polymerase-Associated (PAP) domain; a common feature of non-canonical poly(A) polymerases. Kwak & Wickens, 13 RNA 860 (2007); Martin & Keller, 7 Stem Cell 31 (2007); Saitoh et al., 109 Cell 563 (2002). Catalysis requires a conserved Aspartate triad in the Ntr, and an overexpressed mutant lacking these residues functions as a dominant negative. Hagan et al., 2009. Flanking the active site are three CCHC retroviral-type zinc fingers/zinc knuckles, which are implicated in nucleic acid binding. At the N-terminus of the protein is a region that shares significant homology with the active site, including a proximal PAP domain; however, this region lacks one of the crucial Aspartates predicted to be necessary for catalysis. Instead, this region is most similar to the yeast TRF4 proteins, which carry out cytoplasmic poly(A) RNA polymerase activity. Saitoh et al., 2002. N-terminal to this region is a classical C2H2 zinc finger with no known function. These motifs are known to bind DNA, RNA, or protein. Finally, at the N- and C-termini of Zcchc11 there are two domains of unknown function similar, respectively, to pneumoviridae attachment proteins and the glutamine-rich neurodegenerative disease-associated protein atrophin-1 (FIG. 14).

Figure 14A:
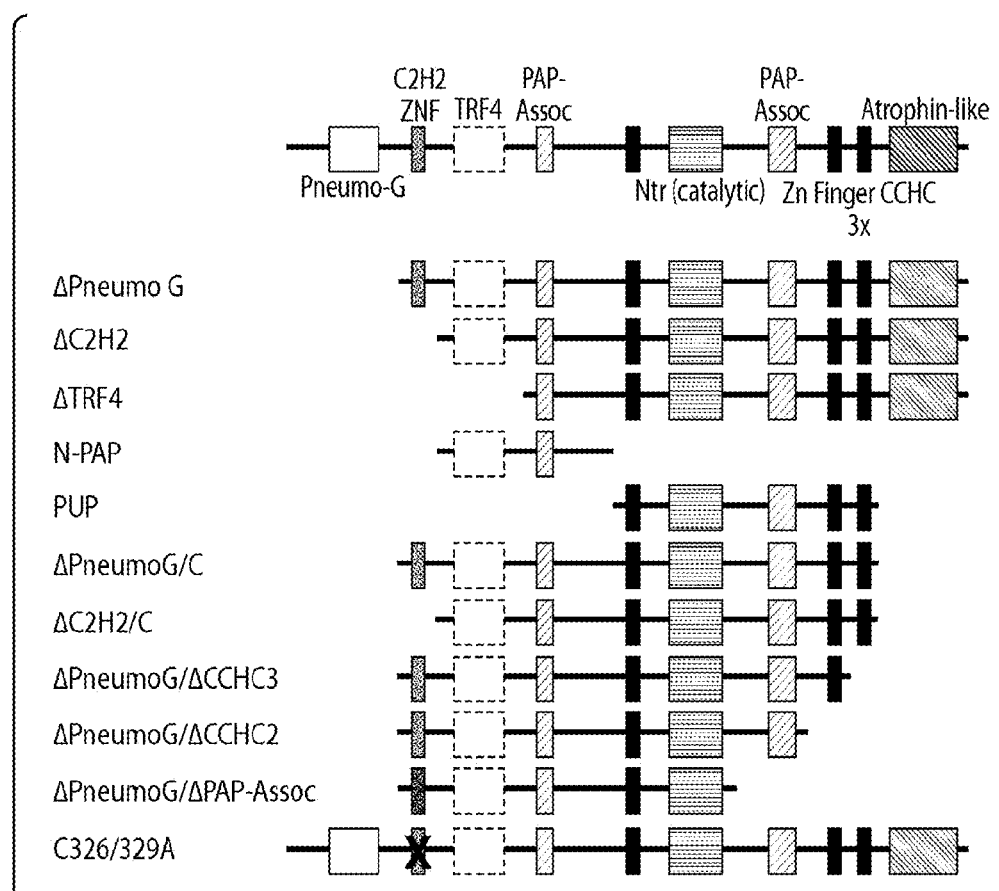
FIGS. 14A-C present the domains of Zcchc11 required for Lin28-mediated pre-let-7 uridylation.
Figure 14B:
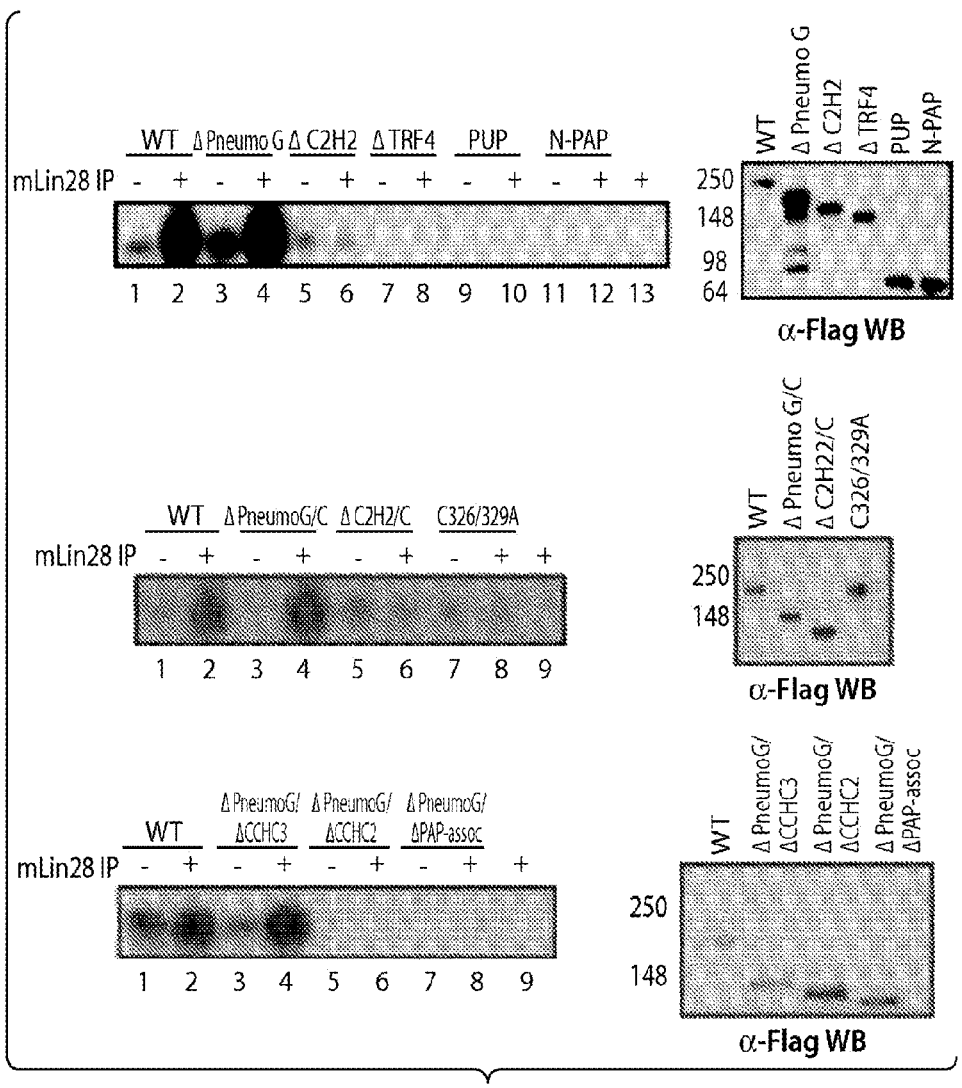

To understand which domains of Zcchc11 are required for uridylation activity, a series of mutant cDNAs were generated and tested the ability of the resulting Flag-immunopurified (Flag IP) proteins to uridylate synthetic pre-let-7 miRNA in vitro. Mutants were generated lacking N- and C-terminal domains or harboring point mutations in conserved residues (FIG. 14A). As described previously, Zcchc11 exhibits a low-level of uridylation against pre-let-7 and this activity is strongly enhanced by the addition of recombinant or immunopurified Lin28. Hagan et al., 2009; Heo et al., 2009. As determined by the incorporation of radiolabeled UTP, the activity of wild type Zcchc11 was compared to each of the series of mutants (FIG. 14B). The serial N-terminal truncations showed that the pneumoviridae (PneumoG) domain was dispensable for both basal level uridylation and activity enhanced by IP Flag-Lin28. Loss of the N-terminal C2H2 domain still allowed for basal activity, but this mutant could no longer support Lin28-enhanced uridylation against pre-let-7, indicating that the C2H2 zinc finger may be essential for the interaction between Lin28 and Zcchc11. Interestingly, when the TRF4 domain was deleted, neither basal nor Lin28-enhanced activities were detected. This result was surprising given the prediction that the TRF4 domain was insufficient to carry out catalytic activity on its own. Indeed, when a fragment of Zcchc11 containing the N-terminal TRF4 domain but lacking the NTR domain was tested, no uridylation activity was detected (FIG. 14B, upper panel, compare lanes 7 and 8 to 11 and 12). All further mutant proteins tested lacking TRF4 failed to support any detectable uridylation activity (FIG. 14B, upper panel, lanes 9 and 10).

To determine if the findings on N-terminal deletions of Zcchc11 could be supported in the context of additional C-terminal truncations, mutants lacking the C-terminal Atrophin-like domain in combination with ΔPneumoG and ΔC2H2 mutants were tested. The Atrophin-like domain was dispensable in these experiments, indicating that it is not required for basal or Lin28-enhanced uridylation by Zcchc11. To confirm that the C2H2 zinc finger per se was required for Lin28-enhanced uridylation, a full-length Zcchc11 cDNA was generated bearing Cysteine to Alanine mutations in the residues predicted to be central to the C2H2 zinc finger (C326/329A). Indeed, this mutant exhibited only basal uridylation activity, as the addition of Lin28 had no impact on its catalysis in vitro. Given that this mutant phenocopied the ΔC2H2 and ΔC2H2/C mutants, we conclude that this zinc finger is required for Lin28-enhanced uridylation in vitro.

Figure 14C:
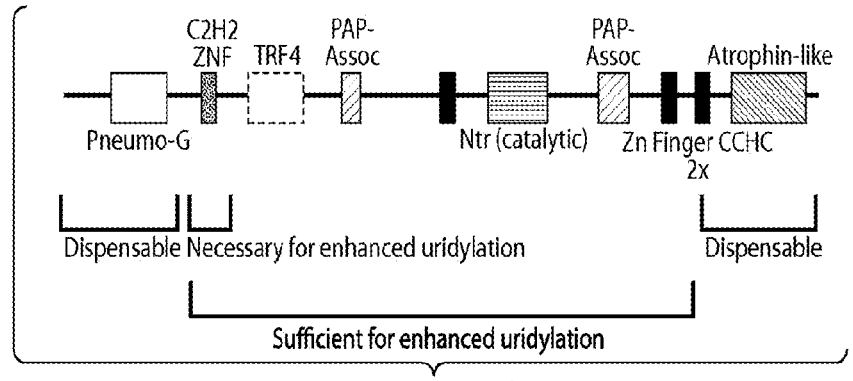
Figure 15:
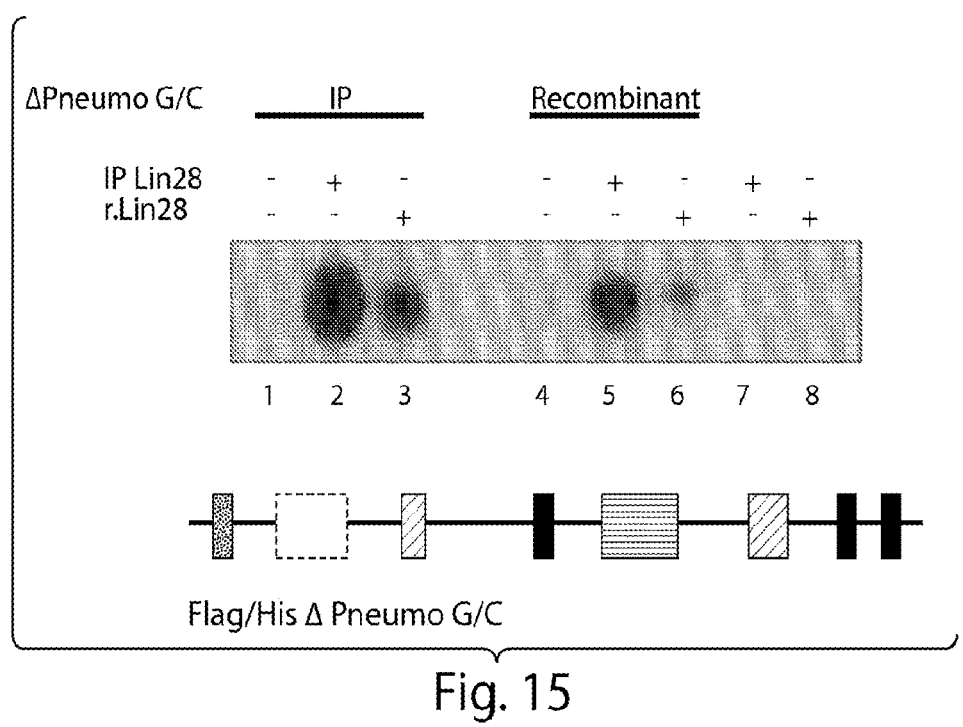
FIG. 15 indicates that Lin28 and Zcchc11 are sufficient for pre-let-7 uridylation. Zcchc11 truncation ΔPneumoG/C purified from either HEK293T (IP) or *E. coli* (Recombinant) was incubated with either Flag-Lin28 (IP) or 6×-His Lin28 (r.Lin28) in a uridylation assay with synthetic pre-let-7g. Below is a schematic representation of the domains present in ΔPneumoG/C.

To define the minimal Zcchc11 mutant that supports Lin28-enhanced uridylation, the requirements of C-terminal domains were examined further. Compared to WT, a mutant lacking the C-terminal-most CCHC zinc finger exhibited robust basal and Lin28-enhanced activity, whereas additionally truncating the adjacent CCHC zinc finger led to no detectable activity, implying that the three CCHC zinc fingers may be required for different aspects of RNA recognition or positioning (FIG. 14B, lower panel). These studies provide insight into the basic mechanism underlying the catalytic nature of Zcchc11 (FIG. 14C).

In vitro reconstitution of Lin28-mediated pre-let-7 uridylation was achieved with recombinant proteins. The experiments described herein suggest that specific domains of Zcchc11 mediate the interaction with Lin28 to uridylate pre-let-7 in vitro. To confirm that these two proteins are sufficient for activity and do not rely on contaminating or accessory factors interacting with the immunopurified proteins, 6x-His Lin28 (r.Lin28) and Flag/6x-His ΔPneumo G/C Zcchc11 were expressed in a purified from E. coli. Compared with immunopurified ΔPneumo G/C Zcchc11, the Flag/6x-His protein uridylated pre-let-7 at the basal level to a similar extent indicating that the Zcchc11 expressed and purified from bacteria is catalytically active. Adding either immunopurified Flag-Lin28 or recombinant 6x-His Lin28 to the reaction similarly enhanced the uridylation of pre-let-7 by either Zcchc11 preparation. Neither of the Lin28 proteins themselves led to detectable levels of uridylated pre-let-7, indicating that labeled products originated from the enzymatic activity of Zcchc11. These experiments show that the combination of Lin28 and Zcchc11 proteins are necessary and sufficient to carry out the robust uridylation of pre-let-7 in vitro.

Figure 16A:
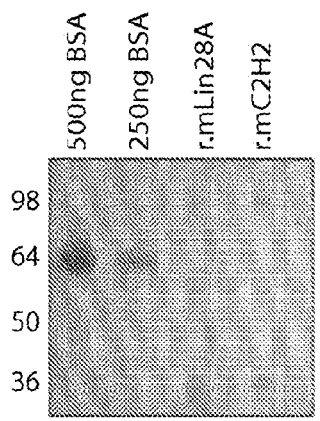
FIGS. 16A-C demonstrate that Lin28 and the C2H2 domain of Zcchc11 synergistically bind pre-let-7.
Figure 16B:
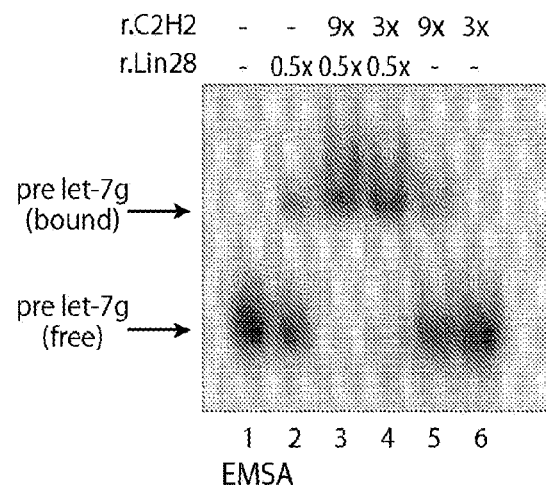

The C2H2 zinc finger of Zcchc11 synergizes with Lin28 to bind pre-let-7. The discovery that Zcchc11 requires its N-terminal C2H2 zinc finger to mediate Lin28-enhanced uridylation suggested that this region is important for physically interacting with either Lin28 or recognizing a Lin28-bound form of pre-let-7. This was tested using electrophoretic mobility shift assays (EMSA) with recombinant 6×-His Lin28 and a fragment of the N-terminus of Zcchc11 containing the C2H2 zinc finger (r.C2H2) (FIG. 16A). As shown previously, incubating r.Lin28 with 5' end-labeled pre-let-7 leads to the formation of a stable complex that can be resolved on a native polyacrylamide gel (Piskounova et al., 2008) (FIG. 16B, lane 2). Compared with r.Lin28, r.C2H2 bound poorly to pre-let-7g alone (FIG. 14B, lanes 5 and 6). When both proteins were combined, however, the intensity of the bound probe was greater than the additive effect of the two proteins singly bound to the probe (FIG. 14B, compare lane 4 to lanes 2 and 6). Although this binding synergy depended on both proteins, there is no detectable ternary complex formation, suggesting that the bound probe is interacting with only one of the two proteins. To further investigate the binding dynamics of Lin28 and the C2H2 zinc finger of Zcchc11, EMSA experiments were conducted using only the terminal loop region of pre-let-7 that is removed by Dicer, more recently termed the pre-element or preE. Nam et al., 147 Cell 1080 (2011); Piskounova et al., 283 J. Biol Chem. 21310 (2008).

Figure 16C:
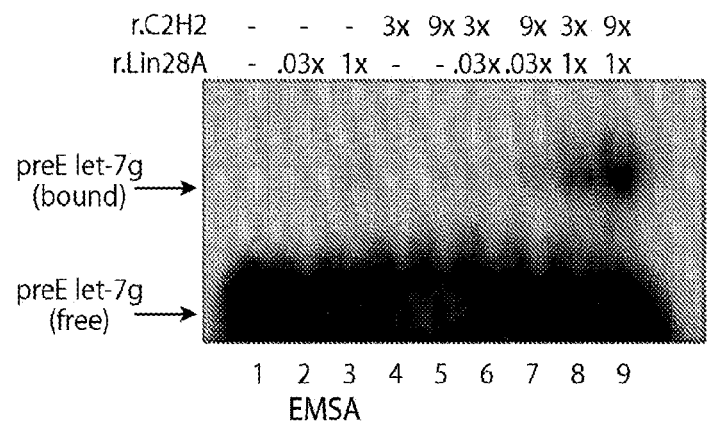

Let-7 preE is sufficient for Lin28 binding and this binding requires RNA sequence and structural information encoded in the preE. Heo et al., 2009; Nam et al., 2011; Newman et al., 2008; Piskounova et al., 2008. To examine more sensitively the relative affinities of both r.Lin28 and r.C2H2, EMSA experiments were carried out at sub-saturating conditions using the preE of let-7g. As shown in FIG. 16C, weak binding of either r.Lin28 or r.C2H2 could be dramatically enhanced by the addition of both proteins (compare lanes 3 and 5 to lane 9). Again, only a single band was observed, indicating a complex composed of pre-let-7 and one of the recombinant proteins. These experiments demonstrate that although binding of either protein can occur, the presence of the second protein increases the affinity for let-7-derived RNAs.

Although the conformational changes underlying this effect have not been detailed, structural studies and RNA footprinting experiments have revealed changes in the preE of various let-7 family members upon binding by Lin28. Desjardins et al., Nucl. Acids Res. (2011); Lightfoot et al., 50 Biochem. 7514 (2011). This change in RNA structure upon binding by Lin28 may allow for specific protein-RNA and/or protein-protein interactions that further alter the RNA or protein structure and permit an increase in C2H2 affinity for the RNA. These results echo the findings from in vitro uridylation assays where Zcchc11 activity is low when incubated with pre-let-7 alone, but dramatically increases in the presence of Lin28. Synergistic binding between Lin28 and the C2H2 zinc finger of Zcchc11 provides greater insight into the mechanism by which the let-7 degradation pathway is controlled and provides further support for the requirement of the C2H2 domain for Lin28-enhanced pre-miRNA uridylation (FIG. 14).

Additionally, the let-7 preE confers Lin28-enhanced pre-miRNA uridylation by Zcchc11. To understand the role of pre-miRNA substrates in Zcchc11-mediated uridylation, which cis-acting RNA elements support uridylation enhanced by Lin28 were explored. Lin28 binding to pre-let-7 requires specific sequence and structural information in both the RNA and the protein. The cold-shock domain (CSD) of Lin28 is inserted into the terminal loop of various pre-let-7 RNAs, and the Lin28 CCHC zinc fingers dimerize to recognize a GGAG motif proximal to the Dicer cleavage site of pre-let-7. Loughlin et al., 2011; Nam et al., 2011.

Figure 17A:
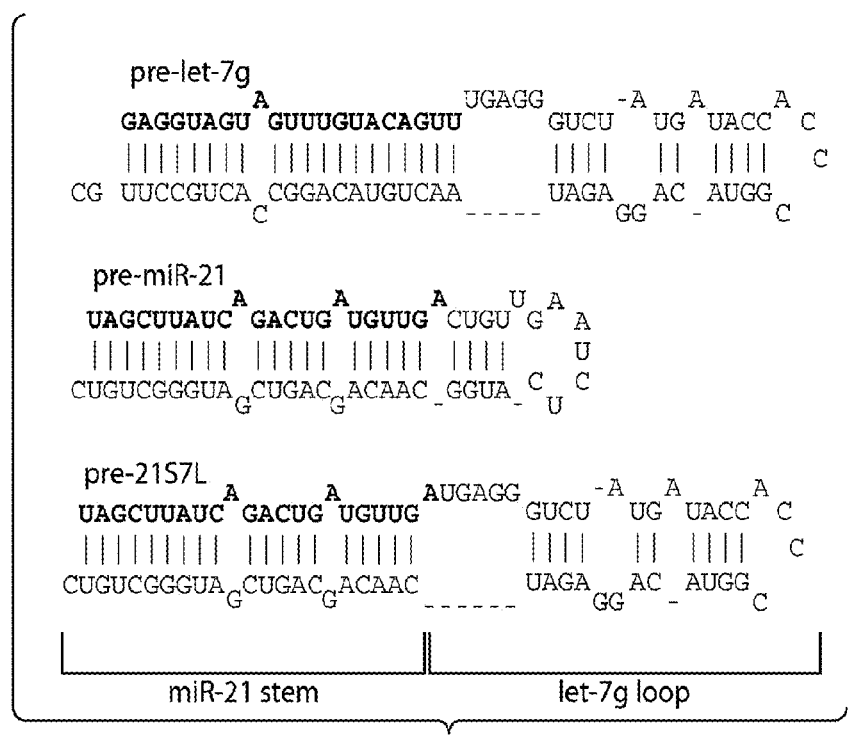
FIGS. 17A-B evidence that the preE of let-7 is sufficient to direct both Lin28 binding and uridylation of pre-let-7.
Figure 17B:
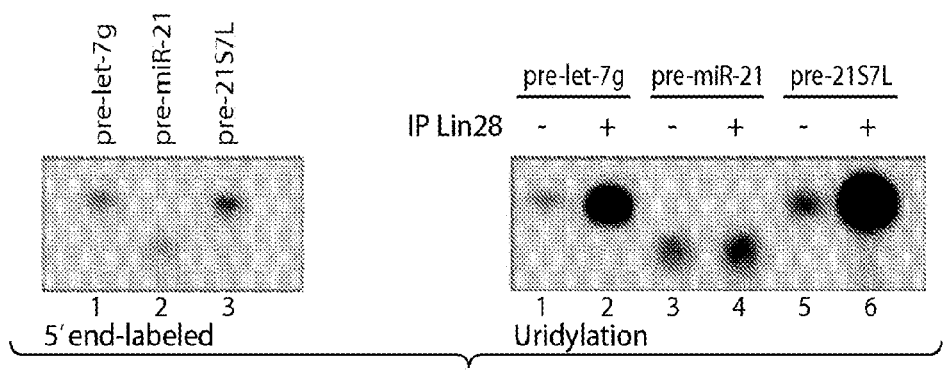

The regions of pre-let-7 required for uridylation by Zcchc11 were identified in the context of the understanding that the let-7 preE is bound by recombinant Lin28 as efficiently as full-length pre-let-7. Piskounova et al., 2008. If Lin28 binding is sufficient to direct Zcchc11-mediated uridylation, then RNA substrates with divergent sequences outside of the let-7 preE should be comparable substrates to pre-let-7. To test this, a synthetic pre-miRNA was generated composed of the preE of let-7g and the stem sequence of miR-21 (pre-21S7L) (FIG. 17A), and compared the uridylation activity of Zcchc11 towards this RNA versus both pre-let-7g and pre-miR-21. As shown in FIG. 17B, pre-let-7g undergoes robust uridylation with the addition of IP Flag-Lin28. miR-21 is uridylated at a basal level similar to that of pre-let-7, but the addition of IP Flag-Lin28 has no effect on uridylation levels as described previously. Hagan et al., 2009. When the chimeric pre-S21L7 is incubated with IP Flag-Lin28, however, it is subjected to enhanced uridylation activity similar to that of WT pre-let-7 (FIG. 174B, compare lanes 5 and 6 to 1 and 2). This result suggests that the effect of Lin28 binding to the preE of pre-let-7 is sufficient to allow targeting and uridylation by Zcchc11.

Figure 18A:
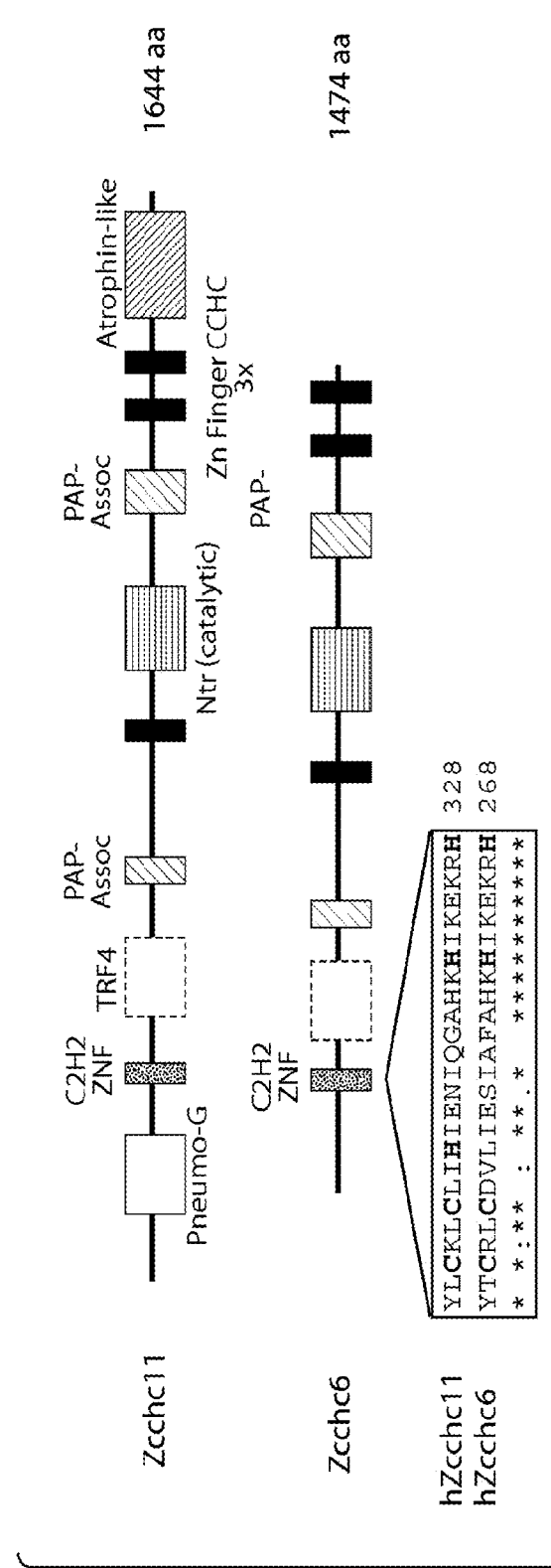
FIGS. 18A-C show that Zcchc11 and Zcchc6 have a highly similar domain organization.
Figures 18B, 18C:
Figure 19A:
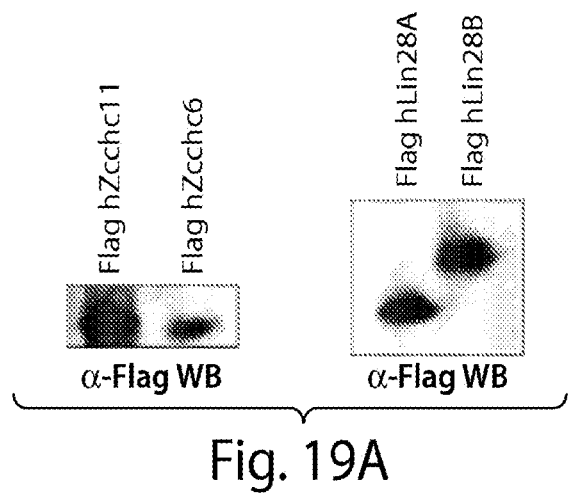
FIGS. 19A-D demonstrate that Zcchc11 and Zcchc6 can both mediate Lin28-dependent pre-let-7 uridylation in vitro.
Figure 19B:
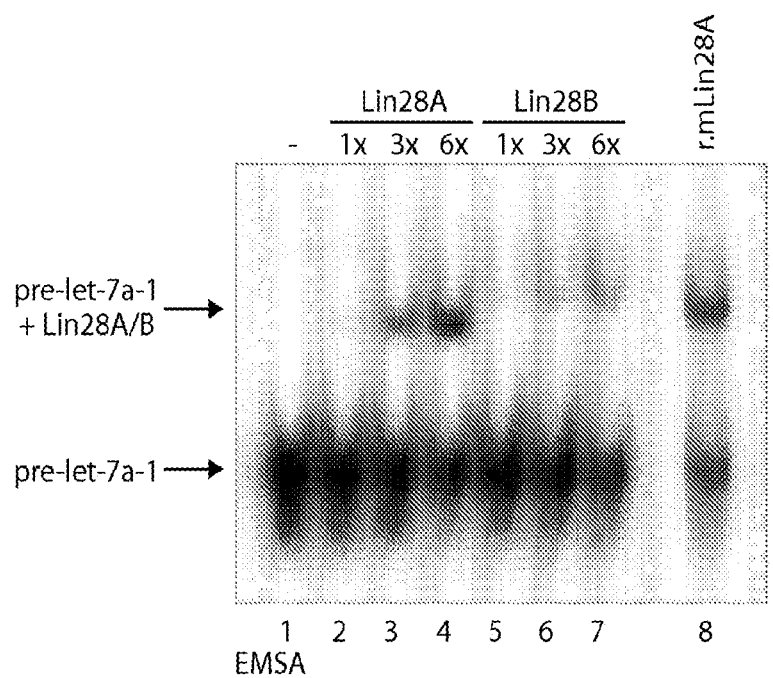
Figure 19C:
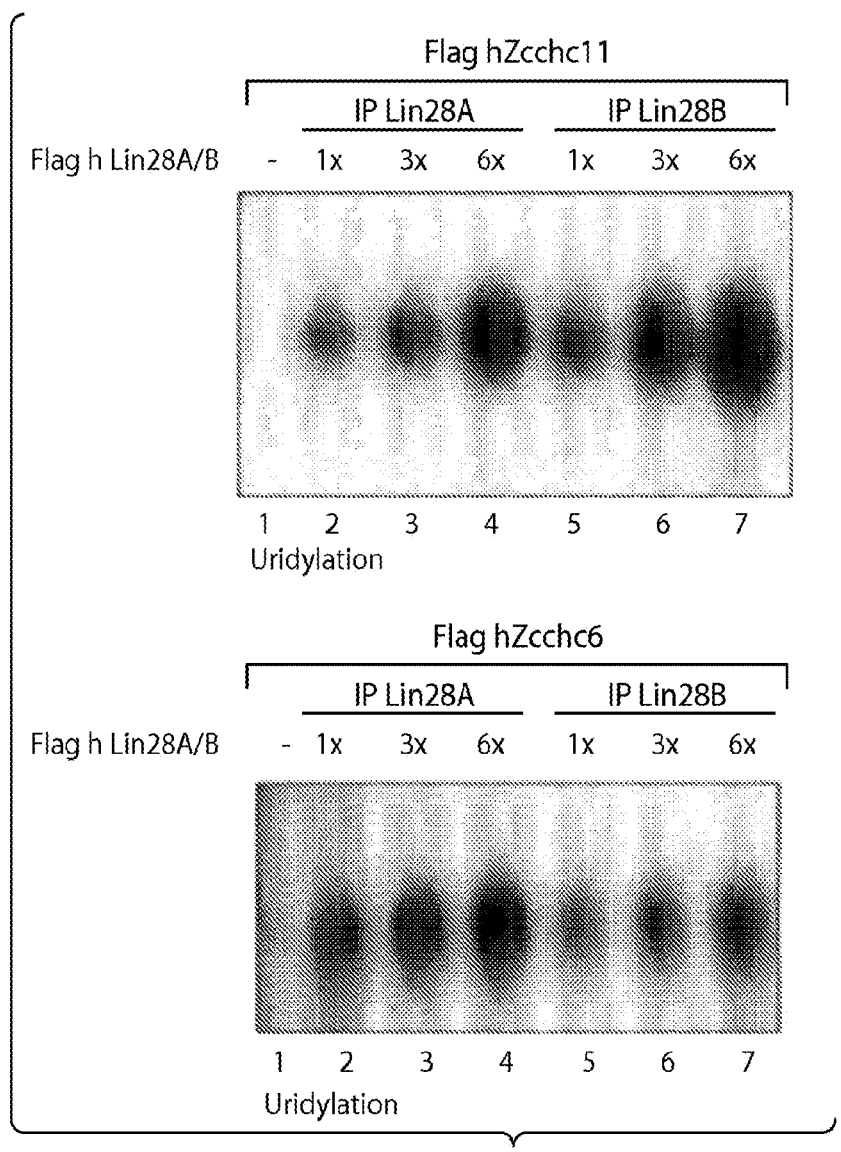
Figure 19D:
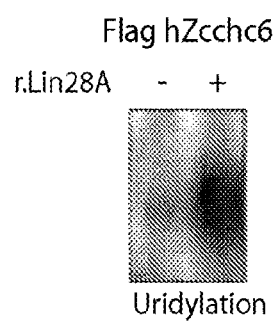

A related TUTase Zcchc6 is functionally redundant with Zcchc11 in vitro. The findings on the domains of Zcchc11 supporting Lin28-mediated uridylation in vitro led to the examination of other TUTases as potential regulators of pre-miRNAs. Among the seven non-canonical poly(A) polymerases encoded in the human genome, Zcchc6 (PAPD6/TUTase 7) has striking homology to Zcchc11 including the domains constituting its active site, its three CCHC zinc fingers, the N-terminal TRF4/PAP-associated domains, and C2H2 zinc finger (FIG. 18A). Importantly, there is extensive conservation between Zcchc11 and Zcchc6 at critical residues in the active site and in the C2H2 zinc finger (FIG. 18A-18C). Whether Zcchc6 shares activity similar to Zcchc11 could be seen by the ability of IP Flag-hZcchc6 to uridylate pre-let-7 in vitro in the absence or presence of Lin28. Similar amounts of Flag-hZcchc11 or Flag-hZcchc6 were used in uridylation assays with Flag-hLin28A and both TUTases were stimulated to an equal extent (FIG. 19A, 19C). To confirm that the effects seen with Flag-hLin28A were not dependent on the paralog of Lin28 used, the stimulatory effect of Flag-hLin28B was tested, because both Lin28 proteins act identically in vitro (FIG. 19A-19C). Heo et al., 2009. In these experiments either Lin28A or Lin28B enhanced the uridylation activity of either TUTase in a dose-dependent manner. The enhancement in hZcchc6 uridylation activity was also observed using r.Lin28, indicating that the this effect was not due to coimmunoprecipating proteins and that Zcchc6 and Zchc11 are functionally indistinguishable in these assays (FIG. 19D).

These in vitro results suggest both TUTases may recognize let-7 precursors in biologically relevant settings. Zcchc6 has previously been shown to have poly(U) activity in vitro (Kwak & Wickens, 2007; Rissland et al., 27 Mol. Cell. Biol. 3612 (2007)), and depletion of Zcchc6 in colon cancer cells led to reduced levels of uridylated mature let-7e. Wyman et al., 21 Genome Res. 1450 (2011). Zcchc6 is also a homolog of C. elegans CDE-1, which uridylates a subset of siRNAs bound by the Argonaute protein CSR-1 and loss of CDE-1 leads to aberrant chromosomal segregation and dysregulation of CSR-1-bound siRNAs. van Wolfswinkel et al., 139 Cell 135 (2009). In spite of these data, this is the first evidence of Zcchc6 uridylating pre-miRNAs and suggests parallel activity with Zcchc11 and a role in the Lin28 pathway.

Figure 20A:
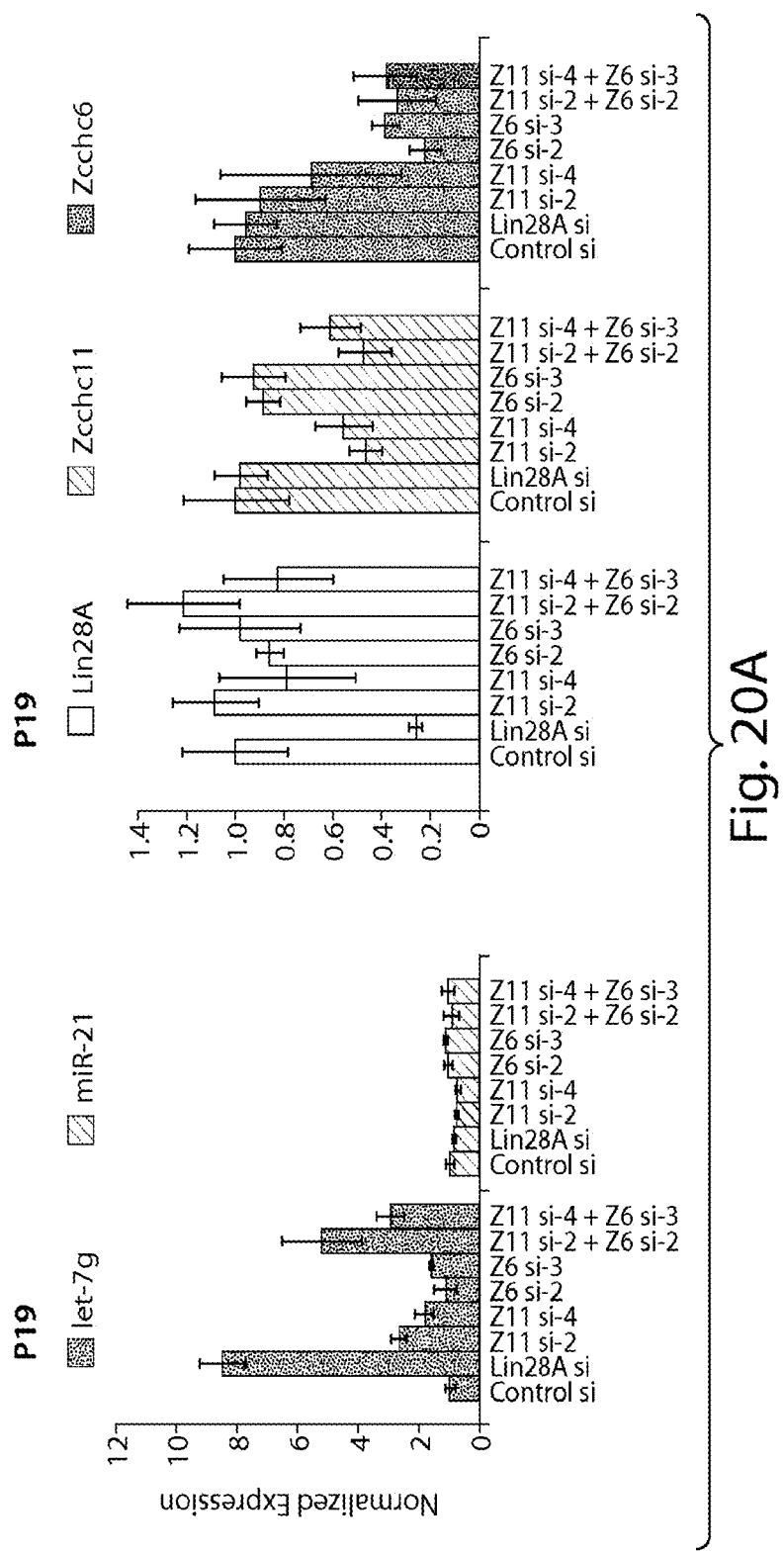
FIGS. 20A-B show that Zcchc11 and Zcchc6 function redundantly to suppress let-7 expression in embryonic cells.
Figure 20B:
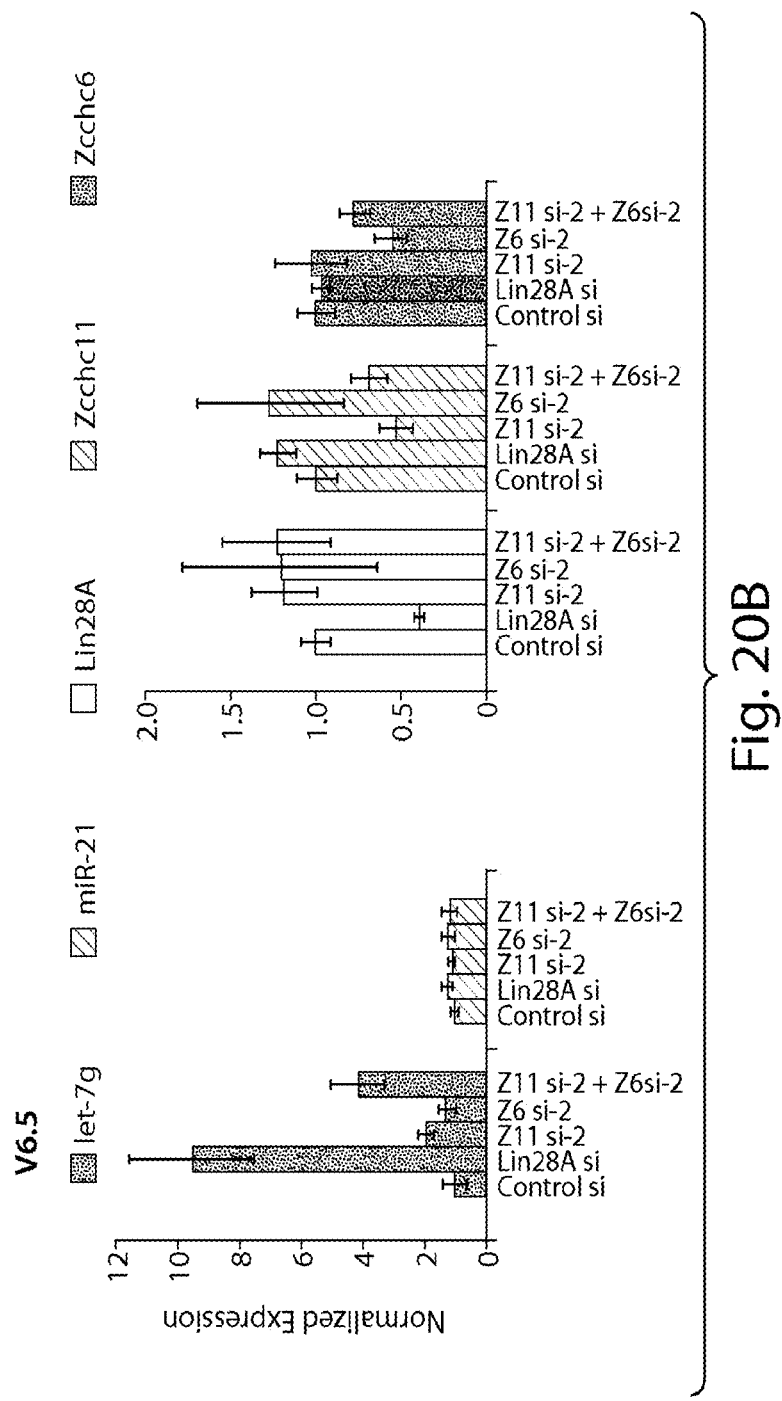

The present invention also demonstrates that Zcchc11 and Zcchc6 redundantly control let-7 biogenesis in embryonic stem cells. Given the findings on the activity of Zcchc6 in vitro, whether Zcchc6 functions in parallel with Zcchc11 in vivo was explored. Zcchc11 depletion in embryonic carcinoma (EC) and embryonic stem (ES) cells led to the coordinate derepression of let-7 miRNAs, while Zcchc6 depletion led to no change in mature let-7 levels. Hagan et al., 2009; Heo et al., 2009. The derepression observed upon Zcchc11 knockdown was generally more modest, however, than the depletion of Lin28 in all cell types tested. Hagan et al., 2009; Heo et al., 2009; Piskounova et al., 2011. One interpretation of this finding is that there are redundant factors working in parallel with Lin28 and Zcchc11 to repress let-7 miRNAs in undifferentiated cell types. Whether Zcchc6 works redundantly with Zcchc11 was tested using siRNAs to deplete both TUTases in P19 and V6.5 cell lines (EC and ES cells, respectively). Upon Zcchc11 knockdown with two independent siRNAs, there was a modest 2- to 3-fold upregulation of mature let-7g, whereas consistent with previous reports, depletion of Zcchc6 with two independent siRNAs led to no significant changes at the level of mature let-7g. When both TUTases were knocked down, however, there was a consistent upregulation in mature let-7 that was more dramatic than either individual knockdown alone (FIG. 20). This trend was specific to let-7 family members, as levels of the unrelated miRNA miR-21 were unchanged. Moreover global profiling revealed that changes in miRNA expression were restricted to let-7 family members. This trend was seen in both P19s and V6.5s, suggesting Zcchc11/Zcchc6 redundancy is a general mechanism of embryonic cells. The synergistic relationship between these two related TUTases, both in vitro and in vivo, could explain the modest effects seen for depletion of either TUTase individually in Lin28-expressing cells and expands the repertoire of miRNA modifying enzymes.

Prior to the instant invention, because Lin28A and Lin28B inhibit let-7 miRNA biogenesis in ESCs and cancer it had been assumed that both proteins block let-7 expression through the same mechanism, by recruiting the TUTase Zcchc11 (TUT4) in the cell cytoplasm to uridylate pre-let-7 and target it for degradation. Moreover these paralogous proteins have been used interchangeably in several in vitro assays. Heo et al., 2009. The present results provide the first evidence that despite their high degree of homology, Lin28A and Lin28B function through distinct mechanisms to block let-7 processing, a finding that has broad implications for the development of new cancer therapies and the potential use of Zcchc11 inhibitors in Lin28A-expressing tumors but not in Lin28B-expressing tumors. This distinction derives from the differential subcellular localization of these two proteins: Lin28A localizes primarily to the cytoplasm, whereas Lin28B contains functional nuclear localization signals and specifically localizes to nucleoli.

Due to the differential subcellular localization of the two proteins, in human cancer cell lines, Lin28A and Lin28B block let-7 processing at different steps of the miRNA-processing pathway. The steps at which let-7 processing is blocked by Lin28 in various different organisms is controversial, however. A recently published report proposes that Lin28 binds pri-let-7 and blocks let-7 expression co-transcriptionally in C. elegans and disputes earlier conclusions that Lin28 functions at steps further downstream in the let-7 biogenesis pathway. Lehrbach et al., 2009); Van Wynsberghe et al., 2011. Others also report that a very small fraction of Lin28A in hESCs localizes to the nucleus and binds pri-let-7 miRNAs, although pre-let-7 is bound abundantly. Van Wynsberghe et al., 2011. This is consistent with the results that demonstrate a small fraction of Lin28A localizes to the nucleus in Igrov1 cell line. Also, Lin28A binds pri-let-7 miRNA, however not as much as Lin28B, and earlier reports have demonstrated that purified Lin28A can inhibit the Microprocessor in vitro. Newman et al., 2008; Viswanathan et al., 2008. Additionally, although the data presented herein demonstrate that Lin28B-mediated repression of let-7 expression is Zcchc11 (TUT4)-independent in multiple different cell-types, it remains possible that in certain contexts or cell-types Lin28B may localize to the cytoplasm and utilize Zcchc11/TUT4 to repress let-7 biogenesis. For example, uridylated pre-let-7 was previously detected in Huh7 cells and Lin28B is reportedly localized to the cytoplasm in Huh7 cells. Guo et al., 2006; Heo et al., 2008.

The present demonstration that the Microprocessor is excluded from nucleoli raises the possibility that sequestration of certain pri-miRNAs to nucleoli by specific RNA-binding proteins may prove to be a more general strategy for the posttranscriptional control of miRNA biogenesis. Previous reports have demonstrated that nucleoli contain machinery responsible for modifying small nucleolar RNAs, for example through RNA methylation or 3' uridylation. Whether these nucleolar mechanisms play a role in pri-miRNA regulation remains to be determined. Boisvert et al., 2007; Matera et al., 2007. It is possible that additional new factors may be involved in sequestering and possibly degrading and/or modifying pri-let-7 miRNAs in the nucleoli in a Lin28B-dependent manner. The identification of such factors could reveal new potential therapeutic targets aimed at restoring let-7 expression in Lin28B-expressing cancers.

The present proof-of-concept studies with human breast and ovarian cancer cell lines demonstrate that inhibition of Zccch11 may represent a possible new therapeutic target for cancer. Indeed, knockdown of Zcchc11 effectively inhibits the tumorigenic capacity and metastatic potential of human breast and ovarian cancer cells and xenografts. Importantly however, the present work also predicts that therapeutic potential of Zcchc11 inhibition is particularly relevant in Lin28A-expressing cancers. Although Lin28A expression is relatively uncommon in several human cancer cell lines, the analysis of primary human colon and breast cancer indicate that upregulation of Lin28A or Lin28B occurs in a large proportion of tumors with approximately equally frequency for each protein. Furthermore, expression of Lin28A or Lin28B seems to distinguish different classes of breast cancers (FIG. 20). Therefore, the identification of small molecule inhibitors of Zcchc11 may lead to the development of novel chemotherapies for Lin28A-expressing cancers.

Recent work examining the role of miRNAs in development and cancer has revealed extensive post-transcriptional control at various levels of miRNA biogenesis. Siomi & Siomi, (2010). Lin28A and Lin28B have emerged as important posttranscriptional regulators of let-7 expression in stem cells, development, metabolism, and disease. Viswanathan & Daley, 2010. In the case of Lin28A, this regulation involves the recruitment of a TUTase Zcchc11 to catalyze the 3' terminal uridylation of pre-let-7 RNAs. Several studies have identified extensive non-templated nucleotide addition to the 3' ends of mature and precursor miRNAs. Ameres et al., 2010; Berezikov et al., 21 Genome Res. 203 (2011); Burroughs et al., 20 Genome Res. 1398 (2010); Chiang et al., 24 Genes Devel. 992 (2010); Heo et al., 2008; Jones et al., 2009; Katoh et al., 23 Genes DEvel. 433 (2009); Lehrbach et al., 2009; Newman et al., 2011. The present embodiments provide the first extensive mechanistic analysis of one of these enzymes, Zcchc11.

More specifically, specific TUTase domains that are required for mediating efficient Lin28-enhanced uridylation of pre-let-7 in vitro have been uncovered. Of the four zinc fingers encoded in Zcchc11, the unique C2H2 zinc finger at the N-terminus of the protein mediates the interaction with Lin28 as point mutations in conserved Cysteine residues of this zinc finger abolish Lin28-enhanced uridylation activity. The TRF4 domain at the N-terminus of Zcchc11, while incapable of supporting uridylation activity on its own, is nonetheless required for activity in vitro. This essential role may explain its significant degree of conservation across taxa. Furthermore, the CCHC zinc fingers, which define a class of at least thirteen mammalian proteins, are differentially required for uridylation activity in vitro. Specifically, the C-terminal-most CCHC zinc finger is dispensable for in vitro activity, while the zinc finger just C-terminal to the active site is required for any detectable activity. Further, there are regions dispensable for Lin28-enhanced uridylation at the N- and C-termini (FIG. 14C). Both of these domains are of unknown function but remain conserved in other organisms.

Because Zcchc11 has been implicated in several other biological pathways, the domains identified as dispensable may be required for other processes. Indeed, a recent study has identified the N-terminal portion of Zcchc11 similar to the N-PAP construct studied above (FIG. 14A) to be sufficient to alter the cell cycle of cultured human cancer cells. Blahna et al., (2011). The present invention unveils critical domains and residues that are required for Lin28-dependent Zcchc11 activity. Though still controversial, the Lin28-mediated control of let-7 expression in C. elegans has also been reported to involve pre-let-7 uridylation. Lehrbach et al., 2009; Van Wynsberghe et al., 2011. Notably, the proposed Zcchc11 ortholog, PUP-2, lacks the C2H2 domain that mediates the functional interaction between Lin28 and Zcchc11 as found herein. Lehrbach et al., 2009. Therefore it remains unclear if and how worm Lin28 recruits PUP-2 to repress let-7 expression.

The N-terminal C2H2 zinc finger of Zcchc11 synergizes with Lin28 to bind pre-let-7g. The requirements of pre-let-7 that mediate Lin28-enhanced activity show that the preE of let-7g to be sufficient to direct this activity. Although Zcchc11 recognizes and uridylates the 3'-end of pre-let-7 family members and other miRNAs, this occurs through a mechanism that is independent of sequence information proximal to the site of uridylation. Instead, Lin28 bound to an intact preE sequence is sufficient to direct robust uridylation of the pre-miRNA. Although the preE used herein contains the Lin28-binding motif of GGAG, this sequence was previously shown to be insufficient in directing uridylation activity towards pre-let-7, as gain-of-function experiments indicated the positioning of the motif relative to the Dicer cleavage site was also essential. Heo et al., 2009. The chimeric pre-21S7L, however, has the GGAG motif positioned not in the preferred site ending four nucleotides (4nt) before the Dicer cleavage site, but only two nucleotides away from this point, suggesting there are other sequence or structural determinants directing Zcchc11-mediated uridylation against pre-let-7 miRNAs. The role of other protein factors giving further specificity can be ruled out because the reaction could be reconstituted from recombinant proteins produced in bacteria, but what defines this level of specificity remains unknown.

Structural studies have uncovered the degree to which the let-7 preE is altered by bound Lin28, revealing a partial unwinding of the duplex region near the site of Dicer cleavage. Nam et al., 2011. Although it is unknown how far this melting proceeds into the stem of pre-let-7, this structural change could alter the RNA so that it is a preferred substrate of Zcchc11. Indeed, a recent structural study showed that the CCHC zinc fingers of Lin28 preferentially bind the single stranded heptad sequence of AGGAGAU (SEQ ID NO:3) in the stem of pre-let-7, providing evidence of sequence-specific RNA binding by zinc finger-containing proteins. Loughlin et al., Nat. Str. Mol. Biol. 2011. Alternatively, pre-let-7-bound Lin28 undergoes a conformational change and this may provide a suitable protein-protein interaction surface between the Lin28-let-7 complex and Zcchc11. Nam et al., 2011. More detailed RNA mutagenesis and/or structural studies examining the interplay between pre-let-7 and these two RNA binding proteins may provide additional insight into precisely how Lin28 functionally enhances C2H2 binding to the let-7 preE. The uridylation and adenylation of mature miRNAs by Zcchc11 has also been reported. Jones et al., 2009; Wyman et al., 2011. Because Zcchc11 exhibits similar basal activity towards unrelated pre-miRNAs (FIG. 17B) there may be other sequence-specific recognition factors that guide Zcchc11 activity towards other RNA substrates including mature miRNAs.

The findings in the present mutational analysis led to the investigation of other putative TUTases, and to the identification of Zcchc6 as a regulator of let-7 expression. One study investigating the potential redundancy between Zcchc11 and Zcchc6 found that only Zcchc11 was capable of binding stem-loop containing histone mRNAs, while Zcchc6 appeared to lack this capacity. Schmidt et al., 2011. In the case of Lin28 and let-7, however, Zcchc6 functioned identically to Zcchc11 in vitro as its enzymatic activity against a synthetic let-7 precursor was enhanced by either Lin28A or Lin28B, as was previously shown for Zcchc11. Heo et al., 2009. Furthermore, Zcchc6 is crucial in efficiently repressing mature let-7 miRNAs in embryonic cells. Although the double knockdown of Zcchc11 and Zcchc6 led to more dramatic let-7 derepression than the loss of either TUTase alone, it still did not reach the levels observed upon Lin28A knockdown. This could be explained by incomplete knockdown of both TUTases or the activity of other as-yet unidentified let-7 repressive factors.

The identification of a second TUTase regulating let-7 turnover may provide valuable insight into the control of let-7 expression in cancer and embryonic stem cell biology. The expression pattern and localization of Zcchc6 are unknown but it is possible that the relative expression levels of these two redundant TUTases will determine the relative contribution of Zcchc6 and Zcchc11 in the Lin28A-mediated control of let-7 expression. In this regard, the present invention shows that Zcchc11 inhibition in Lin28A-driven cancers can block tumor growth in vitro and in vivo, and Zcchc6 may have relevance in this context. Whereas Lin28 proteins might present particular challenges as chemotherapeutic targets due to their non-enzymatic activity, Zcchc11 (and potentially Zcchc6) poses an intriguing possibility as a drug target because of its defined active site and the available structural data regarding non-canonical poly(A) polymerases. Stagno et al., 399 J. Mol. Biol. 464 (2010).

Moreover, the ability to reconstitute this regulatory pathway with recombinant proteins, as shown herein, provides an opportunity to perform in vitro screening to identify small molecule inhibitors of TUTase activity as potential new chemotherapeutic agents. These possibilities allow expansion upon the novel centrality of uridylation in stem cell maintenance and tumor development.

The present invention also provides for modulation of TUTase activities, particularly as these enzymes related to oncogenic pathways. For example, the present embodiments provide for a detailed biochemical analysis including the isolation and characterization TUTase complexes. These experiments provide a detailed understanding of the mechanism of this newly identified oncogenic pathway and is highly relevant to a variety of different Lin28A-expressing human malignancies including Breast, Colon, Ovarian, and Germ cell tumors. The methods described herein are applicable to the screening and characterization of Lin28-TUTase expression, for example, in a large cohort of breast tumors. This information consolidates Lin28 and the TUTase as important diagnostics as well as cancer therapeutic targets.

Emerging data, such as that shown herein, indicate that RNA oligouridylation represents an important aspect of regulated gene expression. The global extent of oligo(U) addition throughout the transcriptome remains to be determined, and the widespread relevance of this RNA modification in the posttranscriptional control of gene expression is unknown. The human and mouse genomes contain seven known or predicted TUTases. Individual TUTases may selectively modify a subset of RNAs. Recent data have demonstrated a role for certain TUTase family members in: (a) the control of histone gene expression during the cell cycle (TUTase 1 and 3), (b) the recycling of small nuclear U6 RNA (U6 TUTase), (c) the Lin28-mediated regulation of let-7 microRNA biogenesis in embryonic stem (ES) cells (TUTase 4), (d) gene silencing by miRNA and siRNA that apparently involves uridylation and also for the control of mature microRNA stability/function, (e) mRNA bulk turnover managed by the fission yeast Cid1 (a putative ortholog of TUTase 7 in mammals), and (f) maintenance of genome stability requiring the uridylation activity of Cde-1/Cid1 gene in C. elegans. When taken together, these reports suggest that certain TUTases may have widespread roles in controlling gene expression and transcript stability. The complete repertoire of RNA under the regulation of each of the known and predicted TUTases remains unknown, however. As shown herein regarding Zcchc11 and Zcchc6, these enzymes display a strong sequence preference for uridylating a subset of mature miRNAs that includes the tumor suppressor let-7 family as well as three other families of miRNAs that have been implicated with various human malignancies. Considering these together with recently published high throughput sequence analyses of miRNAs that identify extensive 3' terminal uridylation of certain miRNAs supports the conclusion that selective uridylation of mature miRNAs with tumor suppressor function, for example by Zccch11 and Zcchc6, represents an important new oncogenic pathway. The present invention will identify other miRNAs that are directly modified by these paralogous TUTases, explore the functional consequences of Zcchc11/Zcchc6-catalyzed 3' terminal uridylation of these miRNAs, and illuminate the importance of this pathway in human cancer. Cell based assays as well as xenograft experiments with both TUTase loss- and gain-of-function will reveal the impact of these newly identified enzymes to human cancer cell biology and will help uncover novel oncogenic pathways the extent of which will be investigated in primary human tumors. Finally, key downstream miRNAs and their target genes will be identified through functional studies to identify those that lead to oncogenic cellular transformation.

Screening can include RNAi-mediated loss of function experiments to deplete TUTases, such as Zcchc11 or Zcchc6, in Lin28A-expressing cancer cells and monitor let-7 expression by qRT-PCR and Northern Blot. The cellular consequences of TUTase knockdown including cell proliferation and colony formation assays can also be examined. A panel of lentiviruses that express shRNAs targeting Lin28A, Zcchc11, and Zcchc6 has been generated. These reagents provide a valuable set of tools to effectively deplete the expression of the relevant proteins in human cancer cells. Thus, these shRNAs can be deployed to examine the molecular and cellular effects of TUTase knockdown in human cancer cells. Importantly, these shRNA constructs are designed to enable the knockdown of both Zcchc11 and Zcchc6 TUTases simultaneously to address any possible redundancy. For this, the shZcchc11 construct includes a puromycin resistance gene and the shZcchc6 construct includes a hygromycin resistance gene. This provides for double antibiotic resistance in transduced cells for knockdown of both Zcchc11 and Zcchc6. The expression pattern of Zcchc11 and Zcchc6 is largely unknown, but relative expression levels of these two redundant TUTases may determine the relative contribution of Zcchc6 and Zcchc11 in the Lin28A-mediated control of let-7 expression. In this regard, as shown herein, Zcchc11 inhibition in Lin28A-driven cancers can block tumor growth. It is therefore important to explore the relevance of Zcchc6 and other TUTases in this context.

In accord with the work presented herein related to Zcchc11, to understand which domains of TUTases are required for uridylation activity, we will generate a series of mutant cDNAs and test the ability of the resulting Flag-immunopurified (Flag IP) proteins to uridylate synthetic pre-let-7 miRNA in vitro. For example, TUTase mutants will be generated lacking N- and C-terminal domains or harboring point mutations in conserved residues. As described herein, Zcchc11 exhibits a low-level of uridylation against pre-let-7 and this activity is strongly enhanced by the addition of recombinant or immunopurified Lin28. As determined by the incorporation of radiolabeled UTP, the activity of wild type TUTases is compared with each of the series of mutant TUTases. These studies provide insight into the basic mechanism underlying the catalytic nature of these TUTases, and identify the minimal domains are preserved in various TUTases.

Additionally, the present embodiments provide for the determination of RNA structural and sequence determinants of TUTase regulation of miRNAs, such as pre-let-7, using a variety of approaches including EMSA, RNase footprinting, and TUTase activity assays with a panel of different RNA substrates. For example, evidence that Zcchc11 requires its N-terminal C2H2 zinc finger to mediate Lin28-enhanced uridylation suggested that this region is important for physically interacting with either Lin28 or recognizing a Lin28-bound form of pre-let-7. This model can be applied to other miRNA models, using electrophoretic mobility shift assays (EMSA) with recombinant 6×-His Lin28 and a fragment of the TUTase containing the site required for synergism, for example, a C2H2 zinc finger (r.C2H2). The relevant fragment is expressed and purified from bacteria as a recombinant protein. As previously shown, incubating r.Lin28 with 5' end-labeled pre-let-7 leads to the formation of a stable complex that can be resolved on a native polyacrylamide gel.

EMSA can be used to measure the relative ability of miRNA-binding proteins and TUTases to bind the respective miRNA, and to explore the possible formation of a ternary ribonucleoprotein complex. Cooperative binding between the miRNA-binding protein (e.g., Lin28) and the TUTase fragment (e.g., C2H2 fragment) can also be explored by performing EMSA experiments with combinations of both proteins at subsaturating concentrations; and further using fragments of the miRNA (e.g., fragments of pre-let-7 RNA). In the model provided by the instant invention, the terminal loop region of the miRNA that is removed by Dicer, more recently termed the pre-element or preE, is useful.

Additionally, RNase footprinting experiments can investigate changes in RNA structure upon binding by the miRNA-binding protein and critical TUTase fragment (e.g., Lin28 and C2H2). This provides insight into the dynamic changes in protein-RNA and/or protein-protein interactions that might help explain the functional interaction between Lin28 and Zcchc11 leading to the Lin28-enhanced TUTase activity. 5' end-labelled pre-let-7g can be analyzed by RNase digestion. Recombinant miRNA-binding proteins and recombinant TUTase proteins are titrated into these in vitro reactions and subsequently perform the RNase digestions. Different RNAses with diverse specificities allows detection of specific cleavage sites that are protected from digestion by the dual proteins, thus indicative of protein binding. Investigating which cis-acting RNA elements support uridylation enhanced by the miRNA-binding protein reveals the role of pre-miRNA substrates in TUTase-mediated uridylation. For example, Lin28 binding to pre-let-7 requires specific sequence and structural information in both the RNA and the protein.

TUTases will be purified from cells and interacting proteins identified to define the composition of TUTase-containing ribonucleoprotein complexes. Biochemical reconstitution assays as well as RNAi-mediated loss-of-function experiments will be used to explore the role of TUTase complex components in the control of miRNA expression and effects on growth and tumorigenicity of miRNA-derepression-associated cancer cell lines. For example, Zcchc11 is present in ~600 KDa protein complex, indicating that the ~180 KDa Zcchc11 protein is a component of a multi-subunit protein complex. In order to gain insight into the mechanism by which TUTases regulate miRNA processing it will be necessary to identify TUTase-interacting proteins. TUTase-associated proteins are identified, to experimentally confirm these interactions, and to assigned to particular complexes. The identification of TUTase-binding partners will enable the biochemically definition of cytoplasmic TUTase complexes and will help uncover the mechanism of posttranscriptional regulation of miRNA-processing in human cancer cells.

Biochemical definition of the composition of rTUTase-containing complexes can be done as shown herein for Zcchc11. Sable cell lines expressing Flag-TUTases are derived, and clones expressing high levels of Flag-tagged protein selected and expanded for large-scale purifications. This approach is an extensively utilized methodology in the lab for protein complex purifications. Because TUTases such as Zcchc11 localize primarily to the cell cytoplasm, it may be necessary to isolate and characterize cytoplasmic TUTase-containing complexes. This often requires >100 mg of protein extract to isolate and identify the TUTase-interacting proteins, which is achieved by growing 100×15 cm plates of Flag-TUTase cells and preparing S100 and nuclear extract. The anticipated protein extract yield is around 200-300 mg S100 extract, from which Flag-TUTase associated proteins are immunoprecipitated. After extensive washes, the Flag-affinity purified material is eluted from the beads using Flag peptide. The protein eluates are typically analyzed by Flag western blot to confirm the purification.

Next, a sample of affinity eluates is resolved by 4%-15% SDS-PAGE and analyzed by silver staining. The silver staining of the affinity eluate reveals coeluting polypeptides. In parallel, immunoprecipitation of naïve cells serves as a control. Comparison of this 'mock' with Flag-TUTase immunoprecipitation will identify bands specifically co-eluting with the TUTases and distinguish them from bands representing any contaminating polypeptides. Precipitation the affinity eluate with trichloroacetic acid (TCA) and resolution of the sample by SDS-PAGE is followed by colloidal blue staining. Individual polypeptides are excised from the gel and subjected to mass spectrometric sequencing performed. The polypeptides that co-purify with the TUTases are sequenced, and this information gives insight into the mechanism of TUTase function. It is likely that several of these peptides correspond to gene products that function in various aspects of RNA metabolism including DEAD box or DEAH box RNA helicases, RNA recognition motifs (RRM), exo- and endo-nucleases, heterogeneous nuclear ribonucleoproteins (HNRPs), or other protein family members involved in RNA-processing and/or stability. In addition, this unbiased purification strategy may yield novel proteins without obvious motifs whose function to date has remained obscure.

Considerable care is taken to determine whether proteins that are identified in the these studies are bona fide components of the TUTase complexes. Several approaches can determine whether a specific protein is tightly associated with a TUTase. For example, antisera against new proteins confirms whether they are present in the immunoprecipitants of Flag antibodies. Also, whether the new proteins co-elute with the TUTase on a gel filtration column is shown by examining the fractions by silver stain and western blot. Further, one can assay for reciprocal co-immunoprecipitation of the new proteins with the TUTase. Additionally, individual cDNAs of some of the new proteins are subcloned to a vector for overexpression of Flag-tagged fusion protein in mammalian cells, and used for the generation of stable cell lines. After screening for expressing clones, cells are expanded for perform large-scale affinity purifications and analyses as described herein. Collectively, these experiments enable establishment of the polypeptide composition of the TUTase complexes and provide the foundation for a detailed functional analysis.

Some of the identified components of the TUTase complex will likely affect miRNA-binding protein/TUTase activity in vitro. The in vitro TUTase activity assay and biochemical reconstitution experiments with purified components to identify factors that are required for miRNA-binding protein-enhanced pre-let-7 uridylation have been established herein. Performing in vitro TUTase assays using cell extracts prepared from control cells and from cells in which complex components have been depleted by RNAi will be a complementary strategy to identify a subset of factors that are specifically required for the action of the TUTase complex. Further assays described herein explore the role of TUTase complex components in the control of let-7 expression and effects on growth and tumorigenicity of Lin28A-expressing cancer cell lines. For these experiments, miRNA binding pretein-expressing cancer cells including T47D (Breast ductal epithelial tumor), and IGROV1 (Ovarian carcinoma) cancer cells are infected with lentiviruses expressing shRNAs to knockdown expression of the relevant genes (e.g., the miRNA-binding protein or the TUTase complex components). For both these well-characterized adherent cancer cell lines, data shows that Lin28A or Zcchc11 depletion leads to elevated let-7 expression and inhibits the colony formation, metastatic potential, and tumorigenic capacity in knockdown cells.

For genes that modulate miRNA-binding protein-TUTase activity, corresponding changes in let-7 miRNA levels are expected when these genes are depleted in cells. Total RNA is extracted from knockdown cells and q.RT-PCR performed (using the TaqMan® system from Applied Biosystems) to measure relative miRNA levels. These assays are performed in parallel for several miRNAs, at least some of which serve as controls. The efficacy of target gene knockdown is confirmed by monitoring the expression of miRNA-binding protein, TUTase and other TUTase complex components, by performing western blots (or by q.RT-PCR if antibodies are unavailable) on cells treated with the individual shRNAs and controls. To reduce any possible off-target effects we will use multiple (at least two) different shRNA or siRNA to knockdown the expression of each target gene. Cell Proliferation, Colony Formation, Invasion, Xenograft Assays on control and knockdown cells (i.e., Lin28A or the TUTase complex components) are performed as described herein.

The present data indicate that Zcchc11 and Zcchc6 not only function with Lin28A to uridylate let-7 precursor RNAs but also selectively uridylate a subset of mature miRNAs in a Lin28-independent manner. The central hypothesis is that Zcchc11/Zcchc6 regulate miRNAs through sequence specific uridylation of mature miRNAs to regulate their stability and/or function. Thus, TUTase activity assays are performed with a panel of synthetic RNAs to determine the RNA sequence requirements for Zcchc11- and Zcchc6-mediated uridylation of mature miRNAs. Results from the TUTase activity assays performed using different RNA substrates uncovered a strong preference of the TUTases Zcchc11 and Zcchc6 for certain mature miRNA sequences. In particular, the mature let-7 miRNA was a preferred substrate for both Zcchc11 (FIG. 21) and Zcchc6.

Figure 21:
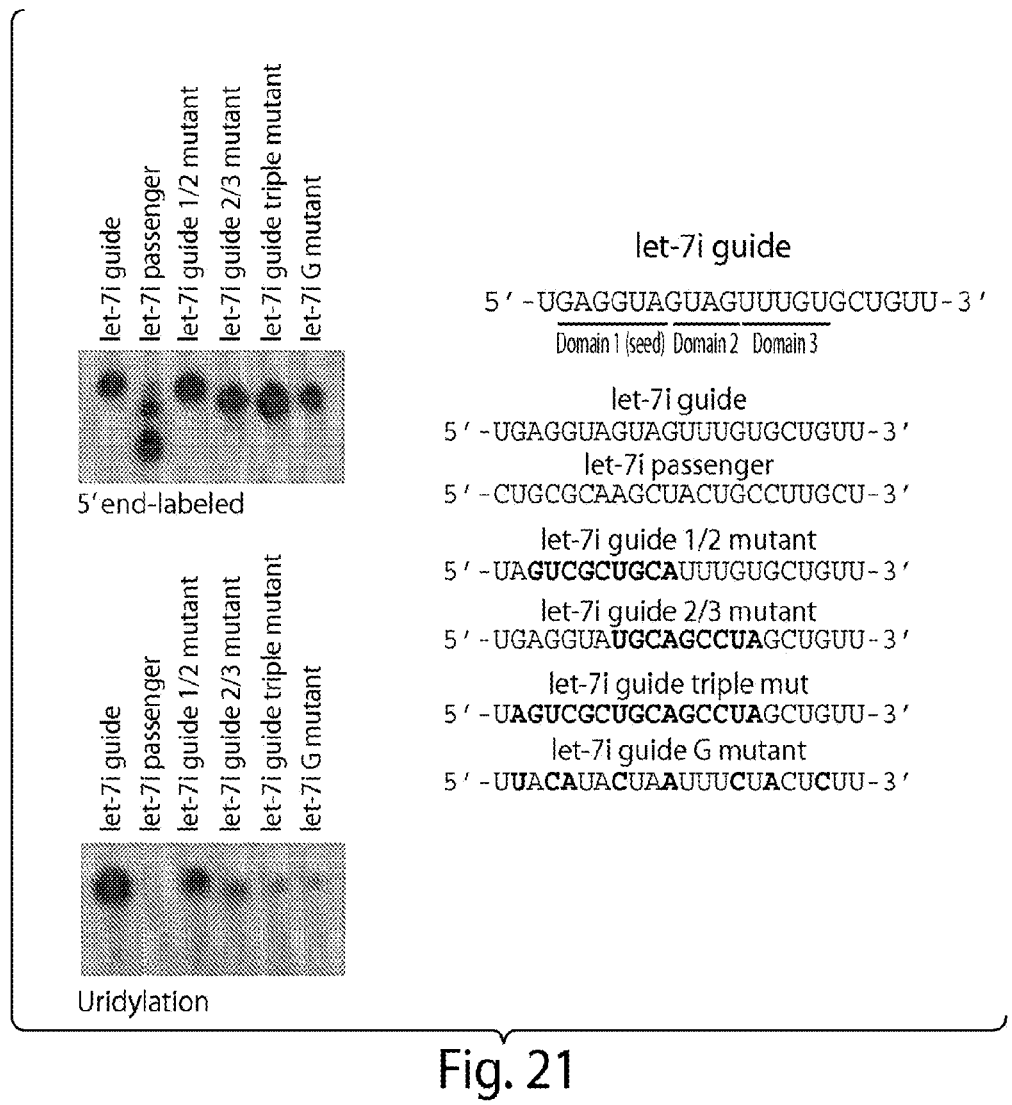
FIG. 21 presents data from RNA sequence requirements for Zcchc11-catalyzed uridylation of mature miRNAs (Top panel) 5'-end labeled RNAs showing equal amounts of RNA. Uridylation assays using Flag-Zcchc11 and the indicated RNA (SEQ ID NOs: 12, 12, 13, 14, 15, 16, and 17 from top to bottom, respectively). (Bottom panels) 5'-end labeled RNAs showing equal amounts of RNA and Uridylation assays using Flag-Zcchc11 and the indicated RNA (SEQ ID NOs: 12, 18 and 19 from top left to bottom left, respectively; SEQ ID NOs. 12, 20, 21 and 22 from top right to bottom right, respectively).
Figure 21:
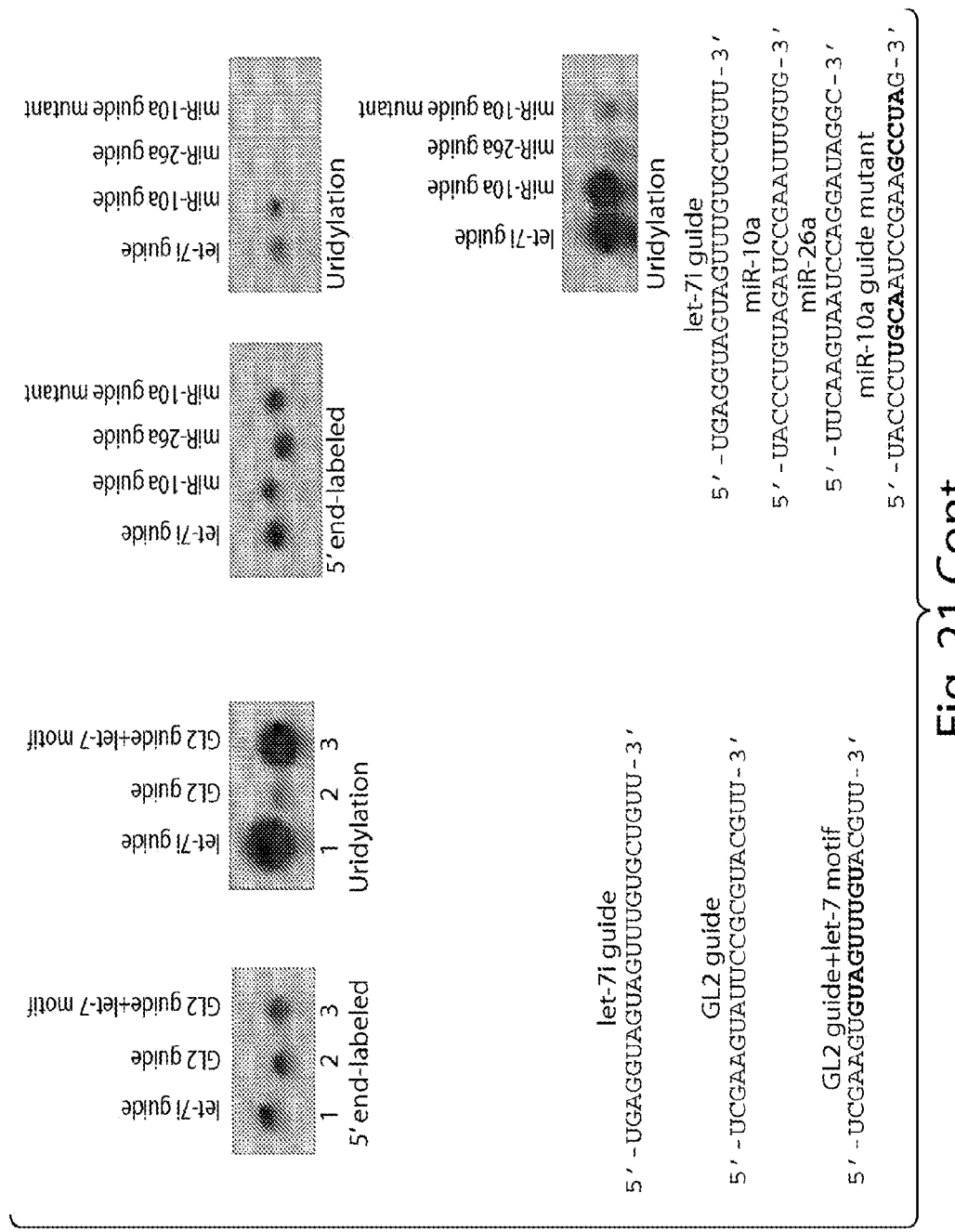

To begin to address the RNA sequence determinants for this substrate preference the primary sequence of let-7 family members was examined. This revealed several regions of conservation, including (as expected) the 5' seed sequence (nt 2-8) as well as other sequence motifs conserved between different let-7 family members and between mouse and human let-7 miRNAs. To determine if any of these sequences were necessary for the RNA preference displayed by Zcchc11 in previous experiments, mutant RNA oligos were designed and tested in vitro. Mutations in the seed and central sequence slightly reduced the substrate preference of Zcchc11 (FIG. 21). Mutations in the central and 3' regions, as well as an RNA oligo that had all three domains mutated, dramatically reduced substrate preference.

Because other RNA-binding proteins with CCHC Zinc fingers preferentially bind GXXG motifs, Zcchc11 might use a similar G-rich motif to recognize sequence information in let-7 guide strands. Interestingly, eliminating all guanine residues in a let-7 guide oligo also severely compromised its ability to serve as a strong Zcchc11 substrate. To confirm the sufficiency of these sequence motifs for substrate preference, an RNA oligo that contained nine nucleotides from the center of let-7 guide were inserted into an unrelated RNA, the Luciferase GL2 siRNA sequence. The activity of Zcchc11 towards this chimeric RNA oligo resembled let-7 guide, and was a drastically better substrate compared to the parental GL2 RNA oligo. Taken together, these results indicate that Zcchc11 uridylates single-stranded RNA in a sequence-specific manner and that this sequence is both necessary and sufficient to confer a strong substrate preference.

A bioinformatic search of all (>1,000) annotated miRNAs in the mouse and human genomes identifies miRNAs that may be similarly recognized by Zcchc11. Because two miRNAs, let-7g and let-7i, contained the perfect sequence GUAGUUUGU (SEQ ID NO:4) was sufficient to confer Zchcc11 substrate specificity, the search was expanded by selecting miRNAs that contained both GUAG and UUGU sequences. A list of all miRNAs with these sequences common to both the human and mouse was generated. Aside from including eight of nine unique let-7 family members, this new list includes seven additional miRNAs that comprise three distinct miRNA families. Several of these miRNAs are known to directly regulate Hox gene expression, including the miR-10, miR-99/100, and the miR-196 families. miR-10a, miR-10b, miR-196a, and miR-196b are encoded within Hox gene clusters, and miR-100 and miR-99a, miR-99b are not. Along with nearly the entire let-7 family, the sequence-specific preference of Zcchc11 and Zcchc6 for these developmentally essential miRNAs may pose a crucial and evolutionarily ancient mode of regulating miRNAs to control development. Importantly, the altered expression of several of these miRNAs is linked with various cancers. Synthetic miR-10a resembles let-7 guide in uridylation assays, and mutations in its conserved motif abolishes this preference (FIG. 21). Similar experiments with a variety of miRNA substrates provides a catalog of the exact sequence preferences of these TUTases, and correlates the data from these in vitro experiments with data generated from the RNA cloning and deep sequencing.

Figure 22:
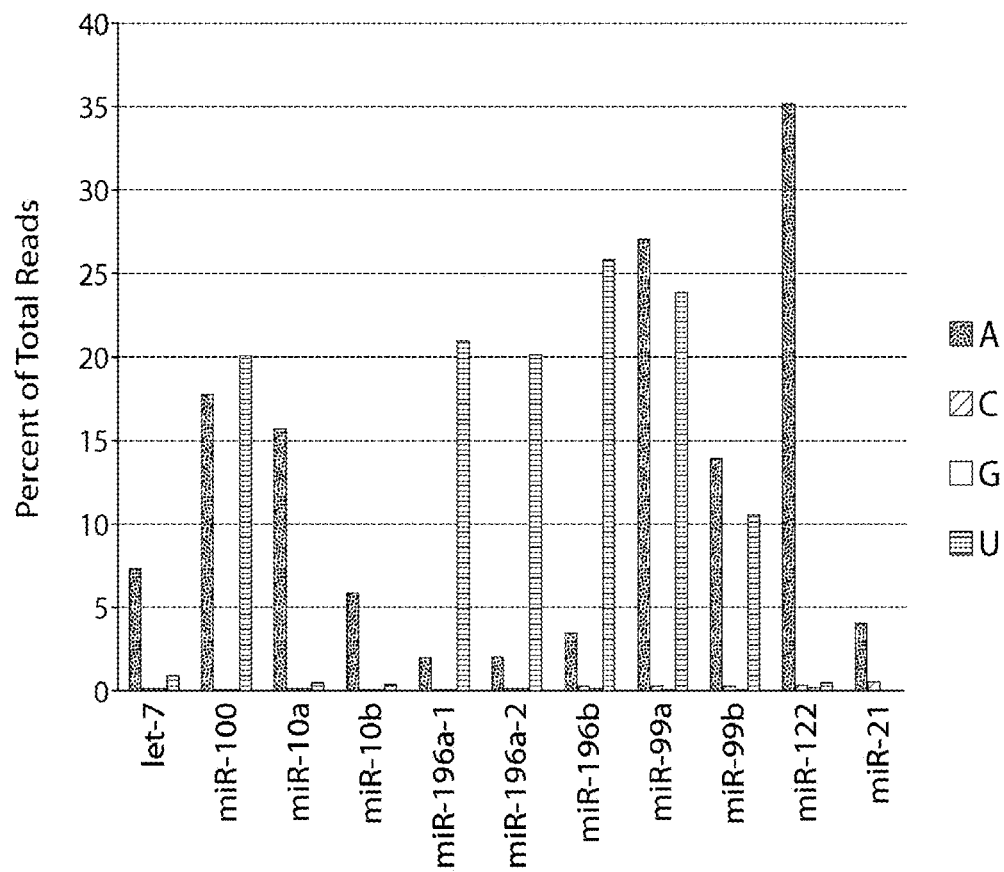
FIG. 22 is a bar graph showing evidence for extensive 3' uridylation of mature miRNAs. A published data set was analyzed for evidence of 3' terminal nucleotide additions for selected miRNA. The bar graph shows the percentage of each miRNA with a terminal (1 or more) nucleotide addition. Sequence reads represent grouped data obtained from all the mouse developmental stages and tissues analyzed in that study.

Another step generates small RNA cDNA libraries from control and TUTase knockdown samples and analyzes the changes in miRNA expression and 3' terminal uridylation by high throughput cDNA sequencing technology. Recent deep sequencing analyses have revealed extensive non-templated (Adenylation or Uridylation) nucleotide addition at the 3'-end of certain mature miRNAs. Though the functional relevance of these modifications and the identity of the RNA terminal transferases mediating these events remain unknown the extent of terminal uridylation is quite extensive for certain miRNAs and seems dynamically regulated in different tissues and mouse developmental stages. A large data set that was recently published from the Bartel lab includes 60 million small RNA sequences cloned from mouse brain, ovary, testes, embryonic stem cells, three embryonic stages, and whole newborns. This data set provides evidence for extensive uridylation of certain miRNAs, including those miRNAs that are preferred substrates for Zcchc11 and Zcchc6 in vitro, whereas other miRNAs such as miR-21 seem to be much less modified (FIG. 22). miR-122, a miRNA that is adenylated by a poly(A) polymerase GLD-1 is included in our analysis since it has been reported that 3' adenylation stabilizes miR-122 levels. An established protocol for RNA cloning and sequencing small RNAs from control and TUTase-depleted cells is used. The data generated helps guide the choice of cell lines, i.e., those cancer cell lines with elevated Zcchc11 and/or Zcchc6 expression. A useful cell line is MCF7 breast cancer cells, which express Zcchc11 but not Lin28A or Lin28B. The basic procedure for small RNAs cloning is established. High throughput screening (using either the Illumina or SOLiD/Applied Biosystems platforms) is performed. This experimental design includes conditions in which each TUTase is knocked down individually as well as combinatorialy to address possible functional redundancy.

Changes miRNA expression is measures, and reporter gene assays monitor miRNA function to identify the consequences of 3' terminal uridylation of mature miRNAs. The experiments identify the extent of TUTase-catalyzed miRNA uridylation in human cancer cell lines. These data provide the foundation for experiments designed to address the functional consequences of miRNA terminal uridylation. Possibilities for miRNA regulation include (a) 3' terminal uridylation regulates miRNA levels, or (b) 3' terminal uridylation regulates miRNA function without altering expression of the miRNA. Although the study of these regulatory pathways is still in its infancy, there is precedence supporting both of these possibilities. These models are tested using q.RT-PCR and Northern blot to monitor possible changes in miRNA expression in TUTase-depleted cells. RNA uridylation targets miRNAs for rapid decay leads to increased miRNA levels in TUTase-depleted cells, whereas the levels of uridylated miRNAs should decrease. Taqman q.RT-PCR assays specifically detect uridylated versions of the mature miRNAs. This serves as a useful tool providing a facile and quantitative means to monitor changes in miRNA uridylation in response to TUTase modulation, and complements the commercially available assays that specifically detect the non-uridylated miRNAs. If miRNA expression is not affected by TUTase knockdown, then miRNA function is tested. miRNA-responsive reporters measure miRNA-mediated posttranscriptional gene silencing. Control and TUTase knockdown cells transfected with Luciferase reporters bearing relevant miRNA-target sequences in the 3'UTR, and the extent of the miRNA-mediated repression is measured by comparing relative Luciferase levels.

If the TUTase(s) impact miRNA function without altering miRNA expression levels, then the molecular basis for this regulatory mechanism is explored. miRNA uridylation may alter the miRNA association with the Argonaute proteins, this can be tested directly by affinity-purifying Argonaute proteins from control- and TUTase-depleted cells and analyzing the associated miRNA by q.RT-PCR and/or Northern blot. Similar experiments to test directly the function of miRNA uridylation can be performed by transfecting TUTase-depleted cells with control or 3' uridylated synthetic miRNAs and measuring Argonaute association as well target gene repression.

The present invention also provides for compositions and methods to determine the oncogenic role of the TUTases. For example, Zcchc11 and Zcchc6 selectively modulate the expression of a subset of miRNAs including the tumor suppressor let-7 family. This regulation likely occurs by both Lin28A-dependent as well as Lin28A-independent mechanisms. Thus, TUTases, such as Zcchc11 and Zcchc6, function as oncogenes and promote cellular transformation. The relevance and scope of this regulatory pathway in cancer biology is analyzed using Lin28A, Lin28B, Zcchc11, and Zcchc6 expression in cancer cell lines, primary human tumors, and corresponding normal tissues using q.RT-PCR, Western blot, and immunohistochemistry. miRNA expression is measured in the same samples by q.RT-PCR and in situ hybridization. Lin28A and Lin28B expression was measured in small cohort of human colon and breast tissues, revealing that Lin28A or Lin28B were upregulated while let-7a was downregulated in colon adenocarcinomas relative to normal colon tissues. In addition, Lin28A was significantly upregulated in HER2-overexpressing breast tumors, while Lin28B was significantly upregulated in triple-negative (ER-, PR-, HER2-) breast tumors. The broader relevance of these findings in breast cancer is extended by measuring Lin28A, Lin28B, and TUTases (such as Zcchc11 and Zcch6) in a much larger cohort of breast tumor samples.

Tumor tissue microarrays are obtained from, for example, the Human Genetics Sample Bank at Ohio State University. These tumor array samples from over 800 patients are readily available as well as corresponding RNA samples from the tumor and adjacent normal breast tissues. This allows measurement of miRNA-binding protein and TUTase (e.g., Lin28A, Lin28B, Zcchc11, and Zcchc6 protein) expression and miRNA levels expression in a large number of lobular and ductal breast carcinomas and normal breast tissues. This allows determination of the prevalence of these genes expression in the two major histologic subtypes of breast cancer and to determine the association between expression of these proteins with important histopathological parameters in breast cancer including ER, PR and HER2 status, grade, tumor size, stage, lymph node status etc. For those samples with follow-up data, whether expression levels of miRNA-binding proteins and the TUTases are associated with outcomes, such as relapse-free and overall survival, is determined. In addition to measuring expression of miRNA-binding protein and TUTase paralogs, the expression levels of the most relevant miRNAs including let-7 si measured. Double-DIG labeled miRCURY LNA™ Detection probes (Exiqon) are used for specific miRNA detection by in situ hybridization. One skilled in the art can generate or buy custom rabbit polyclonal antibodies (Open Biosystems/Thermo Scientific), which can be thoroughly characterized. If developing antibodies for the target TUTase is unsuccessful, one can use q.RT-RCR to measure TUTase expression in breast tissues.

In addition to breast cancers, prostate cancer are a highly relevant tumor. The Zcchc11 mRNA level is elevated in 18/30 (60%) of samples analyzed by q.RT-PCR, and Zcchc11 expression positively correlates with Gleason score. Moreover, analysis of Zcchc6 Microarray expression data in 'Oncomine' revealed elevated (3.2 fold) expression in prostate carcinoma (n=30) compared to normal prostate tissue (P value=3.13E-7) in the data set from Tomlins et al., Nature Genetics 2007, thereby raising the possibility that these TUTases may function redundantly in prostate cancer. The proposed Zcchc11 and Zccch6 expression profiling guides functional studies, as described herein.

RNAi-mediated loss-of function experiments are done in selected cancer cell lines with elevated TUTase expression to characterize and monitor cell proliferation, colony formation, migration, and tumorigenicity. A panel of assays described herein explore the role of the TUTases as potential new oncogenes. For example, whether Zcchc11 and Zcchc6 function as oncogenes in a Lin28A-independent context may be compared in breast and/or prostate cancer cell lines with elevated Zcchc11 and/or Zcchc6 expression that do not express Lin28A or Lin28B (for example MCF-7 breast adenocarcinoma cell line) and used for functional assays designed to examine the role of the TUTases on cell growth and tumorigenicity. For these experiments Zcchc11, Zcchc6, or both Zcchc11 and Zcchc6 (to test possible functional redundancy) are depleted using shRNA, and the effects monitored as described herein.

TUTase gain-of function experiments are correlated with measured effects on cellular transformation. The ability of overexpression of the TUTases, such as Zcchc11 and Zccch6, to induce oncogenic cellular transformation is tested directly, for example the effect of Zcchc11 or Zcchc6 overexpression in MCF10A immortalized breast epithelial cells. Lin28A/B or Src overexpression is used as positive controls. Cells are transduced with lentiviruses expressing the relevant cDNAs. MCF10A cells may become transformed within 48 hours after transduction, and TUTase overexpression may lead to a substantial change in cell morphology. The effects of Zcchc11/Zcchc6 overexpression is tested on the colony formation ability of the transformed MCF10A cells. Xenograft experiments, where control or transformed MCF10A cells are injected into immunodeficient (nu/nu) mice, test the propensity of the injected cells to form of tumors. Overall, these experiments are designed test the hypothesis that elevated TUTase expression leads to cellular transformation.

Further, the mechanism for oncogenesis is explored by examining the involvement of key downstream miRNAs and their respective target mRNAs. The experiments proposed herein may establish the TUTases (Zcchc11 and Zcchc6) as new oncogenes in breast and/or prostate cancer. It may be important to investigate the mechanism for this oncogenic function and to dissect the gene regulatory pathways that are dysregulated by TUTase overexpression in cancer. Genetic rescue experiments are performed, where TUTase levels are manipulated by shRNA-mediated knockdown and, simultaneously, either inhibit the function of individual miRNAs using antisense oligonucleotides to suppress miRNA function (miRCURY LNA antagomiRs from Exiqon) or overexpress individual miRNAs using synthetic miRNA mimics or overexpression plasmids, and monitor the effects on cancer cell growth. Microarrays (e.g., Affymetrix) can be used to measure changes in gene expression in response to manipulation of TUTase levels. Whether these TUTases regulate miRNA expression or function remains to be determined, however in either case the levels of the targets of these miRNAs will be altered. mRNAs with reciprocal expression patterns in the TUTase knockdown and overexpression samples may be considered candidate target genes.

To better distinguish between primary targets and secondary transcriptional effects, Argonaute protein is immunoprecipitated from control and TUTase manipulated samples and the co-purified RNA subjected to RNA-Seq analysis. RNA is isolated from Argonaute immunoprecipitates and multiplexed libraries are generated and sequenced. Reporter gene assays confirm the direct miRNA regulation of selected candidate mRNAs. Luciferase reporter constructs are generated in which the 3'UTR of the candidate gene is subcloned downstream of a luciferase open reading frame. Transient co-transfection of these reporter constructs with the miRNA mimic or antisense inhibitor, followed by analysis of luciferase activity will reveal whether these UTRs contain the necessary sequences for miRNA-mediated suppression. For reporters suppressed by co-transfection with the corresponding miRNA, the putative miRNA seed sequence(s) within the 3'UTR are mutagenized to confirm that the effect observed is caused by a direct interaction. Finally, it is likely that this list of genes that are regulated coordinately with the TUTase will include known and novel genes with oncogenic function. This may be addressed using shRNA to knockdown selected downstream genes and evaluate the impact of this suppression on TUTase-mediated oncogenic transformation.

In addition to cancers, the role of miRNA function in the heart has been addressed by conditionally inhibiting miRNA maturation in the murine heart, and has revealed that miRNAs play an essential role during its development. miRNA expression profiling studies demonstrate that expression levels of specific miRNAs change in diseased human hearts, pointing to their involvement in cardiomyopathies. Furthermore, studies on specific miRNAs in animal models have identified distinct roles for miRNAs both during heart development and under pathological conditions, including the regulation of key factors important for cardiogenesis, the hypertrophic growth response, and cardiac conductance. Further, miRNAs appear to regulate the nervous system. Neural miRNAs are involved at various stages of synaptic development, including dendritogenesis (involving miR-132, miR-134 and miR-124), synapse formation and synapse maturation (where miR-134 and miR-138 are thought to be involved). Some studies find altered miRNA expression in schizophrenia.

An important aspect of the present invention provides for compositions and methods for screening for drugs that restore miRNA expression in cancer, that will likely lead to the development of novel strategies with broad applicability for effective cancer treatment. Let-7 family members are down-regulated in many different tumors. The findings reported herein imply that restoration of let-7 expression is a unique and powerful new strategy for cancer therapy. Lack of an appropriate, safe, and effective delivery methods for regulating let-7 expression, however, is currently a major drawback for implementing such a therapy. The present identification of a novel pathway that selectively inhibits expression of let-7 miRNAs provides an exciting opportunity for the development of novel chemotherapeutic strategies to restore let-7 expression in cancer and supports the hypothesis that inhibition of Lin28A-Zcchc11 in cancer cells will elevate expression of the tumor suppressor let-7 to its physiologic level, leading to reduced expression of multiple let-7 target oncogenes and inhibition of cancer cell proliferation. Drugs that target the miRNA biogenesis pathway remain largely uncharacterized, and no high throughput screening directed towards let-7 miRNA biogenesis has been reported thus far. The present invention provides for the identification and characterization of bioactive chemicals that relieve inhibition of the tumor suppressor let-7 miRNA that is mediated by oncogenic Lin28A and its associated TUTase Zcchc11. One way to identify such potential novel therapeutics is to develop and perform automated high-throughput screening (HTS) assays. The present invention provides for novel HTS approaches to identify drugs that restore let-7 miRNA expression in Lin28A-expressing cancers. Two complementary assays for HTS are envisioned, with the goal of maximizing the chances of a successful outcome: a cell-based system to monitor let-7 expression, and a biochemical assay to identify inhibitors of the TUTase. Hit compounds are validated using a series of secondary screens; the effect of these compounds on cancer cells is examined. This methodology will allows for the translation of basic science discoveries to the development of new and effective cancer treatments. Embodiments provide for the development of novel chemotherapeutic strategies to restore normal let-7 miRNA levels in tumors. "Hit" compounds from high throughput screening will relieve the Lin28A-mediated block in let-7 processing and identify the therapeutic potential of these compounds for human cancer, and thus support the development of novel drug treatments that effectively target the undifferentiated cells within the tumor.

There are several advantages of targeting this pathway as a novel chemotherapeutic strategy: (a) Lin28A is normally expressed primarily in embryonic cells; therefore specific inhibitors of this pathway should offer a good therapeutic window with limited side-effects of any potential cancer treatments. (b) Lin28A is expressed self-renewing stem cells and so specific inhibitors of this pathway will likely target the poorly differentiated and tumor initiating cells. (c) Lin28A selectively and posttranscriptionally inhibits expression of multiple members of the let-7 family miRNAs; and so inhibition of the pathway should lead to the coordinate upregulation of multiple let-7 family members. (d) Lin28A-mediated blockade of let-7 requires an enzymatically active TUTase that should be relatively easy to target with small molecules—for example, by using nucleotide analogs that are already used in the clinic for effective treatment of other diseases. (e) Lin28A is a key component of a feedback loop, so re-expression of let-7 will be self-reinforcing, leading to further elevation of let-7 expression.

A cell-based assay that monitors let-7 activity for HTS involves generating and validating stable cell lines that express a let-7 sensor reporter gene. The cell-based screening utilizes a Luciferase reporter gene, which was engineered to monitor let-7 expression in cultured cells. A Luciferase reporter mRNA harboring a let-7 target sequence in the 3' untranslated region (UTR) can be used to specifically monitor let-7 activity. The psiCHECK-2 vector (Promega) allows generation of reporter constructs containing the let-7 target sequences. This vector has been designed to enable the monitoring of changes in expression of a gene of interest, e.g., a let-7 target, fused to a reporter gene. Renilla luciferase is used as a primary reporter gene that contains multiple cloning sites in the 3'UTR to make the cloning of let-7 target sequences possible. Renilla luciferase expression is driven by SV40 promoter and uses a synthetic poly(A). The psiCHECK-2 vector also possesses a secondary firefly reporter expression cassette that consists of an HSV-TK promoter, a synthetic firefly luciferase gene and an SV40 late poly(A) signal. This cassette has been designed to serve as an intraplasmid normalization reporter. The Renilla luciferase signal thus can be normalized to the firefly luciferase signal. This vector has been widely used as a sensor to test the ability of miRNA to target RNA sequences and to induce posttranscriptional repression of the targeted genes. In order to generate a sensitive reporter assay, a construct in which three let-7 target sequences arranged in tandem was included in the 3'UTR of the Renilla luciferase was generated. These sequences should induce destabilization of the Renilla luciferase transcripts to give a broad window between conditions where the let-7 is expressed or is inhibited by the Lin28 pathway. As a proof-of-principle, the reporter was used to specifically monitor let-7 activity. The data indicate that this let-7 reporter is destabilized by let-7. (FIG. 23).

Relative Luciferase activity was measured in transiently transfected cells. For this, we initially chose Hela cells (that express high levels of let-7 miRNA) as well as P19 embryonal carcinoma cells (in which let-7 expression is blocked by Lin28A). As expected, there was a dramatic destabilization of the let-7 sensor in Hela cells, whereas the same reporter was stable in P19 cells (FIG. 23B). Next, the human lung adenocarcinoma cell line, H1299 (that expresses high levels of Lin28B) was engineered to contain the psiCHECK-2 vector containing the let-7 target sites. This stable H1299 cell line was transfected with plasmid for the expression of a chimeric pri-miRNA in which the terminal loop sequence of pre-let-7 is replaced with that of miR-21 (a miRNA that is not regulated by Lin28). This chimeric construct bypasses Lin28-mediated regulation thus providing a convenient means to ectopically express let-7 in Lin28-expressing cell lines. As expected, expression of let-7 in this H1299 stable cell line resulted in a robust (~5-fold) repression of the Luciferase reporter construct bearing let-7 complementary target sites (FIG. 23C). Stable cells lines containing the let-7 sensor are generated and validated by measuring response to RNAi-mediated Lin28-TUTase depletion. RNAi approaches may be used to monitor the response of each reporter to Lin28A, and Zcchc11 inhibition.

Figure 24A:
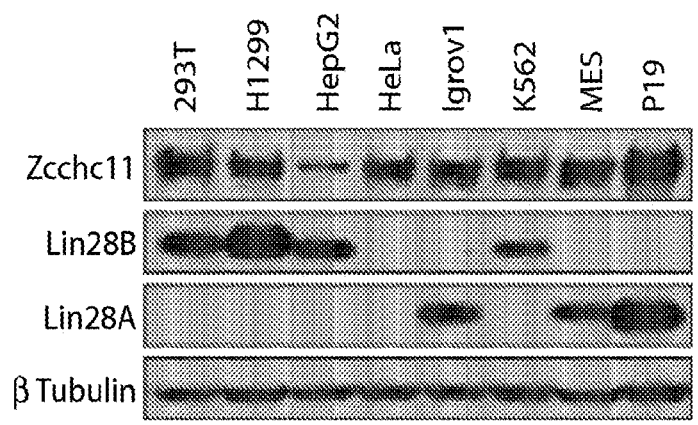
FIGS. 24A-B demonstrate depletion of Lin28-Zcchc11 leads to increased let-7 expression in human cancer cell lines.
Figure 24B:
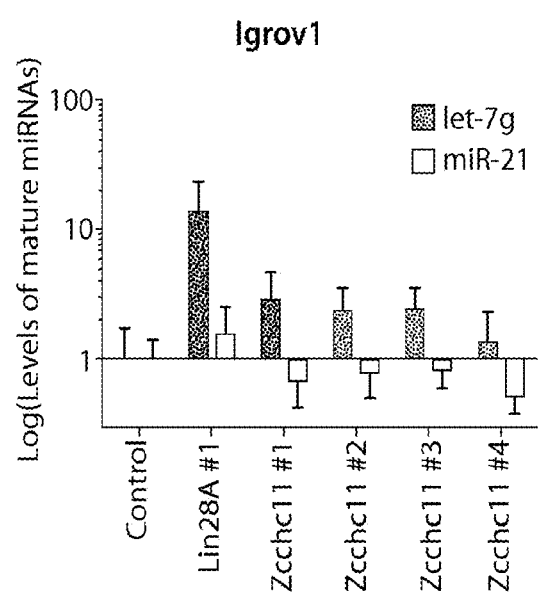

The Dual Luciferase Reporter Assay System (Promega) will be used to prepare cell lysates and to measure sequentially the activity of firefly and then Renilla luciferase. Measurements will be performed using a Synergy 2 luminometer with the Gen5 program (Biotek). The relative light units (RLU) collected for the Renilla luciferase will be normalized to the firefly luciferase RLU. The stable cell line where Lin28A/Zcchc11 inhibits let-7 expression shows relatively high levels of Renilla luciferase. Treatment of a chemical inhibitor that disrupts Lin28A/Zcchc11 repression of let-7 will result in increased let-7 levels and a decrease in relative Renilla luciferase levels. The data demonstrate that shRNA-mediated depletion of Lin28A or Zchcc11 in IGORV1 cells leads to accumulation of let-7 expression (FIG. 24). Establishment of a stable cell line is more convenient and preferred to transiently transfected cells and effectively provides an unlimited source of homogeneous cells in order to achieve a good reproducibility in HTS applications. H1299 (Lung) cancer cells were chosen because they express endogenous Lin28B, but because Lin28A (but not Lin28B) employs the TUTase to selectively repress let-7 expression, one may use Lin28A-expressing cancer cell lines exclusively, for example, well-characterized adherent cancer cell lines expressing Lin28A T47D (Breast ductal epithelial tumor), and IGROV1 (Ovarian carcinoma). For both these cell-types, Zcchc11 depletion inhibits the colony formation, metastatic potential, and tumorigenic capacity.

A transfection protocol is used wherein one plasmid corresponds to the reporter construct based on the psiCheck-2 vector, and the other contains a puromycin resistance marker. Puromycin selection may be advantageous over neomycin selection because of its more potent toxicity to naïve cells. Then, 48 hours after transfection, culture media is replaced with media supplemented with 2.5 µg/mL puromycin and cells will be cultured for 10 to 14 days, with daily replacement of the media to remove dead cells. Stable cell lines are generated from a monoclonal population, necessitating cell colony isolation. Often, polyclonal populations of cell lines stably expressing transgenes tend to lose expression of the transgenic cDNA. After transfection and cell selection, positive clones are screened using luciferase assay and knockdown experiments. The stable cell line with the most significant level of luciferase activity for both luciferases and the most responsive to let-7 levels upon either ectopic let-7 expression, or Lin28A//Zcchc11 knockdown is selected. Several stable clones with the reporter construct containing the Renilla luciferase-3× let-7 have been selected Significant activities are reproducibly recovered for each luciferase and ~5-fold change in Luciferase ratio is obtained with enforced let-7 expression (FIG. 23). Therefore, highly predictable and reproducible responses to let-7 expression and the 5-fold changes in relative Luciferase represent a relatively broad window that provides a clear threshold between positive and negative responses, establishing this strategy for HTS suitability.

A pilot screen using a library of several hundred bioactive compounds can be performed in order to determine the suitability of this cell-based reporter gene system in an automated setting. We will determine whether the stable cell line(s) generated represents a valuable tool for HTS to identify small molecules targeting the Lin28A pathway. The validated cell line are used for HTS of a library of up to two thousand chemicals. A pilot screen can be carried out on the Biomol library from the Institute of Chemistry and Cell Biology (ICCB) at Harvard University. This "Known Bioactives" library (Biomol) set has been validated using other screening assays. Ten thousand cells are plated (in 90 µl) per well of the 96-well assay plates, and control reagents and library compounds will be added 24 hours later. Each compound is tested in duplicate at three different concentrations (0.1, 1, 10 µM). After 48 hours, wells are washed and lysed (20 µl lysis buffer) to allow for assessment of Renilla and Firefly Luciferase levels using the Dual-Luciferase Reporter Assay System (Promega) and a Biotek Synergy2 plate reader. The resulting data is expressed as log 2(RLuc/Fluc). The Z' is calculated for each plate: Z'=1-3*(σCTRL+σDMSO)/|µCTRL-µDMSO|.

Criteria for identifying compounds appear in the 'hit' list if they either have a strong activity at a particular concentration or a consistent activity over at least two concentrations, can be devised because few compounds can be expected to be active over the full dilution range. Candidate hit compounds are validated using a series of secondary screens including q.RT-PCR analysis of let-7 expression, Western Blot analysis of Lin28A and Zcchc11 expression, and in vitro assays for TUTase activity. The most effective compound concentrations is determined from dose curves; effects are monitored by Luciferase activity assays and by q.RT-PCR measurement of let-7 levels. This allows determination of the stable cell line(s) generated represents as a valuable tool for HTS to identify small molecules targeting the Lin28 or TUTase (or both) pathway. Secondary screens may be performed to ascertain compounds that specifically regulate Lin28A-TUTase complex activity.

Putative hits from this primary screen can be evaluated through secondary screens that include dose curves, q.RT-PCR analysis of miRNA expression, Western Blot analysis of Lin28A and Zcchc11 expression, and in vitro TUTase activity assays. These experiments allow for the elimination of false positives, and validation of compounds as regulators of the Lin28 pathway, and for exploration of their mechanism of action. Quantitative analysis of mature miRNA levels by q.RT-PCR may be done as follows: Cells are treated with each compound selected as 'hits' from the primary screen and levels of a let-7 miRNAs analyzed by q.RT-PCR. As shown herein, Lin28A or Zcchc11 knockdown led to accumulation of let-7 in IGROV cells (FIG. 24), and T47D cells. For compounds that modulate Lin28-Zcchc11 expression or activity, corresponding changes in let-7 miRNA levels are expected. Total RNA is extracted from treated cells and q.RT-PCR will be performed using TaqMan assays to measure let-7. These assays will be performed in parallel for several non-let-7 miRNAs such as miR-21 and miR-16 will serve as controls. Additionally, Western Blot Analysis of Lin28A and Zcchc11 expression may be used. Hit compounds from the screen and validated to affect specifically let-7 mature miRNA levels (by q.RT-PCR approaches described above), likely target the Lin28 regulatory pathway in one of two ways; either by altering the expression of Lin28A, or Zcchc11 by somehow influencing the activity of the Lin28-TUTase without directly affecting Lin28-TUTase expression levels. These alternative possibilities are distinguished by secondary screening strategies.

This work allows exploration of the mechanism of action of hit compounds and allows to elimination of compounds that may be acting indirectly. Therefore, the expression of Lin28A, and Zcchc11 is monitored by western blots (and by q.RT-PCR) on cell treated with the individual compounds and mock treated controls. Specific antibodies for the detection of each of the endogenous proteins have been found (FIG. 24A). The corresponding expression plasmids for transient overexpression of epitope tagged proteins are provided herein. These serve as useful tools in the investigation into the effect of compound treatment on Lin28A and Zcchc11 expression. Utilizing the transgenes for ectopic protein expression, as well as analyzing endogenous Lin28A and Zcchc11 protein and mRNA levels (by q.RT-PCR), enable one to distinguish between potential transcriptional versus posttranscriptional regulation. For example, data reveal that Lin28 expression is repressed by let-7 posttranscriptionally whereas other factors such as Myc transcriptionally activate Lin28A expression. Therefore, an analysis of Lin28A and Zcchc11 expression is a possible secondary screens.

In vitro TUTase assays can be employed also. Some of the hit compounds may influence Lin28A-TUTase activity independent of altered expression levels. An in vitro assay is used to identify chemicals that specifically inhibit miRNA biogenesis through targeting the Lin28A-TUTase complex. For in vitro uridylation assays, synthetic pre-let-7 RNA is incubated with the affinity-purified proteins in the presence of [$\alpha$-$^{32}$P]-UTP. By adding individual chemicals identified in the screen to biochemically reconstituted TUTase reactions with purified Lin28A-Zcchc11 complex, or by performing in vitro TUTase assays using cell extracts prepared from treated cells, a subset of chemicals is identified that specifically inhibit the action of the Lin28A-Zcchc11 complex and thereby promote let-7 biogenesis.

The optimized assay also provides for high throughput screening. Depending on the outcome of these pilot experiment, an additional ~400,000 compounds from a chemical diversity set can be screened. The chemical screening can be performed using the services and chemical libraries, such as that available at the Institute of Chemistry and Cell Biology (ICCB)-Longwood, an investigator-initiated screening program that assists academic researchers in carrying out high throughput screening of chemical libraries. High throughput screening capabilities are also offered through the Harvard Stem Cell Institute. The ICCB-Longwood compound collection is continuously growing, and over 400,000 compounds are currently available for screening. One can follow the recommended screening priority for compound libraries according to the ICCB guidelines. The phase of this strategy is to screen the Known Bioactives libraries (6,671 compounds), followed by a selection of ~10,000 compounds from the Natural Product Extracts (48,688 compounds), a selection of ~70,000 most recently plated compounds from the Commercial Libraries (223,041 compounds), followed by ~50,000 recently plated compounds from the Commercial Libraries (223,041 compounds), ~38,000 remaining Natural Product Extracts (48,688 compounds), and finally the remainder of the collection. Details of these libraries are available online. Depending on results from these screens, one may choose to screen additional libraries available through The Chemical Biology Platform of the Broad Institute. The platform team has high-throughput research capabilities in organic synthesis and small-molecule screening. Informatics and computational analysis teams integrate these capabilities. This library comprises over 500,000 compounds and the Chemical Biology Platform participates in the National Cancer Institute's Initiative for Chemical Genetics (ICG).

Figure 25:
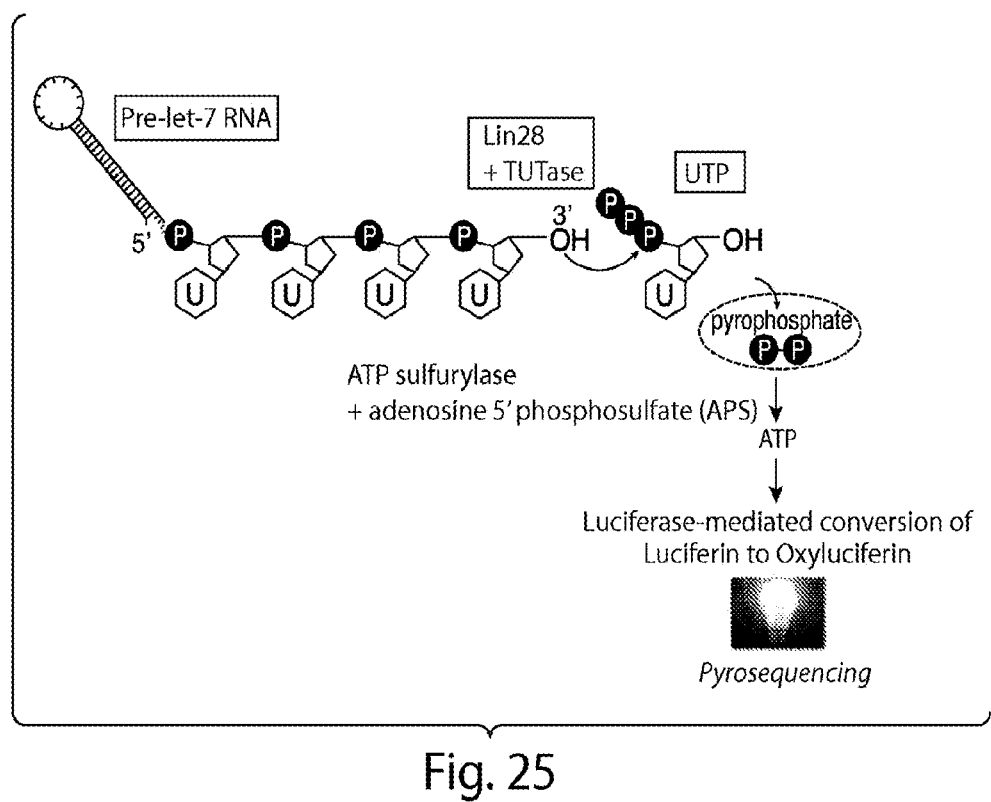
FIG. 25 is a scheme for a high throughput screen assay to monitor TUTase activity.

To establish, validate, and utilize a biochemical assay that monitors TUTase activity for high throughput screening, one can design and optimize in vitro TUTase activity assays using recombinant Lin28A and Zcchc11 proteins and detection methods suitable for HTS, as described herein. Because the activity of the TUTase is likely to be highly 'druggable', the present invention also provides design, optimization, and tily of an in vitro HTS assay that monitors TUTase activity to identify compounds that directly inhibit this enzyme. The reconstituted the in vitro uridylation assay is described herein. Briefly, synthetic pre-let-7 RNA was incubated with the affinity-purified Lin28 and Zcchc11 proteins in the presence of [$\alpha$-$^{32}$P]-UTP. To optimize this assay for HTS, non-radioactive detection methods are advantageous. The incorporation of fluorescent nucleotides (UTP) or measuring levels of pyrophosphate (PPi) that is generated by nucleotide polymerization are alternatives (FIG. 25). The detection of pyrophosphate (PPi) generated by nucleotide polymerization is already commonly utilized for automated massively parallel DNA sequencing (deep-sequencing) technologies. Therefore we anticipate the adaptation of this pyrosequencing approach for monitoring TUTase activity should be feasible and enable high throughput screening.

An abundant supply of purified Lin28 and Zcchc11 (TUTase) proteins are used for the in vitro screening strategy. Highly purified recombinant proteins for these assays can be generated as taught herein. Recombinant Lin28A is expressed in bacteria (His-Lin28A) and purified as described. Using this system, at least 2 mg of highly purified r.Lin28A can be obtained reproducibly from 1 liter of E. coli. For all TUTase activity assays so far described, the source of the TUTase has been Flag-Zcchc11 affinity-purified from cultured human (HEK293) cells. For a HTS approach, it may be necessary to establish conditions for the production of recombinant Zcchc11 protein. The large size of the full-length Zcchc11 protein (>180 kDa) is likely to be prohibitive for its expression and purification from E. coli, but the recombinant C2H2 fragment described herein is advantageous. This truncated protein retains full activity in the present pre-let-7 TUTase assays, and importantly this minimal protein of <120 kDa, is substantially reduced from its original 184 kDa. By using this recombinant protein with recombinant Lin28, the uridylation reaction can be reconstituted in vitro, thereby defining the minimal components of Lin28-mediated pre-let-7 uridylation and enabling the present innovative HTS approach to identify inhibitors of Zcchc11. The purified recombinant proteins are functionally validated by performing TUTase activity assays with radiolabeled pre-let-7 RNA. These proteins are used for the development of the non-radioactive assay. Once these recombinant proteins have been validated, the assay is scaled to the 96- or 384-well format required for HTS. Luciferase measurements can be performed using a Synergy 2 luminometer with the Gen5 program (Biotek). The addition of individual chemicals to TUTase reactions that have been biochemically reconstituted with purified Lin28A-Zcchc11 complex should allow identification of a subset of chemicals that specifically inhibits the action of the Lin28A-Zcchc11 complex and thereby promotes let-7 biogenesis.

A pilot screen is performed on the in vitro assay, using a chemical library that contains a collection of nucleotide analogs. The catalytic activity of the TUTase is inhibited by certain nucleotide analogs, and that the identification of these compounds through HTS will lead to their utility as a novel chemotherapeutic in Lin28A-expressing cancers. There are readily available libraries of such compounds; similar compounds have already been applied in the clinic. For example certain nucleotide analogs have been effectively used for the inhibition of the retroviral reverse transcriptase in HIV therapy, as well as for other viral infections, and in the treatment of certain cancers. As a proof-of-principle experiment we have demonstrated that addition of a chain terminator nucleotide, the analog 2',3'-dideoxy-UTP, effectively inhibits TUTase activity in vitro by preventing oligo-U tail elongation. Thus, 2',3'-dideoxy-UTP serves as a positive control nucleotide analog for the in vitro HTS. Then, putative hits from this primary screen are evaluated through secondary screens that include dose curves, in vitro TUTase activity assays, and analyses of let-7 expression by q.RT-PCR on compound-treated cells. The chemical HTS can be performed using the services and chemical libraries, such as those available at the Institute of Chemistry and Cell Biology (ICCB)-Longwood, an investigator initiated screening program that assists academic researchers in carrying out high-throughput screens of chemical libraries.

To evaluate the efficacy of small molecule inhibitors of the Lin28 pathway as potential chemotherapeutics, identified compounds are tested for their ability to inhibit proliferation, migration, and colony formation of Lin28A-expressing human cancer cells. The validated small molecule inhibitors are examined for their ability to inhibit proliferation of Lin28A-expressing human cancer cell lines. Control cells and compound-treated cells are counted daily using an automated counter for bright field cells. Expression of proliferation markers Ki67 and phospho-Histone H3 can be measured as well. Decreased proliferation of cancer cells is expected in cells in which let-7 expression is restored by chemical treatment.

The effects of hit compounds in colony formation and cell invasion assays are also examined, as described herein. For example, Colony Formation Assay: T47D breast cancer cells and IGROV1 ovarian cancer cells are treated with selected compounds for 24 hours. Triplicate samples of $10^5$ cells from each treatment are mixed 4:1 (v/v) with 2.0% agarose in growth medium for a final concentration of 0.4% agarose. The cell mixture is plated on top of a solidified layer of 0.5% agarose in growth medium. Cells are fed every 6 to 7 days with growth medium containing 0.4% agarose. The number of colonies is counted after 20 days. The experiment is repeated and the statistical significance calculated using Student's t test. Invasion Assays: MDA-MB-231 and T47D breast cancer cells are treated with different compounds for 24 hours. Invasion of matrigel is conducted using standardized conditions with BDBioCoat growth factor reduced MATRIGEL invasion chambers (PharMingen). Assays are conducted per manufacturer's protocol, using 10% FBS as chemoattractant. Non-invading cells on the top-side of the membrane are removed and invading cells are fixed and stained with DAPI, 16 hours-post seeding. Such assays explored the distinct requirements for Zcchc11 in Lin28A- and Lin28B-expressing cancer and established Zcch11 as new therapeutic target in human cancers. The effects of Zcchc11 inhibition on the tumorigenicity and invasiveness of MDA-MB-231 breast cancer cells (Lin28B-expressing cells) relative to T47D breast cancer cells (Lin28A-expressing cells) were compared. Suppression of Zcchc11 expression did not affect let-7a expression in MDA-MB-231 cells, but led to 7-fold increase in mature let-7a levels in T47D cells.

Furthermore, Zcchc11 inhibition did not affect the tumorigenicity and invasiveness of MDA-MB-231 cells, while it suppressed both the colony formation ability and invasiveness of T47D cells. Zcchc11 inhibition had similar effects on the tumor growth of these cell lines in xenografts. For these in vivo experiments, cells were injected subcutaneously in the right flank of athymic nude mice. Tumor growth was monitored every 5 days. In Vivo Ready siRNAs (Ambion Inc.) were mixed with Invivofectamine 2.0 liposomes (Ambion Inc.) and injected intra-peritoneal in a volume of 100 µl at a dose of 5 mg/kg. Specifically, Zcchc11 knockdown did not affect tumor growth of MDA-MB-231, but it suppressed T47D tumor growth. Synthetic let-7a miRNA suppressed both MDA-MB-231 and T47D tumor growth. Also, in the tumors derived from MDA-MB-231 xenografts (day 30), let-7a expression was not affected by inhibition of Zcchc11, while Lin28B suppression increased let-7a levels about 5-fold.

On the other hand, both Zcchc11 and Lin28A inhibition resulted in up-regulation of let-7a expression to similar levels in T47D-derived tumors (day 30). In addition to the breast cancer cells, the effects of Zcchc11 inhibition were tested on tumor growth of several other (liver, lung, ovarian, melanoma, colon) cancer cell types. As above, Zcchc11 inhibition blocked the growth of LIN28A-expressing tumors (Igrov1) (FIG. 11) and did not affect the growth of Lin28B-expressing tumors (HepG2, H1299, SK_MEL_28, CaCO2). Lin28A and Lin28B inhibition suppressed the growth of the corresponding tumors. Taken together, these data suggest that Zcchc11 plays a role in the tumorigenicity and invasiveness of Lin28A-expressing cancer cells. Specificity and Toxicity: The effects of selected compounds on the growth and viability of cells that do not express Lin28A are examined. For example, MCF-10A, non-tumorigenic breast epithelial cells that do not express Lin28A (or Lin28B) are treated with these compounds to monitor the effect on the growth properties of these cells. MCF-10a cells are not expected to be inhibited by the compounds that selectively target the Lin28 pathway. This helps eliminate general cytotoxic compounds from analysis. Similarly, for compounds identified as TUTase inhibitors, they are expected to phenocopy the effects of Zcchc11 depletion in breast cancer cells. Therefore, these compounds should inhibit the growth of T47D, and IGROV1 cells (Lin28A-expressing) but not MDA-MB-231 cells (Lin28B-expressing).

Screen optimization is central to the success of HTS. The present data demonstrate the feasibility of this strategy. Additionally, for example, because two different promoters drive expression of the Firefly and Renilla Luciferase, one might replace one of the promoters so that both Luciferases have the same kind of promoter to eliminate false positives due to differential affect of hits on each promoter. Additionally, to detect enhancement of let-7 activity, turnover of Renilla protein is required (detectable decrease in protein within the 48 hour incubation period) in order to observe changes in RLuc/Fluc ratio. Therefore t½ is a major determinant of screen dynamics and inhibitors of the Lin28 pathway may be easier to find using a longer incubation times. Also, whether some of the 'hit' compounds are simply toxic, affect cell viability, influence cell proliferation, or lead to changes in the cell-cycle requires testing. Whether any of these parameters causes direct or indirect changes in RLuc/Fluc ratio may be examined. For example, it has been reported that miRNA biogenesis may be influenced by cell density. Whether cell confluence changes the RLuc/Fluc ratio is relevant when deciding on hit selection parameters and original cell seeding density. Z scores might not be the best or the sole parameter to use, and the inclusion of additional criteria for hit selection is possible. This optimization is based on the data collected from secondary screens and may be essential for the development of the robust assay for HTS. As part of the compound validation process, to provide extra confidence in the hits, and to try to exclude off-target effects, additional compounds known to act in the same biological pathway may be compared.

Herein, the inventors demonstrate that Lin28A enhances repression of pre-let-7 miRNA by recruiting a TUTase, specifically Zcchc11 and Zcchc6. Inhibition or depletion of such TUTase levels by Zcchc11 shRNA knockdown in a multiple human cancer cell lines which express Lin28 results in the increase in levels of members of the mature let-7 family of tumor-suppressor miRs and a decrease in cell growth, colony forming capacity, and tumor formation.

Accordingly, in discovering that Lin28A recruited TUTase is an inhibitor of miRNA processing and represses biogenesis of let-7 miRNA, which repression contributes to cancer, the inventors have discovered that inhibition of Lin28A-recruited TUTase, e.g., Zcchc11 or Zcchc 6, is a useful target for the treatment or prevention of cancer. Accordingly, one aspect of the present invention relates to a method to treat and/or prevent cancer by inhibition of Lin28A-recruited TUTase.

In some embodiments, the inhibitor agents of Lin28A-recruited TUTase can be, for example, antibodies (polyclonal or monoclonal), neutralizing antibodies, antibody portions, fragments, analogs, variants or derivatives, peptides, proteins, peptide-mimetics, aptamers, oligonucleotides, hormones, small molecules, nucleic acids, nucleic acid analogues, carbohydrates, or analogs, derivatives or variants thereof, that function to inactivate the nucleic acid and/or protein of the gene products identified herein, and those as yet unidentified. Nucleic acids include, for example but not limited to, DNA, RNA, oligonucleotides, peptide nucleic acid (PNA), pseudo-complementary-PNA (pcPNA), locked nucleic acid (LNA), RNAi, microRNAi, siRNA, shRNA etc. The inhibitors can be selected from a group of a chemical, small molecule, chemical entity, nucleic acid sequences, nucleic acid analogues or protein or polypeptide or analogue or fragment thereof. In some embodiments, the nucleic acid is DNA or RNA, and nucleic acid analogues, for example can be PNA, pcPNA and LNA. A nucleic acid may be single or double stranded, and can be selected from a group comprising; nucleic acid encoding a protein of interest, oligonucleotides, PNA, etc. Such nucleic acid sequences include, for example, but not limited to, nucleic acid sequence encoding proteins that act as transcriptional repressors, antisense molecules, ribozymes, small inhibitory nucleic acid sequences, for example but not limited to RNAi, shRNAi, siRNA, micro RNAi (mRNAi), antisense oligonucleotides etc. A protein and/or peptide inhibitor or portion thereof, can be, for example, mutated proteins, therapeutic proteins and recombinant proteins. Proteins and peptides inhibitors can also include for example; mutated proteins, genetically modified proteins, peptides, synthetic peptides, recombinant proteins, chimeric proteins, antibodies, humanized proteins, humanized antibodies, chimeric antibodies, modified proteins and fragments thereof.

As used herein, "gene silencing" or "gene silenced" in reference to an activity of a RNAi molecule, for example a siRNA or miRNA refers to a decrease in the mRNA level in a cell for a target gene by at least about 5%, about 10%, about 20%, about 30%, about 40%, about 50%, about 60%, about 70%, about 80%, about 90%, about 95%, about 99%, about 100% of the mRNA level found in the cell without the presence of the miRNA or RNA interference molecule. In one preferred embodiment, the mRNA levels are decreased by at least about 70%, about 80%, about 90%, about 95%, about 99%, about 100%.

As used herein, the term "RNAi" refers to any type of interfering RNA, including but are not limited to, siRNAi, shRNAi, endogenous microRNA and artificial microRNA. For instance, it includes sequences previously identified as siRNA, regardless of the mechanism of down-stream processing of the RNA (i.e. although siRNAs are believed to have a specific method of in vivo processing resulting in the cleavage of mRNA, such sequences can be incorporated into the vectors in the context of the flanking sequences described herein.

As used herein an "siRNA" refers to a nucleic acid that forms a double stranded RNA, which double stranded RNA has the ability to reduce or inhibit expression of a gene or target gene when the siRNA is present or expressed in the same cell as the target gene, for example where a target gene is Lin28A-recruited TUTase (e.g., Zcchc11 or Zcchc6). The double stranded RNA siRNA can be formed by the complementary strands. In one embodiment, a siRNA refers to a nucleic acid that can form a double stranded siRNA. The sequence of the siRNA can correspond to the full length target gene, or a subsequence thereof. Typically, the siRNA is at least about 15-50 nucleotides in length (e.g., each complementary sequence of the double stranded siRNA is about 15-50 nucleotides in length, and the double stranded siRNA is about 15-50 base pairs in length, preferably about 19-30 base nucleotides, preferably about 20-25 nucleotides in length, e.g., 20, 21, 22, 23, 24, 25, 26, 27, 28, 29, or 30 nucleotides in length.

As used herein "shRNA" or "small hairpin RNA" (also called stem loop) is a type of siRNA. In one embodiment, these shRNAs are composed of a short, e.g. about 19 to about 25 nucleotide, antisense strand, followed by a nucleotide loop of about 5 to about 9 nucleotides, and the analogous sense strand. Alternatively, the sense strand can precede the nucleotide loop structure and the antisense strand can follow.

A "stem-loop structure" refers to a nucleic acid having a secondary structure that includes a region of nucleotides which are known or predicted to form a double strand (stem portion) that is linked on one side by a region of predominantly single-stranded nucleotides (loop portion). The terms "hairpin" and "fold-back" structures are also used herein to refer to stem-loop structures. Such structures are well known in the art and the term is used consistently with its known meaning in the art. The actual primary sequence of nucleotides within the stem-loop structure is not critical to the practice of the invention as long as the secondary structure is present. As is known in the art, the secondary structure does not require exact base-pairing. Thus, the stem may include one or more base mismatches. Alternatively, the base-pairing may be exact, i.e. not include any mismatches. In some instances the precursor microRNA molecule may include more than one stem-loop structure. The multiple stem-loop structures may be linked to one another through a linker, such as, for example, a nucleic acid linker or by a microRNA flanking sequence or other molecule or some combination thereof. The actual primary sequence of nucleotides within the stem-loop structure is not critical as long as the secondary structure is present. As is known in the art, the secondary structure does not require exact base-pairing. Thus, the stem may include one or more base mismatches. Alternatively, the base pairing may not include any mismatches.

As used herein, the term "let-7" refers to the nucleic acid encoding the let-7 miRNA family members and homologues and variants thereof including conservative substitutions, additions, and deletions therein not adversely affecting the structure or function. For example, let-7 refers to the nucleic acid encoding a let-7 family member from humans, including but not limited to, NCBI Accession Nos. AJ421724, AJ421725, AJ421726, AJ421727, AJ421728, AJ421729, AJ421730, AJ421731, AJ421732, and biologically active sequence variants of let-7, including alleles, and in vitro generated derivatives of let-7 that demonstrate let-7 activity.

As used herein, "double stranded RNA" or "dsRNA" refers to RNA molecules that are comprised of two strands. Double-stranded molecules include those comprised of a single RNA molecule that doubles back on itself to form a two-stranded structure. For example, the stem loop structure of the progenitor molecules from which the single-stranded miRNA is derived, called the pre-miRNA (Bartel et al., 116 Cell 281 (2004)), comprises a dsRNA molecule.

The terms "polypeptide" and "protein" are used interchangeably to refer to a polymer of amino acid residues, and for the purposes of the invention are limited to a minimum length of at least 20 amino acids. Oligopeptides, oligomers multimers, and the like, typically refer to longer chains of amino acids and are also composed of linearly arranged amino acids linked by peptide bonds, and whether produced biologically, recombinantly, or synthetically and whether composed of naturally occurring or non-naturally occurring amino acids, are included within this definition. Both full-length proteins and fragments thereof are encompassed by the definition. The terms also include co-translational (e.g., signal peptide cleavage) and post-translational modifications of the polypeptide, such as, for example, disulfide-bond formation, glycosylation, acetylation, phosphorylation, proteolytic cleavage (e.g., cleavage by furins or metalloproteases), and the like. Furthermore, for purposes of the present invention, a "polypeptide" refers to a protein that includes modifications, such as deletions, additions, and substitutions (generally conservative in nature as would be known to a person in the art), to the native sequence, as long as the protein maintains the desired activity. These modifications can be deliberate, as through site-directed mutagenesis, or can be accidental, such as through mutations of hosts that produce the proteins, or errors due to PCR amplification or other recombinant DNA methods. Polypeptides or proteins are composed of linearly arranged amino acids linked by peptide bonds, but in contrast to peptides, has a well-defined conformation. Proteins, as opposed to peptides, generally consist of chains of 15 or more amino acids. For the purposes of the present invention, the term "peptide" as used herein typically refers to a sequence of amino acids of made up of a single chain of D- or L-amino acids or a mixture of D- and L-amino acids joined by peptide bonds. Generally, peptides contain at least two amino acid residues and are less than about 15 amino acids in length.

It will be appreciated that a protein or polypeptide often contain amino acids other than the 20 amino acids commonly referred to as the 20 naturally occurring amino acids, and that many amino acids, including the terminal amino acids, can be modified in a given polypeptide, either by natural processes such as glycosylation and other post-translational modifications, or by chemical modification techniques which are well known in the art. Known modifications which can be present in peptides of the present invention include, but are not limited to, acetylation, acylation, ADP-ribosylation, amidation, covalent attachment of flavin, covalent attachment of a heme moiety, covalent attachment of a polynucleotide or polynucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formulation, gamma-carboxylation, glycation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

The incorporation of non-natural amino acids, including synthetic non-native amino acids, substituted amino acids, or one or more D-amino acids into the peptides (or other components of the composition, with exception for protease recognition sequences) is desirable in certain situations. D-amino acid-containing peptides exhibit increased stability in vitro or in vivo compared to L-amino acid-containing forms. Thus, the construction of peptides incorporating D-amino acids can be particularly useful when greater in vivo or intracellular stability is desired or required. More specifically, D-peptides are resistant to endogenous peptidases and proteases, thereby providing better oral trans-epithelial and transdermal delivery of linked drugs and conjugates, improved bioavailability of membrane-permanent complexes (see below for further discussion), and prolonged intravascular and interstitial lifetimes when such properties are desirable. The use of D-isomer peptides can also enhance transdermal and oral trans-epithelial delivery of linked drugs and other cargo molecules. Additionally, D-peptides cannot be processed efficiently for major histocompatibility complex class II-restricted presentation to T helper cells, and are therefore less likely to induce humoral immune responses in the whole organism. Peptide conjugates can therefore be constructed using, for example, D-isomer forms of cell penetrating peptide sequences, L-isomer forms of cleavage sites, and D-isomer forms of therapeutic peptides. In some embodiments, a polypeptide inhibitor of Lin28A-recruited TUTase can be comprised of D- or L-amino acid residues, as use of naturally occurring L-amino acid residues has the advantage that any breakdown products should be relatively non-toxic to the cell or organism.

In yet a further embodiment, a polypeptide inhibitor of a Lin28A-recruited TUTase can be a retro-inverso peptide. A "retro-inverso peptide" refers to a peptide with a reversal of the direction of the peptide bond on at least one position, i.e., a reversal of the amino- and carboxy-termini with respect to the side chain of the amino acid. Thus, a retro-inverso analogue has reversed termini and reversed direction of peptide bonds while approximately maintaining the topology of the side chains as in the native peptide sequence. The retro-inverso peptide can contain L-amino acids or D-amino acids, or a mixture of L-amino acids and D-amino acids, up to all of the amino acids being the D-isomer. Partial retro-inverso peptide analogues are polypeptides in which only part of the sequence is reversed and replaced with enantiomeric amino acid residues. Because the retro-inverted portion of such an analogue has reversed amino and carboxyl termini, the amino acid residues flanking the retro-inverted portion are replaced by side-chain-analogous .alpha.-substituted geminal-diaminomethanes and malonates, respectively. Retro-inverso forms of cell penetrating peptides have been found to work as efficiently in translocating across a membrane as the natural forms. See Bonelli et al., 24 Intl. J. Pept. Protein Res. 553 (1984); Verdini & Viscomi, 1 J. Chem. Soc. Perkin Trans. 697 (1985); U.S. Pat. No. 6,261, 569. Processes for the solid-phase synthesis of partial retro-inverso peptide analogues have been described (EP 97994-B).

The terms "homology", "identity" and "similarity" refer to the degree of sequence similarity between two peptides or between two optimally aligned nucleic acid molecules. Homology and identity can each be determined by comparing a position in each sequence which can be aligned for purposes of comparison. For example, it is based upon using a standard homology software in the default position, such as BLAST, version 2.2.14. When an equivalent position in the compared sequences is occupied by the same base or amino acid, then the molecules are identical at that position; when the equivalent site occupied by similar amino acid residues (e.g., similar in steric and/or electronic nature such as, for example conservative amino acid substitutions), then the molecules can be referred to as homologous (similar) at that position. Expression as a percentage of homology/similarity or identity refers to a function of the number of similar or identical amino acids at positions shared by the compared sequences, respectfully. A sequence which is "unrelated" or "non-homologous" shares less than 40% identity, though preferably less than 25% identity with the sequences as disclosed herein.

As used herein, the term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T. C, G. U. or I) or residue occurs in both sequences to yield the number of matched positions, dividing the number of matched positions by the total number of positions in the comparison window (i.e., the window size), and multiplying the result by 100 to yield the percentage of sequence identity.

As used herein, the terms "homologous" or "homologues" are used interchangeably, and when used to describe a polynucleotide or polypeptide, indicates that two polynucleotides or polypeptides, or designated sequences thereof, when optimally aligned and compared, for example using BLAST, version 2.2.14 with default parameters for an alignment (see herein) are identical, with appropriate nucleotide insertions or deletions or amino-acid insertions or deletions, in at least 70% of the nucleotides, usually from about 75% to 99%, and more preferably at least about 98 to 99% of the nucleotides. The term "homolog" or "homologous" as used herein also refers to homology with respect to structure and/or function. With respect to sequence homology, sequences are homologs if they are at least 50%, at least 60% at least 70%, at least 80%, at least 90%, at least 95% identical, at least 97% identical, or at least 99% identical. Determination of homologs of the genes or peptides of the present invention can be easily ascertained by the skilled artisan. The term "substantially homologous" refers to sequences that are at least 90%, at least 95% identical, at least 96%, identical at least 97% identical, at least 98% identical or at least 99% identical.

Homologous sequences can be the same functional gene in different species. Determination of homologs of the genes or peptides of the present invention can be easily ascertained by the skilled artisan. For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, for example, by a local homology algorithm (Smith & Waterman, 2 Adv. Appl. Math. 482 (1981)); by the homology alignment algorithm (Needleman & Wunsch, 48 J. Mol. Biol. 443 (1970)); by the search for similarity method (Pearson & Lipman, 85 PNAS 2444 (1988)); by computerized implementations of these algorithms (e.g., GAP, BESTFIT, FASTA, and TFASTA in the Wisconsin Genetics Software Package, Genetics Computer Group, 575 Science Dr., Madison, Wis.); by PILEUP, a simplification of the progressive alignment method (Feng & Doolittle, 25 J. Mol. Evol. 351 (1987)); by BLAST algorithm (Altschul et al., 215 J. Mol. Biol. 403 (1990)); or by visual inspection (see generally Ausubel et al. (eds.), Curr. Prot. Molec. Biol. (4th ed., John Wiley & Sons, New York, 1999)).

The term "variant" as used herein refers to a peptide or nucleic acid that differs from the naturally occurring polypeptide or nucleic acid by one or more amino acid or nucleic acid deletions, additions, substitutions or side-chain modifications, yet retains one or more specific functions or biological activities of the naturally occurring molecule. Amino acid substitutions include alterations in which an amino acid is replaced with a different naturally-occurring or a non-conventional amino acid residue. Such substitutions may be classified as "conservative", in which case an amino acid residue contained in a polypeptide is replaced with another naturally occurring amino acid of similar character either in relation to polarity, side chain functionality or size. Substitutions encompassed by the present invention may also be "non conservative", in which an amino acid residue which is present in a peptide is substituted with an amino acid having different properties, such as naturally-occurring amino acid from a different group (e.g., substituting a charged or hydrophobic amino; acid with alanine), or alternatively, in which a naturally-occurring amino acid is substituted with a non-conventional amino acid. In some embodiments amino acid substitutions are conservative. Also encompassed within the term variant when used with reference to a polynucleotide or polypeptide, refers to a polynucleotide or polypeptide that can vary in primary, secondary, or tertiary structure, as compared to a reference polynucleotide or polypeptide, respectively (e.g., as compared to a wild-type polynucleotide or polypeptide).

Variants can be naturally-occurring, synthetic, recombinant, or chemically modified polynucleotides or polypeptides isolated or generated using methods well known in the art. Variants can include conservative or non-conservative amino acid changes, as described below. Polynucleotide changes can result in amino acid substitutions, additions, deletions, fusions and truncations in the polypeptide encoded by the reference sequence. Variants can also include insertions, deletions or substitutions of amino acids, including insertions and substitutions of amino acids and other molecules) that do not normally occur in the peptide sequence that is the basis of the variant, for example but not limited to insertion of ornithine which do not normally occur in human proteins. The term "conservative substitution," when describing a polypeptide, refers to a change in the amino acid composition of the polypeptide that does not substantially alter the polypeptide's activity. For example, a conservative substitution refers to substituting an amino acid residue for a different amino acid residue that has similar chemical properties. Conservative amino acid substitutions include replacement of a leucine with an isoleucine or valine, an aspartate with a glutamate, or a threonine with a serine. "Conservative amino acid substitutions" result from replacing one amino acid with another having similar structural and/or chemical properties, such as the replacement of a leucine with an isoleucine or valine, an aspartate with a glutamate, or a threonine with a serine. Thus, a "conservative substitution" of a particular amino acid sequence refers to substitution of those amino acids that are not critical for polypeptide activity or substitution of amino acids with other amino acids having similar properties (e.g., acidic, basic, positively or negatively charged, polar or non-polar, etc.) such that the substitution of even critical amino acids does not reduce the activity of the peptide, (i.e. the ability of the peptide to penetrate the BBB). Conservative substitution tables providing functionally similar amino acids are well known in the art. For example, the following six groups each contain amino acids that are conservative substitutions for one another: (1) Alanine (A), Serine (S), Threonine (T); (2) Aspartic acid (D), Glutamic acid (E); (3) Asparagine (N), Glutamine (Q); (4) Arginine (R), Lysine (K); (5) Isoleucine (I), Leucine (L), Methionine (M), Valine (V); and (6) Phenylalanine (F), Tyrosine (Y), Tryptophan (W). See also Creighton, PROTEINS (W. H. Freeman & Company, 1984). In some embodiments, individual substitutions, deletions or additions that alter, add or delete a single amino acid or a small percentage of amino acids can also be considered "conservative substitutions" is the change does not reduce the activity of the peptide (i.e., the ability of a LinA-recruited TUTase polypeptide to process the maturation of miRNA). Insertions or deletions are typically in the range of about one to five amino acids. The choice of conservative amino acids may be selected based on the location of the amino acid to be substituted in the peptide, for example if the amino acid is on the exterior of the peptide and expose to solvents, or on the interior and not exposed to solvents.

In alternative embodiments, one can select the amino acid which will substitute an existing amino acid based on the location of the existing amino acid, i.e., its exposure to solvents (i.e., if the amino acid is exposed to solvents or is present on the outer surface of the peptide or polypeptide as compared to internally localized amino acids not exposed to solvents). Selection of such conservative amino acid substitutions are well known in the art. Accordingly, one can select conservative amino acid substitutions suitable for amino acids on the exterior of a protein or peptide (i.e. amino acids exposed to a solvent), for example, but not limited to, the following substitutions can be used: substitution of Y with F, T with S or K, P with A, E with D or Q, N with D or G, R with K, G with N or A, T with S or K, D with N or E, I with L or V, F with Y, S with T or A, R with K, G with N or A, K with R, A with S, K or P.

The term "functional" when used in conjunction with "derivative" or "variant" refers to a molecule such as a protein which possess a biological activity (either functional or structural) that is substantially similar to a biological activity of the entity or molecule its is a functional derivative or functional variant thereof. The term functional derivative is intended to include the fragments, analogues or chemical derivatives of a molecule. A molecule is said to be "substantially similar" to another molecule if both molecules have substantially similar structures or if both molecules possess a similar biological activity, for example if both molecules are able to deliver a target antigen to the cytosol of a cell in the absence of PA and without being fused to the target antigen. Thus, provided that two molecules possess a similar activity, they are considered variants and are encompassed for use as disclosed herein, even if the structure of one of the molecules not found in the other, or if the sequence of amino acid residues is not identical. Thus, provided that two molecules possess a similar biological activity, they are considered variants as that term is used herein even if the structure of one of the molecules not found in the other, or if the sequence of amino acid residues is not identical.

The term "disease" or "disorder" is used interchangeably herein, refers to any alternation in state of the body or of some of the organs, interrupting or disturbing the performance of the functions and/or causing symptoms such as discomfort, dysfunction, distress, or even death to the person afflicted or those in contact with a person. A disease or disorder can also related to a distemper, ailing, ailment, malady, disorder, sickness, illness, complaint, inderdisposion, affection.

The term "malignancy" and "cancer" are used interchangeably herein, refers to diseases that are characterized by uncontrolled, abnormal growth of cells. Cancer cells can spread locally or through the bloodstream and lymphatic system to other parts of the body. The term "malignancy" or "cancer" are used interchangeably herein and refers to any disease of an organ or tissue in mammals characterized by poorly controlled or uncontrolled multiplication of normal or abnormal cells in that tissue and its effect on the body as a whole. Cancer diseases within the scope of the definition comprise benign neoplasms, dysplasias, hyperplasias as well as neoplasms showing metastatic growth or any other transformations like e.g. leukoplakias which often precede a breakout of cancer. The term "tumor" or "tumor cell" are used interchangeably herein, refers to the tissue mass or tissue type of cell that is undergoing abnormal proliferation.

A "cancer cell" refers to a cancerous, pre-cancerous or transformed cell, either in vivo, ex vivo, and in tissue culture, that has spontaneous or induced phenotypic changes that do not necessarily involve the uptake of new genetic material. Although transformation can arise from infection with a transforming virus and incorporation of new genomic nucleic acid, or uptake of exogenous nucleic acid, it can also arise spontaneously or following exposure to a carcinogen, thereby mutating an endogenous gene. Transformation/cancer is associated with, e.g., morphological changes, immortalization of cells, aberrant growth control, foci formation, anchorage dependence, proliferation, malignancy, contact inhibition and density limitation of growth, growth factor or serum dependence, tumor specific markers levels, invasiveness, tumor growth or suppression in suitable animal hosts such as nude mice, and the like, in vitro, in vivo, and ex vivo. See also Freshney, Culture Animal Cells: A Man. Basic Tech. (3rd ed., 1994).

The term "biological sample" as used herein may mean a sample of biological tissue or fluid that comprises nucleic acids. Such samples include, but are not limited to, tissue isolated from animals. Biological samples may also include sections of tissues such as biopsy and autopsy samples, frozen sections taken for histologic purposes, blood, plasma, serum, sputum, stool, tears, mucus, hair, and skin. Biological samples also include explants and primary and/or transformed cell cultures derived from patient tissues. A biological sample may be provided by removing a sample of cells from an animal, but can also be accomplished by using previously isolated cells (e.g., isolated by another person, at another time, and/or for another purpose), or by performing the methods of the invention in vivo. As used herein, the term "biological sample" also refers to a cell or population of cells or a quantity of tissue or fluid from a subject. "Biological sample" can also refer to cells or tissue analyzed in vivo, i.e., without removal from the subject. The term "tissue" is intended to include intact cells, blood, blood preparations such as plasma and serum, bones, joints, muscles, smooth muscles, and organs.

The terms "patient", "subject" and "individual" are used interchangeably herein, and refer to an animal, particularly a human, to whom treatment, including prophylactic treatment is provided. The term "subject" as used herein refers to human and non-human animals, such as apes, monkeys, horses, cattle, sheep, goats, dogs, cats, rabbits, guinea pigs, rats, and mice. In one embodiment, the subject is human. In another embodiment, the subject is an experimental animal or animal substitute as a disease model.

The term "gene" used herein can be a genomic gene comprising transcriptional and/or translational regulatory sequences and/or a coding region and/or non-translated sequences (e.g., introns, 5'- and 3'-untranslated sequences and regulatory sequences). The coding region of a gene can be a nucleotide sequence coding for an amino acid sequence or a functional RNA, such as tRNA, rRNA, catalytic RNA, siRNA, miRNA and antisense RNA. A gene can also be an mRNA or cDNA corresponding to the coding regions (e.g., exons and miRNA) optionally comprising 5'- or 3' untranslated sequences linked thereto. A gene can also be an amplified nucleic acid molecule produced in vitro comprising all or a part of the coding region and/or 5'- or 3'-untranslated sequences linked thereto.

The term "nucleic acid" or "oligonucleotide" or "polynucleotide" used herein can mean at least two nucleotides covalently linked together. As will be appreciated by those in the art, the depiction of a single strand also defines the sequence of the complementary strand. Thus, a nucleic acid also encompasses the complementary strand of a depicted single strand. As will also be appreciated by those in the art, many variants of a nucleic acid can be used for the same purpose as a given nucleic acid. Thus, a nucleic acid also encompasses substantially identical nucleic acids and complements thereof. As will also be appreciated by those in the art, a single strand provides a probe for a probe that can hybridize to the target sequence under stringent hybridization conditions. Thus, a nucleic acid also encompasses a probe that hybridizes to a "target" under stringent hybridization conditions. Nucleic acids can be single stranded or double stranded, or can contain portions of both double stranded and single stranded sequence. The nucleic acid can be DNA, both genomic and cDNA, RNA, or a hybrid, where the nucleic acid can contain combinations of deoxyribo- and ribo-nucleotides, and combinations of bases including uracil, adenine, thymine, cytosine, guanine, inosine, xanthine hypoxanthine, isocytosine and isoguanine. Nucleic acids can be obtained by chemical synthesis methods or by recombinant methods.

A nucleic acid will generally contain phosphodiester bonds, although nucleic acid analogs can be included that can have at least one different linkage, e.g., phosphoramidate, phosphorothioate, phosphorodithioate, or O-methylphosphoroamidite linkages and peptide nucleic acid backbones and linkages. Other analog nucleic acids include those with positive backbones; non-ionic backbones, and non-ribose backbones, including those described in U.S. Pat. No. 5,235,033 and U.S. Pat. No. 5,034,506. Nucleic acids containing one or more non-naturally occurring or modified nucleotides are also included within one definition of nucleic acids. The modified nucleotide analog can be located for example at the 5'-end and/or the 3'-end of the nucleic acid molecule. Representative examples of nucleotide analogs can be selected from sugar- or backbone-modified ribonucleotides. It should be noted, however, that also nucleobase-modified ribonucleotides, i.e. ribonucleotides, containing a non naturally occurring nucleobase instead of a naturally occurring nucleobase such as uridines or cytidines modified at the 5-position, e.g., 5-(2-amino)propyl uridine, 5-bromo uridine; adenosines and guanosines modified at the 8-position, e.g., 8-bromo guanosine; deaza nucleotides, e.g., 7 deaza-adenosine; O- and N-alkylated nucleotides, e.g., N6-methyl adenosine are suitable. The 2' OH-group can be replaced by a group selected from H, OR, Rhalo, SH, SR, $NH_2$, NHR, $NR_2$ or CN, wherein R is C1-C6 alkyl, alkenyl or alkynyl and halo is F, Cl, Br, or I. Modifications of the ribose-phosphate backbone can be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs can be made.

The term "agent" refers to any entity which is normally absent or not present at the levels being administered, in the cell. Agent may be selected from a group comprising; chemicals; small molecules; nucleic acid sequences; nucleic acid analogues; proteins; peptides; aptamers; antibodies; or fragments thereof. A nucleic acid sequence may be RNA or DNA, and may be single or double stranded, and can be selected from a group comprising; nucleic acid encoding a protein of interest, oligonucleotides, nucleic acid analogues, for example peptide-nucleic acid (PNA), pseudo-complementary PNA (pc-PNA), locked nucleic acid (LNA), etc. Such nucleic acid sequences include, for example, but not limited to, nucleic acid sequence encoding proteins, for example that act as transcriptional repressors, antisense molecules, ribozymes, small inhibitory nucleic acid sequences, for example but not limited to RNAi, shRNAi, siRNA, micro RNAi (mRNAi), antisense oligonucleotides etc. A protein and/or peptide or fragment thereof can be any protein of interest, for example, but not limited to; mutated proteins; therapeutic proteins; truncated proteins, wherein the protein is normally absent or expressed at lower levels in the cell. Proteins can also be selected from a group comprising; mutated proteins, genetically engineered proteins, peptides, synthetic peptides, recombinant proteins, chimeric proteins, antibodies, midibodies, tribodies, humanized proteins, humanized antibodies, chimeric antibodies, modified proteins and fragments thereof. The agent may be applied to the media, where it contacts the cell and induces its effects. Alternatively, the agent may be intracellular within the cell as a result of introduction of the nucleic acid sequence into the cell and its transcription resulting in the production of the nucleic acid and/or protein environmental stimuli within the cell. In some embodiments, the agent is any chemical, entity or moiety, including without limitation synthetic and naturally-occurring non-proteinaceous entities. In certain embodiments the agent is a small molecule having a chemical moiety. For example, chemical moieties included unsubstituted or substituted alkyl, aromatic, or heterocyclyl moieties including macrolides, leptomycins and related natural products or analogues thereof. Agents can be known to have a desired activity and/or property, or can be selected from a library of diverse compounds.

As used herein, the term "treating" includes reducing or alleviating at least one adverse effect or symptom of a condition, disease or disorder associated with inappropriate proliferation, for example cancer. As used herein, the term treating is used to refer to the reduction of a symptom and/or a biochemical marker of in appropriate proliferation, for example a reduction in at lease one biochemical marker of cancer by at least 10%. For example, a reduction in a biochemical marker of cancer, for example a reduction in, as an illustrative example only, at least one of the following biomarkers; CD44, telomerase, TGF-α, TGF-α, erbB-2, erbB-3, MUC1, MUC2, MUC5, CK20, PSA, CA125 or FOBT by at least 10%; or a reduction in the rate of proliferation of the cancer cells by 10%, would be considered effective treatments by the methods as disclosed herein. As alternative examples, a reduction in a symptom of cancer, for example, a slowing of the rate of growth of the cancer by 10%, or a cessation of the increase in tumor size, or a reduction in the size of a tumor by 10% or a reduction in the tumor spread (i.e. tumor metastasis) by 10% would also be considered as affective treatments by the methods as disclosed herein.

The term "effective amount" as used herein refers to the amount of at least one agent of pharmaceutical composition to reduce or stop at least one symptom of the abnormal proliferation, for example a symptom of a cancer or malignancy. For example, an effective amount using the methods as disclosed herein would be considered as the amount sufficient to reduce a symptom of the abnormal proliferation, for example at least one symptom of a cancer or malignancy by at least 10%. An effective amount as used herein would also include an amount sufficient to prevent or delay the development of a symptom of the disease, alter the course of a symptom disease (for example but not limited to, slow the progression of a symptom of the disease), or reverse a symptom of the disease.

As used herein, the terms "administering," and "introducing" are used interchangeably and refer to the placement of the agents into a subject by a method or route which results in at least partial localization of the agents at a desired site. The compounds of the present invention can be administered by any appropriate route which results in an effective treatment in the subject.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the formulation.

The term "vector" refers to a nucleic acid molecule capable of transporting another nucleic acid to which it has been linked. Vectors capable of directing the expression of genes and/or nucleic acid sequence to which they are operatively linked are referred to herein as "expression vectors". In general, expression vectors of utility in recombinant DNA techniques are often in the form of "plasmids" which refer to circular double stranded DNA loops which, in their vector form are not bound to the chromosome. Other expression vectors can be used in different embodiments of the invention, for example, but are not limited to, plasmids, episomes, bacteriophages or viral vectors, and such vectors can integrate into the host's genome or replicate autonomously in the particular cell. Other forms of expression vectors known by those skilled in the art which serve the equivalent functions can also be used. Expression vectors comprise expression vectors for stable or transient expression encoding the DNA. A vector can be a plasmid, bacteriophage, bacterial artificial chromosome or yeast artificial chromosome. A vector can be a DNA or RNA vector. A vector can be either a self replicating extrachromosomal vector or a vector which integrate into a host genome.

The term "gene product(s)" as used herein refers to include RNA transcribed from a gene, or a polypeptide encoded by a gene or translated from RNA.

The term "inhibition" or "inhibit" when referring to the gene expression and/or activity or protein of a TUTase recruited by Lin28A, such as Zcchc11 or Zcchc6, or a functional domain thereof, refers to a reduction or prevention in the level of its function or a reduction of its gene expression product.

In some embodiments, agents that inhibit TUTases recruited by Lin28 are nucleic acids. Nucleic acid inhibitors of Lin28-recruited TUTases are for example, but not are limited to, RNA interference-inducing molecules, for example but are not limited to siRNA, dsRNA, stRNA, shRNA and modified versions thereof, where the RNA interference molecule silences the gene expression of a TUTase such as Zcchc11 or Zcchc6. In some embodiments, the nucleic acid inhibitor is an anti-sense oligonucleic acid, or a nucleic acid analogue, for example but are not limited to DNA, RNA, peptide-nucleic acid (PNA), pseudo-complementary PNA (pc-PNA), or locked nucleic acid (LNA) and the like. In alternative embodiments, the nucleic acid is DNA or RNA, and nucleic acid analogues, for example PNA, pcPNA and LNA. A nucleic acid can be single or double stranded, and can be selected from a group comprising nucleic acid encoding a protein of interest, oligonucleotides, PNA, etc. Such nucleic acid sequences include, for example, but are not limited to, nucleic acid sequence encoding proteins that act as transcriptional repressors, antisense molecules, ribozymes, small inhibitory nucleic acid sequences, for example but are not limited to RNAi, shRNAi, siRNA, micro RNAi (mRNAi), antisense oligonucleotides, etc. In general, RNA interference technology is well known in the art, as are methods of delivering RNA interfering agents. See, e.g., U.S. Patent Pub. No. 2010/0221226.

In some embodiments, the method as disclosed herein are useful for the treatment of any disease or disorder characterized by lack or reduced expression of tumor suppressor miRNAs, for example but not limited to let-7 family miRNA, that are mediated by miRNA-binding protein-recruited 3' terminal uridylyl transferases (TUTases), such as Zcchc11 or Zcchc6 or a functional domain thereof.

In one embodiment, a pharmaceutical composition as disclosed herein comprises at least one agent which is an inhibitor of a Lin28A-recruited TUTase can be administered for treatment or prevention of breast cancer. In some embodiments, the pharmaceutical composition as disclosed herein which comprises at least one agent inhibitor of Lin28A-recruited TUTase can be administered for treatment or prevention of, for example but not limited to, breast cancer or prostate cancer.

In addition, the agents and pharmaceutical compositions as disclosed herein comprising inhibitors of a Lin28A-recruited TUTase can also be used for prophylactic treatment of cancer. There are hereditary conditions and/or environmental situations (e.g., exposure to carcinogens) known in the art that predispose an individual to developing cancers, or subjects identified to have increased expression of Lin28A as compared to a reference sample. Under these circumstances, it may be beneficial to treat these individuals with therapeutically effective doses of an agent which inhibit Lin28A-TUTase, such as Zcchc11 or Zcchc6, to reduce the risk of developing cancers. Determination of Lin28A-associated risk is known in the art, as is monitoring Lin28 levels in Lin28-associated cancers. See U.S. Patent Pub. No. 2010/0221266.

In some embodiments, the agents and pharmaceutical compositions as disclosed herein comprising at least one inhibitor of Lin28A-recruited TUTase can be administered in therapeutically effective dosages alone or in combination with at least one other adjuvant cancer therapy such as surgery, chemotherapy, radiotherapy, thermotherapy, immunotherapy, hormone therapy, anti-cancer agent or laser therapy, to provide a beneficial effect, e.g. reducing tumor size, slowing rate of tumor growth, reducing cell proliferation of the tumor, promoting cancer cell death, inhibiting angiogenesis, inhibiting metastasis, or otherwise improving overall clinical condition, without necessarily eradicating the cancer.

The term "chemotherapeutic agent" or "chemotherapy agent" are used interchangeably herein and refers to an agent that can be used in the treatment of cancers and neoplasms, for example brain cancers and gliomas and that is capable of treating such a disorder. In some embodiments, a chemotherapeutic agent can be in the form of a prodrug which can be activated to a cytotoxic form. Chemotherapeutic agents are commonly known by persons of ordinary skill in the art and are encompassed for use in the present invention. For example, chemotherapeutic drugs for the treatment of tumors and gliomas include, but are not limited to: temozolomide (Temodar), procarbazine (Matulane), and lomustine (CCNU). Chemotherapy given intravenously (by IV, via needle inserted into a vein) includes vincristine (Oncovin or Vincasar PFS), cisplatin (Platinol), carmustine (BCNU, BiCNU), and carboplatin (Paraplatin), Mexotrexate (Rheumatrex or Trexall), irinotecan (CPT-11); erlotinib; oxalipatin; anthracyclins-idarubicin and daunorubicin; doxorubicin; alkylating agents such as melphalan and chlorambucil; cisplatinum, methotrexate, and alkaloids such as vindesine and vinblastine.

In another embodiment, the present invention encompasses combination therapy in which subjects identified as having, or increased risk of developing cancer by having increased levels of Lin28A protein or expression as compared to a reference level using the methods as disclosed herein are administered an anti-cancer combination therapy where combinations of anti-cancer agents are used are used in combination with cytostatic agents, anti-VEGF and/or p53 reactivation agent. A cytostatic agent is any agent capable of inhibiting or suppressing cellular growth and multiplication. Examples of cytostatic agents used in the treatment of cancer are paclitaxel, 5-fluorouracil, 5-fluorouridine, mitomycin-C, doxorubicin, and zotarolimus. Other cancer therapeutics include inhibitors of matrix metalloproteinases such as marimastat, growth factor antagonists, signal transduction inhibitors and protein kinase C inhibitors.

The compositions as disclosed herein used in connection with the treatment methods of the present invention are administered and dosed in accordance with good medical practice, taking into account the clinical condition of the individual subject, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including, but not limited to, improved survival rate or more rapid recovery, or improvement or elimination of symptoms and other indicators as are selected as appropriate measures by those skilled in the art.

An agent that inhibits a TUTas recruited by Lin28A can be used as a medicament or used to formulate a pharmaceutical composition with one or more of the utilities disclosed herein. In some embodiments, an agent which inhibits Lin28A-recruited TUTase can be administered in vitro to cells in culture, in vivo to cells in the body, or ex vivo to cells outside of a subject that can later be returned to the body of the same individual or another. Such cells can be disaggregated or provided as solid tissue.

In some embodiments, an agent that inhibits Lin28A-recruited TUTase can be used to produce a medicament or other pharmaceutical compositions. Use of the compositions as disclosed herein comprising an agent inhibiting Lin28-recruited TUTase can further comprise a pharmaceutically acceptable carrier and/or additional components useful for delivering the composition to a subject. Such pharmaceutically acceptable carrier and/or additional components are well known in the art. Addition of such carriers and other components to the agents as disclosed herein is well within the level of skill in this art.

Suitable choices in amounts and timing of doses, formulation, and routes of administration can be made with the goals of achieving a favorable response in the subject with cancer, for example a subject with cancer or a subject at risk thereof (i.e., efficacy), and avoiding undue toxicity or other harm thereto (i.e., safety). Therefore, "effective" refers to such choices that involve routine manipulation of conditions to achieve a desired effect.

The embodiments of the invention described herein are further described by the following numbered paragraphs:

1. A composition for inhibiting Lin28A-mediated let-7 repression comprising an agent that inhibits the interaction of Lin28A with 3' terminal uridylyl transferase (TUTase) or a functional portion thereof.

2. The composition of paragraph 1, wherein the TUTase is Zcchc11 or Zcchc6.

3. A method of inhibiting Lin28A-mediated let-7 repression in a cell comprising contacting said cell with an inhibitor of TUTase.

4. A method of increasing the expression level of let-7 in a tissue in a subject comprising administering a therapeutically effective amount of an inhibitor of a Lin28A-recruited TUTase and a pharmaceutically acceptable carrier, whereby the amount of let-7 in the tissue is increased in the presence of the inhibitor relative to in the absence of the inhibitor.

5. A system for high throughput screening of agents that derepress let-7 expression comprising: a recombinant functional domain of TUTase Zcchc11 or Zcchc6; a recombinant functional domain of Lin28A; a let-7 miRNA precursor; a means for monitoring 3' terminal uridylyl transferase activity; wherein an agent that derepresses let-7 expression inhibits TUTase activity compared with an agent that does not derepress let-7 expression.

6. A method of treating of a Lin28A-expressing cancer in a subject in need thereof, comprising administering a therapeutically effective amount of an inhibitor of a TUTase and a pharmaceutically acceptable carrier, whereby the growth of the Lin28A-expressing cancer is reduced in the presence of the inhibitor.

7. A method of treatment of cancer in a subject in need thereof, the method comprising measuring the level of expression of Lin28A in a cancerous tissue obtained from the subject; and administering a therapeutically effective amount of an inhibitor of a TUTase to the subject when the cancerous tissue is positive for Lin28A expression.

8. A method of inhibiting tumor growth in a subject in need thereof comprising administering a therapeutically effective amount of an inhibitor of a TUTase and a pharmaceutically acceptable carrier, whereby tumor growth is inhibited in the presence of the inhibitor.

9. A method of preventing tumor or cancer metastasis in a subject in need thereof comprising administering a therapeutically effective amount of an inhibitor of a TUTase and a pharmaceutically acceptable carrier, whereby tumor or cancer metastasis is inhibited in the presence of the inhibitor.

10. The method of paragraph 8 or 9, wherein the tumor or cancer in the subject expresses Lin28A.

11. The method of paragraph 8 or 9, further comprising measuring the level of expression of Lin28A in a in a sample of cancerous tissue obtained from the subject prior to administering the TUTase inhibitor.

12. The method of any one of paragraphs 6-11, wherein the TUTase is Zcchc11 or Zcchc6.

13. The method of any one of paragraphs 6-12, wherein the inhibitor inhibits the expression of Zcchc11 or Zcchc6.

14. The method of any one of paragraphs 6-13, wherein the inhibitor inhibits the activity of Zcchc11 or Zcchc6.

15. The method of any one of paragraphs 6-14, wherein the inhibitor is selected from the group consisting of an antibody or a portion, derivative, analog, fragment or variant thereof, a RNA interference molecule, a small molecule, a peptide and an aptamer.

16. The method of paragraph 15, wherein the inhibitor is a RNA interference molecule.

17. The method of paragraph 16, wherein the RNA interference molecule is a short-hairpin RNA.

18. The method of paragraph 17, wherein the RNA interference molecule is a short-hairpin RNA directed specifically against the Zcchc11 gene or the Zcchc6 gene.

19. The method of any one of paragraphs 6-18, wherein the cancer is colon, breast, ovarian, or prostate cancer.

20. A method of increasing the expression level of let-7a in a tissue in a subject comprising administering a therapeutically effective amount of an inhibitor of a TUTase and a pharmaceutically acceptable carrier, whereby the amount of let-7a in the tissue is increased in the presence of the inhibitor relative to in the absence of the inhibitor.

21. The method of paragraph 20, wherein the tissue is colon, prostate, ovarian, or breast tissue.

22. The method of paragraph 20, wherein the subject is diagnosed with cancer.

23. The method of paragraph 21, wherein the tissue is a cancerous tissue.

24. The method of any one of paragraphs 20-23, wherein the tissue in the subject expresses Lin28A.

25. The method of paragraph 20 further comprising measuring the level of expression of Lin28A in a sample of the tissue obtained from the subject prior to administering the inhibitor.

26. The method of any one of paragraphs 20-25, wherein the TUTase is Zcchc11 or Zcchc6.

27. The method of any one of paragraphs 20-26, wherein the inhibitor inhibits the expression of Zcchc11 or Zcchc6.

28. The method of any one of paragraphs 20-27, wherein the inhibitor inhibits the activity of Zcchc11 or Zcchc6.

29. The method of any one of paragraphs 20-28, wherein the inhibitor is selected from the group consisting of an antibody, a portion of an antibody, a RNA interference molecule, a small molecule, a peptide, and an aptamer.

30. The method of paragraph 29, wherein the inhibitor is a RNA interference molecule.

31. The method of paragraph 30, wherein the RNA interference molecule is a short-hairpin RNA.

32. The method of paragraph 25, wherein the RNA interference molecule is a short-hairpin RNA directed specifically against the Zcchc11 gene.

33. The method of paragraph 25, wherein the RNA interference molecule is a short-hairpin RNA directed specifically against the Zcchc6 gene.

34. The method of any one of paragraphs 20-33, wherein the expression level of let-7a level in the tissue is increased by at least 2-fold.

35. The method of any one of paragraphs 20-33, wherein the expression level of let-7a level in the tissue is increased by about 2- to about 10-fold.

EXAMPLES

Example 1

Characterization of the Molecular Mechanisms of the Lin28/Let-7 Axis

Cloning:

Myc-Lin28A and -Lin28B were cloned into pBK-EF1. Lin28A, Lin28B, and Lin28BDNLS#1 were cloned into pFLAG-CMV2 vector (Sigma). Lin28BD NoLSDNLS#1 was generated by site-directed mutagenesis using the Quick Change kit (Stratagene). Lin28A, Lin28B, Lin28BDNLS#1, and Lin28BD NoLSDNLS#1 were cloned into CT-GFP-Topo (Invitrogen). NLS#1 and NLS#2 oligos were annealed before ligating into CT-GFP-Topo. N-terminal Cherry-DGCR8 fusion construct was generated by subcloning Cherry cDNA into p3xFLAG-CMV14-DGCR8. Gregory et al., 2004. Lin28A and Lin28B were subcloned into Pet21 for His-tagged recombinant protein expression. Pri-let-7g was previously reported. Viswanathan et al., 2008). Cloning primers are listed in Table 1:

TABLE 1

| Primers | | SEQ ID NO: |
|---|---|---|
| Cloning to pBK-EF1 | | |
| Myc-Lin28A AgeI For | TGCAGACCGGTGAGCAGAAACTCATAAGCGAAGAGGACCTGGGCTCCGTGTCCAACCAG | 23 |
| Myc-Lin28A HindIII Rev | GACATGAAGCTTTCAATTCTGTGCCTCCGGGAG | 24 |
| Myc-Lin28B AgeI For | TGCAGACCGGTGAGCAGAAACTCATAAGCGAAGAGGACCTGGCCGAAGGCGGGGCTAG | 25 |
| Myc-Lin28B XbaI Rev | TACGATTCTAGATTATGTCTTTTTCCTTTTTTGAACTGAAGGC | 26 |
| Myc-Lin28BΔNLS#1 Rev | AGTCTATCTAGATTAGCTTTGCTCTTCTGGTGC | 27 |

TABLE 1-continued

| Primers | | SEQ ID NO: |
|---|---|---|
| Site-directed mutagenesis Lin28B NoLS | | |
| Lin28B Mut1 For | GACACTACAGGGAAGAGGACCAGGGGGAGATAG | 28 |
| Lin28B Mut1 Rev | CTATCTCCCCCTGGTCCTCTTCCCTGTAGTGTC | 29 |
| Lin28B Mut2 For | GGAAGTGAAAGAGGACCCGGAGGGAAGACACTA | 30 |
| Lin28B Mut2 Rev | TAGTGTCTTCCCTCCGGGTCCTCTTTCACTTCC | 31 |
| Cloning to pFlag-CMV2 | | |
| Lin28A XbaI For | TATCGATCTAGAGGCTCCGTGTCCAACCAGCAG | 32 |
| Lin28A BamHI Rev | TATCGAGGATCCTTAATTCTGTGCCTCCGGGAGCAGGG | 33 |
| Lin28B XbaI For | TATCGATCTAGAGCCGAAGGCGGGGCTAGCAAAG | 34 |
| Lin28B BamHI Rev | CTCGCAGGATCCTTATGTCTTTTTCCTTTTTTGAACTG | 35 |
| Lin28BΔNLS#1 BamHI Rev | CGTCAGGGATCCTTAGCTTTGCTCTTCTGGTGC | 36 |
| Cloning Primers for CT-GFP-Topo | | |
| Lin28A For | GCCGCCATGGGCTCCGTGTCCAACCAGC | 37 |
| Lin28A Rev | CATTCTGTGCCTCCGGGAGCAG | 38 |
| Lin28B For | GCCGCCATGGCCGAAGGCGGGGCTAGC | 39 |
| Lin28B Rev | CTGTCTTTTTCCTTTTTTGAACTG | 40 |
| Lin28BΔNLS#1 Rev | AAACTGAAGGCCCCTTTTTGC | 41 |
| NLS#1For | GCCGCCATGAAAAAGGGGCCTTCAGTTCAAAAAAGGAAAAAGACAGA | 42 |
| NLS#1Rev | TCTGTCTTTTTCCTTTTTTGAACTGAAGGCCCCTTTTTCATGGCGGCA | 43 |
| NLS#2For | GCCGCCATGGGAAGAAGACCCAAAGGGAAGACACTACAGAAAAGAAAACCAAAGGA | 44 |
| NLS#2Rev | CCTTTGGTTTTCTTTTCTGTAGTGTCTTCCCTTTGGGTCTTCTTCCCATGGCGGCA | 45 |
| Cloning to Pet21a(+) | | |
| His-Lin28A-BamHI For | GGATCCcatcatcaccatcaccacGGCTCCGTGTCCAACCAGCAG | 46 |
| Lin28A-NotI Rev | GCGGCCGCTTACAGTTTGCGTACCAATAAG | 47 |
| His-Lin28B-BamHI For | GGATCCcatcatcaccatcaccacGCCGAAGGCGGGGCTAGCAAAG | 48 |
| Lin28B-NotI Rev | TTATGTCTTTTTCCTTTTTTGAAC | 49 |

TABLE 1-continued

Primers

| | | SEQ ID NO: |
|---|---|---|
| q.RT-PCR Primers | | |
| hsa-pri-let-7g For | AGCGCTCCGTTTCCTTTT | 50 |
| hsa-pri-let-7g Rev | CCCCACTTGGCAGCTG | 51 |
| hsa-pri-let-7a-1 For | CCTGGATGTTCTCTTCACTG | 52 |
| hsa-pri-let-7a-1 For | GCCTGGATGCAGACTTTTCT | 53 |
| hsa-pri-mir-21 For | GCTTATCAGACTGATGTTGACTG | 54 |
| hsa-pri-mir-21 Rev | CAGCCCATCGACTGGTG | 55 |
| U6 For | CTCGCTTCGGCAGCACA | 56 |
| U6 Rev | AACGCTTCACGAATTTGCGT | 57 |
| Lin28A For | AAGCGCAGATCAAAAGGAGA | 58 |
| Lin28A Rev | CTGATGCTCTGGCAGAAGTG | 59 |
| Lin28B For | TGATAAACCGAGAGGGAAGC | 60 |
| Lin28B Rev | TGTGAATTCCACTGGTTCTCC | 61 |
| GAPDH For | ATGTTCGTCATGGGTGTGAA | 62 |
| GAPDH Rev | GGTGCTAAGCAGTTGGTGGT | 63 |

TABLE 2 shRNAs used for knockdown

| Control shRNA#1 | ACCGGCAACAAGATGAAGAGCACCAACTCGAGT TGGTGCTCTTCATCTTGTTGTTTTGAATTC | SEQ ID NO: 64 |
| Control shRNA#2 | ACCGGGCCCGCAAGCTGACCCTGAAGTTCATTC AAGAGATGAACTTCAGGgTCAGCTTGCTTTTTG AATTC | SEQ ID NO: 65 |
| Control shRNA#3 | ACCGGGTCGGCTTACGGCGGTGATTTCTCGAGA AATCACCGCCGTAAGCCGACTTTTTGAATTC | SEQ ID NO: 66 |
| Zcchc11 shRNA #1 | ACCGGGTCAGTTACATTCAGCAGAAACTCGAGT TTCTGCTGAATGTAACTGACTTTTTGAATTC | SEQ ID NO: 67 |
| Zcchc11 shRNA #2 | ACCGGCGTGATAGTGATCTGGATATTCTCGAGA ATATCCAGATCACTATCACGTTTTTGAATTC | SEQ ID NO: 68 |
| Zcchc11 shRNA #3 | ACCGGGCTTCTGACCTTAATGATGATCTCGAGA TCATCATTAAGGTCAGAAGCTTTTTGAATTC | SEQ ID NO: 69 |
| Zcchc11 shRNA #4 | ACCGGGCAACAGACATGTACAGATAACTCGAGT TATCTGTACATGTCTGTTGCTTTTTGAATTC | SEQ ID NO: 70 |
| Lin28A shRNA | ACCGGGAACCCTTCCATGTGCAGCTTTTCAAG CTGCACATGGAAGGGTTCCTTTTTTGAATTC | SEQ ID NO: 71 |
| Lin28B shRNA | CCGGGCCTTGAGTCAATACGGGTAACTCGAGTT ACCCGTATTGACTCAAGGCTTTTTG | SEQ ID NO: 72 |

Immunoprecipitation and Western Blotting:

Whole cell lysates were prepared using lysis buffer (20 mM Tris/pH8.0, 137 mM NaCl, 1 mM EDTA, 1% Triton X100, 10% Glycerol, 1.5 mM MgCl2, 1 mM DTT, with protease inhibitors (Roche)). Flag-immunoprecipitations were done using Flag-agarose beads (Sigma) for 90 min at 4° C. Beads were washed with Buffer containing 300 mM KCl (BC300). Elutions were done with Flag peptide (Sigma). Anti-Flag-HRP Antibody (Sigma, A8592) was used at 1:1000 dilution in 5% milk for an hr. For myc-immunoprecipitation, myc-antibody (Covance, PRB-150C) was added to Protein G-agarose beads (Sigma). Myc-IP was performed overnight at 4° C. Anti-myc antibody was used at 1:1000 in 5% milk. Secondary anti-mouse IgG-HRP (Sigma, A9044) was used in 2.5% milk at 1:10000 dilution for an hr. For endogenous protein western blots, concentration of cell lysates was measured using Bradford reagent (Biorad).

The following antibodies were used: Lin28A (Cell Signaling, 3978), Lin28B (Cell Signaling, 4196), Zcchc11 (Protein Tech Group, 18980-1-AP), DGCR8 (Protein Tech Group, 10996-1-AP) at 1:1000 and β-Tubulin (Abcam AB6046) at and 1:5000. Secondary anti-rabbit IgG-HRP (Sigma #A9169) secondary antibodies were used at 1:10, 000 dilutions in 2.5% milk. Antibody against Zcchc11 (Imgenex, IMX-3587) was used at 1:1,000 and a donkey anti-goat IgG-HRP (Santa Cruz, sc-2033) secondary antibody was used at 1:5,000. Antibody for Fibrillarin (Abcam, ab18380) was used at 1:1,000 in 5% milk, and anti-mouse IgG-HRP (Sigma) was used at 1:10,000 in 2.5% milk.

Cell Culture:

HEK293, Hela, H1299, Igrov1, HepG2, T47D, MDA-MB-231, CaCO2, and SK_Mel_28 cells were maintained in DMEM (Gibco, Invitrogen), supplemented with 10% FBS, Pen/Strep, L-Glutamine and Non-essential Amino Acids (Gibco, Invitrogen). K562 cell line was grown in IMDM (Gibco, Invitrogen) with the same supplements. MCF10A cells containing the ER-Src fusion protein were grown in DMEM/F12 medium supplemented with 5% donor HS, 20 ng/ml epidermal growth factor (EGF), 10 mg/ml insulin, 100 mg/ml hydrocortisone, 1 ng/ml cholera toxin, and 50 units/ml pen/strep, with the addition of puromycin. Iliopoulos et al., 2009). To induce transformation, the Src oncogene was activated by the addition of 1 mM tamoxifen (Sigma, St. Louis) to confluent cell cultures.

Subcellular Fractionation:

Cellular fractionation was done with the NE-PER Nuclear and Cytoplasmic Extraction Kit (Pierce). Cells were grown on 3.5 mm dishes and harvested per manufacturer's instructions. Large-scale fractionation of Nucleoli was performed as as follows: Cells pellets were resuspended in an equal volume of buffer A [10 mM Tris, (pH 8.0), 1.5 mM MgCl2, 10 mM KCl, 0.5 mM DTT, 0.2 mM PMSF]. Cells were incubated for 10 min on the rotator, pelleted and resuspended in 2 vol. of buffer A. Cells were manually homogenized with a pestle, spun down to pellet the nuclei. Nuclei were resuspended in buffer C [20 mM Tris, (pH 7.9), 25% Glycerol, 0.42M NaCl, 1.5 mM MgCl2, 0.2 mM EDTA, 0.5 mM DTT, 0.5 mM PMSF] and homogenized with a pestle. Nuclei were incubated on the rotator for 30 min at 4° C., and spun down at 12,000 rpm for 30 min to pellet nucleoli. Nucleoli were resuspended in buffer E [50 mM Tris, (pH 7.9), 25% Glycerol, 0.5 mM EDTA, 5 mM MgCl$_2$], homogenized with a pestle and spun down to separate the soluble and insoluble fractions. The nucleolar pellet fraction was resuspended in Lysis buffer (20 mM Tris (pH 8.0), 137 mM NaCl, 1 mM EDTA, 1% Triton X100, 10% Glycerol, 1.5 mM MgCl$_2$, 1 mM DTT, with protease inhibitors (Roche)].

RNA Extraction and qPCR:

RNA was harvested from cells and from xenograft tumors on day 30 using Trizol (Invitrogen) per manufacturer's instructions. TaqMan miRNA assays (Applied Biosystems) were used to quantify mature miRNA expression as described previously (Hagan et al., 2009). Pri-miRNA levels were analyzed by qPCR. First, gene specific cDNA was made with the reverse primer for each pri-miRNA, using SuperScriptIII cDNA Synthesis Kit (Invitrogen). cDNA was used for qPCR with iQ SYBRGreen Supermix (BioRad). U6 was used as a normalizer.

Recombinant Lin28A and Lin28B Protein Purification and EMSA:

Transformed BL21-CodonPlus® Competent bacteria (Stratagene) were grown to an OD600 nm of 0.4-0.6. Expression was induced 100 µM IPTG for 2-3 hours. Cell pellets were resuspended in cold lysis buffer [20 mM imidazole pH 8.0 in PBS, 0.1% Phenylmethyl sulfonyl fluoride (PMSF)] and sonicated. Cleared lysates were incubated with Ni-NTA beads and after 90 min incubation at 4° C. the beads were washed with 80-column-vol. wash buffer [10 mM Tris (pH 7.8), 50 mM imidazole pH 8.0, 500 mM NaCl, 0.1% PMSF). Bound His-tagged proteins were eluted from the column with 1 volume elution buffer [10 mM Tris (pH 7.8), 500 mM imidazole pH 8.0, 500 mM NaCl, 0.1% fresh PMSF] and dialyzed overnight against BC100 [20 mM Tris-HCl (pH 7.8), 100 mM KCl, 0.2 mM EDTA, 10% glycerol]. EMSA with end-labeled synthetic pre-let-7 RNA was performed as described but without competitor yeast tRNA (Piskounova et al., 2008). Briefly, reactions were set up in binding buffer [50 mM Tris, (pH7.5), 100 mM NaCl, 10 mM βMe, 20 U RNaseIN (Promega)] with 0.5 nM end-labeled pre-let-7g and incubated for 45 min at room temperature. Bound complexes were resolved on native 5% polyacrylamide gels and visualized by radiography. Band intensities of scanned gels were quantified using ImageJ software and used to calculate percentage of probe bound. Graph-Pad Prism was used to plot the data. For both recombinant Lin28A and Lin288B, the percent active protein was EMSA with purified His-Lin28A/B was performed as described but without competitor yeast tRNA. Piskounova et al., 2008. Complexes were resolved on native 3.5% or 5% polyacrylamide gels and visualized by autoradiography. Band intensities of scanned gels were quantified using ImageJ software and used to calculate percentage of probe bound. Graph-Pad Prism was used to plot data. Percent active protein was determined using stoichiometric binding reactions as described in Ryder et al. (2008) Hills equation for specific binding with one site, $Y=Bmax*X^h= ðKD^h+X^h Þ$, was used to calculate KD.

RNA-Immunoprecipitation (RIP):

Hela cells were transfected with Flag-constructs of Lin28A and Lin28B, or empty Flag-plasmid for 48 hr. Flag-immunoprecipitations were done using Flag-agarose beads (Sigma) for 90 min at 4° C. Beads were washed with BC500. RNA was eluted from the beads with Trizol. RNA was extracted following manufacturer's protocol. Pri-microRNA levels were analyzed by q.RT-PCR. Error was shown as SEM, n=3.

Immunofluorescence:

Cells were grown on coverslips for 24-48 hr, before fixing with 4% paraformaldehyde for 20 min at room temperature. Cells were then blocked and permeabilized with 5% serum with 0.2% Triton for 20 min at room temperature. Cells were incubated at 4° C. overnight with primary antibodies at 1:400 dilutions. The next day, cells were washed with PBS and incubated with the secondary antibodies at 1:400 dilution for 1 hr (Invitrogen, Anti-mouse A21202, Anti-Rabbit A21207), in the dark at room temperature. The cover slips were mounted with Vectashield mounting solution with DAPI (VectorLabs). For GFP-fusions, the Topo CT-GFP cloning kit (Invitrogen) was used. Cells were transfected with GFP-fusion constructs, and after 48 hr fixed as described above. Cells were washed with PBS three times, the last wash contained 0.2% Triton. Coverslips were mounted as described herein.

Phase-Contrast Images:

In order to study the morphological changes and phenotypic transformation of MCF10A ER-Src TAM-induced (36 hr) cells, phase-contrast pictures were taken in a microscope (10× objective). Furthermore, phase-contrast pictures were taken MCF10A ER-Src cells induced by TAM for 36 h and simultaneously treated with an siRNA against Lin28B (siLin28B) (100 nM), a monoclonal antibody against IL6 (Ab-IL6) (2 ug/ml) (Mab206, R&D Systems) or a siRNA against Zcchc11 (siZcchc11#1) (100 nM). Cell morphology was assessed by phase contrast microscopy (10× objective), and percentage of transformed ER-Src cells was calculated by evaluation of cell morphology by Metamorph v5.0 software.

Colony Formation Assay:

MDA-MB-231 cells and T47D cells were transfected with different siRNAs for 48 hr. Triplicate samples of 105 cells from each cell line were mixed 4:1 (v/v) with 2.0% agarose in growth medium for a final concentration of 0.4% agarose. The cell mixture was plated on top of a solidified layer of 0.5% agarose in growth medium. Cells were fed every 6 to 7 days with growth medium containing 0.4% agarose. The number of colonies was counted after 20 days.

MCF10A ER-Src transformed cells, MDA-MB-231 cells and T47D cells were transfected with different siRNAs for 48 hr. The siRNAs used in this experiment were the following: i) siRNA negative control (siRNA NC) (100 nM), (cat no. AM4611, Ambion Inc); ii) siRNA against Zcchc11 (siZcchc11#1) (100 nM) (cat no. s23551, Ambion Inc); iii) siRNA against Zcchc11 (siZcchc11#2) (100 nM) (cat no. s23553, Ambion Inc); iv) siRNA against Lin28B (siLin28B) (100 nM) (cat no. s52477, Ambion Inc); v) siRNA against Lin28A (siLin28A) (100 nM) (cat no. s36195, Ambion Inc). Then, triplicate samples of $10^5$ cells from each cell line were mixed 4:1 (v/v) with 2.0% agarose in growth medium for a final concentration of 0.4% agarose. The cell mixture was plated on top of a solidified layer of 0.5% agarose in growth medium. Cells were fed every 6 to 7 days with growth medium containing 0.4% agarose. The number of colonies was counted after 20 days. The experiment was repeated thrice and the statistical significance was calculated using Student's t test.

Interleukin 6 ELISA Assay:

The concentration of interleukin 6 released to the supernatant of MCF10A ER-Src TAM-treated (36 hr) cells treated together with 100 nM siRNA NC, or siZcchc11#1 or siZcchc11#2 or siLin28B was measured via IL6 ELISA assays (cat no. D6050), according to manufacturer instructions (R&D Systems).

Invasion Assays:

invasion assays were performed in MDA-MB-231, and T47D breast cancer cells were transfected with different siRNAs for 16 hr. Invasion of matrigel was conducted by using standardized conditions with BDBioCoat growth factor-reduced MATRIGEL invasion chambers (PharMingen). Assays were conducted per manufacturer's protocol, using 10% FBS as chemoattractant. Noninvading cells on the top side of the membrane were removed, whereas invading cells were fixed and stained with 40-6-diamidino-2-phenylindole (DAPI, Vector Laboratories Inc.), 16 hr post-seeding.

Mouse Experiments:

(a) 5×10⁶ MCF10A ER-Src TAM-treated (36 h) cells were injected subcutaneously in the right flank of athymic nude mice (Charles River Laboratories). Tumor growth was monitored every 5 days and tumor volumes were calculated by the equation $V(mm^3)=a \times b2/2$, where a is the largest diameter and b is the perpendicular diameter. When the tumors reached a size of ~100 mm3 (day 15) were randomly distributed in four groups (5 mice/group). The first group was used as control (non-treated), the second group was i.p treated with 5 mg/kg siRNA negative control, the third group was i.p treated with 5 mg/kg siZcchc11#1 and the fourth group was i.p. treated with 5 mg/kg siLin28B. Tumor volumes were monitored for 45 days.

(b) 2×10⁶ MDA-MB-231 cells were injected subcutaneously in the right flank of athymic nude mice (Charles River Laboratories). Tumor growth was monitored every five days. When the tumors reached a size of ~100 mm3 (day 15) were randomly distributed in five groups (5 mice/group). The first group was used as control (non-treated), the second group was i.p treated with 5 mg/kg siRNA negative control, the third group was i.p treated with 5 mg/kg siZcchc11#1 and the fourth group was i.p. treated with 5 mg/kg siLin28B and the fifth group was i.p. treated with 5 mg/kg let-7a microRNA. Tumor volumes were monitored for 45 days.

(c) 2×10⁶ T47D cells were injected subcutaneously in the right flank of athymic nude mice (Charles River Laboratories). Tumor growth was monitored every 5 days. When the tumors reached a size of ~100 mm³ (day 15) were randomly distributed in five groups (5 mice/group). The first group was used as control (non-treated), the second group was i.p treated with 5 mg/kg siRNA negative control, the third group was i.p treated with 5 mg/kg siZcchc11#1 and the fourth group was i.p. treated with 5 mg/kg siLin28A and the fifth group was i.p. treated with 5 mg/kg let-7a microRNA. Tumor volumes were monitored for 45 days.

(d) 10⁶ HepG2 cells were injected subcutaneously in the right flank of athymic nude mice (Charles River Laboratories). Tumor growth was monitored every five days. When the tumors reached a size of ~200 mm3 (day 15) were randomly distributed in four groups (5 mice/group). The first group was used as control (non-treated), the second group was i.p treated with 5 mg/kg siRNA negative control, the third group was i.p treated with 5 mg/kg siZcchc11#1 and the fourth group was i.p. treated with 5 mg/kg siLin28B. Tumor volumes were monitored for 45 days.

(e) 5×10⁶ H1299 cells were injected subcutaneously in the right flank of athymic nude mice (Charles River Laboratories). Tumor growth was monitored every 5 days. When the tumors reached a size of ~200 mm3 (day 15) were randomly distributed in four groups (5 mice/group). The first group was used as control (non-treated), the second group was i.p treated with 5 mg/kg siRNA negative control, the third group was i.p treated with 5 mg/kg siZcchc11#1 and the fourth group was i.p. treated with 5 mg/kg siLin28B. Tumor volumes were monitored for 45 days.

(f) 2×10⁶ Igrov1 cells were injected subcutaneously in the right flank of athymic nude mice (Charles River Laboratories). Tumor growth was monitored every five days. When the tumors reached a size of ~180 mm3 (day 15) were randomly distributed in four groups (5 mice/group). The first group was used as control (non-treated), the second group was i.p treated with 5 mg/kg siRNA negative control, the third group was i.p treated with 5 mg/kg siZcchc11#1 and the fourth group was i.p. treated with 5 mg/kg siLin28A. Tumor volumes were monitored for 45 days.

(g) 5×10⁶ SK_MEL_28 melanoma cells were injected subcutaneously in the right flank of athymic nude mice (Charles River Laboratories). Tumor growth was monitored every five days. When the tumors reached a size of ~200 mm3 (day 15) were randomly distributed in four groups (5 mice/group). The first group was used as control (non-treated), the second group was i.p treated with 5 mg/kg siRNA negative control, the third group was i.p treated with 5 mg/kg siZcchc11#1 and the fourth group was i.p. treated with 5 mg/kg siLin28B. Tumor volumes were monitored for 45 days.

(h) 5×10⁶ CaCO2 colon cancer cells were injected subcutaneously in the right flank of athymic nude mice (Charles River Laboratories). Tumor growth was monitored every five days. When the tumors reached a size of ~180 mm3 (day 15) were randomly distributed in four groups (5 mice/group). The first group was used as control (non-treated), the second group was i.p treated with 5 mg/kg siRNA negative control, the third group was i.p treated with 5 mg/kg siZcchc11#1 and the fourth group was i.p. treated with 5 mg/kg siLin28B. Tumor volumes were monitored for 45 days.

All the experiments described here used In Vivo Ready siRNAs from Ambion Inc which are high-quality siRNAs that are purified especially for introduction into animals. Each siRNA strand is individually purified by HPLC, desalted, and annealed with its complementary strand. In Vivo Ready siRNAs are then further purified using a process that removes excess salt via a semi-permeable membrane. The result is a highly pure siRNA with minimal salt content, suitable for in vivo applications. These siRNAs are then filtered through a 0.2-µm pre-sterilized filter and tested for the presence of endotoxin. Next, we mixed the siRNAs with Invivofectamine 2.0 liposomes (Ambion Inc) and injected them in mice in a volume of 100 ul using a 20 G needle. The experiments described above were performed in accordance with Dana-Farber Institutional Animal Care and Use Committee procedures and guidelines.

Real-Time RT-PCR Analysis for Human Cancer Tissues:

Real-time RT-PCR was performed to determine the expression levels of let-7a in human colon and breast normal tissues and carcinomas. RNA was isolated, using Trizol (15596-026, Invitrogen). Reverse Transcription was carried out using the Universal cDNA synthesis kit (203300). Real-time PCR was carried out in triplicate using the SYBR Green master mix (203450) and primer for let-7a (204775, Exiqon) in a CFX384 Real Time PCR detection system (Bio-Rad). Let-7a expression levels were normalized to the levels of U6 snRNA (203907, Exiqon). Furthermore, RNAs were purchased from Origene from the following cancer tissues (8 renal cell carcinomas, 8 hepatocellular carcinomas, 8 squamous cell lung carcinomas, 8 ovarial adenocarcinomas, 8 prostate adenocarcinomas, 8 papillary thyroid carcinomas) and were used to test Lin28A and Lin28B mRNA expression levels. Real time RT-PCR was employed to determine the expression levels of Lin28A and Lin28B. Reverse Transcription was carried out using the Retroscript Kit (AM1710, Applied Biosystems). Real time PCR for was carried out using IQ SYBR Green supermix (170-8882, Bio-Rad). Glyceraldehyde-3-phosphate dehydrogenase (GAPDH) was used as the internal control.

NF-kB/p65 ActivELISA Assay:

The NF-kB/p65 ActivELISA Kit measured nuclear p65 levels in nuclear protein lysates derived from 12 breast cancer tissues purchased from AMS Biotechnology Inc and Biochain Inc. The anti-p65 antibody coated plate captures free p65 and the amount of bound p65 is detected by adding a second anti-p65 antibody followed by alkaline phosphatase (AKP)-conjugated secondary antibody using colorimetric detection in an ELISA plate reader at absorbance 405 nm. Each sample was loaded on triplicate and data are presented as mean±SD.

In Situ microRNA Hybridization:

Double-DIG labeled Mircury LNA Detection probe for the detection of hsa-let-7 (1800-15, Exiqon) by in situ hybridization, was used as previously described (Iliopoulos et al., 2009) with modifications. Sections of colon adenocarcinomas and adjacent uninvolved tissues were deparaffinized with xylene (3×5 min), followed by treatment with serial dilutions of ethanol (3×100%, 2×96% and 3×70%) and by two changes of DEPC-PBS. Tissues were then digested with proteinase K (15 μg/ml) for 20 min at 37° C., rinsed with 3×DEPC-PBS. Sections were dehydrated with 2×70%, 2×96% and 2×100% ethanol, air-dried and hybridized for 1 hour with the hsa-let-7 probe (40 nM) or the double-DIG labeled U6 Control Probe (99002-15) diluted in microRNA ISH buffer (90000, Exiqon), at 54° C. Following hybridization, sections were rinsed twice with 5×SSC, 2×1×SSC and 3×0.2×SSC, 5 min each, at 54° C., and PBS. The slides were incubated with blocking solution (11585762001, Roche) for 15 min and then with anti-DIG antibody (1:800) in 2% sheep serum (013-000-121, Jackson Immunoresearch) blocking solution for 1 hour, at RT. Following three washes with PBS-T (PBS, 0.1% Tween-20), slides were incubated with the AP substrate buffer (NBT-BCIP tablet [11697471001, Roche] in 10 ml 0.2 mM Levamisole [31742, Fluka]) for 2 hr at 30° C. in the dark. The reaction was stopped with two washes of AP stop solution (50 mM Tris-HCl, 150 mM NaCl, 10 mM KCl) and 2 washes with water. Tissues were counter stained with Nuclear Fast Red for 1 min and rinsed with water. At the end, sections were dehydrated with 2×70%, 2×96% and 2×100% ethanol and mounted with coverslips in Eukitt mounting medium (361894G, VWR). Images were captured with a Nikon 80i Upright Microscope equipped with a Nikon Digital Sight DS-Fi1 color camera, using the NIS-Elements image acquisition software. All images were captured and processed using identical settings.

Immunohistochemistry:

Sections of the colon adenocarcinomas and adjacent uninvolved tissues were deparaffinised with xylene (3×5 min) followed by treatment with serial dilutions of ethanol (100%, 100%, 95% and 95%, 10 min each) and by two changes of ddH2O. Antigen unmasking was achieved by boiling the slides (95-99° C.) for 10 min, in 10 mM sodium citrate, pH 6.0. Sections were then rinsed three times with ddH2O, immersed in 3% $H_2O_2$ for 10 min, washed twice with ddH2O and once with TBS-T (TBS, 0.1% Tween-20) and blocked for 1 hour with blocking solution (5% normal goat serum [5425, Cell Signaling Technology] in TBS-T). Lin28A (3978, Cell Signaling Technology) and Lin28B (LS-B3423, LSBio) antibodies were diluted 1:50 in signal stain antibody diluent (8112, Cell Signaling Technology) and 1:100 in blocking solution respectively, and incubated with the sections overnight at 4° C. Following incubation with the antibodies, sections were washed three times, 5 min each, with TBS-T and incubated for 1 hour at room temperature with anti-rabbit biotin antibody (LS-D1, LSBio) diluted in blocking solution (1:300). Sections were washed three times, 5 min each, with TBS-T, incubated with the Vectastain ABC-AP reagent (AK-5000) for 30 min, washed and stained with the Vector Red Alkaline Phosphatase Substrate Kit (SK-5100), and with the hematoxylin QS counterstain (H-3404, Vector Laboratories). Finally tissues were dehydrated and mounted in Eukitt medium.

Human Tissues and RNAs:

Thirty normal colon tissues and 45 colon adenocarcinomas were collected from the translational pathology core laboratory of the Department of Pathology at UCLA. All subjects gave informed consent, and the study was approved by the UCLA Institutional Review Board. RNAs from twelve normal mammary tissues and 33 breast cancer tissues were purchased from Origene Inc. The ER, PR, and HER2 status for each of these breast carcinomas was known. Additional RNAs were purchased from Origene (8 each of renal cell carcinomas, hepatocellular carcinomas, squamous cell lung carcinomas, ovarial adenocarcinomas, prostate adenocarcinomas, papillary thyroid carcinomas).

Example 2

Molecular Characterization of Lin28/TUTase/Let-7 Interactions

Cloning:

All mZcchc11 mammalian-expression mutants were cloned into the XhoI and SalI sites of pBK_2× Flag EF1 vector. C326/329A mutant Zcchc11 was generated by site-directed mutagenesis using the QuickChange kit (Stratagene). hZcchc6 was amplified from HEK293 cDNA and cloned into the HindIII and BamHI sites of pFLAG-CMV2 (Sigma). For recombinant protein expression ΔPneumoG/C mZcchc11 was cloned into the SalI and NotI sites of pETDUET-1. Recombinant mZcchc11 C2H2 was cloned into the EcoRI and HindIII sites of pETDUET-1. Expression constructs for Flag-m.Lin28A, Flag-Lin28A, Flag-Lin28B, recombinant His-Lin28A, Flag-hZcchc11 wild-type and D1026/1028A mutant were described previously (Hagan et al., 2009; Piskounova et al., 2011; Piskounova et al., 2008; Viswanathan et al., 2008). Cloning primers are listed in Supplementary Table 3:

TABLE 3

| TUTase Lin28 cloning primers | |
|---|---|
| mZcchc11 ΔPneumo G XhoI F | TGCCGCCTCGAGGTTTCTATGGA-TAAAAGGAAGA GTGAA (SEQ ID NO: 73) |
| mZcchc11 N-PAP (ΔC2H2) XhoI F | TGCCGCCTCGAGCTTCGGTCTCTTCCATCTC-CTT (SEQ ID NO: 74) |
| mZcchc11 ΔTftF4 SalI F | TGCCGCCTCGAGTGCTTACTTGGAAGTTG-GATTG AAGG (SEQ ID NO: 75) |
| mZcchc11 N-PAP SalI ft | TGCCGCGTCGACTTGCTTTAAGTCACTGC-CTCCA C (SEQ ID NO: 76) |
| mZcchc11 PUP XhoI F | TGCCGCCTCGAGTCCCAGGAATTATATTAT-GTGT TTGATAAGTT (SEQ ID NO: 77) |
| mZcchc11 PUP (ΔC) SalI ft | TGCCGCGTCGACTTCTGAAGACTGTCTGGTC-CTT ATG (SEQ ID NO: 78) |
| mZcchc11 ΔCCHC3 SalI ft | GTCGACGTCACGGGAGTCTTTTTCTTCTTC (SEQ ID NO: 79) |

TABLE 3-continued

TUTase Lin28 cloning primers

| | |
|---|---|
| mZcchc11 ΔCCHC2 SalI ft | TGCCGCGTCGACATGATTCAAGT-CAAAAGGATCTTCAATTG (SEQ ID NO: 80) |
| mZcchc11 ΔPAP-Assoc SalI ft | GTCGACTCTCTGCGGAATCTGCTTCCC (SEQ ID NO: 81) |
| mZcchc11 C326/329A F | TGCCGCTATCTAGCCAAACTTGCCTTAAT-TCACATT (SEQ ID NO: 82) |
| mZcchc11 C326/329A ft | AATGTGAATTAAGGCAAGTTTGGCTAGA-TAGCGGCA (SEQ ID NO: 83) |
| mZcchc11 ΔPneumo G/C | CGATGCGTCGACGACTACAAGGATGACGAT-GACAAAGTTTCTA (SEQ ID NO: 84) |
| SalI Flag recomb. F | TGGATAAAAGGAAGAGTGAA (SEQ ID NO: 85) |
| mZcchc11 ΔPneumo G/C NotI Flag recomb. ft | GCGGCCGCTTCTGAAGACTGTCTGGTCCTTATG (SEQ ID NO: 86) |
| mZcchc11 r.C2H2 EcoftI F | GTAGCGGAATTCGTTTGTTTCTATGGA-TAAAAGGAAGAGTGAA (SEQ ID NO: 87) |
| mZcchc11 r.C2H2 HindIII ft | GTCGATAAGCTTTCCTTGTTCTTTT-GCTAACTCAACAAC (SEQ ID NO: 88) |
| hZcchc6 HindIII F | GGTACTGGGCAAAGCTTTGCAG (SEQ ID NO: 89) |
| hZcchc6 BamHI ft | CGTAGCGGATCCTTATGATTCCTGCTGGGTC-CTC (SEQ ID NO: 90) |
| mZcchc11 qPCft F | GAAGACAGAAACAGACAACCAAG (SEQ ID NO: 91) |
| mZcchc11 qPCft ft | CCTCCAAAGCAAAATCCAGTG (SEQ ID NO: 92) |
| mLin28 qPCft F | AGGCGGTGGAGTTCACCTTTAAGA (SEQ ID NO: 93) |
| mLin28 qPCft ft | AGCTTGCATTCCTTGGCATGATGG (SEQ ID NO: 94) |
| mActin qPCft F | CAGAAGGAGATTACTGCTCTGGCT (SEQ ID NO: 95) |
| mActin qPCft ft | TACTCCTGCTTGCTGATCCACATC (SEQ ID NO: 96) |
| mZcchc6 used taqman primer set (ABI, Mm00463475_m1) | |

Immunoprecipitation and Recombinant Protein Production:

Expression plasmids for Flag-Zcchc11, Flag-Zcch6, Flag-Lin28A, or Flag-Lin28B were transfected into HEK293T cells using Lipofectamine 2000 (Invitrogen). Cells were harvested in lysis buffer (20 mM Tris-HCl, pH 8.0, 137 mM NaCl, 1 mM EDTA, 1% Triton x100, 10% Glycerol, 1.5 mM MgCl$_2$, 5 mM DTT, 0.2 mM PMSF). Protein was purified using anti-Flag M2 beads (Sigma), eluted using Flag peptide (Sigma) and confirmed by Western Blot analysis, with a mouse anti-Flag antibody (Sigma). For recombinant protein production: Transformed BL21-Codon-Plus® Competent bacteria (Stratagene) were grown to an OD600 nm of 0.4-0.6. Recombinant protein expression (r.Lin28A, r.Zcchc11, and r.C2H2) was induced with 100 µM IPTG for 2-3 hr. Cell pellets were resuspended in cold lysis buffer [20 mM imidazole pH 8.0 in PBS, 0.1% Phenylmethyl sulfonyl fluoride (PMSF)] and sonicated. Cleared lysates were incubated with Ni-NTA beads and after 90 min incubation at 4° C. the beads were washed with 80 bead volumes wash buffer [10 mM Tris (pH 7.8), 50 mM imidazole pH 8.0, 500 mM NaCl, 0.1% PMSF, 1 mM DTT). Bound His-tagged proteins were eluted from the column with 1 volume elution buffer [10 mM Tris (pH 7.8), 500 mM imidazole pH 8.0, 500 mM NaCl, 1 mM DTT, 0.1% fresh PMSF] and dialyzed overnight against BC100 [20 mM Tris-HCl (pH 7.8), 100 mM KCl, 0.2 mM EDTA, 10% glycerol]. Proteins were further purified by size exclusion chromatography using a Superose 6 gel filtration column (20 mM Tris-HCl (pH 7.8), 500 mM KCl, 0.2 mM EDTA, 0.2% NP40, 10% glycerol) and peak fractions were dialyzed overnight against BC100 and stored at 4° C.

In Vitro Uridylation Assay:

Purified proteins were incubated with 4 pmol of unlabelled synthetic RNA (Dharmacon) for 1 hour at 37° C. in a 30 µl reaction mixture containing 100 mM KCl, 20 mM Tris-HCl pH 7.6, 10% Glycerol, 125 nM [α-$^{32}$P]UTP, 3.2 mM MgCl2, 40 U RNasin ribonuclease inhibitor (Promega). Products were resolved on 15% denaturing polyacrylamide gels and bands were detected by autoradiography.

Electrophoretic Mobility Shift Analysis:

EMSA with purified His-Lin28A and His-C2H2 domain of Zcchc11 was performed with end-labeled synthetic pre-let-7 as described but without competitor yeast tRNA (Piskounova et al., 2008). Briefly, reactions were set up in binding buffer [50 mM Tris, (pH7.5), 100 mM NaCl, 10 mM βMe, 20 U RNasin (Promega)] with 0.5 nM or 5 nM end-labeled pre-let-7g and incubated for 60 min at room temperature. Bound complexes were resolved on native 5% polyacrylamide gels and visualized by autoradiography.

In Vivo Knockdowns and Quantitative RT-PCR:

The indicated siRNAs (see Table 4) were reverse transfected in either P19 or feeder-free V6.5 mouse embryonic stem cells using Lipofectamine2000 in 6 well plates, according to the manufacturer's protocol (Invitrogen).

TABLE 4 siRNAs

| | |
|---|---|
| Lin28 si #1 | GGGUUGUGAUGACAGGCAAUU (SEQ ID NO: 97) |
| Zcchc11 si #2 | GGGCUAAGCUGUGCUAUAU (SEQ ID NO: 98) |
| Zcchc11 si #4 | CCAAAGUGCCUAUUGUAAA (SEQ ID NO: 99) |
| Zcchc6 si #2 | AGAUCAGGCUUCAACGUAA (SEQ ID NO: 100) |
| Zcchc6 si #3 | GAAAGUGAGGCGACGGAGA (SEQ ID NO: 101) |

Total RNA was isolated 60 hours post-transfection using TriZol reagent (Invitrogen). To analyze relative mRNA levels, 2 µg of total RNA was reverse transcribed using random hexamers and SuperScriptIII (Invitrogen). MiRNAs were reverse transcribed from 10 ng total RNA using gene-specific stem-loop RT primers (Applied Biosystems). Relative levels of miRNAs were determined by TaqMan based real-time PCR, snoRNA-142 for normalization. For quantitative analysis of mRNA levels real-time RT-PCR was performed with either SYBR green or Taqman assays. Actin was used as control. For global microRNA profiling, the TaqMan Rodent MicroRNA A Array v2.0 was used with 350 ng total RNA as starting material for the multiplex RT with pre-amplification, according to manufacturer's directions (Applied Biosystems). The resulting data was normalized to the U6 snRNA.

We claim:

1. A method of high throughput screening of agents that derepress let-7 expression, the method comprising:
   providing a recombinant functional domain of mammalian terminal uridyly transferase (TUTase) ZCCHC11 or ZCCHC6, a recombinant functional domain of mammalian Lin28A, and a let-7 miRNA precursor in an assay;
   adding an agent to said assay;
   monitoring 3' TUTase activity; and
   identifying the agent as an agent that derepresses let-7 expression if it inhibits TUTase activity as compared to an agent that does not derepress let-7 expression.

2. The method of claim 1, wherein the assay is an in vitro assay.

3. The method of claim 1, wherein the assay is a cell-based assay.

4. The method of claim 1, wherein the agent is a compound from a compound library.

5. The method of claim 4, wherein the compound library is a chemical library, a bioactive compound library, or a natural product extract library.

6. The method of claim 1, wherein the TUTase is ZCCHC 11.

7. The method of claim 1, wherein the TUTase is ZCCHC 6.

8. The method of claim 1, wherein the functional domain of mammalian TUTase comprises a N-terminal C2H2 zinc finger.

* * * * *

UNITED STATES PATENT AND TRADEMARK OFFICE
CERTIFICATE OF CORRECTION

| | | |
|---|---|---|
| PATENT NO. | : 9,938,354 B2 | Page 1 of 1 |
| APPLICATION NO. | : 14/269041 | |
| DATED | : April 10, 2018 | |
| INVENTOR(S) | : Richard I. Gregory et al. | |

It is certified that error appears in the above-identified patent and that said Letters Patent is hereby corrected as shown below:

In the Specification

At Column 1, Line 18, please replace the paragraph titled "FEDERAL FUNDING" with the following paragraph:
FEDERALLY SPONSORED RESEARCH
This invention was made with government support under Grant Number GM086386, awarded by the National Institutes of Health. The Government has certain rights in the invention.

Signed and Sealed this
Fifth Day of March, 2024

Katherine Kelly Vidal
*Director of the United States Patent and Trademark Office*